(12) United States Patent
Sun

(10) Patent No.: US 8,129,388 B2
(45) Date of Patent: Mar. 6, 2012

(54) THERAPEUTIC AGENTS USEFUL FOR TREATING PAIN

(75) Inventor: Qun Sun, Princeton, NJ (US)

(73) Assignee: Purde Pharma L.P., Stamford, CT (US)

( * ) Notice: Subject to any disclaimer, the term of this patent is extended or adjusted under 35 U.S.C. 154(b) by 0 days.

(21) Appl. No.: 13/158,267

(22) Filed: Jun. 10, 2011

(65) Prior Publication Data

US 2011/0281876 A1 Nov. 17, 2011

Related U.S. Application Data

(60) Continuation of application No. 12/846,689, filed on Jul. 29, 2010, now Pat. No. 7,964,606, which is a division of application No. 11/386,058, filed on Mar. 20, 2006, now Pat. No. 7,799,807, which is a continuation of application No. PCT/US2004/030824, filed on Sep. 21, 2004.

(60) Provisional application No. 60/504,679, filed on Sep. 22, 2003.

(51) Int. Cl.
*C07D 403/12* (2006.01)
*A61K 31/497* (2006.01)

(52) U.S. Cl. ............... 514/252.01; 544/238; 544/241

(58) Field of Classification Search ............ 544/238, 544/241; 514/252.01
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,039,680 A | 8/1991 | Imperato et al. | |
| 5,059,595 A | 10/1991 | Le Grazie | |
| 5,073,543 A | 12/1991 | Marshall et al. | |
| 5,075,341 A | 12/1991 | Mendelson et al. | |
| 5,120,548 A | 6/1992 | McClelland et al. | |
| 5,198,459 A | 3/1993 | Imperato et al. | |
| 5,232,934 A | 8/1993 | Downs | |
| 5,294,624 A | 3/1994 | Fuse et al. | |
| 5,354,556 A | 10/1994 | Sparks et al. | |
| 5,442,064 A | 8/1995 | Pieper et al. | |
| 5,556,837 A | 9/1996 | Nestler et al. | |
| 5,556,838 A | 9/1996 | Mayer et al. | |
| 5,574,052 A | 11/1996 | Rose et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,698,155 A | 12/1997 | Grosswald et al. | |
| 5,733,566 A | 3/1998 | Lewis | |
| 5,762,925 A | 6/1998 | Sagen | |
| 5,840,720 A | 11/1998 | Chen | |
| 6,136,839 A | 10/2000 | Isakson et al. | |
| 6,204,284 B1 | 3/2001 | Beer et al. | |
| 6,239,267 B1 | 5/2001 | Duckworth et al. | |
| 6,326,385 B1 | 12/2001 | Wickenden et al. | |
| 6,335,180 B1 | 1/2002 | Julius et al. | |
| 6,406,908 B1 | 6/2002 | McIntyre et al. | |
| 6,495,550 B2 | 12/2002 | McNaughton-Smith et al. | |
| 6,974,818 B2 | 12/2005 | Kyle et al. | |
| 7,767,677 B2 | 8/2010 | Kamboj et al. | |
| 7,772,254 B2 | 8/2010 | Sun | |
| 7,799,807 B2 | 9/2010 | Sun | |
| 7,964,606 B2 | 6/2011 | Sun | |
| 7,994,177 B2 | 8/2011 | Sun | |
| 2001/0049444 A1 | 12/2001 | McNaughton-Smith et al. | |
| 2003/0153596 A1 | 8/2003 | Suh et al. | |
| 2004/0110802 A1 | 6/2004 | Thorarensen et al. | |
| 2004/0259931 A1 | 12/2004 | Goodfellow et al. | |
| 2005/0130954 A1 | 6/2005 | Mitchell et al. | |
| 2005/0222161 A1 | 10/2005 | Moriya et al. | |
| 2005/0222410 A1 | 10/2005 | Stokes et al. | |
| 2006/0100245 A1 | 5/2006 | Bakthavatchalam et al. | |
| 2006/0142333 A1 | 6/2006 | MacDonald et al. | |
| 2006/0235022 A1 | 10/2006 | Sun | |
| 2006/0241117 A1 | 10/2006 | Sun | |
| 2010/0317670 A1 | 12/2010 | Sun | |

FOREIGN PATENT DOCUMENTS

| | | |
|---|---|---|
| DE | 100 10 422 | 9/2001 |
| DE | 10010422 A1 * | 9/2001 |
| EP | 0 533 267 | 3/1993 |
| GB | 2 276 162 | 9/1994 |
| GB | 2 276 163 | 9/1994 |
| WO | WO 94/05153 | 3/1994 |
| WO | WO 98/20867 | 5/1998 |
| WO | WO 00/39117 | 7/2000 |
| WO | WO 03/087057 | 10/2003 |
| WO | WO 2004/056774 | 7/2004 |
| WO | WO 2004/058762 | 7/2004 |
| WO | WO 2004/072069 | 8/2004 |
| WO | WO 2004/106285 | 12/2004 |
| WO | WO 2005/003101 | 1/2005 |
| WO | WO 2005/016323 | 2/2005 |

OTHER PUBLICATIONS

Amadji et al., "Chirons in the 1,3-dioxane series: Stereospecific cross-coupling reactions and chirality transfers," *Tettrahedron* 9 : 1657-60 (1998).

(Continued)

*Primary Examiner* — Kahsay T Habte
(74) *Attorney, Agent, or Firm* — Dechert LLP

(57) ABSTRACT

The present invention discloses compounds of formula:

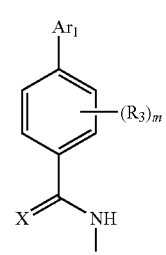

(I)

where $Ar_1$, $Ar_2$, X, $R_3$, and m are as disclosed herein or a pharmaceutically acceptable salt thereof (a "Phenylene Compound"); compositions comprising an effective amount of a Phenylene Compound; and methods for treating pain and other conditions in an animal comprising administering to an animal in need thereof an effective amount of a Phenylene Compound.

23 Claims, No Drawings

OTHER PUBLICATIONS

Bartho et al., "Involvement of capsaicin-sensitive neurones in hyperalgesia and enhanced opioid antinociception in inflammation," *Naunyn-Schmiedeberg's Archives Pharmacol.* 342:666-670 (1990).

Berkow et al., "Crohn's Disease," *The Merck Manual of Medical Information* 528-530 (1997).

Berkow et al., "Irritable Bowel Syndrome," *The Merck Manual of Medical Information* 525-526 (1997).

Berkow et al., "Peptic Ulcer," *The Merck Manual of Medical Information* 496-500 (1997).

Berkow et al., "Seizure Disorders," *The Merck Manual of Medical Information*, pp. 345-350 (1997).

Berkow et al., "Stroke," *The Merck Manual of Medical Information*, pp. 352-355 (1997).

Berkow et al., "Ulcerative Colitis," *The Merck Manual of Medical Information* 530-532 (1997).

Berkow et al., "Urinary Incontinence," *The Merck Manual of Medical Information* 631-634 (1997).

Bevan et al., "Vanilloid Receptors: Pivotal Molecules in Nocciception," *Current Opinions in CPNS investigational Drugs* 2(2):178-185 (2000).

Billotte, "Synthesis of C-substituted cyclic amines using azacycloalkyl organozinc reagents," *Synlett.* pp. 379-380 (Apr. 1998).

Brunton, "Agents for control of gastric acidity and treatment of peptic ulcers," *Goodman and Gilman's The Pharmacological Basis of Therapeutics*, pp. 901-915 (J. Hardman and L. Limbird eds., $9^{th}$ ed. 1996).

Buchwald et al., "Long-term, continuous intravenous heparin administration by an implantable infusion pump in ambulatory patients with recurrent venous thrombosis," *Surgery* 88:507-516 (1980).

Chiamulera et al., "Reinforcing and locomotor stimulant effects of cocaine are absent in mGluR5 null mutant mice," *Nature Neurosci* 4(9):873-874 (2001).

*Controlled Drug Bioavailability, Drug Product Design and Performance* (Smolen and Ball eds., 1984).

Cooke, "Glycopyrrolate in bladder dysfunction," *SA Medical J.* 63:3 (1983).

D'Amour et al, "A method for determining loss of pain sensation," *J. Pharmacol Exp. Ther.* 72:74-79 (1941).

Di Marzo et al., "Endovanilloid signaling in pain," *Current Opinion in Neurobiology* 12:372-379 (2002).

Dogrul et al., "Peripheral and spinal antihyperalgesic activity of SIB-1757, a metabotropic glutamate receptor (mGluR$_5$) antagonist, in experimental neuropathic pain in rats," *Neurosci. Lett.* 292(2):115-118 (2000).

During et al., "Controlled release of dopamine from a polymeric brain implant: In vivo characterization," *Ann. Neurol.* 25:351-356 (1989).

Fillon et al., "Electrosynthesis of functionalized organodizinc compound from aromatic dihalides via a cobalt catalysis in acetonitrile/pyridine as solvent," *Tett. Lett.* 42:3843-46 (2001).

Foley, "Pain," *Cecil Textbook of Medicine*, pp. 100-107 (1996).

Fundytus et al., "Antisense oligonucleotide knockdown of mGluR$_1$ alleviates hyperalgesia and allodynia associated with chronic inflammation," *Pharmacol., Biochem. & Behavior* 73:401-410 (2002).

Fundyius et al., "In vivo antinociceptive activity of anti-rat mGluR$_1$ and mGluR$_5$ antibodies in rats," *NeuroReport* 9:731-735 (1998).

Fundytus et al., "Knockdown of spinal metabotropic glutamate receptor 1 (mGluR$_1$) alleviates pain and restores opioid efficacy after nerve injury in rats," *Brit J. Pharmacol.* 132:354-367 (2001).

Fundytus, "Glutamate receptors and nociception implications for the drug-treatment of pain," *CNS Drugs* 15:29-58 (2001).

Goodson, In *Medical Applications of Controlled Release*, vol. 2, pp. 115-138 (1984).

Greene et al., *Protective Groups in Organic Synthesis*, 309-405 (2d ed. 1991).

Greene, "Protection for the hydroxyl group including 1,2- and 1,3-diols," *Protective Groups in Organic Synthesis* pp. 10-86 (1981).

Grupp et al., "Protection against hypoxia-reoxygenation in the absence of poly (ADP-ribose) synthetase in isolated working hearts," *J. Mol. Cell Cardiol.* 31:297-303 (1999).

Hanson, "Analgesic, antipyretic and anti-inflammatory drugs," *Remington: The Science and Practice of Pharmacy* vol. II, pp. 1196-1221 (A.R. Gennaro ed. 19th ed. 1995).

Hargreaves et al., "A new and sensitive method for measuring thermal nociception in cutaneous hyperalgesia," *Pain* 32(1):77-88 (1988).

Howard et al., "Intracerebral drug delivery in rats with lesion-induced memory deficits," *J. Neurosurg.* 71:105 (1989).

Insel, "Analgesic-antipyretic and anti-inflammatory agents and drugs employed in the treatment of gout," in *Goodman & Gilman's The Pharmacological Basis of Therapeutics* pp. 617-657 (Molinhoff and Ruddon eds., $9^{th}$ ed 1996).

Kim, "An experimental model for peripheral neuropathy produced by segmental spinal nerve ligation in the rat," *Pain* 50(3):355-363 (1992).

Langer et al., "Chemical and physical structure of polymers as carriers for controlled release of bioactive agents: A review," *J. Macromol. Sci. Rev. Macromol. Chem.* C23(1):61-126 (1983).

Langer, "New methods of drug delivery," *Science* 249:1527-1533 (1990).

Levin et al., "Direct measurement of the anticholinergic activity of a series of pharmacological compounds on the canine and rabbit urinary bladder," *J. Urology* 128:396-398 (1982).

Levy et al., "Inhibition of calcification of bioprosthetic heart valves by local controlled-release diphosphonate," *Science* 228:190-192 (1985).

Lopez-Rodriquez et al., "VR1 Receptor Modulators as Potential Drugs for Neuropathic Pain," *Mini-Revs in Medicinal Chem.* 3(7):729-748 (2003).

Masu et al., "Sequence and expression of a metabotropic glutamate receptor," *Nature* 349:760-765 (1991).

*Medical Applications of Controlled Release* (Langer and Wise eds., 1974).

Miller et al, "Growth factor upregulation of phosphoinositide-coupled metabotropic glutamate receptor in cortical astrocytes," *J. Neurosci.* 15(9):6103-6109 (1995).

Mirakhur et al., "Glycopyrrolate: Pharmacology and clinical use," *Anaesthesia* 38:1195-1204 (1983).

Ossowska et al., "Blockade of the metabotropic glutamate receptor subtype 5 (mGluR5) produces antiparkinsonian-like effects in rats," *Neuropharmacol.* 41:413-420 (2001).

Pomonis et al., "N-(4-Tertiarybutylphenyl)-4-(3-chlorophyridin-2-yl)tetrahydropyrazine-1(2H)-carbox-amide (BCTC), a Novel, Orally Effective Vanilloid Receptor 1 Antagonist with Analgesic Properties: II. In Vivo Characterization in Rat Models of Inflammatory and Neuropathic Pain" *J. Pharmacol. Exper. Therapeutics* 306(1):387-393 (2003).

Radebough et al., "Preformulation," *Remington's Pharmaceutical Sciences*, pp. 1447-1676 (Alfonso R. Gennaro ed., 19th ed. 1995).

Saudek et al., "A preliminary trial of the programmable implantable medication system for insulin delivery," *New Engl. J. Med.* 321:574-579 (1989).

Sefton, "Implantable pumps," *CRC Crit. Ref Biomed. Eng.* 14:201-240 (1987).

Seltzer at al., "A novel behavioral model of neuropathic pain disorders produced in rats by partial sciatic nerve injury," *Pain* 43:205-218 (1990).

Smith et al., *March's Advanced Organic Chemistry: Reaction Mechanisms and Structure*, pp. 805-807 ($5^{th}$ ed. 2001).

Smith et al., *March's Advanced Organic Chemistry: Reaction Mechanisms and Structure*, pp. 1184-1185 ($5^{th}$ ed. 2001).

Spooren at al., "Novel allosteric antagonists shed light on mGlu$_5$ receptors and CNS disorders," *Trends Pharmacol. Sci.* 22(7):331-337 (2001).

Stein, "Unilateral inflammation of the hindpaw in rats as a model of prolonged noxious stimulation: Alterations in behavior and nociceptive thresholds," *Pharmacol. Biochem. Behavior* 31:451-455 (1988).

Szallasi et al., "The Cloned Rat Vanilloid Receptor VR1 Mediates Both R-Type Binding and C-Type Calcium Response in Dorsal Root Ganglion Neurons," *Molec. Pharmacol.* 56:581-587 (1999).

Szallasi et al., "Vanilloid (Capsaicin) Receptors and Mechanisma," *Pharmacol. Revs.* 51(2):159-211 (1999).

Tatarczynska et al., "Potential anxiolytic- and antidepressant-like effects of MPEP, a potent, selective and systemically active mGlu5 receptor antagonist," *Brit J. Pharmacol.* 132(7):1423-1430 (2001).

Treat et al, "Liposome encapsulated doxorubicin—preliminary results of phase I and phase II trials," *Liposomes in the Therapy of Infectious Disease and Cancer*, pp. 353-365 (1989).

Treit, "Animal models for the study of anti-anxiety agents: A review," *Neurosci. Biobehavioral Revs.* 9(2):203-222 (1985).

Walker et al., "Metabotropic glutamate receptor subtype 5 (mGlu5) and nociceptive function. I. Selective blockade of mGlu5 receptors in models of acute, persistent and chronic pain," *Neuropharmacol.* 40:1-9 (2000).

Wang et al., "High Affinity Antagonists of the Vanilloid Receptor," *Mol. Pharmacol.* 62:(4):947-956 (2002).

Wein, "Pharmacology of incontinence," *Urologic Clinics of North America* 22(3):557-577 (1995).

Wrigglesworth et al., "Capsaicin-like Agonists," *Drugs of the Future* 23(5):531-538 (1998).

Searth Report of EP 08011788.0-2117, Dec. 15, 2005, Euro-Celtique S.A.

Hales et al., "Novel Inhibitors of Prolyl 4-Hydroxylase," *J. Med. Chem.* 36:3853-3858 (1993).

Wang et al., "High Affinity Antagonists of the Vanilloid Receptor," *Mol Pharmacol.* 62:947-956 (2002).

Toth et al., "Design of a High-Affinity Competitive Antagonist of the Vanilloid Receptor Selective for the Calcium Entry-Linked Receptor Population," *Mol Pharmacol.* 65:282-291 (2004).

* cited by examiner

SEQUENCE LISTING

```
<160> NUMBER OF SEQ ID NOS: 2

<210> SEQ ID NO 1
<211> LENGTH: 32
<212> TYPE: DNA
<213> ORGANISM: Artificial Sequence
<220> FEATURE:
<223> OTHER INFORMATION: Human VR1 forward primer

<400> SEQUENCE: 1
gaagatcttc gctggttgca cactgggcca ca                                      32

<210> SEQ ID NO 2
<211> LENGTH: 32
<212> TYPE: DNA
```

```
<213> ORGANISM: Artificial Sequence
<220> FEATURE:
<223> OTHER INFORMATION: Human VR1 reverse primer

<400> SEQUENCE: 2
gaagatcttc ggggacagtg acggttggat gt                                32
```

THERAPEUTIC AGENTS USEFUL FOR TREATING PAIN

This application is a continuation of application Ser. No. 12/846,689, filed Jul. 29, 2010, now U.S. Pat. No. 7,964,606, which is a divisional of application Ser. No. 11/386,058, filed Mar. 20, 2006, now U.S. Pat. No. 7,799,807, which is a continuation of International patent application serial no. PCT/US2004/030824, filed Sep. 21, 2004, which claims the benefit under 35 U.S.C. §119(e) of provisional application No. 60/504,679, filed Sep. 22, 2003, the contents of all of which are incorporated herein by reference.

1. FIELD OF THE INVENTION

The present invention relates to Phenylene Compounds, compositions comprising an effective amount of a Phenylene Compound and methods for treating or preventing a Condition such as pain comprising administering to an animal in need thereof an effective amount of a Phenylene Compound.

2. BACKGROUND OF THE INVENTION

Pain is the most common symptom for which patients seek medical advice and treatment. Pain can be acute or chronic. While acute pain is usually self-limited, chronic pain persists for 3 months or longer and can lead to significant changes in a patient's personality, lifestyle, functional ability and overall quality of life (K. M. Foley, Pain, in Cecil Textbook of Medicine 100-107 (J. C. Bennett and F. Plum eds., 20th ed. 1996)).

Moreover, chronic pain can be classified as either nociceptive or neuropathic. Nociceptive pain includes tissue injury-induced pain and inflammatory pain such as that associated with arthritis. Neuropathic pain is caused by damage to the peripheral or central nervous system and is maintained by aberrant somatosensory processing. There is a large body of evidence relating activity at both Group I mGluRs (mGluR1 and mGluR5) (M. E. Fundytus, CNS Drugs 15:29-58 (2001)) and vanilloid receptors (VR1) (V. Di Marzo et al., Current Opinion in Neurobiology 12:372-379 (2002)) to pain processing. Inhibiting mGluR1 or mGluR5 reduces pain, as shown by in vivo treatment with antibodies selective for either mGluR1 or mGluR5, where neuropathic pain in rats was attenuated (M. E. Fundytus et al., NeuroReport 9:731-735 (1998)). It has also been shown that antisense oligonucleotide knockdown of mGluR1 alleviates both neuropathic and inflammatory pain (M. E. Fundytus et al., British Journal of Pharmacology 132:354-367 (2001); M. E. Fundytus et al., Pharmacology, Biochemistry & Behavior 73:401-410 (2002)). Small molecule antagonists for mGluR5-attenuated pain in in vivo animal models are disclosed in, e.g., K. Walker et al., Neuropharmacology 40:1-9 (2000) and A. Dogrul et al., Neuroscience Letters 292:115-118 (2000)).

Nociceptive pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. Id. In addition to the above-listed treatments, neuropathic pain, which can be difficult to treat, has also been treated with anti-epileptics (e.g., gabapentin, carbamazepine, valproic acid, topiramate, phenyloin), NMDA antagonists (e.g., ketamine, dextromethorphan), topical lidocaine (for post-herpetic neuralgia), and tricyclic antidepressants (e.g., fluoxetine, sertraline and amitriptyline).

Pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. Id.

Urinary incontinence ("UI") is uncontrollable urination, generally caused by bladder-detrusor-muscle instability. UI affects people of all ages and levels of physical health, both in health care settings and in the community at large. Physiologic bladder contraction results in large part from acetylcholine-induced stimulation of post-ganglionic muscarinic-receptor sites on bladder smooth muscle. Treatments for UI include the administration of drugs having bladder-relaxant properties, which help to control bladder-detrusor-muscle overactivity. For example, anticholinergics such as propantheline bromide and glycopyrrolate, and combinations of smooth-muscle relaxants such as a combination of racemic oxybutynin and dicyclomine or an anticholinergic, have been used to treat UI (See, e.g., A. J. Wein, Urol. Clin. N. Am. 22:557-577 (1995); Levin et al., J. Urol. 128:396-398 (1982); Cooke et al., S. Afr. Med. J. 63:3 (1983); R. K. Mirakhur et al., Anaesthesia 38:1195-1204 (1983)). These drugs are not effective, however, in all patients having uninhibited bladder contractions. Administration of anticholinergic medications represent the mainstay of this type of treatment.

None of the existing commercial drug treatments for UI has achieved complete success in all classes of UI patients, nor has treatment occurred without significant adverse side effects. For example, drowsiness, dry mouth, constipation, blurred vision, headaches, tachycardia, and cardiac arrhythmia, which are related to the anticholinergic activity of traditional anti-UI drugs, can occur frequently and adversely affect patient compliance. Yet despite the prevalence of unwanted anticholinergic effects in many patients, anticholinergic drugs are currently prescribed for patients having UI. The Merck Manual of Medical Information 631-634 (R. Berkow ed., 1997).

About 1 in 10 people develop an ulcer. Ulcers develop as a result of an imbalance between acid-secretory factors, also known as "aggressive factors," such as stomach acid, pepsin, and Helicobacter pylori infection, and local mucosal-protective factors, such as secretion of bicarbonate, mucus, and prostaglandins.

Treatment of ulcers typically involves reducing or inhibiting the aggressive factors. For example, antacids such as aluminum hydroxide, magnesium hydroxide, sodium bicarbonate, and calcium bicarbonate can be used to neutralize stomach acids. Antacids, however, can cause alkalosis, leading to nausea, headache, and weakness. Antacids can also interfere with the absorption of other drugs into the blood stream and cause diarrhea.

$H_2$ antagonists, such as cimetidine, ranitidine, famotidine, and nizatidine, are also used to treat ulcers. $H_2$ antagonists promote ulcer healing by reducing gastric acid and digestive-enzyme secretion elicited by histamine and other $H_2$ agonists in the stomach and duodenum. $H_2$ antagonists, however, can cause breast enlargement and impotence in men, mental changes (especially in the elderly), headache, dizziness, nausea, myalgia, diarrhea, rash, and fever.

$H^+$, $K^+$-ATPase inhibitors such as omeprazole and lansoprazole are also used to treat ulcers. $H^+$, $K^+$-ATPase inhibitors inhibit the production of enzymes used by the stomach to secrete acid. Side effects associated with $H^+$, $K^+$-ATPase inhibitors include nausea, diarrhea, abdominal colic, headache, dizziness, somnolence, skin rashes, and transient elevations of plasma activities of aminotransferases.

Sucraflate is also used to treat ulcers. Sucraflate adheres to epithelial cells and is believed to form a protective coating at the base of an ulcer to promote healing. Sucraflate, however, can cause constipation, dry mouth, and interfere with the absorption of other drugs.

Antibiotics are used when *Helicobacter pylori* is the underlying cause of the ulcer. Often antibiotic therapy is coupled with the administration of bismuth compounds such as bismuth subsalicylate and colloidal bismuth citrate. The bismuth compounds are believed to enhance secretion of mucous and $HCO_3^-$, inhibit pepsin activity, and act as an antibacterial against *H. pylori*. Ingestion of bismuth compounds, however, can lead to elevated plasma concentrations of $Bi^{+3}$ and can interfere with the absorption of other drugs.

Prostaglandin analogues, such as misoprostal, inhibit secretion of acid and stimulate the secretion of mucous and bicarbonate and are also used to treat ulcers, especially ulcers in patients who require nonsteroidal anti-inflammatory drugs. Effective oral doses of prostaglandin analogues, however, can cause diarrhea and abdominal cramping. In addition, some prostaglandin analogues are abortifacients.

Carbenoxolone, a mineral corticoid, can also be used to treat ulcers. Carbenoxolone appears to alter the composition and quantity of mucous, thereby enhancing the mucosal barrier. Carbenoxolone, however, can lead to $Na^+$ and fluid retention, hypertension, hypokalemia, and impaired glucose tolerance.

Muscarinic cholinergic antagonists such as pirenzapine and telenzapine can also be used to reduce acid secretion and treat ulcers. Side effects of muscarinic cholinergic antagonists include dry mouth, blurred vision, and constipation. *The Merck Manual of Medical Information* 496-500 (R. Berkow ed., 1997) and *Goodman and Gilman's The Pharmacological Basis of Therapeutics* 901-915 (J. Hardman and L. Limbird eds., $9^{th}$ ed. 1996).

Inflammatory-bowel disease ("IBD") is a chronic disorder in which the bowel becomes inflamed, often causing recurring abdominal cramps and diarrhea. The two types of IBD are Crohn's disease and ulcerative colitis.

Crohn's disease, which can include regional enteritis, granulomatous ileitis, and ileocolitis, is a chronic inflammation of the intestinal wall. Crohn's disease occurs equally in both sexes and is more common in Jews of eastern-European ancestry. Most cases of Crohn's disease begin before age 30 and the majority start between the ages of 14 and 24. The disease typically affects the full thickness of the intestinal wall. Generally the disease affects the lowest portion of the small intestine (ileum) and the large intestine, but can occur in any part of the digestive tract.

Early symptoms of Crohn's disease are chronic diarrhea, crampy abdominal pain, fever, loss of appetite, and weight loss. Complications associated with Crohn's disease include the development of intestinal obstructions, abnormal connecting channels (fistulas), and abscesses. The risk of cancer of the large intestine is increased in people who have Crohn's disease. Often Crohn's disease is associated with other disorders such as gallstones, inadequate absorption of nutrients, amyloidosis, arthritis, episcleritis, aphthous stomatitis, erythema nodosum, pyoderma gangrenosum, ankylosing spondylitis, sacroilitis, uveitis, and primary sclerosing cholangitis. There is no known cure for Crohn's disease.

Cramps and diarrhea, side effects associated with Crohn's disease, can be relieved by anticholinergic drugs, diphenoxylate, loperamide, deodorized opium tincture, or codeine. Generally, the drug is taken orally before a meal.

Broad-spectrum antibiotics are often administered to treat the symptoms of Crohn's disease. The antibiotic metronidazole is often administered when the disease affects the large intestine or causes abscesses and fistulas around the anus. Long-term use of metronidazole, however, can damage nerves, resulting in pins-and-needles sensations in the arms and legs. Sulfasalazine and chemically related drugs can suppress mild inflammation, especially in the large intestine. These drugs, however, are less effective in sudden, severe flare-ups. Corticosteroids, such as prednisone, reduce fever and diarrhea and relieve abdominal pain and tenderness. Long-term corticosteroid therapy, however, invariably results in serious side effects such as high blood-sugar levels, increased risk of infection, osteoporosis, water retention, and fragility of the skin. Drugs such as azathioprine and mercaptourine can compromise the immune system and are often effective for Crohn's disease in patients that do not respond to other drugs. These drugs, however, usually need 3 to 6 months before they produce benefits and can cause serious side effects such as allergy, pancreatitis, and low white-blood-cell count.

When Crohn's disease causes the intestine to be obstructed or when abscesses or fistulas do not heal, surgery can be necessary to remove diseased sections of the intestine. Surgery, however, does not cure the disease, and inflammation tends to recur where the intestine is rejoined. In almost half of the cases a second operation is needed. *The Merck Manual of Medical Information* 528-530 (R. Berkow ed., 1997).

Ulcerative colitis is a chronic disease in which the large intestine becomes inflamed and ulcerated, leading to episodes of bloody diarrhea, abdominal cramps, and fever. Ulcerative colitis usually begins between ages 15 and 30, however, a small group of people have their first attack between ages 50 and 70. Unlike Crohn's disease, ulcerative colitis never affects the small intestine and does not affect the full thickness of the intestine. The disease usually begins in the rectum and the sigmoid colon and eventually spreads partially or completely throughout the large intestine. The cause of ulcerative colitis is unknown. Treatment of ulcerative colitis is directed to controlling inflammation, reducing symptoms, and replacing lost fluids and nutrients.

Irritable-bowel syndrome ("IBS") is a disorder of motility of the entire gastrointestinal tract, causing abdominal pain, constipation, and/or diarrhea. IBS affects three-times more women than men.

There are two major types of IBS. The first type, spastic-colon type, is commonly triggered by eating, and usually produces periodic constipation and diarrhea with pain. Mucous often appears in the stool. The pain can come in bouts of continuous dull aching pain or cramps, usually in the lower abdomen. The person suffering from spastic-colon type IBS can also experience bloating, gas, nausea, headache, fatigue, depression, anxiety, and difficulty concentrating. The second type of IBS usually produces painless diarrhea or constipation. The diarrhea can begin suddenly and with extreme urgency. Often the diarrhea occurs soon after a meal and can sometimes occur immediately upon awakening.

Treatment of IBS typically involves modification of an IBS-patient's diet. Often it is recommended that an IBS patient avoid beans, cabbage, sorbitol, and fructose. A low-fat, high-fiber diet can also help some IBS patients. Regular physical activity can also help keep the gastrointestinal tract functioning properly. Drugs such as propantheline that slow the function of the gastrointestinal tract are generally not effective for treating IBS. Antidiarrheal drugs, such as diphenoxylate and loperamide, help with diarrhea. *The Merck Manual of Medical Information* 525-526 (R. Berkow ed., 1997).

Certain pharmaceutical agents have been administered for treating addiction. U.S. Pat. No. 5,556,838 to Mayer et al. discloses the use of nontoxic NMDA-blocking agents co-administered with an addictive substance to prevent the development of tolerance or withdrawal symptoms. U.S. Pat. No. 5,574,052 to Rose et al. discloses co-administration of an addictive substance with an antagonist to partially block the pharmacological effects of the addictive substance. U.S. Pat. No. 5,075,341 to Mendelson et al. discloses the use of a mixed opiate agonist/antagonist to treat cocaine and opiate addiction. U.S. Pat. No. 5,232,934 to Downs discloses administration of 3-phenoxypyridine to treat addiction. U.S. Pat. Nos. 5,039,680 and 5,198,459 to Imperato et al. disclose using a serotonin antagonist to treat chemical addiction. U.S. Pat. No. 5,556,837 to Nestler et. al. discloses infusing BDNF or NT-4 growth factors to inhibit or reverse neurological adaptive changes that correlate with behavioral changes in an addicted individual. U.S. Pat. No. 5,762,925 to Sagan discloses implanting encapsulated adrenal medullary cells into an animal's central nervous system to inhibit the development of opioid intolerance. U.S. Pat. No. 6,204,284 to Beer et al. discloses racemic (±)-1-(3,4-dichlorophenyl)-3-azabicyclo[3.1.0]hexane for use in the prevention or relief of a withdrawal syndrome resulting from addiction to drugs and for the treatment of chemical dependencies.

Without treatment, Parkinson's disease progresses to a rigid akinetic state in which patients are incapable of caring for themselves. Death frequently results from complications of immobility, including aspiration pneumonia or pulmonary embolism. Drugs commonly used for the treatment of Parkinson's disease include carbidopa/levodopa, pergolide, bromocriptine, selegiline, amantadine, and trihexyphenidyl hydrochloride. There remains, however, a need for drugs useful for the treatment of Parkinson's disease and having an improved therapeutic profile.

Anxiety is a fear, apprehension or dread of impending danger often accompanied by restlessness, tension, tachycardia and dyspnea. Currently, benzodiazepines are the most commonly used anti-anxiety agents for generalized anxiety disorder. Benzodiazepines, however, carry the risk of producing impairment of cognition and skilled motor functions, particularly in the elderly, which can result in confusion, delerium, and falls with fractures. Sedatives are also commonly prescribed for treating anxiety. The azapirones, such as buspirone, are also used to treat moderate anxiety. The azapirones, however, are less useful for treating severe anxiety accompanied with panic attacks.

Epilepsy is a disorder characterized by the tendency to have recurring seizures. Examples of drugs for treating a seizure and epilepsy include carbamazepine, ethosuximide, gabapentin, lamotrigine, phenobarbital, phenyloin, primidone, valproic acid, trimethadione, benzodiazepines, γ-vinyl GABA, acetazolamide, and felbamate. Anti-seizure drugs, however, can have side effects such as drowsiness; hyperactivity; hallucinations; inability to concentrate; central and peripheral nervous system toxicity, such as nystagmus, ataxia, diplopia, and vertigo; gingival hyperplasia; gastrointestinal disturbances such as nausea, vomiting, epigastric pain, and anorexia; endocrine effects such as inhibition of antidiuretic hormone, hyperglycemia, glycosuria, osteomalacia; and hypersensitivity such as scarlatiniform rash, morbilliform rash, Stevens-Johnson syndrome, systemic lupus erythematosus, and hepatic necrosis; and hematological reactions such as red-cell aplasia, agranulocytosis, thrombocytopenia, aplastic anemia, and megaloblastic anemia. *The Merck Manual of Medical Information* 345-350 (R. Berkow ed., 1997).

Symptoms of strokes vary depending on what part of the brain is affected. Symptoms include loss or abnormal sensations in an arm or leg or one side of the body, weakness or paralysis of an arm or leg or one side of the body, partial loss of vision or hearing, double vision, dizziness, slurred speech, difficulty in thinking of the appropriate word or saying it, inability to recognize parts of the body, unusual movements, loss of bladder control, imbalance, and falling, and fainting. The symptoms can be permanent and can be associated with coma or stupor. Examples of drugs for treating strokes include anticoagulants such as heparin, drugs that break up clots such as streptokinase or tissue plasminogen activator, and drugs that reduce swelling such as mannitol or corticosteroids. *The Merck Manual of Medical Information* 352-355 (R. Berkow ed., 1997).

Pruritus is an unpleasant sensation that prompts scratching. Conventionally, pruritus is treated by phototherapy with ultraviolet B or PUVA or with therapeutic agents such as naltrexone, nalmefene, danazol, tricyclics, and antidepressants.

Selective antagonists of the metabotropic glutamate receptor 5 ("mGluR5") have been shown to exert analgesic activity in in vivo animal models (K. Walker et al., *Neuropharmacology* 40:1-9 (2000) and A. Dogrul et al., *Neuroscience Letters*, 292(2):115-118 (2000)).

Selective antagonists of the mGluR5 receptor have also been shown to exert anxiolytic and anti-depressant activity in in vivo animal models (E. Tatarczynska et al., *Br. J. Pharmacol.* 132(7):1423-1430 (2001) and P. J. M. Will et al., *Trends in Pharmacological Sciences* 22(7):331-37 (2001)).

Selective antagonists of the mGluR5 receptor have also been shown to exert anti-Parkinson activity in vivo (K. J. Ossowska et al., *Neuropharmacology* 41(4):413-20 (2001) and P. J. M. Will et al., *Trends in Pharmacological Sciences* 22(7):331-37 (2001)).

Selective antagonists of the mGluR5 receptor have also been shown to exert anti-dependence activity in vivo (C. Chiamulera et al., *Nature Neuroscience* 4(9):873-74 (2001)).

U.S. Pat. No. 6,495,550 to McNaughton-Smith et al. discloses pyridine substituted benzanilides useful as openers of potassium ion channels.

International publication no. WO 94/05153 discloses substituted benzene compounds useful as herbicides.

International publication no. WO 04/058762 discloses substituted 9-membered bicyclic compounds useful as MK-2 inhibitors.

United Kingdom Application No. GB 2 276 162 discloses aniline and benzanilide compounds useful for treating disorders of the central nervous system, endocrine disorders, and sexual dysfunction.

United Kingdom Application No. GB 2 276 163 discloses pyridine compounds useful for treating disorders of the central nervous system, endocrine disorders, and sexual dysfunction.

European Application No. EP 533267 discloses benzanilide compounds useful as 5-HT1D antagonists.

U.S. published patent application no. US 2003/0153596 to Young Ger Suh discloses thiourea derivatives useful as a modulator for vanilloid receptors.

There is a need in the art for compounds that are useful for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression in an animal Citation of any reference in Section 2 of this application is not to be construed as an admission that such reference is prior art to the present application.

3. SUMMARY OF THE INVENTION

The present invention encompasses compounds of formula (I):

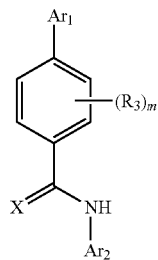

and pharmaceutically acceptable salts thereof, where
Ar$_1$ is

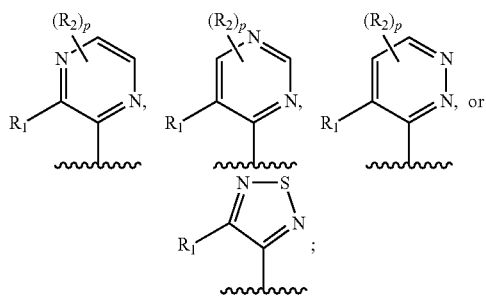

Ar$_2$ is

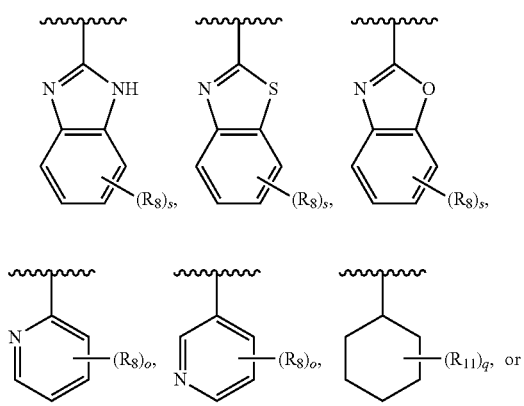

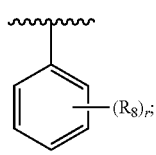

X is O or S;

R$_1$ is -halo, —CH$_3$, —C(halo)$_3$, —CH(halo)$_2$, or —CH$_2$(halo);

each R$_2$ is independently:
(a) -halo, —OH, —NH$_2$, —CN, or —NO$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_5$ groups; or
(c) -phenyl, -naphthyl, —(C$_{14}$)aryl or -(5- to 10-membered)heteroaryl, each of which is unsubstituted or substituted with one or more R$_6$ groups;

each R$_3$ is independently:
(a) -halo, —CN, —OH, —NO$_2$, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, (C$_8$-C$_{14}$)tricycloalkenyl, -(3- to 7-membered)heterocycle, or -(7- to 10-membered)bicycloheterocycle, each of which is unsubstituted or substituted with one or more R$_5$ groups; or
(c) -phenyl, -naphthyl, —(C$_{14}$)aryl or -(5- to 10-membered)heteroaryl, each of which is unsubstituted or substituted with one or more R$_6$ groups;

each R$_5$ is independently —CN, —OH, —(C$_1$-C$_6$)alkyl, —(C$_2$-C$_6$)alkenyl, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_B$, or —S(O)$_2$R$_7$;

each R$_6$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, —CH$_2$(halo), —CN, —OH, -halo, —N$_3$, —NO$_2$, N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each R$_7$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, or CH$_2$(halo);

each R$_8$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —COR$_7$, —C(O)OR$_7$, —OC(O)R$_7$, —OC(O)OR$_7$, —SR$_7$, —S(O)R$_B$, or —S(O)$_2$R$_7$;

each R$_{11}$ is independently —(C$_1$-C$_6$)alkyl, —(C$_2$-C$_6$)alkenyl, —(C$_2$-C$_6$)alkynyl, (C$_3$-C$_8$)cycloalkyl, —(C$_5$-C$_8$)cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_B$, or —S(O)$_2$R$_7$;

each halo is independently —F, —Cl, —Br, or —I;
m is an integer ranging from 0 to 4;
o is an integer ranging from 0 to 4;
p is an integer ranging from 0 to 2;
q is an integer ranging from 0 to 6;
r is an integer ranging from 0 to 5; and
s is an integer ranging from 0 to 4.

The invention further encompasses compounds of formula (II):

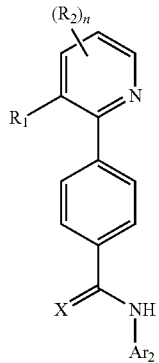

(II)

and pharmaceutically acceptable salts thereof, where

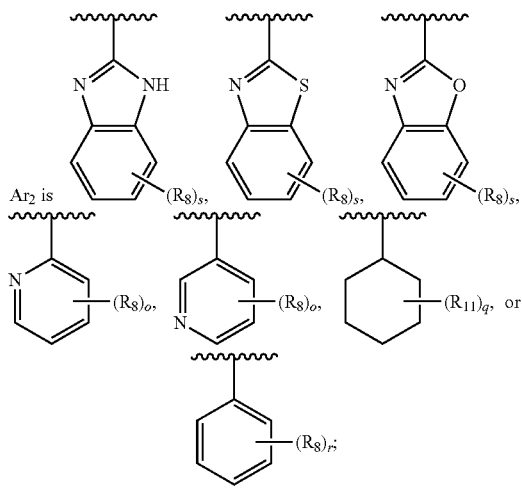

Ar₂ is

X is O or S;
R₁ is -halo, —CH₃, —C(halo)₃, —CH(halo)₂, or —CH₂(halo);
each R₂ is independently:
(a) -halo, —OH, —NH₂, —CN, or —NO₂;
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or (7- to 10-membered)bicycloheterocycle, each of which is unsubstituted or substituted with one or more R₅ groups; or
(c) -phenyl, -naphthyl, —($C_{14}$)aryl or -(5- to 10-membered)heteroaryl, each of which is unsubstituted or substituted with one or more R₆ groups;
each R₅ is independently —CN, —OH, —($C_1$-$C_6$)alkyl, —($C_2$-$C_6$)alkenyl, -halo, —N₃, —NO₂, —N(R₇)₂, —CH=NR₇, —NR₇OH, —OR₇, —COR₇, —C(O)OR₇, —OC(O)R₇, —OC(O)OR₇, —SR₇, —S(O)R₇, or —S(O)₂R₇;
each R₆ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)₃, —CH(halo)₂, —CH₂(halo), —CN, —OH, -halo, —N₃, —NO₂, N(R₇)₂, —CH=NR₇, —NR₇OH, —OR₇, —COR₇, —C(O)OR₇, —OC(O)R₇, —OC(O)OR₇, —SR₇, —S(O)R_B, or —S(O)₂R₇;
each R₇ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)₃, —CH(halo)₂, or CH₂(halo);
each R₈ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)₃, —CH(halo)₂, —CH₂(halo), —CN, —OH, -halo, —N₃, —NO₂, —N(R₇)₂, —CH=NR₇, —NR₇OH, —OR₇, —COR₇, —C(O)OR₇, —OC(O)R₇, —OC(O)OR₇, —SR₇, —S(O)R₇, or —S(O)₂R₇;
each R₁₁ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)₃, —CH(halo)₂, —CH₂(halo), —CN, —OH, -halo, —N₃, —NO₂, —N(R₇)₂, —CH=NR₇, —NR₇OH, —OR₇, —COR₇, —C(O)OR₇, —OC(O)R₇, —OC(O)OR₇, —SR₇, —S(O)R_T, or —S(O)₂R₇;
each halo is independently —F, —Cl, —Br, or —I;
n is an integer ranging from 0 to 3;
o is an integer ranging from 0 to 4;
q is an integer ranging from 0 to 6;
r is an integer ranging from 0 to 5; and
s is an integer ranging from 0 to 4.

A compound of formula (I) or (II) or a pharmaceutically acceptable salt thereof (a "Phenylene Compound") is useful for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression (each being a "Condition") in an animal.

The invention also relates to compositions comprising an effective amount of a Phenylene Compound and a pharmaceutically acceptable carrier or excipient. The compositions are useful for treating or preventing a Condition in an animal.

The invention further relates to methods for treating a Condition, comprising administering to an animal in need thereof an effective amount of a Phenylene Compound.

The invention further relates to methods for preventing a Condition, comprising administering to an animal in need thereof an effective amount of a Phenylene Compound.

The invention still further relates to methods for inhibiting Vanilloid Receptor 1 ("VR1") function in a cell, comprising contacting a cell capable of expressing VR1 with an effective amount of a Phenylene Compound.

The invention still further relates to methods for inhibiting mGluR5 function in a cell, comprising contacting a cell capable of expressing mGluR5 with an effective amount of a Phenylene Compound.

The invention still further relates to methods for inhibiting metabotropic glutamate receptor 1 ("mGluR1") function in a cell, comprising contacting a cell capable of expressing mGluR1 with an effective amount of a Phenylene Compound.

The invention still further relates to methods for preparing a composition, comprising the step of admixing a Phenylene Compound and a pharmaceutically acceptable carrier or excipient.

The invention still further relates to a kit comprising a container containing an effective amount of a Phenylene Compound.

The present invention can be understood more fully by reference to the following detailed description and illustrative examples, which are intended to exemplify non-limiting embodiments of the invention.

4. DETAILED DESCRIPTION OF THE INVENTION

4.1 Phenylene Compounds of Formula (I)

As stated above, the present invention encompasses Phenylene Compounds of Formula (I)

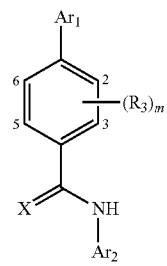
(I)

where $Ar_1$, $Ar_2$, $R_3$, X, and m are defined above for the Phenylene Compounds of formula (I).

In one embodiment, $Ar_1$ is a pyrimidyl group.
In another embodiment, $Ar_1$ is a pyrazinyl group.
In another embodiment, $Ar_1$ is a pyridazinyl group.
In another embodiment, $Ar_1$ is a thiadiazolyl group.
In another embodiment, X is O.
In another embodiment, X is S.
In another embodiment, $Ar_2$ is a benzoimidazolyl group.
In another embodiment, $Ar_2$ is a benzothiazolyl group.
In another embodiment, $Ar_2$ is a benzooxazolyl group.
In another embodiment, $Ar_2$ is

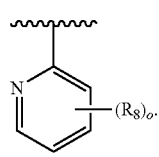

In another embodiment, $Ar_2$ is

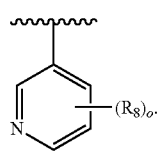

In another embodiment, $Ar_2$ is

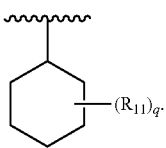

In another embodiment, $Ar_2$ is

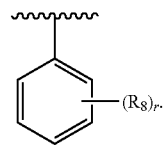

In another embodiment, m is 0.
In another embodiment, m is 1.
In another embodiment, m is 2.
In another embodiment, m is 3.
In another embodiment, m is 4.
In another embodiment, p is 0.
In another embodiment, p is 1.
In another embodiment, p is 2.
In another embodiment, o is 0.
In another embodiment, o is 1.
In another embodiment, o is 2.
In another embodiment, o is 3.
In another embodiment, o is 4.
In another embodiment, q is 0.
In another embodiment, q is 1.
In another embodiment, q is 2.
In another embodiment, q is 3.
In another embodiment, q is 4.
In another embodiment, q is 5.
In another embodiment, q is 6.
In another embodiment, r is 0.
In another embodiment, r is 1.
In another embodiment, r is 2.
In another embodiment, r is 3.
In another embodiment, r is 4.
In another embodiment, r is 5.
In another embodiment, s is 0.
In another embodiment, s is 1.
In another embodiment, s is 2.
In another embodiment, s is 3.
In another embodiment, s is 4.
In another embodiment, s is 5.
In another embodiment, $R_1$ is -halo.
In another embodiment, $R_1$ is —Cl.
In another embodiment, $R_1$ is —Br.
In another embodiment, $R_1$ is —I.
In another embodiment, $R_1$ is —F.
In another embodiment, $R_1$ is —$CH_3$.
In another embodiment, $R_1$ is —C(halo)$_3$.
In another embodiment, $R_1$ is —CH(halo)$_2$.
In another embodiment, $R_1$ is —$CH_2$(halo).
In another embodiment, p is 1 and $R_2$ is -halo, —OH, —$NH_2$, —CN, or —$NO_2$.
In another embodiment, p is 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{10}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.
In another embodiment, p is 1 and $R_2$ is -phenyl, -naphthyl, —($C_{14}$)aryl or -(5- to 10-membered)heteroaryl, each of which is unsubstituted or substituted with one or more $R_6$ groups.
In another embodiment, m is 1 and $R_3$ is -halo, —CN, —OH, —$NO_2$, or —$NH_2$.
In another embodiment, m is 1 and $R_3$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_5$ groups.

In another embodiment, m is 1 and R$_3$ is -phenyl, -naphthyl, —(C$_{14}$)aryl or -(5- to 10-membered)heteroaryl, each of which is unsubstituted or substituted with one or more R$_6$ groups.

In another embodiment, m is 1 and R$_3$ is —(C$_1$-C$_{10}$)alkyl.
In another embodiment, m is 1 and R$_3$ is —CH$_3$.
In another embodiment, m is 1 and R$_3$ is -halo.
In another embodiment, m is 1 and R$_3$ is —Cl.
In another embodiment, m is 1 and R$_3$ is —Br.
In another embodiment, m is 1 and R$_3$ is —I.
In another embodiment, m is 1 and R$_3$ is —F.
In another embodiment, Ar$_2$ is a benzothiazolyl group and s is 1.
In another embodiment, Ar$_2$ is a benzoimidazolyl group and s is 1.
In another embodiment, Ar$_2$ is a benzooxazolyl group and s is 1.
In another embodiment, Ar$_2$ is

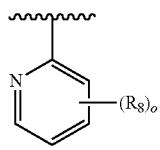

and o is 1.

In another embodiment, Ar$_2$ is

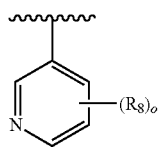

and o is 1.

In another embodiment, Ar$_2$ is

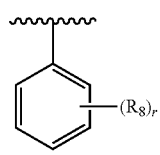

and r is 1.

In another embodiment, Ar$_2$ is

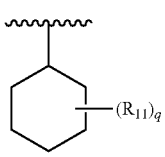

and q is 1.

In another embodiment, Ar$_2$ is a benzothiazolyl group, s is 1, and R$_8$ is -halo or —(C$_1$-C$_6$) alkyl.

In another embodiment, Ar$_2$ is a benzoimidazolyl group, s is 1, and R$_8$ is -halo or —(C$_1$-C$_6$) alkyl.

In another embodiment, Ar$_2$ is a benzooxazolyl group, s is 1, and R$_8$ is -halo or —(C$_1$-C$_6$) alkyl.

In another embodiment, Ar$_2$ is

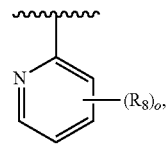

o is 1, and R$_8$ is -halo or —(C$_1$-C$_6$) alkyl.

In another embodiment, Ar$_2$ is

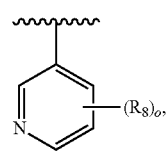

o is 1, and R$_8$ is -halo or —(C$_1$-C$_6$) alkyl.

In another embodiment, Ar$_2$ is

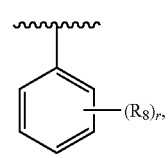

r is 1, and R$_8$ is -halo or —(C$_1$-C$_6$) alkyl.

In another embodiment, Ar$_2$ is

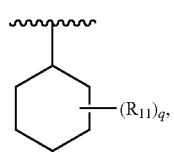

q is 1, and R$_{11}$ is -halo or —(C$_1$-C$_6$) alkyl.

In another embodiment, Ar$_2$ is

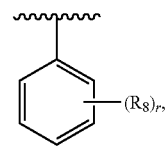

r is 1, and R$_8$ is at the para-position of the phenyl ring.

In another embodiment, Ar$_1$ is a pyrazinyl group, X is O, m is 0, and Ar$_2$ is a benzothiazolyl group.

In another embodiment, Ar$_1$ is a pyrazinyl group, X is O, m is 0, and Ar$_2$ is a benzooxazolyl group.

In another embodiment, Ail is a pyrazinyl group, X is O, m is 0, and Ar$_2$ is a benzoimidazolyl group.

In another embodiment, Ar₁ is a pyrazinyl group, X is O, m is 0, and Ar₂ is

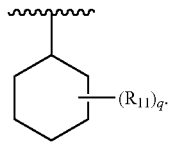

In another embodiment, Ar₁ is a pyrazinyl group, X is O, m is 0, and Ar₂ is

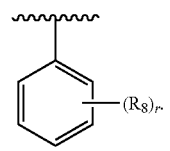

In another embodiment, Ar₁ is a pyrazinyl group, X is O, m is 0, and Ar₂ is

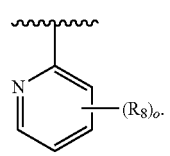

In another embodiment, Ar₁ is a pyrazinyl group, X is O, m is 0, and Ar₂ is

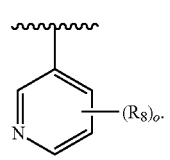

In another embodiment, Ar₁ is a pyrazinyl group, X is O, r is 1, m is 0, Ar₂ is

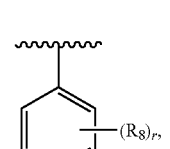

and R₈ is a —(C₁-C₆)alkyl. In another embodiment, the —(C₁-C₆)alkyl is substituted at the phenyl group's para-position. In another embodiment, the —(C₁-C₆)alkyl is a tert-butyl group. In another embodiment, the —(C₁-C₆)alkyl is a tert-butyl group and is substituted at the phenyl group's para-position. In another embodiment, the —(C₁-C₆)alkyl is an iso-propyl group. In another embodiment, the —(C₁-C₆)alkyl is an iso-propyl group and is substituted at the phenyl group's para-position.

In another embodiment, Ar₁ is a pyrazinyl group, X is O, r is 1, m is 0, Ar₂ is

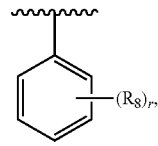

and R₈ is —CF₃. In another embodiment, the —CF₃ is substituted at the phenyl group's 4-position.

In another embodiment, Ar₁ is a pyrazinyl group, X is O, r is 1, m is 0, Ar₂ is

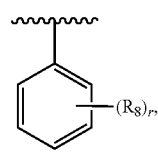

and R₈ is -halo. In another embodiment, the -halo is substituted at the phenyl group's para-position. In another embodiment, -halo is —Cl. In another embodiment, -halo is —Cl and is substituted at the phenyl group's para-position. In another embodiment, -halo is —Br. In another embodiment, -halo is —Br and is substituted at the phenyl group's para-position. In another embodiment, -halo is —I. In another embodiment, -halo is —I and is substituted at the phenyl group's para-position. In another embodiment, -halo is —F. In another embodiment, -halo is —F and is substituted at the phenyl group's para-position.

In another embodiment, Ar₁ is a pyrimidinyl group, X is O, m is 0, and Ar₂ is a benzothiazolyl group.

In another embodiment, Ar₁ is a pyrimidinyl group, X is O, m is 0, and Ar₂ is a benzooxazolyl group.

In another embodiment, Ar₁ is a pyrimidinyl group, X is O, m is 0, and Ar₂ is a benzoimidazolyl group.

In another embodiment, Ar₁ is a pyrimidinyl group, X is O, m is 0, and Ar₂ is

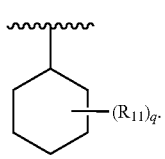

In another embodiment, Ar₁ is a pyrimidinyl group, X is O, m is 0, and Ar₂ is

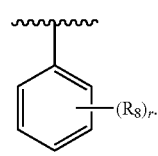

In another embodiment, Ar$_1$ is a pyrimidinyl group, X is O, m is 0, and Ar$_2$ is

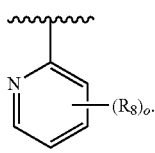

In another embodiment, Ar$_1$ is a pyrimidinyl group, X is O, m is 0, and Ar$_2$ is

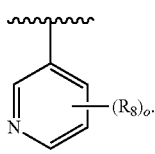

In another embodiment, Ar$_1$ is a pyrimidinyl group, X is O, r is 1, m is 0, Ar$_2$ is

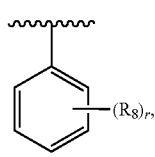

and R$_8$ is a —(C$_1$-C$_6$)alkyl. In another embodiment, the —(C$_1$-C$_6$)alkyl is substituted at the phenyl group's para-position. In another embodiment, the —(C$_1$-C$_6$)alkyl is a tert-butyl group. In another embodiment, the —(C$_1$-C$_6$)alkyl is a tert-butyl group and is substituted at the phenyl group's para-position. In another embodiment, the —(C$_1$-C$_6$)alkyl is an iso-propyl group. In another embodiment, the —(C$_1$-C$_6$)alkyl is an iso-propyl group and is substituted at the phenyl group's para-position.

In another embodiment, Ar$_1$ is a pyrimidinyl group, X is O, r is 1, m is 0, Ar$_2$ is

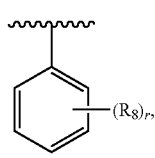

and R$_8$ is —CF$_3$. In another embodiment, the —CF$_3$ is substituted at the phenyl group's 4-position In another embodiment, Ar$_1$ is a pyrimidinyl group, X is O, r is 1, m is 0, Ar$_2$ is

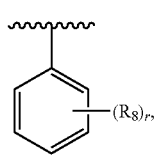

and R$_8$ is -halo. In another embodiment, the -halo is substituted at the phenyl group's para-position. In another embodiment, -halo is —Cl. In another embodiment, -halo is —Cl and is substituted at the phenyl group's para-position. In another embodiment, -halo is —Br. In another embodiment, -halo is —Br and is substituted at the phenyl group's para-position. In another embodiment, -halo is —I. In another embodiment, -halo is —I and is substituted at the phenyl group's para-position. In another embodiment, -halo is —F. In another embodiment, -halo is —F and is substituted at the phenyl group's para-position.

In another embodiment, Ar$_1$ is a pyridazinyl group, X is O, m is 0, and Ar$_2$ is a benzothiazolyl group.

In another embodiment, Ar$_1$ is a pyridazinyl group, X is O, m is 0, and Ar$_2$ is a benzooxazolyl group.

In another embodiment, Ar$_1$ is a pyridazinyl group, X is O, m is 0, and Ar$_2$ is a benzoimidazolyl group.

In another embodiment, Ar$_1$ is a pyridazinyl group, X is O, m is 0, and Ar$_2$ is

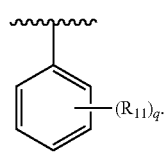

In another embodiment, Ar$_1$ is a pyridazinyl group, X is O, m is 0, and Ar$_2$ is

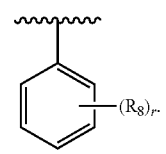

In another embodiment, Ar$_1$ is a pyridazinyl group, X is O, m is 0, and Ar$_2$ is

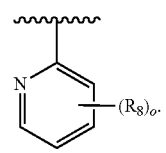

In another embodiment, Ar$_1$ is a pyridazinyl group, X is O, m is 0, and Ar$_2$ is

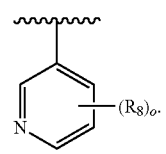

In another embodiment, $Ar_1$ is a pyridazinyl group, X is O, r is 1, m is 0, $Ar_2$ is

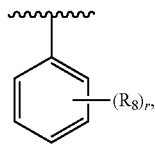

and $R_8$ is a —($C_1$-$C_6$)alkyl. In another embodiment, the —($C_1$-$C_6$)alkyl is substituted at the phenyl group's para-position. In another embodiment, the —($C_1$-$C_6$)alkyl is a tert-butyl group. In another embodiment, the —($C_1$-$C_6$)alkyl is a tert-butyl group and is substituted at the phenyl group's para-position. In another embodiment, the —($C_1$-$C_6$)alkyl is an iso-propyl group. In another embodiment, the —($C_1$-$C_6$)alkyl is an iso-propyl group and is substituted at the phenyl group's para-position.

In another embodiment, $Ar_1$ is a pyridazinyl group, X is O, r is 1, m is 0, $Ar_2$ is

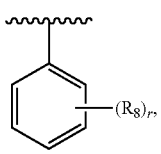

and $R_8$ is —$CF_3$. In another embodiment, the —$CF_3$ is substituted at the phenyl group's para-position.

In another embodiment, $Ar_1$ is a pyridazinyl group, X is O, r is 1, m is 0, $Ar_2$ is

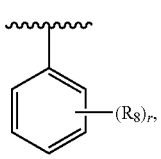

and $R_8$ is -halo. In another embodiment, the -halo is substituted at the phenyl group's para-position. In another embodiment, -halo is —Cl. In another embodiment, -halo is —Cl and is substituted at the phenyl group's para-position. In another embodiment, -halo is —Br. In another embodiment, -halo is —Br and is substituted at the phenyl group's para-position. In another embodiment, -halo is —I. In another embodiment, -halo is —I and is substituted at the phenyl group's para-position. In another embodiment, -halo is —F. In another embodiment, -halo is —F and is substituted at the phenyl group's para-position.

In another embodiment, $Ar_1$ is a thiadiazolyl group, X is O, m is 0, and $Ar_2$ is a benzothiazolyl group.

In another embodiment, $Ar_1$ is a thiadiazolyl group, X is O, m is 0, and $Ar_2$ is a benzooxazolyl group.

In another embodiment, $Ar_1$ is a thiadiazolyl group, X is O, m is 0, and $Ar_2$ is a benzoimidazolyl group.

In another embodiment, $Ar_1$ is a thiadiazolyl group, X is O, m is 0, and $Ar_2$ is

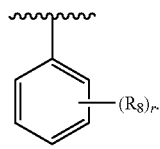

In another embodiment, $Ar_1$ is a thiadiazolyl group, X is O, m is 0, and $Ar_2$ is

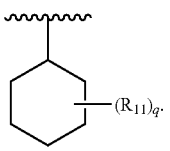

In another embodiment, $Ar_1$ is a thiadiazolyl group, X is O, m is 0, and $Ar_2$ is

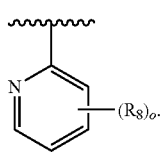

In another embodiment, $Ar_1$ is a thiadiazolyl group, X is O, m is 0, and $Ar_2$ is

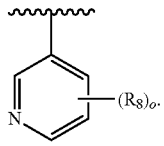

In another embodiment, $Ar_1$ is a thiadiazolyl group, X is O, r is 1, m is 0, $Ar_2$ is

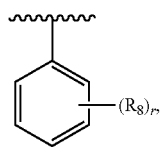

and $R_8$ is a —($C_1$-$C_6$)alkyl. In another embodiment, the —($C_1$-$C_6$)alkyl is substituted at the phenyl group's para-position. In another embodiment, the —($C_1$-$C_6$)alkyl is a tert-butyl group. In another embodiment, the —($C_1$-$C_6$)alkyl is a tert-butyl group and is substituted at the phenyl group's para-position. In another embodiment, the —($C_1$-$C_6$)alkyl is an iso-propyl group. In another embodiment, the —($C_1$-$C_6$)alkyl is an iso-propyl group and is substituted at the phenyl group's para-position.

In another embodiment, $Ar_1$ is a thiadiazolyl group, X is O, r is 1, m is 0, $Ar_2$ is and $R_8$ is —$CF_3$. In another embodiment, the —$CF_3$ is substituted at the phenyl group's para-position.

In another embodiment, $Ar_1$ is a thiadiazolyl group, X is O, r is 1, m is 0, $Ar_2$ is and $R_8$ is -halo. In another embodiment, the -halo is substituted at the phenyl group's para-position. In another embodiment, -halo is —Cl. In another embodiment, -halo is —Cl and is substituted at the phenyl group's para-position. In another embodiment, -halo is —Br. In another embodiment, -halo is —Br and is substituted at the phenyl group's para-position. In another embodiment, -halo is —I. In another embodiment, -halo is —I and is substituted at the phenyl group's para-position. In another embodiment, -halo is —F. In another embodiment, -halo is —F and is substituted at the phenyl group's para-position.

In the Phenylene Compounds that have an $R_3$ group, the $R_3$ group can be attached to the carbon atom at the 2-, 3-, 5- and/or 6-position of the phenylene ring. In one embodiment, an $R_3$ group is attached to the carbon at the 2-position of the phenylene ring. In another embodiment, an $R_3$ group is attached to the carbon at the 3-position of the phenylene ring. In another embodiment, an $R_3$ group is attached to the carbon at the 5-position of the phenylene ring. In another embodiment, an $R_3$ group is attached to the carbon at the 6-position of the phenylene ring.

In another embodiment, an $R_3$ group is a —$(C_1$-$C_{10})$alkyl group and the $R_3$ group is attached to the carbon at the 2-position of the phenylene ring. In another embodiment, an $R_3$ group is a —$(C_1$-$C_{10})$alkyl group and the $R_3$ group is attached to the carbon at the 3-position of the phenylene ring. In another embodiment, an $R_3$ group is a —$(C_1$-$C_{10})$alkyl group and the $R_3$ group is attached to the carbon at the 5-position of the phenylene ring. In another embodiment, an $R_3$ group is a —$(C_1$-$C_{10})$alkyl group and the $R_3$ group is attached to the carbon at the 6-position of the phenylene ring.

In another embodiment, an $R_3$ group is —$CH_3$ and the $R_3$ group is attached to the carbon at the 2-position of the phenylene ring. In another embodiment, an $R_3$ group is —$CH_3$ and the $R_3$ group is attached to the carbon at the 3-position of the phenylene ring. In another embodiment, an $R_3$ group is —$CH_3$ and the $R_3$ group is attached to the carbon at the 5-position of the phenylene ring. In another embodiment, an $R_3$ group is —$CH_3$ and the $R_3$ group is attached to the carbon at the 6-position of the phenylene ring.

In another embodiment, an $R_3$ group is -halo and the $R_3$ group is attached to the carbon at the 2-position of the phenylene ring. In another embodiment, an $R_3$ group is -halo and the $R_3$ group is attached to the carbon at the 3-position of the phenylene ring. In another embodiment, an $R_3$ group is -halo and the $R_3$ group is attached to the carbon at the 5-position of the phenylene ring. In another embodiment, an $R_3$ group is -halo and the $R_3$ group is attached to the carbon at the 6-position of the phenylene ring.

In another embodiment, an $R_3$ group is —Cl and the $R_3$ group is attached to the carbon at the 2-position of the phenylene ring. In another embodiment, an $R_3$ group is —Cl and the $R_3$ group is attached to the carbon at the 3-position of the phenylene ring. In another embodiment, an $R_3$ group is —Cl and the $R_3$ group is attached to the carbon at the 5-position of the phenylene ring. In another embodiment, an $R_3$ group is —Cl and the $R_3$ group is attached to the carbon at the 6-position of the phenylene ring.

In another embodiment, an $R_3$ group is —Br and the $R_3$ group is attached to the carbon at the 2-position of the phenylene ring. In another embodiment, an $R_3$ group is —Br and the $R_3$ group is attached to the carbon at the 3-position of the phenylene ring. In another embodiment, an $R_3$ group is —Br and the $R_3$ group is attached to the carbon at the 5-position of the phenylene ring. In another embodiment, an $R_3$ group is —Br and the $R_3$ group is attached to the carbon at the 6-position of the phenylene ring.

In another embodiment, an $R_3$ group is —F and the $R_3$ group is attached to the carbon at the 2-position of the phenylene ring. In another embodiment, an $R_3$ group is —F and the $R_3$ group is attached to the carbon at the 3-position of the phenylene ring. In another embodiment, an $R_3$ group is —F and the $R_3$ group is attached to the carbon at the 5-position of the phenylene ring. In another embodiment, an $R_3$ group is —F and the $R_3$ group is attached to the carbon at the 6-position of the phenylene ring.

In another embodiment, an $R_3$ group is —I and the $R_3$ group is attached to the carbon at the 2-position of the phenylene ring. In another embodiment, an $R_3$ group is —I and the $R_3$ group is attached to the carbon at the 3-position of the phenylene ring. In another embodiment, an $R_3$ group is —I and the $R_3$ group is attached to the carbon at the 5-position of the phenylene ring. In another embodiment, an $R_3$ group is —I and the $R_3$ group is attached to the carbon at the 6-position of the phenylene ring.

In another embodiment, m is 1, the $R_3$ group is a —$(C_1$-$C_{10})$alkyl group, and the $R_3$ group is attached to the carbon at the 2-position of the phenylene ring. In another embodiment, m is 1, the $R_3$ group is a —$(C_1$-$C_{10})$alkyl group, and the $R_3$ group is attached to the carbon at the 3-position of the phenylene ring.

In another embodiment, m is 1, the $R_3$ group is —$CH_3$, and the $R_3$ group is attached to the carbon at the 2-position of the phenylene ring. In another embodiment, m is 1, the $R_3$ group is —$CH_3$, and the $R_3$ group is attached to the carbon at the 3-position of the phenylene ring.

In another embodiment, m is 1, the $R_3$ group is -halo, and the $R_3$ group is attached to the carbon at the 2-position of the phenylene ring. In another embodiment, m is 1, the $R_3$ group is -halo, and the $R_3$ group is attached to the carbon at the 3-position of the phenylene ring.

In another embodiment, m is 1, the $R_3$ group is —Cl, and the $R_3$ group is attached to the carbon at the 2-position of the phenylene ring. In another embodiment, m is 1, the $R_3$ group is —Cl, and the $R_3$ group is attached to the carbon at the 3-position of the phenylene ring.

In another embodiment, m is 1, the $R_3$ group is —Br, and the $R_3$ group is attached to the carbon at the 2-position of the phenylene ring. In another embodiment, m is 1, the $R_3$ group is —Br, and the $R_3$ group is attached to the carbon at the 3-position of the phenylene ring.

In another embodiment, m is 1, the $R_3$ group is —F, and the $R_3$ group is attached to the carbon at the 2-position of the phenylene ring. In another embodiment, m is 1, the $R_3$ group is —F, and the $R_3$ group is attached to the carbon at the 3-position of the phenylene ring.

In another embodiment, m is 1, the $R_3$ group is —I, and the $R_3$ group is attached to the carbon at the 2-position of the phenylene ring. In another embodiment, m is 1, the $R_3$ group is —I, and the $R_3$ group is attached to the carbon at the 3-position of the phenylene ring.

4.2 Phenylene Compounds of Formula (II)

The invention also relates to Phenylene Compounds of formula (II)

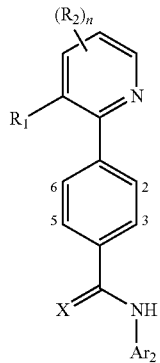

where $R_1$, $R_2$, $Ar_2$, X, and n are defined above for the Phenylene Compounds of formula (II).

In one embodiment, X is O.

In another embodiment, X is S.

In another embodiment, $Ar_2$ is a benzoimidazolyl group.

In another embodiment, $Ar_2$ is a benzothiazolyl group.

In another embodiment, $Ar_2$ is a benzooxazolyl group.

In another embodiment, $Ar_2$ is

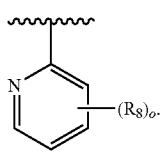

In another embodiment, $Ar_2$ is

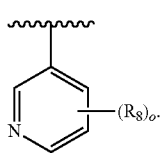

In another embodiment, $Ar_2$ is

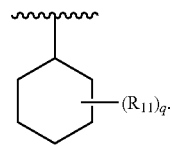

In another embodiment, $Ar_2$ is

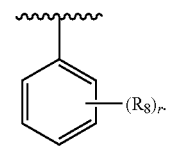

In another embodiment, n is 0.
In another embodiment, n is 1.
In another embodiment, n is 2.
In another embodiment, n is 3.
In another embodiment, o is 0.
In another embodiment, o is 1.
In another embodiment, o is 2.
In another embodiment, o is 3.
In another embodiment, o is 4.
In another embodiment, q is 0.
In another embodiment, q is 1.
In another embodiment, q is 2.
In another embodiment, q is 3.
In another embodiment, q is 4.
In another embodiment, q is 5.
In another embodiment, q is 6.
In another embodiment, r is 0.
In another embodiment, r is 1.
In another embodiment, r is 2.
In another embodiment, r is 3.
In another embodiment, r is 4.
In another embodiment, r is 5.
In another embodiment, s is 0.
In another embodiment, s is 1.
In another embodiment, s is 2.
In another embodiment, s is 3.
In another embodiment, s is 4.
In another embodiment, $R_1$ is -halo.
In another embodiment, $R_1$ is —Cl.
In another embodiment, $R_1$ is —Br.
In another embodiment, $R_1$ is —I.
In another embodiment, $R_1$ is —F.
In another embodiment, $R_1$ is $CH_3$.
In another embodiment, $R_1$ is —C(halo)$_3$.
In another embodiment, $R_1$ is —CH(halo)$_2$.
In another embodiment, $R_1$ is —CH$_2$(halo).

In another embodiment, n is 1 and $R_2$ is -halo, —OH, —NH$_2$, —CN, or —NO$_2$.

In another embodiment, n is 1 and $R_2$ is —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{10}$)bicycloalkenyl, —(C$_8$-C$_{10}$)tricycloalkenyl, -(3- to 7-membered)heterocycle, or -(7- to 10-membered)bicycloheterocycle, each of which is unsubstituted or substituted with one or more $R_5$ groups.

In another embodiment, n is 1 and $R_2$ is -phenyl, -naphthyl, —(C$_{14}$)aryl or -(5- to 10-membered)heteroaryl, each of which is unsubstituted or substituted with one or more $R_6$ groups.

In another embodiment, $Ar_2$ is a benzothiazolyl group and s is 1.

In another embodiment, $Ar_2$ is a benzoimidazolyl group and s is 1.

In another embodiment, $Ar_2$ is a benzooxazolyl group and s is 1.

In another embodiment, $Ar_2$ is

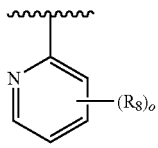

and o is 1.

In another embodiment, $Ar_2$ is

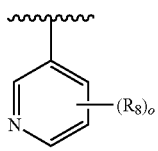

and o is 1.

In another embodiment, $Ar_2$ is

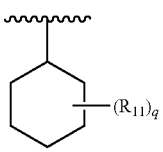

and q is 1.

In another embodiment, $Ar_2$ is

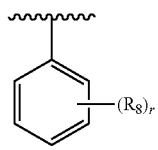

and r is 1.

In another embodiment, $Ar_2$ is a benzothiazolyl group, s is 1, and $R_8$ is -halo or —$(C_1-C_6)$ alkyl.

In another embodiment, $Ar_2$ is a benzoimidazolyl group, s is 1, and $R_8$ is -halo or —$(C_1-C_6)$ alkyl.

In another embodiment, $Ar_2$ is a benzooxazolyl group, s is 1, and $R_8$ is -halo or —$(C_1-C_6)$ alkyl.

In another embodiment, $Ar_2$ is

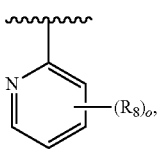

o is 1, and $R_8$ is -halo or —$(C_1-C_6)$ alkyl.

In another embodiment, $Ar_2$ is

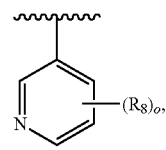

o is 1, and $R_8$ is -halo or —$(C_1-C_6)$ alkyl.

In another embodiment, $Ar_2$ is

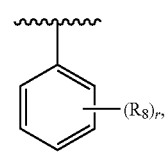

r is 1, and $R_8$ is -halo or —$(C_1-C_6)$ alkyl.

In another embodiment, $Ar_2$ is

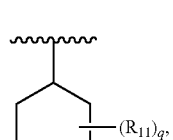

q is 1, and $R_{11}$ is -halo or —$(C_1-C_6)$ alkyl.

In another embodiment, $Ar_2$ is

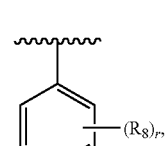

r is 1, and $R_8$ is at the para-position of the phenyl ring.

In another embodiment, X is O, and $Ar_2$ is a benzothiazolyl group.

In another embodiment, X is O, and $Ar_2$ is a benzooxazolyl group.

In another embodiment, X is O, and $Ar_2$ is a benzoimidazolyl group.

In another embodiment, X is O, and $Ar_2$ is

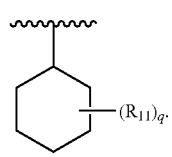

In another embodiment, X is O, and $Ar_2$ is.

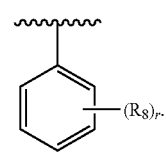

In another embodiment, X is O, and Ar₂ is

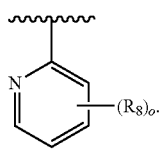

In another embodiment, X is O, and Ar₂ is

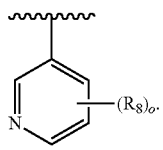

In another embodiment, X is O, r is 1, Ar₂ is

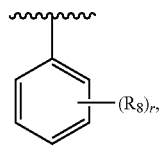

and $R_8$ is a —(C₁-C₆)alkyl. In another embodiment, the —(C₁-C₆)alkyl is substituted at the phenyl group's para-position. In another embodiment, the —(C₁-C₆)alkyl is a tert-butyl group. In another embodiment, the —(C₁-C₆)alkyl is a tert-butyl group and is substituted at the phenyl group's para-position. In another embodiment, the —(C₁-C₆)alkyl is an iso-propyl group. In another embodiment, the —(C₁-C₆)alkyl is an iso-propyl group and is substituted at the phenyl group's para-position.

In another embodiment, X is O, r is 1, Ar₂ is

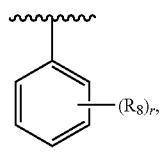

and $R_8$ is —CF₃. In another embodiment, the —CF₃ is substituted at the phenyl group's para-position.

In another embodiment, X is O, r is 1, Ar₂ is

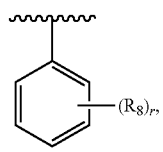

and $R_8$ is -halo. In another embodiment, the -halo is substituted at the phenyl group's para-position. In another embodiment, -halo is —Cl. In another embodiment, -halo is —Cl and is substituted at the phenyl group's para-position. In another embodiment, -halo is —Br. In another embodiment, -halo is —Br and is substituted at the phenyl group's para-position. In another embodiment, -halo is —I. In another embodiment, -halo is —I and is substituted at the phenyl group's para-position. In another embodiment, -halo is —F. In another embodiment, -halo is —F and is substituted at the phenyl group's para-position.

Optical isomers of the Phenylene Compounds can be obtained by known techniques such as chiral chromatography or formation of diastereomeric salts from an optically active acid or base.

In addition, one or more hydrogen, carbon or other atoms of a Phenylene Compound can be replaced by an isotope of the hydrogen, carbon or other atoms. Such compounds, which are encompassed by the present invention, are useful as research and diagnostic tools in metabolism pharmacokinetic studies and in binding assays.

4.3 Illustrative Phenylene Compounds

Illustrative Phenylene Compounds are listed below in Tables 1-10.

For the chemical structure depicted, e.g., at the head of each of Tables 1-5, a is independently 0 or 1. When a=0, the group at the "a" position is —H. When a=1, the group at the "a" position ($R_{8a}$) is other than —H, i.e., is $R_8$.

For the chemical structure depicted, e.g., at the head of each of Tables 6-10, a is independently 0 or 1. When a=0, the group at the "a" position is —H. When a=1, the group at the "a" position (($R_8$)$_a$) is other than —H, i.e., is $R_8$.

For the chemical structure depicted, e.g., at the head of each of Tables 6-10, b is independently 0 or 1. When b=0, the group at the "b" position is —H. When b=1, the group at the "b" position (($R_8$)$_b$) is other than —H, i.e., is $R_8$.

TABLE 1

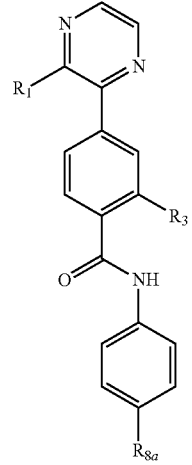

(Ia)

and pharmaceutically acceptable salts thereof, where:

| Compound | R₁ | $R_{8a}$ |
|---|---|---|
| A1 (a, b, c, d, e, and f) | —Cl | —H |
| A2 (a, b, c, d, e, and f) | —Cl | -tert-butyl |
| A3 (a, b, c, d, e, and f) | —Cl | -iso-butyl |
| A4 (a, b, c, d, e, and f) | —Cl | -sec-butyl |
| A5 (a, b, c, d, e, and f) | —Cl | -iso-propyl |
| A6 (a, b, c, d, e, and f) | —Cl | -n-propyl |
| A7 (a, b, c, d, e, and f) | —Cl | -cyclohexyl |
| A8 (a, b, c, d, e, and f) | —Cl | -tert-butoxy |
| A9 (a, b, c, d, e, and f) | —Cl | -iso-propoxy |
| A10 (a, b, c, d, e, and f) | —Cl | —CF₃ |
| A11 (a, b, c, d, e, and f) | —Cl | —OCF₃ |
| A12 (a, b, c, d, e, and f) | —Cl | —Cl |
| A13 (a, b, c, d, e, and f) | —Cl | —Br |

TABLE 1-continued

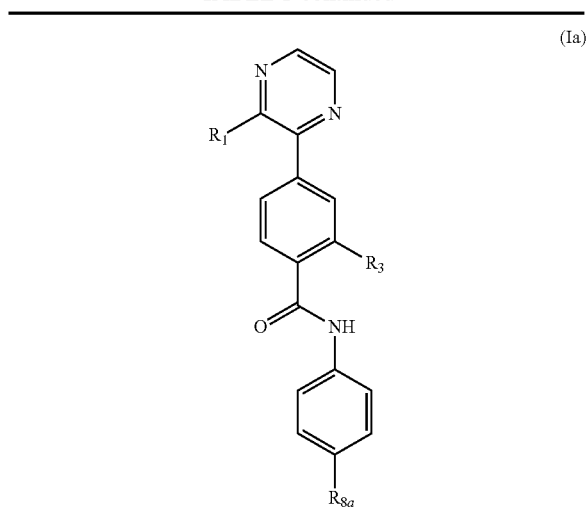

(Ia)

and pharmaceutically acceptable salts thereof, where:

| Compound | $R_1$ | $R_{8a}$ |
|---|---|---|
| A14 (a, b, c, d, e, and f) | —Cl | —I |
| A15 (a, b, c, d, e, and f) | —Cl | -n-butyl |
| A16 (a, b, c, d, e, and f) | —Cl | -n-propyl |
| A17 (a, b, c, d, e, and f) | —F | —H |
| A18 (a, b, c, d, e, and f) | —F | -tert-butyl |
| A19 (a, b, c, d, e, and f) | —F | -iso-butyl |
| A20 (a, b, c, d, e, and f) | —F | -sec-butyl |
| A21 (a, b, c, d, e, and f) | —F | -iso-propyl |
| A22 (a, b, c, d, e, and f) | —F | -n-propyl |
| A23 (a, b, c, d, e, and f) | —F | -cyclohexyl |
| A24 (a, b, c, d, e, and f) | —F | -tert-butoxy |
| A25 (a, b, c, d, e, and f) | —F | -iso-propoxy |
| A26 (a, b, c, d, e, and f) | —F | —CF$_3$ |
| A27 (a, b, c, d, e, and f) | —F | —OCF$_3$ |
| A28 (a, b, c, d, e, and f) | —F | —Cl |
| A29 (a, b, c, d, e, and f) | —F | —Br |
| A30 (a, b, c, d, e, and f) | —F | —I |
| A31 (a, b, c, d, e, and f) | —F | -n-butyl |
| A32 (a, b, c, d, e, and f) | —F | -n-propyl |
| A33 (a, b, c, d, e, and f) | —CH$_3$ | —H |
| A34 (a, b, c, d, e, and f) | —CH$_3$ | -iso-butyl |
| A35 (a, b, c, d, e, and f) | —CH$_3$ | -tert-butyl |
| A36 (a, b, c, d, e, and f) | —CH$_3$ | -sec-butyl |
| A37 (a, b, c, d, e, and f) | —CH$_3$ | -iso-propyl |
| A38 (a, b, c, d, e, and f) | —CH$_3$ | -n-propyl |
| A39 (a, b, c, d, e, and f) | —CH$_3$ | -cyclohexyl |
| A40 (a, b, c, d, e, and f) | —CH$_3$ | -tert-butoxy |
| A41 (a, b, c, d, e, and f) | —CH$_3$ | -iso-propoxy |
| A42 (a, b, c, d, e, and f) | —CH$_3$ | —CF$_3$ |
| A43 (a, b, c, d, e, and f) | —CH$_3$ | —OCF$_3$ |
| A44 (a, b, c, d, e, and f) | —CH$_3$ | —Cl |
| A45 (a, b, c, d, e, and f) | —CH$_3$ | —Br |
| A46 (a, b, c, d, e, and f) | —CH$_3$ | —I |
| A47 (a, b, c, d, e, and f) | —CH$_3$ | -n-butyl |
| A48 (a, b, c, d, e, and f) | —CH$_3$ | -n-propyl |
| A49 (a, b, c, d, e, and f) | —CF$_3$ | —H |
| A50 (a, b, c, d, e, and f) | —CF$_3$ | -tert-butyl |
| A51 (a, b, c, d, e, and f) | —CF$_3$ | -iso-butyl |
| A52 (a, b, c, d, e, and f) | —CF$_3$ | -sec-butyl |
| A53 (a, b, c, d, e, and f) | —CF$_3$ | -iso-propyl |
| A54 (a, b, c, d, e, and f) | —CF$_3$ | -n-propyl |
| A55 (a, b, c, d, e, and f) | —CF$_3$ | -cyclohexyl |
| A56 (a, b, c, d, e, and f) | —CF$_3$ | -tert-butoxy |
| A57 (a, b, c, d, e, and f) | —CF$_3$ | -iso-propoxy |
| A58 (a, b, c, d, e, and f) | —CF$_3$ | —CF$_3$ |
| A59 (a, b, c, d, e, and f) | —CF$_3$ | —OCF$_3$ |
| A60 (a, b, c, d, e, and f) | —CF$_3$ | —Cl |
| A61 (a, b, c, d, e, and f) | —CF$_3$ | —Br |
| A62 (a, b, c, d, e, and f) | —CF$_3$ | —I |
| A63 (a, b, c, d, e, and f) | —CF$_3$ | -n-butyl |
| A64 (a, b, c, d, e, and f) | —CF$_3$ | -n-propyl |
| A65 (a, b, c, d, e, and f) | —CHF$_2$ | -tert-butyl |
| A66 (a, b, c, d, e, and f) | —CHF$_2$ | —H |

TABLE 1-continued

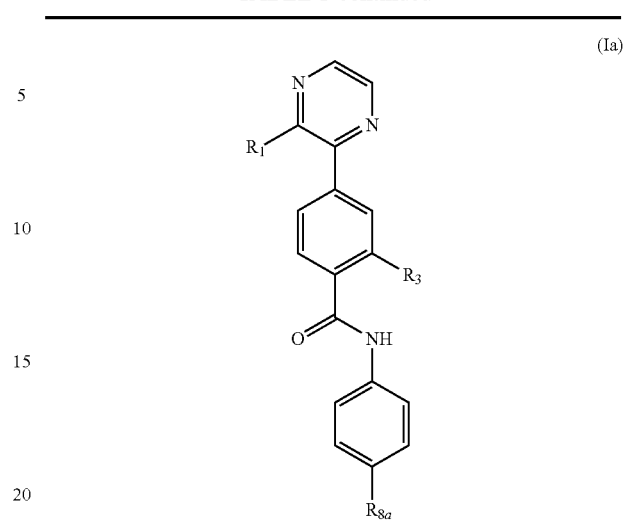

(Ia)

and pharmaceutically acceptable salts thereof, where:

| Compound | $R_1$ | $R_{8a}$ |
|---|---|---|
| A67 (a, b, c, d, e, and f) | —CHF$_2$ | -iso-butyl |
| A68 (a, b, c, d, e, and f) | —CHF$_2$ | -sec-butyl |
| A69 (a, b, c, d, e, and f) | —CHF$_2$ | -iso-propyl |
| A70 (a, b, c, d, e, and f) | —CHF$_2$ | -n-propyl |
| A71 (a, b, c, d, e, and f) | —CHF$_2$ | -cyclohexyl |
| A72 (a, b, c, d, e, and f) | —CHF$_2$ | -tert-butoxy |
| A73 (a, b, c, d, e, and f) | —CHF$_2$ | -iso-propoxy |
| A74 (a, b, c, d, e, and f) | —CHF$_2$ | —CF$_3$ |
| A75 (a, b, c, d, e, and f) | —CHF$_2$ | —OCF$_3$ |
| A76 (a, b, c, d, e, and f) | —CHF$_2$ | —Cl |
| A77 (a, b, c, d, e, and f) | —CHF$_2$ | —Br |
| A78 (a, b, c, d, e, and f) | —CHF$_2$ | —I |
| A79 (a, b, c, d, e, and f) | —CHF$_2$ | -n-butyl |
| A80 (a, b, c, d, e, and f) | —CHF$_2$ | -n-propyl |
| A81 (a, b, c, d, e, and f) | —Br | —H |
| A82 (a, b, c, d, e, and f) | —Br | -tert-butyl |
| A83 (a, b, c, d, e, and f) | —Br | -iso-butyl |
| A84 (a, b, c, d, e, and f) | —Br | -sec-butyl |
| A85 (a, b, c, d, e, and f) | —Br | -iso-propyl |
| A86 (a, b, c, d, e, and f) | —Br | -n-propyl |
| A87 (a, b, c, d, e, and f) | —Br | -cyclohexyl |
| A88 (a, b, c, d, e, and f) | —Br | -tert-butoxy |
| A89 (a, b, c, d, e, and f) | —Br | -iso-propoxy |
| A90 (a, b, c, d, e, and f) | —Br | —CF$_3$ |
| A91 (a, b, c, d, e, and f) | —Br | —OCF$_3$ |
| A92 (a, b, c, d, e, and f) | —Br | —Cl |
| A93 (a, b, c, d, e, and f) | —Br | —Br |
| A94 (a, b, c, d, e, and f) | —Br | —I |
| A95 (a, b, c, d, e, and f) | —Br | -n-butyl |
| A96 (a, b, c, d, e, and f) | —Br | -n-propyl |
| A97 (a, b, c, d, e, and f) | —I | -tert-butyl |
| A98 (a, b, c, d, e, and f) | —I | —H |
| A99 (a, b, c, d, e, and f) | —I | -iso-butyl |
| A100 (a, b, c, d, e, and f) | —I | -sec-butyl |
| A101 (a, b, c, d, e, and f) | —I | -iso-propyl |
| A102 (a, b, c, d, e, and f) | —I | -n-propyl |
| A103 (a, b, c, d, e, and f) | —I | -cyclohexyl |
| A104 (a, b, c, d, e, and f) | —I | -tert-butoxy |
| A105 (a, b, c, d, e, and f) | —I | -iso-propoxy |
| A106 (a, b, c, d, e, and f) | —I | —CF$_3$ |
| A107 (a, b, c, d, e, and f) | —I | —OCF$_3$ |
| A108 (a, b, c, d, e, and f) | —I | —Cl |
| A109 (a, b, c, d, e, and f) | —I | —Br |

TABLE 1-continued

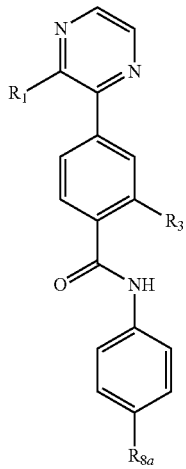

(Ia)

and pharmaceutically acceptable salts thereof, where:

| Compound | R₁ | R₈ₐ |
|---|---|---|
| A110 (a, b, c, d, e, and f) | —I | —I |
| A111 (a, b, c, d, e, and f) | —I | -n-butyl |
| A112 (a, b, c, d, e, and f) | —I | -n-propyl |

In the column labeled "Compound":
(a) means that R₃ is —CH₃;
(b) means that R₃ is —Cl;
(c) means that R₃ is —Br;
(d) means that R₃ is —I;
(e) means that R₃ is —F; and
(f) means that R₃ is —H, i.e., in formula (I) m = 0.

TABLE 2

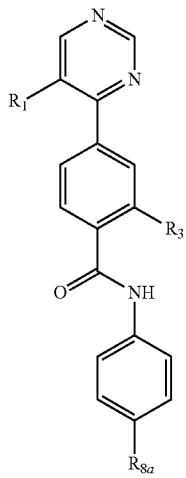

(Ib)

and pharmaceutically acceptable salts thereof, where:

| Compound | R₁ | R₈ₐ |
|---|---|---|
| B1 (a, b, c, d, e, and f) | —Cl | —H |
| B2 (a, b, c, d, e, and f) | —Cl | -tert-butyl |
| B3 (a, b, c, d, e, and f) | —Cl | -iso-butyl |
| B4 (a, b, c, d, e, and f) | —Cl | -sec-butyl |
| B5 (a, b, c, d, e, and f) | —Cl | -iso-propyl |
| B6 (a, b, c, d, e, and f) | —Cl | -n-propyl |
| B7 (a, b, c, d, e, and f) | —Cl | -cyclohexyl |
| B8 (a, b, c, d, e, and f) | —Cl | -tert-butoxy |
| B9 (a, b, c, d, e, and f) | —Cl | -iso-propoxy |
| B10 (a, b, c, d, e, and f) | —Cl | —CF₃ |

TABLE 2-continued

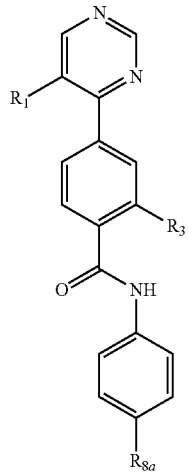

(Ib)

and pharmaceutically acceptable salts thereof, where:

| Compound | R₁ | R₈ₐ |
|---|---|---|
| B11 (a, b, c, d, e, and f) | —Cl | —OCF₃ |
| B12 (a, b, c, d, e, and f) | —Cl | —Cl |
| B13 (a, b, c, d, e, and f) | —Cl | —Br |
| B14 (a, b, c, d, e, and f) | —Cl | —I |
| B15 (a, b, c, d, e, and f) | —Cl | -n-butyl |
| B16 (a, b, c, d, e, and f) | —Cl | -n-propyl |
| B17 (a, b, c, d, e, and f) | —F | —H |
| B18 (a, b, c, d, e, and f) | —F | -tert-butyl |
| B19 (a, b, c, d, e, and f) | —F | -iso-butyl |
| B20 (a, b, c, d, e, and f) | —F | -sec-butyl |
| B21 (a, b, c, d, e, and f) | —F | -iso-propyl |
| B22 (a, b, c, d, e, and f) | —F | -n-propyl |
| B23 (a, b, c, d, e, and f) | —F | -cyclohexyl |
| B24 (a, b, c, d, e, and f) | —F | -tert-butoxy |
| B25 (a, b, c, d, e, and f) | —F | -iso-propoxy |
| B26 (a, b, c, d, e, and f) | —F | —CF₃ |
| B27 (a, b, c, d, e, and f) | —F | —OCF₃ |
| B28 (a, b, c, d, e, and f) | —F | —Cl |
| B29 (a, b, c, d, e, and f) | —F | —Br |
| B30 (a, b, c, d, e, and f) | —F | —I |
| B31 (a, b, c, d, e, and f) | —F | -n-butyl |
| B32 (a, b, c, d, e, and f) | —F | -n-propyl |
| B33 (a, b, c, d, e, and f) | —CH₃ | —H |
| B34 (a, b, c, d, e, and f) | —CH₃ | -iso-butyl |
| B35 (a, b, c, d, e, and f) | —CH₃ | -tert-butyl |
| B36 (a, b, c, d, e, and f) | —CH₃ | -sec-butyl |
| B37 (a, b, c, d, e, and f) | —CH₃ | -iso-propyl |
| B38 (a, b, c, d, e, and f) | —CH₃ | -n-propyl |
| B39 (a, b, c, d, e, and f) | —CH₃ | -cyclohexyl |
| B40 (a, b, c, d, e, and f) | —CH₃ | -tert-butoxy |
| B41 (a, b, c, d, e, and f) | —CH₃ | -iso-propoxy |
| B42 (a, b, c, d, e, and f) | —CH₃ | —CF₃ |
| B43 (a, b, c, d, e, and f) | —CH₃ | —OCF₃ |
| B44 (a, b, c, d, e, and f) | —CH₃ | —Cl |
| B45 (a, b, c, d, e, and f) | —CH₃ | —Br |
| B46 (a, b, c, d, e, and f) | —CH₃ | —I |
| B47 (a, b, c, d, e, and f) | —CH₃ | -n-butyl |
| B48 (a, b, c, d, e, and f) | —CH₃ | -n-propyl |
| B49 (a, b, c, d, e, and f) | —CF₃ | —H |
| B50 (a, b, c, d, e, and f) | —CF₃ | -tert-butyl |
| B51 (a, b, c, d, e, and f) | —CF₃ | -iso-butyl |
| B52 (a, b, c, d, e, and f) | —CF₃ | -sec-butyl |
| B53 (a, b, c, d, e, and f) | —CF₃ | -iso-propyl |
| B54 (a, b, c, d, e, and f) | —CF₃ | -n-propyl |
| B55 (a, b, c, d, e, and f) | —CF₃ | -cyclohexyl |
| B56 (a, b, c, d, e, and f) | —CF₃ | -tert-butoxy |
| B57 (a, b, c, d, e, and f) | —CF₃ | -iso-propoxy |
| B58 (a, b, c, d, e, and f) | —CF₃ | —CF₃ |
| B59 (a, b, c, d, e, and f) | —CF₃ | —OCF₃ |
| B60 (a, b, c, d, e, and f) | —CF₃ | —Cl |
| B61 (a, b, c, d, e, and f) | —CF₃ | —Br |
| B62 (a, b, c, d, e, and f) | —CF₃ | —I |

TABLE 2-continued

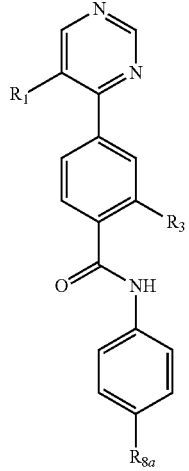

(Ib)

and pharmaceutically acceptable salts thereof, where:

| Compound | R₁ | R₈ₐ |
|---|---|---|
| B63 (a, b, c, d, e, and f) | —CF₃ | -n-butyl |
| B64 (a, b, c, d, e, and f) | —CF₃ | -n-propyl |
| B65 (a, b, c, d, e, and f) | —CHF₂ | -tert-butyl |
| B66 (a, b, c, d, e, and f) | —CHF₂ | —H |
| B67 (a, b, c, d, e, and f) | —CHF₂ | -iso-butyl |
| B68 (a, b, c, d, e, and f) | —CHF₂ | -sec-butyl |
| B69 (a, b, c, d, e, and f) | —CHF₂ | -iso-propyl |
| B70 (a, b, c, d, e, and f) | —CHF₂ | -n-propyl |
| B71 (a, b, c, d, e, and f) | —CHF₂ | -cyclohexyl |
| B72 (a, b, c, d, e, and f) | —CHF₂ | -tert-butoxy |
| B73 (a, b, c, d, e, and f) | —CHF₂ | -iso-propoxy |
| B74 (a, b, c, d, e, and f) | —CHF₂ | —CF₃ |
| B75 (a, b, c, d, e, and f) | —CHF₂ | —OCF₃ |
| B76 (a, b, c, d, e, and f) | —CHF₂ | —Cl |
| B77 (a, b, c, d, e, and f) | —CHF₂ | —Br |
| B78 (a, b, c, d, e, and f) | —CHF₂ | —I |
| B79 (a, b, c, d, e, and f) | —CHF₂ | -n-butyl |
| B80 (a, b, c, d, e, and f) | —CHF₂ | -n-propyl |
| B81 (a, b, c, d, e, and f) | —Br | —H |
| B82 (a, b, c, d, e, and f) | —Br | -tert-butyl |
| B83 (a, b, c, d, e, and f) | —Br | -iso-butyl |
| B84 (a, b, c, d, e, and f) | —Br | -sec-butyl |
| B85 (a, b, c, d, e, and f) | —Br | -iso-propyl |
| B86 (a, b, c, d, e, and f) | —Br | -n-propyl |
| B87 (a, b, c, d, e, and f) | —Br | -cyclohexyl |
| B88 (a, b, c, d, e, and f) | —Br | -tert-butoxy |
| B89 (a, b, c, d, e, and f) | —Br | -iso-propoxy |
| B90 (a, b, c, d, e, and f) | —Br | —CF₃ |
| B91 (a, b, c, d, e, and f) | —Br | —OCF₃ |
| B92 (a, b, c, d, e, and f) | —Br | —Cl |
| B93 (a, b, c, d, e, and f) | —Br | —Br |
| B94 (a, b, c, d, e, and f) | —Br | —I |
| B95 (a, b, c, d, e, and f) | —Br | -n-butyl |
| B96 (a, b, c, d, e, and f) | —Br | -n-propyl |
| B97 (a, b, c, d, e, and f) | —I | -tert-butyl |
| B98 (a, b, c, d, e, and f) | —I | —H |
| B99 (a, b, c, d, e, and f) | —I | -iso-butyl |
| B100 (a, b, c, d, e, and f) | —I | -sec-butyl |
| B101 (a, b, c, d, e, and f) | —I | -iso-propyl |
| B102 (a, b, c, d, e, and f) | —I | -n-propyl |
| B103 (a, b, c, d, e, and f) | —I | -cyclohexyl |
| B104 (a, b, c, d, e, and f) | —I | -tert-butoxy |
| B105 (a, b, c, d, e, and f) | —I | -iso-propoxy |
| B106 (a, b, c, d, e, and f) | —I | —CF₃ |
| B107 (a, b, c, d, e, and f) | —I | —OCF₃ |
| B108 (a, b, c, d, e, and f) | —I | —Cl |
| B109 (a, b, c, d, e, and f) | —I | —Br |
| B110 (a, b, c, d, e, and 1) | —I | —I |
| B111 (a, b, c, d, e, and f) | —I | -n-butyl |
| B112 (a, b, c, d, e, and f) | —I | -n-propyl |

In the column labeled "Compound":

TABLE 2-continued

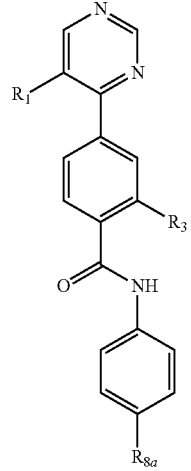

(Ib)

and pharmaceutically acceptable salts thereof, where:

(a) means that R₃ is —CH₃;
(b) means that R₃ is —Cl;
(c) means that R₃ is —Br;
(d) means that R₃ is —I;
(e) means that R₃ is —F; and
(f) means that R₃ is —H, i.e., in formula (I) m = 0.

TABLE 3

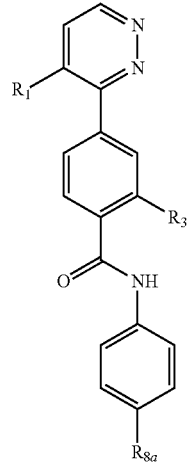

(Ic)

and pharmaceutically acceptable salts thereof, where:

| Compound | R₁ | R₈ₐ |
|---|---|---|
| C1 (a, b, c, d, e, and f) | —Cl | —H |
| C2 (a, b, c, d, e, and f) | —Cl | -tert-butyl |
| C3 (a, b, c, d, e, and f) | —Cl | -iso-butyl |
| C4 (a, b, c, d, e, and f) | —Cl | -sec-butyl |
| C5 (a, b, c, d, e, and f) | —Cl | -iso-propyl |
| C6 (a, b, c, d, e, and f) | —Cl | -n-propyl |
| C7 (a, b, c, d, e, and f) | —Cl | -cyclohexyl |
| C8 (a, b, c, d, e, and f) | —Cl | -tert-butoxy |
| C9 (a, b, c, d, e, and f) | —Cl | -iso-propoxy |
| C10 (a, b, c, d, e, and f) | —Cl | —CF₃ |
| C11 (a, b, c, d, e, and f) | —Cl | —OCF₃ |
| C12 (a, b, c, d, e, and f) | —Cl | —Cl |
| C13 (a, b, c, d, e, and f) | —Cl | —Br |
| C14 (a, b, c, d, e, and f) | —Cl | —I |
| C15 (a, b, c, d, e, and f) | —Cl | -n-butyl |

TABLE 3-continued

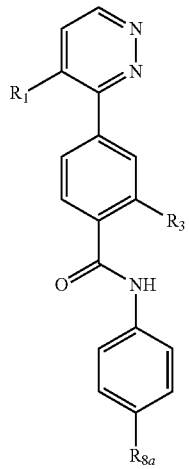

(Ic)

and pharmaceutically acceptable salts thereof, where:

| Compound | R₁ | R₈ₐ |
|---|---|---|
| C16 (a, b, c, d, e, and f) | —Cl | -n-propyl |
| C17 (a, b, c, d, e, and f) | —F | —H |
| C18 (a, b, c, d, e, and f) | —F | -tert-butyl |
| C19 (a, b, c, d, e, and f) | —F | -iso-butyl |
| C20 (a, b, c, d, e, and f) | —F | -sec-butyl |
| C21 (a, b, c, d, e, and f) | —F | -iso-propyl |
| C22 (a, b, c, d, e, and f) | —F | -n-propyl |
| C23 (a, b, c, d, e, and f) | —F | -cyclohexyl |
| C24 (a, b, c, d, e, and D | —F | -tert-butoxy |
| C25 (a, b, c, d, e, and f) | —F | -iso-propoxy |
| C26 (a, b, c, d, e, and f) | —F | —CF₃ |
| C27 (a, b, c, d, e, and f) | —F | —OCF₃ |
| C28 (a, b, c, d, e, and f) | —F | —Cl |
| C29 (a, b, c, d, e, and f) | —F | —Br |
| C30 (a, b, c, d, e, and f) | —F | —I |
| C31 (a, b, c, d, e, and f) | —F | -n-butyl |
| C32 (a, b, c, d, e, and f) | —F | -n-propyl |
| C33 (a, b, c, d, e, and f) | —CH₃ | —H |
| C34 (a, b, c, d, e, and f) | —CH₃ | -iso-butyl |
| C35 (a, b, c, d, e, and f) | —CH₃ | -tert-butyl |
| C36 (a, b, c, d, e, and f) | —CH₃ | -sec-butyl |
| C37 (a, b, c, d, e, and f) | —CH₃ | -iso-propyl |
| C38 (a, b, c, d, e, and f) | —CH₃ | -n-propyl |
| C39 (a, b, c, d, e, and f) | —CH₃ | -cyclohexyl |
| C40 (a, b, c, d, e, and f) | —CH₃ | -tert-butoxy |
| C41 (a, b, c, d, e, and f) | —CH₃ | -iso-propoxy |
| C42 (a, b, c, d, e, and f) | —CH₃ | —CF₃ |
| C43 (a, b, c, d, e, and f) | —CH₃ | —OCF₃ |
| C44 (a, b, c, d, e, and f) | —CH₃ | —Cl |
| C45 (a, b, c, d, e, and f) | —CH₃ | —Br |
| C46 (a, b, c, d, e, and f) | —CH₃ | —I |
| C47 (a, b, c, d, e, and f) | —CH₃ | -n-butyl |
| C48 (a, b, c, d, e, and f) | —CH₃ | -n-propyl |
| C49 (a, b, c, d, e, and f) | —CF₃ | —H |
| C50 (a, b, c, d, e, and f) | —CF₃ | -tert-butyl |
| C51 (a, b, c, d, e, and f) | —CF₃ | -iso-butyl |
| C52 (a, b, c, d, e, and f) | —CF₃ | -sec-butyl |
| C53 (a, b, c, d, e, and f) | —CF₃ | -iso-propyl |
| C54 (a, b, c, d, e, and f) | —CF₃ | -n-propyl |
| C55 (a, b, c, d, e, and f) | —CF₃ | -cyclohexyl |
| C56 (a, b, c, d, e, and f) | —CF₃ | -tert-butoxy |
| C57 (a, b, c, d, e, and f) | —CF₃ | -iso-propoxy |
| C58 (a, b, c, d, e, and f) | —CF₃ | —CF₃ |
| C59 (a, b, c, d, e, and f) | —CF₃ | —OCF₃ |
| C60 (a, b, c, d, e, and f) | —CF₃ | —Cl |
| C61 (a, b, c, d, e, and f) | —CF₃ | —Br |
| C62 (a, b, c, d, e, and f) | —CF₃ | —I |
| C63 (a, b, c, d, e, and f) | —CF₃ | -n-butyl |
| C64 (a, b, c, d, e, and f) | —CF₃ | -n-propyl |
| C65 (a, b, c, d, e, and f) | —CHF₂ | -tert-butyl |
| C66 (a, b, c, d, e, and f) | —CHF₂ | —H |
| C67 (a, b, c, d, e, and f) | —CHF₂ | -iso-butyl |
| C68 (a, b, c, d, e, and f) | —CHF₂ | -sec-butyl |

TABLE 3-continued

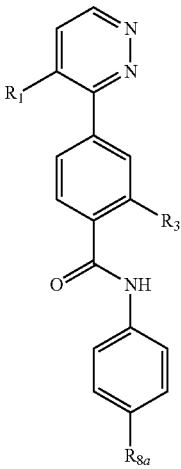

(Ic)

and pharmaceutically acceptable salts thereof, where:

| Compound | R₁ | R₈ₐ |
|---|---|---|
| C69 (a, b, c, d, e, and f) | —CHF₂ | -iso-propyl |
| C70 (a, b, c, d, e, and f) | —CHF₂ | -n-propyl |
| C71 (a, b, c, d, e, and f) | —CHF₂ | -cyclohexyl |
| C72 (a, b, c, d, e, and f) | —CHF₂ | -tert-butoxy |
| C73 (a, b, c, d, e, and f) | —CHF₂ | -iso-propoxy |
| C74 (a, b, c, d, e, and f) | —CHF₂ | —CF₃ |
| C75 (a, b, c, d, e, and f) | —CHF₂ | —OCF₃ |
| C76 (a, b, c, d, e, and f) | —CHF₂ | —Cl |
| C77 (a, b, c, d, e, and f) | —CHF₂ | —Br |
| C78 (a, b, c, d, e, and f) | —CHF₂ | —I |
| C79 (a, b, c, d, e, and f) | —CHF₂ | -n-butyl |
| C80 (a, b, c, d, e, and f) | —CHF₂ | -n-propyl |
| C81 (a, b, c, d, e, and f) | —Br | —H |
| C82 (a, b, c, d, e, and f) | —Br | -tert-butyl |
| C83 (a, b, c, d, e, and f) | —Br | -iso-butyl |
| C84 (a, b, c, d, e, and f) | —Br | -sec-butyl |
| C85 (a, b, c, d, e, and f) | —Br | -iso-propyl |
| C86 (a, b, c, d, e, and f) | —Br | -n-propyl |
| C87 (a, b, c, d, e, and f) | —Br | -cyclohexyl |
| C88 (a, b, c, d, e, and f) | —Br | -tert-butoxy |
| C89 (a, b, c, d, e, and f) | —Br | -iso-propoxy |
| C90 (a, b, c, d, e, and f) | —Br | —CF₃ |
| C91 (a, b, c, d, e, and f) | —Br | —OCF₃ |
| C92 (a, b, c, d, e, and f) | —Br | —Cl |
| C93 (a, b, c, d, e, and f) | —Br | —Br |
| C94 (a, b, c, d, e, and f) | —Br | —I |
| C95 (a, b, c, d, e, and f) | —Br | -n-butyl |
| C96 (a, b, c, d, e, and f) | —Br | -n-propyl |
| C97 (a, b, c, d, e, and f) | —I | -tert-butyl |
| C98 (a, b, c, d, e, and f) | —I | —H |
| C99 (a, b, c, d, e, and f) | —I | -iso-butyl |
| C100 (a, b, c, d, e, and f) | —I | -sec-butyl |
| C101 (a, b, c, d, e, and f) | —I | -iso-propyl |
| C102 (a, b, c, d, e, and f) | —I | -n-propyl |
| C103 (a, b, c, d, e, and f) | —I | -cyclohexyl |
| C104 (a, b, c, d, e, and f) | —I | -tert-butoxy |
| C105 (a, b, c, d, e, and f) | —I | -iso-propoxy |
| C106 (a, b, c, d, e, and f) | —I | —CF₃ |
| C107 (a, b, c, d, e, and f) | —I | —OCF₃ |
| C108 (a, b, c, d, e, and f) | —I | —Cl |
| C109 (a, b, c, d, e, and f) | —I | —Br |
| C110 (a, b, c, d, e, and f) | —I | —I |
| C111 (a, b, c, d, e, and f) | —I | -n-butyl |
| C112 (a, b, c, d, e, and f) | —I | -n-propyl |

In the column labeled "Compound":
(a) means that R₃ is —CH₃;
(b) means that R₃ is —Cl;
(c) means that R₃ is —Br;
(d) means that R₃ is —I;
(e) means that R₃ is —F; and
(f) means that R₃ is —H, i.e., in formula (I) m = 0.

TABLE 4

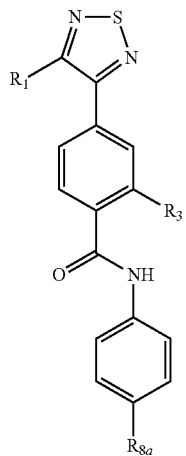

(Id)

and pharmaceutically acceptable salts thereof, where:

| Compound | $R_1$ | $R_{8a}$ |
|---|---|---|
| D1 (a, b, c, d, e, and f) | —Cl | —H |
| D2 (a, b, c, d, e, and f) | —Cl | -tert-butyl |
| D3 (a, b, c, d, e, and f) | —Cl | -iso-butyl |
| D4 (a, b, c, d, e, and f) | —Cl | -sec-butyl |
| D5 (a, b, c, d, e, and f) | —Cl | -iso-propyl |
| D6 (a, b, c, d, e, and f) | —Cl | -n-propyl |
| D7 (a, b, c, d, e, and f) | —Cl | -cyclohexyl |
| D8 (a, b, c, d, e, and f) | —Cl | -tert-butoxy |
| D9 (a, b, c, d, e, and f) | —Cl | -iso-propoxy |
| D10 (a, b, c, d, e, and f) | —Cl | —$CF_3$ |
| D11 (a, b, c, d, e, and f) | —Cl | —$OCF_3$ |
| D12 (a, b, c, d, e, and f) | —Cl | —Cl |
| D13 (a, b, c, d, e, and f) | —Cl | —Br |
| D14 (a, b, c, d, e, and f) | —Cl | —I |
| D15 (a, b, c, d, e, and f) | —Cl | -n-butyl |
| D16 (a, b, c, d, e, and f) | —Cl | -n-propyl |
| D17 (a, b, c, d, e, and f) | —F | —H |
| D18 (a, b, c, d, e, and f) | —F | -tert-butyl |
| D19 (a, b, c, d, e, and f) | —F | -iso-butyl |
| D20 (a, b, c, d, e, and f) | —F | -sec-butyl |
| D21 (a, b, c, d, e, and f) | —F | -iso-propyl |
| D22 (a, b, c, d, e, and f) | —F | -n-propyl |
| D23 (a, b, c, d, e, and f) | —F | -cyclohexyl |
| D24 (a, b, c, d, e, and f) | —F | -tert-butoxy |
| D25 (a, b, c, d, e, and f) | —F | -iso-propoxy |
| D26 (a, b, c, d, e, and f) | —F | —$CF_3$ |
| D27 (a, b, c, d, e, and f) | —F | —$OCF_3$ |
| D28 (a, b, c, d, e, and f) | —F | —Cl |
| D29 (a, b, c, d, e, and f) | —F | —Br |
| D30 (a, b, c, d, e, and f) | —F | —I |
| D31 (a, b, c, d, e, and f) | —F | -n-butyl |
| D32 (a, b, c, d, e, and f) | —F | -n-propyl |
| D33 (a, b, c, d, e, and f) | —$CH_3$ | —H |
| D34 (a, b, c, d, e, and f) | —$CH_3$ | -iso-butyl |
| D35 (a, b, c, d, e, and f) | —$CH_3$ | -tert-butyl |
| D36 (a, b, c, d, e, and f) | —$CH_3$ | -sec-butyl |
| D37 (a, b, c, d, e, and f) | —$CH_3$ | -iso-propyl |
| D38 (a, b, c, d, e, and f) | —$CH_3$ | -n-propyl |
| D39 (a, b, c, d, e, and f) | —$CH_3$ | -cyclohexyl |
| D40 (a, b, c, d, e, and f) | —$CH_3$ | -tert-butoxy |
| D41 (a, b, c, d, e, and f) | —$CH_3$ | -iso-propoxy |
| D42 (a, b, c, d, e, and f) | —$CH_3$ | —$CF_3$ |
| D43 (a, b, c, d, e, and f) | —$CH_3$ | —$OCF_3$ |
| D44 (a, b, c, d, e, and f) | —$CH_3$ | —Cl |
| D45 (a, b, c, d, e, and f) | —$CH_3$ | —Br |
| D46 (a, b, c, d, e, and f) | —$CH_3$ | —I |
| D47 (a, b, c, d, e, and f) | —$CH_3$ | -n-butyl |
| D48 (a, b, c, d, e, and f) | —$CH_3$ | -n-propyl |
| D49 (a, b, c, d, e, and f) | —$CF_3$ | —H |
| D50 (a, b, c, d, e, and f) | —$CF_3$ | -tert-butyl |
| D51 (a, b, c, d, e, and f) | —$CF_3$ | -iso-butyl |
| D52 (a, b, c, d, e, and f) | —$CF_3$ | -sec-butyl |
| D53 (a, b, c, d, e, and f) | —$CF_3$ | -iso-propyl |
| D54 (a, b, c, d, e, and f) | —$CF_3$ | -n-propyl |
| D55 (a, b, c, d, e, and f) | —$CF_3$ | -cyclohexyl |
| D56 (a, b, c, d, e, and f) | —$CF_3$ | -tert-butoxy |
| D57 (a, b, c, d, e, and f) | —$CF_3$ | -iso-propoxy |
| D58 (a, b, c, d, e, and f) | —$CF_3$ | —$CF_3$ |
| D59 (a, b, c, d, e, and f) | —$CF_3$ | —$OCF_3$ |
| D60 (a, b, c, d, e, and f) | —$CF_3$ | —Cl |
| D61 (a, b, c, d, e, and f) | —$CF_3$ | —Br |
| D62 (a, b, c, d, e, and f) | —$CF_3$ | —I |
| D63 (a, b, c, d, e, and f) | —$CF_3$ | -n-butyl |
| D64 (a, b, c, d, e, and f) | —$CF_3$ | -n-propyl |
| D65 (a, b, c, d, e, and f) | —$CHF_2$ | -tert-butyl |
| D66 (a, b, c, d, e, and f) | —$CHF_2$ | —H |
| D67 (a, b, c, d, e, and f) | —$CHF_2$ | -iso-butyl |
| D68 (a, b, c, d, e, and f) | —$CHF_2$ | -sec-butyl |
| D69 (a, b, c, d, e, and f) | —$CHF_2$ | -iso-propyl |
| D70 (a, b, c, d, e, and f) | —$CHF_2$ | -n-propyl |
| D71 (a, b, c, d, e, and f) | —$CHF_2$ | -cyclohexyl |
| D72 (a, b, c, d, e, and f) | —$CHF_2$ | -tert-butoxy |
| D73 (a, b, c, d, e, and f) | —$CHF_2$ | -iso-propoxy |
| D74 (a, b, c, d, e, and f) | —$CHF_2$ | —$CF_3$ |
| D75 (a, b, c, d, e, and f) | —$CHF_2$ | —$OCF_3$ |
| D76 (a, b, c, d, e, and f) | —$CHF_2$ | —Cl |
| D77 (a, b, c, d, e, and f) | —$CHF_2$ | —Br |
| D78 (a, b, c, d, e, and f) | —$CHF_2$ | —I |
| D79 (a, b, c, d, e, and f) | —$CHF_2$ | -n-butyl |
| D80 (a, b, c, d, e, and f) | —$CHF_2$ | -n-propyl |
| D81 (a, b, c, d, e, and f) | —Br | —H |
| D82 (a, b, c, d, e, and f) | —Br | -tert-butyl |
| D83 (a, b, c, d, e, and f) | —Br | -iso-butyl |
| D84 (a, b, c, d, e, and f) | —Br | -sec-butyl |
| D85 (a, b, c, d, e, and f) | —Br | -iso-propyl |
| D86 (a, b, c, d, e, and f) | —Br | -n-propyl |
| D87 (a, b, c, d, e, and f) | —Br | -cyclohexyl |
| D88 (a, b, c, d, e, and f) | —Br | -tert-butoxy |
| D89 (a, b, c, d, e, and f) | —Br | -iso-propoxy |
| D90 (a, b, c, d, e, and f) | —Br | —$CF_3$ |
| D91 (a, b, c, d, e, and f) | —Br | —$OCF_3$ |
| D92 (a, b, c, d, e, and f) | —Br | —Cl |
| D93 (a, b, c, d, e, and f) | —Br | —Br |
| D94 (a, b, c, d, e, and f) | —Br | —I |
| D95 (a, b, c, d, e, and f) | —Br | -n-butyl |
| D96 (a, b, c, d, e, and f) | —Br | -n-propyl |
| D97 (a, b, c, d, e, and f) | —I | -tert-butyl |
| D98 (a, b, c, d, e, and f) | —I | —H |
| D99 (a, b, c, d, e, and f) | —I | -iso-butyl |
| D100 (a, b, c, d, e, and f) | —I | -sec-butyl |
| D101 (a, b, c, d, e, and f) | —I | -iso-propyl |
| D102 (a, b, c, d, e, and f) | —I | -n-propyl |
| D103 (a, b, c, d, e, and f) | —I | -cyclohexyl |
| D104 (a, b, c, d, e, and f) | —I | -tert-butoxy |
| D105 (a, b, c, d, e, and f) | —I | -iso-propoxy |
| D106 (a, b, c, d, e, and f) | —I | —$CF_3$ |

TABLE 4-continued

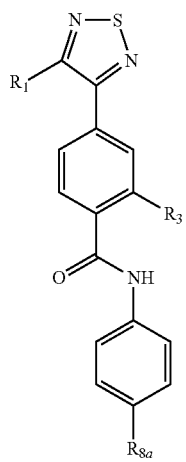

(Id)

and pharmaceutically acceptable salts thereof, where:

| Compound | $R_1$ | $R_{8a}$ |
|---|---|---|
| D107 (a, b, c, d, e, and f) | —I | —OCF$_3$ |
| D108 (a, b, c, d, e, and f) | —I | —Cl |
| D109 (a, b, c, d, e, and f) | —I | —Br |
| D110 (a, b, c, d, e, and f) | —I | —I |
| D111 (a, b, c, d, e, and f) | —I | -n-butyl |
| D112 (a, b, c, d, e, and f) | —I | -n-propyl |

In the column labeled "Compound":
(a) means that $R_3$ is —CH$_3$;
(b) means that $R_3$ is —Cl;
(c) means that $R_3$ is —Br;
(d) means that $R_3$ is —I;
(e) means that $R_3$ is —F; and
(f) means that $R_3$ is —H, i.e., in formula (I) m = 0.

TABLE 5

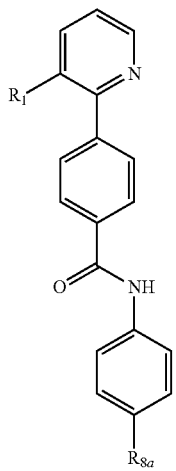

(IIa)

and pharmaceutically acceptable salts thereof, where:

| Compound | $R_1$ | $R_{8a}$ |
|---|---|---|
| E1 | —Cl | —H |
| E2 | —Cl | -tert-butyl |
| E3 | —Cl | -iso-butyl |
| E4 | —Cl | -sec-butyl |
| E5 | —Cl | -iso-propyl |
| E6 | —Cl | -n-propyl |
| E7 | —Cl | -cyclohexyl |
| E8 | —Cl | -tert-butoxy |

TABLE 5-continued

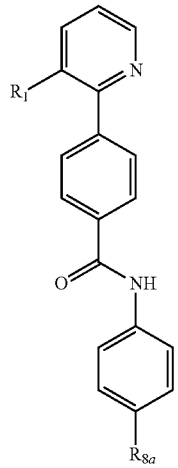

(IIa)

and pharmaceutically acceptable salts thereof, where:

| Compound | $R_1$ | $R_{8a}$ |
|---|---|---|
| E9 | —Cl | -iso-propoxy |
| E10 | —Cl | —CF$_3$ |
| E11 | —Cl | —OCF$_3$ |
| E12 | —Cl | —Cl |
| E13 | —Cl | —Br |
| E14 | —Cl | —I |
| E15 | —Cl | -n-butyl |
| E16 | —Cl | -n-propyl |
| E17 | —F | —H |
| E18 | —F | -tert-butyl |
| E19 | —F | -iso-butyl |
| E20 | —F | -sec-butyl |
| E21 | —F | -iso-propyl |
| E22 | —F | -n-propyl |
| E23 | —F | -cyclohexyl |
| E24 | —F | -tert-butoxy |
| E25 | —F | -iso-propoxy |
| E26 | —F | —CF$_3$ |
| E27 | —F | —OCF$_3$ |
| E28 | —F | —Cl |
| E29 | —F | —Br |
| E30 | —F | —I |
| E31 | —F | -n-butyl |
| E32 | —F | -n-propyl |
| E33 | —CH$_3$ | —H |
| E34 | —CH$_3$ | -iso-butyl |
| E35 | —CH$_3$ | -tert-butyl |
| E36 | —CH$_3$ | -sec-butyl |
| E37 | —CH$_3$ | -iso-propyl |
| E38 | —CH$_3$ | -n-propyl |
| E39 | —CH$_3$ | -cyclohexyl |
| E40 | —CH$_3$ | -tert-butoxy |
| E41 | —CH$_3$ | -iso-propoxy |
| E42 | —CH$_3$ | —CF$_3$ |
| E43 | —CH$_3$ | —OCF$_3$ |
| E44 | —CH$_3$ | —Cl |
| E45 | —CH$_3$ | —Br |
| E46 | —CH$_3$ | —I |
| E47 | —CH$_3$ | -n-butyl |
| E48 | —CH$_3$ | -n-propyl |
| E49 | —CF$_3$ | —H |
| E50 | —CF$_3$ | -tert-butyl |
| E51 | —CF$_3$ | -iso-butyl |
| E52 | —CF$_3$ | -sec-butyl |
| E53 | —CF$_3$ | -iso-propyl |
| E54 | —CF$_3$ | -n-propyl |
| E55 | —CF$_3$ | -cyclohexyl |
| E56 | —CF$_3$ | -tert-butoxy |
| E57 | —CF$_3$ | -iso-propoxy |
| E58 | —CF$_3$ | —CF$_3$ |
| E59 | —CF$_3$ | —OCF$_3$ |
| E60 | —CF$_3$ | —Cl |
| E61 | —CF$_3$ | —Br |

TABLE 5-continued

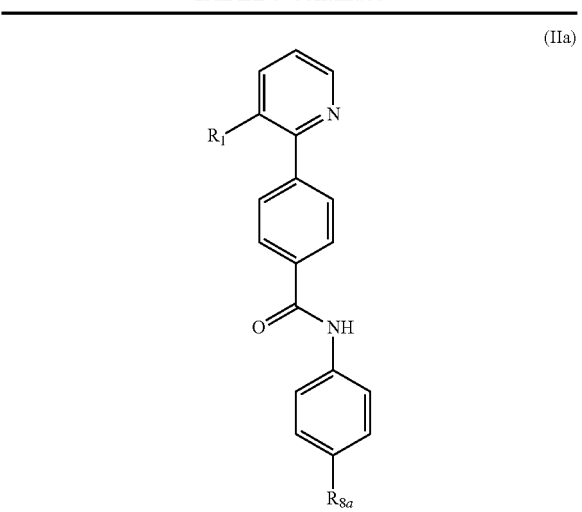
(IIa)

and pharmaceutically acceptable salts thereof, where:

| Compound | R₁ | R₈ₐ |
|---|---|---|
| E62 | —CF₃ | —I |
| E63 | —CF₃ | -n-butyl |
| E64 | —CF₃ | -n-propyl |
| E65 | —CHF₂ | -tert-butyl |
| E66 | —CHF₂ | —H |
| E67 | —CHF₂ | -iso-butyl |
| E68 | —CHF₂ | -sec-butyl |
| E69 | —CHF₂ | -iso-propyl |
| E70 | —CHF₂ | -n-propyl |
| E71 | —CHF₂ | -cyclohexyl |
| E72 | —CHF₂ | -tert-butoxy |
| E73 | —CHF₂ | -iso-propoxy |
| E74 | —CHF₂ | —CF₃ |
| E75 | —CHF₂ | —OCF₃ |
| E76 | —CHF₂ | —Cl |
| E77 | —CHF₂ | —Br |
| E78 | —CHF₂ | —I |
| E79 | —CHF₂ | -n-butyl |
| E80 | —CHF₂ | -n-propyl |
| E81 | —Br | —H |
| E82 | —Br | -tert-butyl |
| E83 | —Br | -iso-butyl |
| E84 | —Br | -sec-butyl |
| E85 | —Br | -iso-propyl |
| E86 | —Br | -n-propyl |
| E87 | —Br | -cyclohexyl |
| E88 | —Br | -tert-butoxy |
| E89 | —Br | -iso-propoxy |
| E90 | —Br | —CF₃ |
| E91 | —Br | —OCF₃ |
| E92 | —Br | —Cl |
| E93 | —Br | —Br |
| E94 | —Br | —I |
| E95 | —Br | -n-butyl |
| E96 | —Br | -n-propyl |
| E97 | —I | -tert-butyl |
| E98 | —I | —H |
| E99 | —I | -iso-butyl |
| E100 | —I | -sec-butyl |
| E101 | —I | -iso-propyl |
| E102 | —I | -n-propyl |
| E103 | —I | -cyclohexyl |
| E104 | —I | -tert-butoxy |
| E105 | —I | -iso-propoxy |
| E106 | —I | —CF₃ |
| E107 | —I | —OCF₃ |
| E108 | —I | —Cl |
| E109 | —I | —Br |
| E110 | —I | —I |
| E111 | —I | -n-butyl |
| E112 | —I | -n-propyl |

TABLE 6

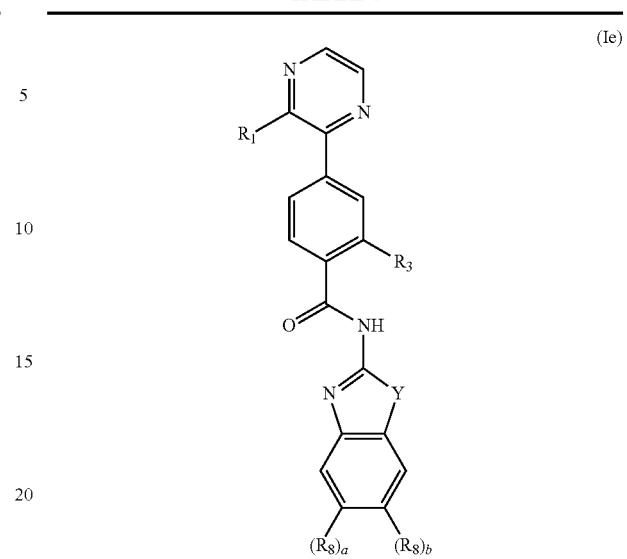
(Ie)

and pharmaceutically acceptable salts thereof, where:

| Compound | Y | R₁ | (R₈)ₐ | (R₈)ᵦ |
|---|---|---|---|---|
| F1 (a, b, c, d, e, and f) | S | —Cl | —Cl | —H |
| F2 (a, b, c, d, e, and f) | S | —Cl | —Br | —H |
| F3 (a, b, c, d, e, and f) | S | —Cl | —F | —H |
| F4 (a, b, c, d, e, and f) | S | —Cl | —CH₃ | —H |
| F5 (a, b, c, d, e, and f) | S | —Cl | —CF₃ | —H |
| F6 (a, b, c, d, e, and f) | S | —Cl | —OCH₃ | —H |
| F7 (a, b, c, d, e, and f) | S | —Cl | —OCH₂CH₃ | —H |
| F8 (a, b, c, d, e, and f) | S | —Cl | —OCF₃ | —H |
| F9 (a, b, c, d, e, and f) | S | —Cl | -tert-butyl | —H |
| F10 (a, b, c, d, e, and f) | S | —Cl | -iso-propyl | —H |
| F11 (a, b, c, d, e, and f) | S | —Cl | —CH₃ | —CH₃ |
| F12 (a, b, c, d, e, and f) | S | —Cl | —H | —H |
| F13 (a, b, c, d, e, and f) | S | —Cl | —H | —Cl |
| F14 (a, b, c, d, e, and f) | S | —Cl | —H | —Br |
| F15 (a, b, c, d, e, and f) | S | —Cl | —H | —F |
| F16 (a, b, c, d, e, and f) | S | —Cl | —H | —CH₃ |
| F17 (a, b, c, d, e, and f) | S | —Cl | —H | —CF₃ |
| F18 (a, b, c, d, e, and f) | S | —Cl | —H | —OCH₃ |
| F19 (a, b, c, d, e, and f) | S | —Cl | —H | —OCH₂CH₃ |
| F20 (a, b, c, d, e, and f) | S | —Cl | —H | —OCF₃ |
| F21 (a, b, c, d, e, and f) | S | —Cl | —H | -tert-butyl |
| F22 (a, b, c, d, e, and f) | S | —Cl | —H | -iso-propyl |
| F23 (a, b, c, d, e, and f) | S | —CH₃ | —Cl | —H |
| F24 (a, b, c, d, e, and f) | S | —CH₃ | —Br | —H |
| F25 (a, b, c, d, e, and f) | S | —CH₃ | —F | —H |
| F26 (a, b, c, d, e, and f) | S | —CH₃ | —CH₃ | —H |
| F27 (a, b, c, d, e, and f) | S | —CH₃ | —CF₃ | —H |
| F28 (a, b, c, d, e, and f) | S | —CH₃ | —OCH₃ | —H |
| F29 (a, b, c, d, e, and f) | S | —CH₃ | —OCH₂CH₃ | —H |
| F30 (a, b, c, d, e, and f) | S | —CH₃ | —OCF₃ | —H |
| F31 (a, b, c, d, e, and f) | S | —CH₃ | -tert-butyl | —H |
| F32 (a, b, c, d, e, and f) | S | —CH₃ | -iso-propyl | —H |
| F33 (a, b, c, d, e, and f) | S | —CH₃ | —CH₃ | —CH₃ |
| F34 (a, b, c, d, e, and f) | S | —CH₃ | —H | —H |
| F35 (a, b, c, d, e, and f) | S | —CH₃ | —H | —Cl |
| F36 (a, b, c, d, e, and f) | S | —CH₃ | —H | —Br |
| F37 (a, b, c, d, e, and f) | S | —CH₃ | —H | —F |
| F38 (a, b, c, d, e, and f) | S | —CH₃ | —H | —CH₃ |
| F39 (a, b, c, d, e, and f) | S | —CH₃ | —H | —CF₃ |
| F40 (a, b, c, d, e, and f) | S | —CH₃ | —H | —OCH₃ |
| F41 (a, b, c, d, e, and f) | S | —CH₃ | —H | —OCH₂CH₃ |
| F42 (a, b, c, d, e, and f) | S | —CH₃ | —H | —OCF₃ |
| F43 (a, b, c, d, e, and f) | S | —CH₃ | —H | -tert-butyl |
| F44 (a, b, c, d, e, and f) | S | —CH₃ | —H | -iso-propyl |
| F45 (a, b, c, d, e, and f) | S | —CF₃ | —Cl | —H |
| F46 (a, b, c, d, e, and f) | S | —CF₃ | —Br | —H |
| F47 (a, b, c, d, e, and f) | S | —CF₃ | —F | —H |
| F48 (a, b, c, d, e, and f) | S | —CF₃ | —CH₃ | —H |
| F49 (a, b, c, d, e, and f) | S | —CF₃ | —CF₃ | —H |
| F50 (a, b, c, d, e, and f) | S | —CF₃ | —OCH₃ | —H |
| F51 (a, b, c, d, e, and f) | S | —CF₃ | —OCH₂CH₃ | —H |

TABLE 6-continued

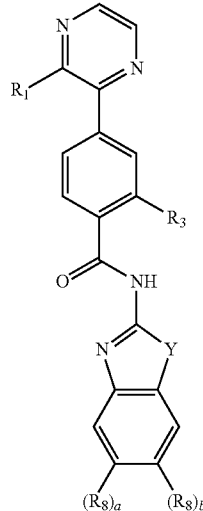

(Ie)

and pharmaceutically acceptable salts thereof, where:

| Compound | Y | $R_1$ | $(R_8)_a$ | $(R_8)_b$ |
|---|---|---|---|---|
| F52 (a, b, c, d, e, and f) | S | —$CF_3$ | —$OCF_3$ | —H |
| F53 (a, b, c, d, e, and f) | S | —$CF_3$ | -tert-butyl | —H |
| F54 (a, b, c, d, e, and f) | S | —$CF_3$ | -iso-propyl | —H |
| F55 (a, b, c, d, e, and f) | S | —$CF_3$ | —$CH_3$ | —$CH_3$ |
| F56 (a, b, c, d, e, and f) | S | —$CF_3$ | —H | —H |
| F57 (a, b, c, d, e, and f) | S | —$CF_3$ | —H | —Cl |
| F58 (a, b, c, d, e, and f) | S | —$CF_3$ | —H | —Br |
| F59 (a, b, c, d, e, and f) | S | —$CF_3$ | —H | —F |
| F60 (a, b, c, d, e, and f) | S | —$CF_3$ | —H | —$CH_3$ |
| F61 (a, b, c, d, e, and f) | S | —$CF_3$ | —H | —$CF_3$ |
| F62 (a, b, c, d, e, and f) | S | —$CF_3$ | —H | —$OCH_3$ |
| F63 (a, b, c, d, e, and f) | S | —$CF_3$ | —H | —$OCH_2CH_3$ |
| F64 (a, b, c, d, e, and f) | S | —$CF_3$ | —H | —$OCF_3$ |
| F65 (a, b, c, d, e, and f) | S | —$CF_3$ | —H | -tert-butyl |
| F66 (a, b, c, d, e, and f) | S | —$CF_3$ | —H | -iso-propyl |
| F67 (a, b, c, d, e, and f) | S | —$CHF_2$ | —Cl | —H |
| F68 (a, b, c, d, e, and f) | S | —$CHF_2$ | —Br | —H |
| F69 (a, b, c, d, e, and f) | S | —$CHF_2$ | —F | —H |
| F70 (a, b, c, d, e, and f) | S | —$CHF_2$ | —$CH_3$ | —H |
| F71 (a, b, c, d, e, and f) | S | —$CHF_2$ | —$CF_3$ | —H |
| F72 (a, b, c, d, e, and f) | S | —$CHF_2$ | —$OCH_3$ | —H |
| F73 (a, b, c, d, e, and f) | S | —$CHF_2$ | —$OCH_2CH_3$ | —H |
| F74 (a, b, c, d, e, and f) | S | —$CHF_2$ | —$OCF_3$ | —H |
| F75 (a, b, c, d, e, and f) | S | —$CHF_2$ | -tert-butyl | —H |
| F76 (a, b, c, d, e, and f) | S | —$CHF_2$ | -iso-propyl | —H |
| F77 (a, b, c, d, e, and f) | S | —$CHF_2$ | —$CH_3$ | —$CH_3$ |
| F78 (a, b, c, d, e, and f) | S | —$CHF_2$ | —H | —H |
| F79 (a, b, c, d, e, and f) | S | —$CHF_2$ | —H | —Cl |
| F80 (a, b, c, d, e, and f) | S | —$CHF_2$ | —H | —Br |
| F81 (a, b, c, d, e, and f) | S | —$CHF_2$ | —H | —F |
| F82 (a, b, c, d, e, and f) | S | —$CHF_2$ | —H | —$CH_3$ |
| F83 (a, b, c, d, e, and f) | S | —$CHF_2$ | —H | —$CF_3$ |
| F84 (a, b, c, d, e, and f) | S | —$CHF_2$ | —H | —$OCH_3$ |
| F85 (a, b, c, d, e, and f) | S | —$CHF_2$ | —H | —$OCH_2CH_3$ |
| F86 (a, b, c, d, e, and f) | S | —$CHF_2$ | —H | —$OCF_3$ |
| F87 (a, b, c, d, e, and f) | S | —$CHF_2$ | —H | -tert-butyl |
| F88 (a, b, c, d, e, and f) | S | —$CHF_2$ | —H | -iso-propyl |
| F89 (a, b, c, d, e, and f) | S | —Br | —$OCF_3$ | —H |
| F90 (a, b, c, d, e, and f) | S | —Br | —Cl | —H |
| F91 (a, b, c, d, e, and f) | S | —Br | —F | —H |
| F92 (a, b, c, d, e, and f) | S | —Br | —$CH_3$ | —H |
| F93 (a, b, c, d, e, and f) | S | —Br | —$CF_3$ | —H |
| F94 (a, b, c, d, e, and f) | S | —Br | —$OCH_3$ | —H |
| F95 (a, b, c, d, e, and f) | S | —Br | —$OCH_2CH_3$ | —H |
| F96 (a, b, c, d, e, and f) | S | —Br | —$OCF_3$ | —H |
| F97 (a, b, c, d, e, and f) | S | —Br | -tert-butyl | —H |
| F98 (a, b, c, d, e, and f) | S | —Br | -iso-propyl | —H |
| F99 (a, b, c, d, e, and f) | S | —Br | —$CH_3$ | —$CH_3$ |
| F100 (a, b, c, d, e, and f) | S | —Br | —H | —H |
| F101 (a, b, c, d, e, and f) | S | —Br | —H | —Cl |
| F102 (a, b, c, d, e, and f) | S | —Br | —H | —Br |
| F103 (a, b, c, d, e, and f) | S | —Br | —H | —F |
| F104 (a, b, c, d, e, and f) | S | —Br | —H | —$CH_3$ |
| F105 (a, b, c, d, e, and f) | S | —Br | —H | —$CF_3$ |
| F106 (a, b, c, d, e, and f) | S | —Br | —H | —$OCH_3$ |
| F107 (a, b, c, d, e, and f) | S | —Br | —H | —$OCH_2CH_3$ |
| F108 (a, b, c, d, e, and f) | S | —Br | —H | —$OCF_3$ |
| F109 (a, b, c, d, e, and f) | S | —Br | —H | -tert-butyl |
| F110 (a, b, c, d, e, and f) | S | —Br | —H | -iso-propyl |
| F111 (a, b, c, d, e, and f) | S | —I | —Cl | —H |
| F112 (a, b, c, d, e, and f) | S | —I | —Br | —H |
| F113 (a, b, c, d, e, and f) | S | —I | —F | —H |
| F114 (a, b, c, d, e, and f) | S | —I | —$CH_3$ | —H |
| F115 (a, b, c, d, e, and f) | S | —I | —$CF_3$ | —H |
| F116 (a, b, c, d, e, and f) | S | —I | —$OCH_3$ | —H |
| F117 (a, b, c, d, e, and f) | S | —I | —$OCH_2CH_3$ | —H |
| F118 (a, b, c, d, e, and f) | S | —I | —$OCF_3$ | —H |
| F119 (a, b, c, d, e, and f) | S | —I | -tert-butyl | —H |
| F120 (a, b, c, d, e, and f) | S | —I | -iso-propyl | —H |
| F121 (a, b, c, d, e, and f) | S | —I | —$CH_3$ | —$CH_3$ |
| F122 (a, b, c, d, e, and f) | S | —I | —H | —H |
| F123 (a, b, c, d, e, and f) | S | —I | —H | —Cl |
| F124 (a, b, c, d, e, and f) | S | —I | —H | —Br |
| F125 (a, b, c, d, e, and f) | S | —I | —H | —F |
| F126 (a, b, c, d, e, and f) | S | —I | —H | —$CH_3$ |
| F127 (a, b, c, d, e, and f) | S | —I | —H | —$CF_3$ |
| F128 (a, b, c, d, e, and f) | S | —I | —H | —$OCH_3$ |
| F129 (a, b, c, d, e, and f) | S | —I | —H | —$OCH_2CH_3$ |
| F130 (a, b, c, d, e, and f) | S | —I | —H | —$OCF_3$ |
| F131 (a, b, c, d, e, and f) | S | —I | —H | -tert-butyl |
| F132 (a, b, c, d, e, and f) | S | —I | —H | -iso-propyl |
| F133 (a, b, c, d, e, and f) | O | —Cl | —Cl | —H |
| F134 (a, b, c, d, e, and f) | O | —Cl | —Br | —H |
| F135 (a, b, c, d, e, and f) | O | —Cl | —F | —H |
| F136 (a, b, c, d, e, and f) | O | —Cl | —$CH_3$ | —H |
| F137 (a, b, c, d, e, and f) | O | —Cl | —$CF_3$ | —H |
| F138 (a, b, c, d, e, and f) | O | —Cl | —$OCH_3$ | —H |
| F139 (a, b, c, d, e, and f) | O | —Cl | —$OCH_2CH_3$ | —H |
| F140 (a, b, c, d, e, and f) | O | —Cl | —$OCF_3$ | —H |
| F141 (a, b, c, d, e, and f) | O | —Cl | -tert-butyl | —H |
| F142 (a, b, c, d, e, and f) | O | —Cl | -iso-propyl | —H |
| F143 (a, b, c, d, e, and f) | O | —Cl | —$CH_3$ | —$CH_3$ |
| F144 (a, b, c, d, e, and f) | O | —Cl | —H | —H |
| F145 (a, b, c, d, e, and f) | O | —Cl | —H | —$CH_3$ |
| F146 (a, b, c, d, e, and f) | O | —Cl | —H | —Cl |
| F147 (a, b, c, d, e, and f) | O | —Cl | —H | —Br |
| F148 (a, b, c, d, e, and f) | O | —Cl | —H | —F |
| F149 (a, b, c, d, e, and f) | O | —Cl | —H | —$CF_3$ |
| F150 (a, b, c, d, e, and f) | O | —Cl | —H | —$OCH_3$ |
| F151 (a, b, c, d, e, and f) | O | —Cl | —H | —$OCH_2CH_3$ |
| F152 (a, b, c, d, e, and f) | O | —Cl | —H | —$OCF_3$ |
| F153 (a, b, c, d, e, and f) | O | —Cl | —H | -tert-butyl |

TABLE 6-continued (Ie)

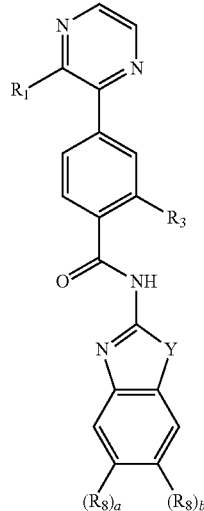

and pharmaceutically acceptable salts thereof, where:

| Compound | Y | R$_1$ | (R$_8$)$_a$ | (R$_8$)$_b$ |
|---|---|---|---|---|
| F154 (a, b, c, d, e, and f) | O | —Cl | —H | -iso-propyl |
| F155 (a, b, c, d, e, and f) | O | —CH$_3$ | —Cl | —H |
| F156 (a, b, c, d, e, and f) | O | —CH$_3$ | —Br | —H |
| F157 (a, b, c, d, e, and f) | O | —CH$_3$ | —F | —H |
| F158 (a, b, c, d, e, and f) | O | —CH$_3$ | —CH$_3$ | —H |
| F159 (a, b, c, d, e, and f) | O | —CH$_3$ | —CF$_3$ | —H |
| F160 (a, b, c, d, e, and f) | O | —CH$_3$ | —OCH$_3$ | —H |
| F161 (a, b, c, d, e, and f) | O | —CH$_3$ | —OCH$_2$CH$_3$ | —H |
| F162 (a, b, c, d, e, and f) | O | —CH$_3$ | —OCF$_3$ | —H |
| F163 (a, b, c, d, e, and f) | O | —CH$_3$ | -tert-butyl | —H |
| F164 (a, b, c, d, e, and f) | O | —CH$_3$ | -iso-propyl | —H |
| F165 (a, b, c, d, e, and f) | O | —CH$_3$ | —CH$_3$ | —CH$_3$ |
| F166 (a, b, c, d, e, and f) | O | —CH$_3$ | —H | —H |
| F167 (a, b, c, d, e, and f) | O | —CH$_3$ | —H | —Cl |
| F168 (a, b, c, d, e, and f) | O | —CH$_3$ | —H | —Br |
| F169 (a, b, c, d, e, and f) | O | —CH$_3$ | —H | —F |
| F170 (a, b, c, d, e, and f) | O | —CH$_3$ | —H | —CH$_3$ |
| F171 (a, b, c, d, e, and f) | O | —CH$_3$ | —H | —CF$_3$ |
| F172 (a, b, c, d, e, and f) | O | —CH$_3$ | —H | —OCH$_3$ |
| F173 (a, b, c, d, e, and f) | O | —CH$_3$ | —H | —OCH$_2$CH$_3$ |
| F174 (a, b, c, d, e, and f) | O | —CH$_3$ | —H | —OCF$_3$ |
| F175 (a, b, c, d, e, and f) | O | —CH$_3$ | —H | -tert-butyl |
| F176 (a, b, c, d, e, and f) | O | —CH$_3$ | —H | -iso-propyl |
| F177 (a, b, c, d, e, and f) | O | —CF$_3$ | —Cl | —H |
| F178 (a, b, c, d, e, and f) | O | —CF$_3$ | —Br | —H |
| F179 (a, b, c, d, e, and f) | O | —CF$_3$ | —F | —H |
| F180 (a, b, c, d, e, and f) | O | —CF$_3$ | —CH$_3$ | —H |
| F181 (a, b, c, d, e, and f) | O | —CF$_3$ | —CF$_3$ | —H |
| F182 (a, b, c, d, e, and f) | O | —CF$_3$ | —OCH$_3$ | —H |
| F183 (a, b, c, d, e, and f) | O | —CF$_3$ | —OCH$_2$CH$_3$ | —H |
| F184 (a, b, c, d, e, and f) | O | —CF$_3$ | —OCF$_3$ | —H |
| F185 (a, b, c, d, e, and f) | O | —CF$_3$ | -tert-butyl | —H |
| F186 (a, b, c, d, e, and f) | O | —CF$_3$ | -iso-propyl | —H |
| F187 (a, b, c, d, e, and f) | O | —CF$_3$ | —CH$_3$ | —CH$_3$ |
| F188 (a, b, c, d, e, and f) | O | —CF$_3$ | —H | —H |
| F189 (a, b, c, d, e, and f) | O | —CF$_3$ | —H | —Cl |
| F190 (a, b, c, d, e, and f) | O | —CF$_3$ | —H | —Br |
| F191 (a, b, c, d, e, and f) | O | —CF$_3$ | —H | —F |
| F192 (a, b, c, d, e, and f) | O | —CF$_3$ | —H | —CH$_3$ |
| F193 (a, b, c, d, e, and f) | O | —CF$_3$ | —H | —CF$_3$ |
| F194 (a, b, c, d, e, and f) | O | —CF$_3$ | —H | —OCH$_3$ |
| F195 (a, b, c, d, e, and f) | O | —CF$_3$ | —H | —OCH$_2$CH$_3$ |
| F196 (a, b, c, d, e, and f) | O | —CF$_3$ | —H | —OCF$_3$ |
| F197 (a, b, c, d, e, and f) | O | —CF$_3$ | —H | -tert-butyl |
| F198 (a, b, c, d, e, and f) | O | —CF$_3$ | —H | -iso-propyl |
| F199 (a, b, c, d, e, and f) | O | —CHF$_2$ | —Cl | —H |
| F200 (a, b, c, d, e, and f) | O | —CHF$_2$ | —Br | —H |
| F201 (a, b, c, d, e, and f) | O | —CHF$_2$ | —F | —H |
| F202 (a, b, c, d, e, and f) | O | —CHF$_2$ | —CH$_3$ | —H |
| F203 (a, b, c, d, e, and f) | O | —CHF$_2$ | —CF$_3$ | —H |
| F204 (a, b, c, d, e, and f) | O | —CHF$_2$ | —OCH$_3$ | —H |
| F205 (a, b, c, d, e, and f) | O | —CHF$_2$ | —OCH$_2$CH$_3$ | —H |
| F206 (a, b, c, d, e, and f) | O | —CHF$_2$ | —OCF$_3$ | —H |
| F207 (a, b, c, d, e, and f) | O | —CHF$_2$ | -tert-butyl | —H |
| F208 (a, b, c, d, e, and f) | O | —CHF$_2$ | -iso-propyl | —H |
| F209 (a, b, c, d, e, and f) | O | —CHF$_2$ | —CH$_3$ | —CH$_3$ |
| F210 (a, b, c, d, e, and f) | O | —CHF$_2$ | —H | —H |
| F211 (a, b, c, d, e, and f) | O | —CHF$_2$ | —H | —Cl |
| F212 (a, b, c, d, e, and f) | O | —CHF$_2$ | —H | —Br |
| F213 (a, b, c, d, e, and f) | O | —CHF$_2$ | —H | —F |
| F214 (a, b, c, d, e, and f) | O | —CHF$_2$ | —H | —CH$_3$ |
| F215 (a, b, c, d, e, and f) | O | —CHF$_2$ | —H | —CF$_3$ |
| F216 (a, b, c, d, e, and f) | O | —CHF$_2$ | —H | —OCH$_3$ |
| F217 (a, b, c, d, e, and f) | O | —CHF$_2$ | —H | —OCH$_2$CH$_3$ |
| F218 (a, b, c, d, e, and f) | O | —CHF$_2$ | —H | —OCF$_3$ |
| F219 (a, b, c, d, e, and f) | O | —CHF$_2$ | —H | -tert-butyl |
| F220 (a, b, c, d, e, and f) | O | —CHF$_2$ | —H | -iso-propyl |
| F221 (a, b, c, d, e, and f) | O | —Br | —Br | —H |
| F222 (a, b, c, d, e, and f) | O | —Br | —Cl | —H |
| F223 (a, b, c, d, e, and f) | O | —Br | —F | —H |
| F224 (a, b, c, d, e, and f) | O | —Br | —CH$_3$ | —H |
| F225 (a, b, c, d, e, and f) | O | —Br | —CF$_3$ | —H |
| F226 (a, b, c, d, e, and f) | O | —Br | —OCH$_3$ | —H |
| F227 (a, b, c, d, e, and f) | O | —Br | —OCH$_2$CH$_3$ | —H |
| F228 (a, b, c, d, e, and f) | O | —Br | —OCF$_3$ | —H |
| F229 (a, b, c, d, e, and f) | O | —Br | -tert-butyl | —H |
| F230 (a, b, c, d, e, and f) | O | —Br | -iso-propyl | —H |
| F231 (a, b, c, d, e, and f) | O | —Br | —CH$_3$ | —CH$_3$ |
| F232 (a, b, c, d, e, and f) | O | —Br | —H | —H |
| F233 (a, b, c, d, e, and f) | O | —Br | —H | —Cl |
| F234 (a, b, c, d, e, and f) | O | —Br | —H | —Br |
| F235 (a, b, c, d, e, and f) | O | —Br | —H | —F |
| F236 (a, b, c, d, e, and f) | O | —Br | —H | —CH$_3$ |
| F237 (a, b, c, d, e, and f) | O | —Br | —H | —CF$_3$ |
| F238 (a, b, c, d, e, and f) | O | —Br | —H | —OCH$_3$ |
| F239 (a, b, c, d, e, and f) | O | —Br | —H | —OCH$_2$CH$_3$ |
| F240 (a, b, c, d, e, and f) | O | —Br | —H | —OCF$_3$ |
| F241 (a, b, c, d, e, and f) | O | —Br | —H | -tert-butyl |
| F242 (a, b, c, d, e, and f) | O | —Br | —H | -iso-propyl |
| F243 (a, b, c, d, e, and f) | O | —I | —Cl | —H |
| F244 (a, b, c, d, e, and f) | O | —I | —Br | —H |
| F245 (a, b, c, d, e, and f) | O | —I | —F | —H |
| F246 (a, b, c, d, e, and f) | O | —I | —CH$_3$ | —H |
| F247 (a, b, c, d, e, and f) | O | —I | —CF$_3$ | —H |
| F248 (a, b, c, d, e, and f) | O | —I | —OCH$_3$ | —H |
| F249 (a, b, c, d, e, and f) | O | —I | —OCH$_2$CH$_3$ | —H |
| F250 (a, b, c, d, e, and f) | O | —I | —OCF$_3$ | —H |
| F251 (a, b, c, d, e, and f) | O | —I | -tert-butyl | —H |
| F252 (a, b, c, d, e, and f) | O | —I | -iso-propyl | —H |
| F253 (a, b, c, d, e, and f) | O | —I | —CH$_3$ | —CH$_3$ |
| F254 (a, b, c, d, e, and f) | O | —I | —H | —H |
| F255 (a, b, c, d, e, and f) | O | —I | —H | —Cl |

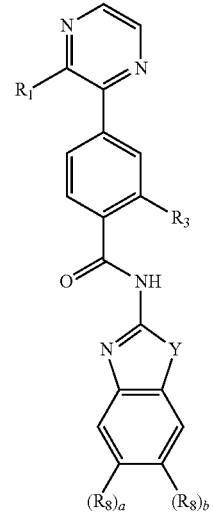

TABLE 6-continued

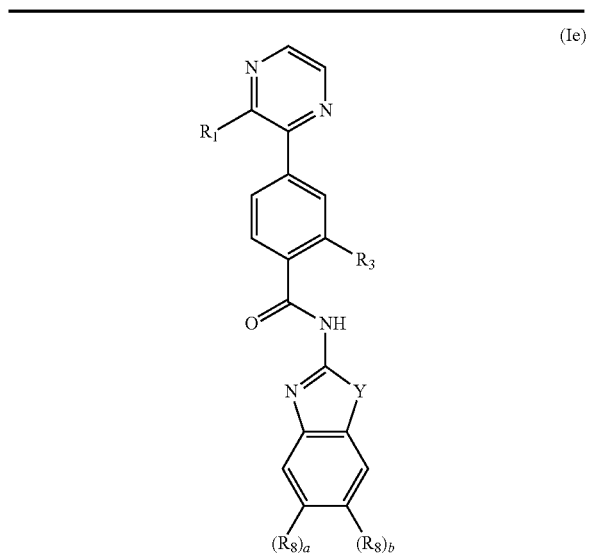

(Ie)

and pharmaceutically acceptable salts thereof, where:

| Compound | Y | R₁ | (R₈)ₐ | (R₈)ᵦ |
|---|---|---|---|---|
| F256 (a, b, c, d, e, and f) | O | —I | —H | —Br |
| F257 (a, b, c, d, e, and f) | O | —I | —H | —F |
| F258 (a, b, c, d, e, and f) | O | —I | —H | —CH₃ |
| F259 (a, b, c, d, e, and f) | O | —I | —H | —CF₃ |
| F260 (a, b, c, d, e, and f) | O | —I | —H | —OCH₃ |
| F261 (a, b, c, d, e, and f) | O | —I | —H | —OCH₂CH₃ |
| F262 (a, b, c, d, e, and f) | O | —I | —H | —OCF₃ |
| F263 (a, b, c, d, e, and f) | O | —I | —H | -tert-butyl |
| F264 (a, b, c, d, e, and f) | O | —I | —H | -iso-propyl |
| F265 (a, b, c, d, e, and f) | NH | —Cl | —Cl | —H |
| F266 (a, b, c, d, e, and f) | NH | —Cl | —Br | —H |
| F267 (a, b, c, d, e, and f) | NH | —Cl | —F | —H |
| F268 (a, b, c, d, e, and f) | NH | —Cl | —CH₃ | —H |
| F269 (a, b, c, d, e, and f) | NH | —Cl | —CF₃ | —H |
| F270 (a, b, c, d, e, and f) | NH | —Cl | —OCH₃ | —H |
| F271 (a, b, c, d, e, and f) | NH | —Cl | —OCH₂CH₃ | —H |
| F272 (a, b, c, d, e, and f) | NH | —Cl | —OCF₃ | —H |
| F273 (a, b, c, d, e, and f) | NH | —Cl | -tert-butyl | —H |
| F274 (a, b, c, d, e, and f) | NH | —Cl | -iso-propyl | —H |
| F275 (a, b, c, d, e, and f) | NH | —Cl | —CH₃ | —CH₃ |
| F276 (a, b, c, d, e, and f) | NH | —Cl | —H | —H |
| F277 (a, b, c, d, e, and f) | NH | —Cl | —H | —CH₃ |
| F278 (a, b, c, d, e, and f) | NH | —Cl | —H | —Cl |
| F279 (a, b, c, d, e, and f) | NH | —Cl | —H | —Br |
| F280 (a, b, c, d, e, and f) | NH | —Cl | —H | —F |
| F281 (a, b, c, d, e, and f) | NH | —Cl | —H | —CF₃ |
| F282 (a, b, c, d, e, and f) | NH | —Cl | —H | —OCH₃ |
| F283 (a, b, c, d, e, and f) | NH | —Cl | —H | —OCH₂CH₃ |
| F284 (a, b, c, d, e, and f) | NH | —Cl | —H | —OCF₃ |
| F285 (a, b, c, d, e, and f) | NH | —Cl | —H | -tert-butyl |
| F286 (a, b, c, d, e, and f) | NH | —Cl | —H | -iso-propyl |
| F287 (a, b, c, d, e, and f) | NH | —CH₃ | —Cl | —H |
| F288 (a, b, c, d, e, and f) | NH | —CH₃ | —Br | —H |
| F289 (a, b, c, d, e, and f) | NH | —CH₃ | —F | —H |
| F290 (a, b, c, d, e, and f) | NH | —CH₃ | —CH₃ | —H |
| F291 (a, b, c, d, e, and f) | NH | —CH₃ | —CF₃ | —H |
| F292 (a, b, c, d, e, and f) | NH | —CH₃ | —OCH₃ | —H |
| F293 (a, b, c, d, e, and f) | NH | —CH₃ | —OCH₂CH₃ | —H |
| F294 (a, b, c, d, e, and f) | NH | —CH₃ | —OCF₃ | —H |
| F295 (a, b, c, d, e, and f) | NH | —CH₃ | -tert-butyl | —H |
| F296 (a, b, c, d, e, and f) | NH | —CH₃ | -iso-propyl | —H |
| F297 (a, b, c, d, e, and f) | NH | —CH₃ | —CH₃ | —CH₃ |
| F298 (a, b, c, d, e, and f) | NH | —CH₃ | —H | —H |
| F299 (a, b, c, d, e, and f) | NH | —CH₃ | —H | —Cl |
| F300 (a, b, c, d, e, and f) | NH | —CH₃ | —H | —Br |
| F301 (a, b, c, d, e, and f) | NH | —CH₃ | —H | —F |
| F302 (a, b, c, d, e, and f) | NH | —CH₃ | —H | —CH₃ |
| F303 (a, b, c, d, e, and f) | NH | —CH₃ | —H | —CF₃ |
| F304 (a, b, c, d, e, and f) | NH | —CH₃ | —H | —OCH₃ |
| F305 (a, b, c, d, e, and f) | NH | —CH₃ | —H | —OCH₂CH₃ |
| F306 (a, b, c, d, e, and f) | NH | —CH₃ | —H | —OCF₃ |

TABLE 6-continued

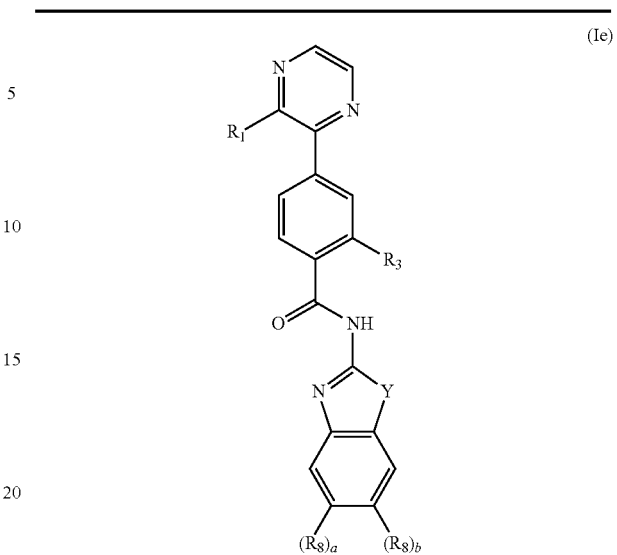

(Ie)

and pharmaceutically acceptable salts thereof, where:

| Compound | Y | R₁ | (R₈)ₐ | (R₈)ᵦ |
|---|---|---|---|---|
| F307 (a, b, c, d, e, and f) | NH | —CH₃ | —H | -tert-butyl |
| F308 (a, b, c, d, e, and f) | NH | —CH₃ | —H | -iso-propyl |
| F309 (a, b, c, d, e, and f) | NH | —CF₃ | —Cl | —H |
| F310 (a, b, c, d, e, and f) | NH | —CF₃ | —Br | —H |
| F311 (a, b, c, d, e, and f) | NH | —CF₃ | —F | —H |
| F312 (a, b, c, d, e, and f) | NH | —CF₃ | —CH₃ | —H |
| F313 (a, b, c, d, e, and f) | NH | —CF₃ | —CF₃ | —H |
| F314 (a, b, c, d, e, and f) | NH | —CF₃ | —OCH₃ | —H |
| F315 (a, b, c, d, e, and f) | NH | —CF₃ | —OCH₂CH₃ | —H |
| F316 (a, b, c, d, e, and f) | NH | —CF₃ | —OCF₃ | —H |
| F317 (a, b, c, d, e, and f) | NH | —CF₃ | -tert-butyl | —H |
| F318 (a, b, c, d, e, and f) | NH | —CF₃ | -iso-propyl | —H |
| F319 (a, b, c, d, e, and f) | NH | —CF₃ | —CH₃ | —CH₃ |
| F320 (a, b, c, d, e, and f) | NH | —CF₃ | —H | —H |
| F321 (a, b, c, d, e, and f) | NH | —CF₃ | —H | —Cl |
| F322 (a, b, c, d, e, and f) | NH | —CF₃ | —H | —Br |
| F323 (a, b, c, d, e, and f) | NH | —CF₃ | —H | —F |
| F324 (a, b, c, d, e, and f) | NH | —CF₃ | —H | —CH₃ |
| F325 (a, b, c, d, e, and f) | NH | —CF₃ | —H | —CF₃ |
| F326 (a, b, c, d, e, and f) | NH | —CF₃ | —H | —OCH₃ |
| F327 (a, b, c, d, e, and f) | NH | —CF₃ | —H | —OCH₂CH₃ |
| F328 (a, b, c, d, e, and f) | NH | —CF₃ | —H | —OCF₃ |
| F329 (a, b, c, d, e, and f) | NH | —CF₃ | —H | -tert-butyl |
| F330 (a, b, c, d, e, and f) | NH | —CF₃ | —H | -iso-propyl |
| F331 (a, b, c, d, e, and f) | NH | —CHF₂ | —Cl | —H |
| F332 (a, b, c, d, e, and f) | NH | —CHF₂ | —Br | —H |
| F333 (a, b, c, d, e, and f) | NH | —CHF₂ | —F | —H |
| F334 (a, b, c, d, e, and f) | NH | —CHF₂ | —CH₃ | —H |
| F335 (a, b, c, d, e, and f) | NH | —CHF₂ | —CF₃ | —H |
| F336 (a, b, c, d, e, and f) | NH | —CHF₂ | —OCH₃ | —H |
| F337 (a, b, c, d, e, and f) | NH | —CHF₂ | —OCH₂CH₃ | —H |
| F338 (a, b, c, d, e, and f) | NH | —CHF₂ | —OCF₃ | —H |
| F339 (a, b, c, d, e, and f) | NH | —CHF₂ | -tert-butyl | —H |
| F340 (a, b, c, d, e, and f) | NH | —CHF₂ | -iso-propyl | —H |
| F341 (a, b, c, d, e, and f) | NH | —CHF₂ | —CH₃ | —CH₃ |
| F342 (a, b, c, d, e, and f) | NH | —CHF₂ | —H | —H |
| F343 (a, b, c, d, e, and f) | NH | —CHF₂ | —H | —Cl |
| F344 (a, b, c, d, e, and f) | NH | —CHF₂ | —H | —Br |
| F345 (a, b, c, d, e, and f) | NH | —CHF₂ | —H | —F |
| F346 (a, b, c, d, e, and f) | NH | —CHF₂ | —H | —CH₃ |
| F347 (a, b, c, d, e, and f) | NH | —CHF₂ | —H | —CF₃ |
| F348 (a, b, c, d, e, and f) | NH | —CHF₂ | —H | —OCH₃ |
| F349 (a, b, c, d, e, and f) | NH | —CHF₂ | —H | —OCH₂CH₃ |
| F350 (a, b, c, d, e, and f) | NH | —CHF₂ | —H | —OCF₃ |
| F351 (a, b, c, d, e, and f) | NH | —CHF₂ | —H | -tert-butyl |
| F352 (a, b, c, d, e, and f) | NH | —CHF₂ | —H | -iso-propyl |
| F353 (a, b, c, d, e, and f) | NH | —Br | —Br | —H |
| F354 (a, b, c, d, e, and f) | NH | —Br | —Cl | —H |
| F355 (a, b, c, d, e, and f) | NH | —Br | —F | —H |
| F356 (a, b, c, d, e, and f) | NH | —Br | —CH₃ | —H |
| F357 (a, b, c, d, e, and f) | NH | —Br | —CF₃ | —H |

TABLE 6-continued (Ie)

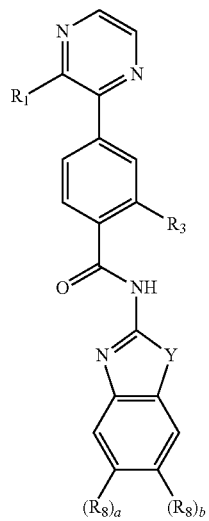

and pharmaceutically acceptable salts thereof, where:

| Compound | Y | R$_1$ | (R$_8$)$_a$ | (R$_8$)$_b$ |
|---|---|---|---|---|
| F358 (a, b, c, d, e, and f) | NH | —Br | —OCH$_3$ | —H |
| F359 (a, b, c, d, e, and f) | NH | —Br | —OCH$_2$CH$_3$ | —H |
| F360 (a, b, c, d, e, and f) | NH | —Br | —OCF$_3$ | —H |
| F361 (a, b, c, d, e, and f) | NH | —Br | -tert-butyl | —H |
| F362 (a, b, c, d, e, and f) | NH | —Br | -iso-propyl | —H |
| F363 (a, b, c, d, e, and f) | NH | —Br | —CH$_3$ | —CH$_3$ |
| F364 (a, b, c, d, e, and f) | NH | —Br | —H | —H |
| F365 (a, b, c, d, e, and f) | NH | —Br | —H | —Cl |
| F366 (a, b, c, d, e, and f) | NH | —Br | —H | —Br |
| F367 (a, b, c, d, e, and f) | NH | —Br | —H | —F |
| F368 (a, b, c, d, e, and f) | NH | —Br | —H | —CH$_3$ |
| F369 (a, b, c, d, e, and f) | NH | —Br | —H | —CF$_3$ |
| F370 (a, b, c, d, e, and f) | NH | —Br | —H | —OCH$_3$ |
| F371 (a, b, c, d, e, and f) | NH | —Br | —H | —OCH$_2$CH$_3$ |
| F372 (a, b, c, d, e, and f) | NH | —Br | —H | —OCF$_3$ |
| F373 (a, b, c, d, e, and f) | NH | —Br | —H | -tert-butyl |
| F374 (a, b, c, d, e, and f) | NH | —Br | —H | -iso-propyl |
| F375 (a, b, c, d, e, and f) | NH | —I | —Cl | —H |
| F376 (a, b, c, d, e, and f) | NH | —I | —Br | —H |
| F377 (a, b, c, d, e, and f) | NH | —I | —F | —H |
| F378 (a, b, c, d, e, and f) | NH | —I | —CH$_3$ | —H |
| F379 (a, b, c, d, e, and f) | NH | —I | —CF$_3$ | —H |
| F380 (a, b, c, d, e, and f) | NH | —I | —OCH$_3$ | —H |
| F381 (a, b, c, d, e, and f) | NH | —I | —OCH$_2$CH$_3$ | —H |
| F382 (a, b, c, d, e, and f) | NH | —I | —OCF$_3$ | —H |
| F383 (a, b, c, d, e, and f) | NH | —I | -tert-butyl | —H |
| F384 (a, b, c, d, e, and f) | NH | —I | -iso-propyl | —H |
| F385 (a, b, c, d, e, and f) | NH | —I | —CH$_3$ | —CH$_3$ |
| F386 (a, b, c, d, e, and f) | NH | —I | —H | —H |
| F387 (a, b, c, d, e, and f) | NH | —I | —H | —Cl |
| F388 (a, b, c, d, e, and f) | NH | —I | —H | —Br |
| F389 (a, b, c, d, e, and f) | NH | —I | —H | —F |
| F390 (a, b, c, d, e, and f) | NH | —I | —H | —CH$_3$ |
| F391 (a, b, c, d, e, and f) | NH | —I | —H | —CF$_3$ |
| F392 (a, b, c, d, e, and f) | NH | —I | —H | —OCH$_3$ |
| F393 (a, b, c, d, e, and f) | NH | —I | —H | —OCH$_2$CH$_3$ |
| F394 (a, b, c, d, e, and f) | NH | —I | —H | —OCF$_3$ |
| F395 (a, b, c, d, e, and f) | NH | —I | —H | -tert-butyl |
| F396 (a, b, c, d, e, and f) | NH | —I | —H | -iso-propyl |

In the column labeled "Compound":
(a) means that R$_3$ is —CH$_3$;
(b) means that R$_3$ is —Cl;
(c) means that R$_3$ is —Br;
(d) means that R$_3$ is —I;
(e) means that R$_3$ is —F; and
(f) means that R$_3$ is —H, i.e., in formula (I) m = 0.

TABLE 7

(If)

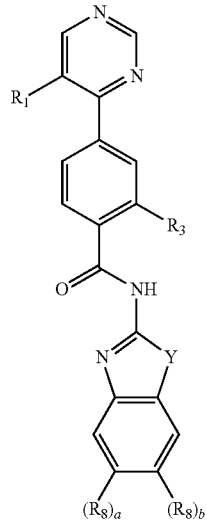

and pharmaceutically acceptable salts thereof, where:

| Compound | Y | R$_1$ | (R$_8$)$_a$ | (R$_8$)$_b$ |
|---|---|---|---|---|
| G1 (a, b, c, d, e, and f) | S | —Cl | —Cl | —H |
| G2 (a, b, c, d, e, and f) | S | —Cl | —Br | —H |
| G3 (a, b, c, d, e, and f) | S | —Cl | —F | —H |
| G4 (a, b, c, d, e, and f) | S | —Cl | —CH$_3$ | —H |
| G5 (a, b, c, d, e, and f) | S | —Cl | —CF$_3$ | —H |
| G6 (a, b, c, d, e, and f) | S | —Cl | —OCH$_3$ | —H |
| G7 (a, b, c, d, e, and f) | S | —Cl | —OCH$_2$CH$_3$ | —H |
| G8 (a, b, c, d, e, and f) | S | —Cl | —OCF$_3$ | —H |
| G9 (a, b, c, d, e, and f) | S | —Cl | -tert-butyl | —H |
| G10 (a, b, c, d, e, and f) | S | —Cl | -iso-propyl | —H |
| G11 (a, b, c, d, e, and f) | S | —Cl | —CH$_3$ | —CH$_3$ |
| G12 (a, b, c, d, e, and f) | S | —Cl | —H | —H |
| G13 (a, b, c, d, e, and f) | S | —Cl | —H | —Cl |
| G14 (a, b, c, d, e, and f) | S | —Cl | —H | —Br |
| G15 (a, b, c, d, e, and f) | S | —Cl | —H | —F |
| G16 (a, b, c, d, e, and f) | S | —Cl | —H | —CH$_3$ |
| G17 (a, b, c, d, e, and f) | S | —Cl | —H | —CF$_3$ |
| G18 (a, b, c, d, e, and f) | S | —Cl | —H | —OCH$_3$ |
| G19 (a, b, c, d, e, and f) | S | —Cl | —H | —OCH$_2$CH$_3$ |
| G20 (a, b, c, d, e, and f) | S | —Cl | —H | —OCF$_3$ |
| G21 (a, b, c, d, e, and f) | S | —Cl | —H | -tert-butyl |
| G22 (a, b, c, d, e, and f) | S | —Cl | —H | -iso-propyl |
| G23 (a, b, c, d, e, and f) | S | —CH$_3$ | —Cl | —H |
| G24 (a, b, c, d, e, and f) | S | —CH$_3$ | —Br | —H |
| G25 (a, b, c, d, e, and f) | S | —CH$_3$ | —F | —H |
| G26 (a, b, c, d, e, and f) | S | —CH$_3$ | —CH$_3$ | —H |
| G27 (a, b, c, d, e, and f) | S | —CH$_3$ | —CF$_3$ | —H |
| G28 (a, b, c, d, e, and f) | S | —CH$_3$ | —OCH$_3$ | —H |
| G29 (a, b, c, d, e, and f) | S | —CH$_3$ | —OCH$_2$CH$_3$ | —H |
| G30 (a, b, c, d, e, and f) | S | —CH$_3$ | —OCF$_3$ | —H |
| G31 (a, b, c, d, e, and f) | S | —CH$_3$ | -tert-butyl | —H |
| G32 (a, b, c, d, e, and f) | S | —CH$_3$ | -iso-propyl | —H |
| G33 (a, b, c, d, e, and f) | S | —CH$_3$ | —CH$_3$ | —CH$_3$ |
| G34 (a, b, c, d, e, and f) | S | —CH$_3$ | —H | —H |
| G35 (a, b, c, d, e, and f) | S | —CH$_3$ | —H | —Cl |
| G36 (a, b, c, d, e, and f) | S | —CH$_3$ | —H | —Br |
| G37 (a, b, c, d, e, and f) | S | —CH$_3$ | —H | —F |
| G38 (a, b, c, d, e, and f) | S | —CH$_3$ | —H | —CH$_3$ |
| G39 (a, b, c, d, e, and f) | S | —CH$_3$ | —H | —CF$_3$ |
| G40 (a, b, c, d, e, and f) | S | —CH$_3$ | —H | —OCH$_3$ |
| G41 (a, b, c, d, e, and f) | S | —CH$_3$ | —H | —OCH$_2$CH$_3$ |
| G42 (a, b, c, d, e, and f) | S | —CH$_3$ | —H | —OCF$_3$ |
| G43 (a, b, c, d, e, and f) | S | —CH$_3$ | —H | -tert-butyl |
| G44 (a, b, c, d, e, and f) | S | —CH$_3$ | —H | -iso-propyl |
| G45 (a, b, c, d, e, and f) | S | —CF$_3$ | —Cl | —H |
| G46 (a, b, c, d, e, and f) | S | —CF$_3$ | —Br | —H |
| G47 (a, b, c, d, e, and f) | S | —CF$_3$ | —F | —H |
| G48 (a, b, c, d, e, and f) | S | —CF$_3$ | —CH$_3$ | —H |
| G49 (a, b, c, d, e, and f) | S | —CF$_3$ | —CF$_3$ | —H |
| G50 (a, b, c, d, e, and f) | S | —CF$_3$ | —OCH$_3$ | —H |

TABLE 7-continued

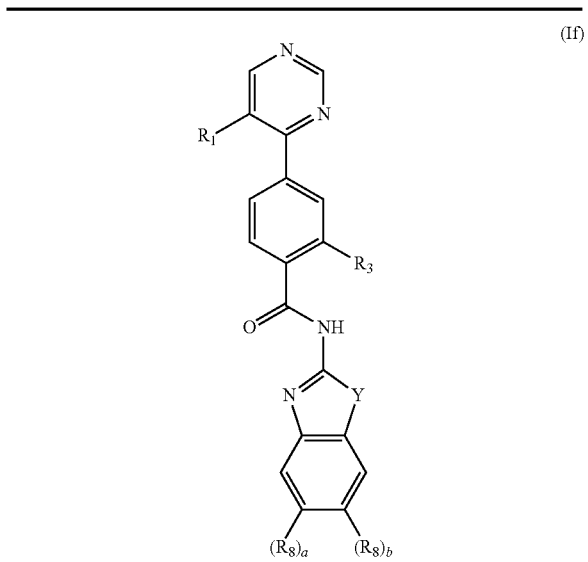

(If)

and pharmaceutically acceptable salts thereof, where:

| Compound | Y | $R_1$ | $(R_8)_a$ | $(R_8)_b$ |
|---|---|---|---|---|
| G51 (a, b, c, d, e, and f) | S | —$CF_3$ | —$OCH_2CH_3$ | —H |
| G52 (a, b, c, d, e, and f) | S | —$CF_3$ | —$OCF_3$ | —H |
| G53 (a, b, c, d, e, and f) | S | —$CF_3$ | -tert-butyl | —H |
| G54 (a, b, c, d, e, and f) | S | —$CF_3$ | -iso-propyl | —H |
| G55 (a, b, c, d, e, and f) | S | —$CF_3$ | —$CH_3$ | —$CH_3$ |
| G56 (a, b, c, d, e, and f) | S | —$CF_3$ | —H | —H |
| G57 (a, b, c, d, e, and f) | S | —$CF_3$ | —H | —Cl |
| G58 (a, b, c, d, e, and f) | S | —$CF_3$ | —H | —Br |
| G59 (a, b, c, d, e, and f) | S | —$CF_3$ | —H | —F |
| G60 (a, b, c, d, e, and f) | S | —$CF_3$ | —H | —$CH_3$ |
| G61 (a, b, c, d, e, and f) | S | —$CF_3$ | —H | —$CF_3$ |
| G62 (a, b, c, d, e, and f) | S | —$CF_3$ | —H | —$OCH_3$ |
| G63 (a, b, c, d, e, and f) | S | —$CF_3$ | —H | —$OCH_2CH_3$ |
| G64 (a, b, c, d, e, and f) | S | —$CF_3$ | —H | —$OCF_3$ |
| G65 (a, b, c, d, e, and f) | S | —$CF_3$ | —H | -tert-butyl |
| G66 (a, b, c, d, e, and f) | S | —$CF_3$ | —H | -iso-propyl |
| G67 (a, b, c, d, e, and f) | S | —$CHF_2$ | —Cl | —H |
| G68 (a, b, c, d, e, and f) | S | —$CHF_2$ | —Br | —H |
| G69 (a, b, c, d, e, and f) | S | —$CHF_2$ | —F | —H |
| G70 (a, b, c, d, e, and f) | S | —$CHF_2$ | —$CH_3$ | —H |
| G71 (a, b, c, d, e, and f) | S | —$CHF_2$ | —$CF_3$ | —H |
| G72 (a, b, c, d, e, and f) | S | —$CHF_2$ | —$OCH_3$ | —H |
| G73 (a, b, c, d, e, and f) | S | —$CHF_2$ | —$OCH_2CH_3$ | —H |
| G74 (a, b, c, d, e, and f) | S | —$CHF_2$ | —$OCF_3$ | —H |
| G75 (a, b, c, d, e, and f) | S | —$CHF_2$ | -tert-butyl | —H |
| G76 (a, b, c, d, e, and f) | S | —$CHF_2$ | -iso-propyl | —H |
| G77 (a, b, c, d, e, and f) | S | —$CHF_2$ | —$CH_3$ | —$CH_3$ |
| G78 (a, b, c, d, e, and f) | S | —$CHF_2$ | —H | —H |
| G79 (a, b, c, d, e, and f) | S | —$CHF_2$ | —H | —Cl |
| G80 (a, b, c, d, e, and f) | S | —$CHF_2$ | —H | —Br |
| G81 (a, b, c, d, e, and f) | S | —$CHF_2$ | —H | —F |
| G82 (a, b, c, d, e, and f) | S | —$CHF_2$ | —H | —$CH_3$ |
| G83 (a, b, c, d, e, and f) | S | —$CHF_2$ | —H | —$CF_3$ |
| G84 (a, b, c, d, e, and f) | S | —$CHF_2$ | —H | —$OCH_3$ |
| G85 (a, b, c, d, e, and f) | S | —$CHF_2$ | —H | —$OCH_2CH_3$ |
| G86 (a, b, c, d, e, and f) | S | —$CHF_2$ | —H | —$OCF_3$ |
| G87 (a, b, c, d, e, and f) | S | —$CHF_2$ | —H | -tert-butyl |
| G88 (a, b, c, d, e, and f) | S | —$CHF_2$ | —H | -iso-propyl |
| G89 (a, b, c, d, e, and f) | S | —Br | —Br | —H |
| G90 (a, b, c, d, e, and f) | S | —Br | —Cl | —H |
| G91 (a, b, c, d, e, and f) | S | —Br | —F | —H |
| G92 (a, b, c, d, e, and f) | S | —Br | —$CH_3$ | —H |
| G93 (a, b, c, d, e, and f) | S | —Br | —$CF_3$ | —H |
| G94 (a, b, c, d, e, and f) | S | —Br | —$OCH_3$ | —H |
| G95 (a, b, c, d, e, and f) | S | —Br | —$OCH_2CH_3$ | —H |
| G96 (a, b, c, d, e, and f) | S | —Br | —$OCF_3$ | —H |
| G97 (a, b, c, d, e, and f) | S | —Br | -tert-butyl | —H |
| G98 (a, b, c, d, e, and f) | S | —Br | -iso-propyl | —H |
| G99 (a, b, c, d, e, and f) | S | —Br | —$CH_3$ | —$CH_3$ |
| G100 (a, b, c, d, e, and f) | S | —Br | —H | —H |
| G101 (a, b, c, d, e, and f) | S | —Br | —H | —Cl |
| G102 (a, b, c, d, e, and f) | S | —Br | —Fl | —Br |
| G103 (a, b, c, d, e, and f) | S | —Br | —H | —F |
| G104 (a, b, c, d, e, and f) | S | —Br | —H | —$CH_3$ |
| G105 (a, b, c, d, e, and f) | S | —Br | —H | —$CF_3$ |
| G106 (a, b, c, d, e, and f) | S | —Br | —H | —$OCH_3$ |
| G107 (a, b, c, d, e, and f) | S | —Br | —H | —$OCH_2CH_3$ |
| G108 (a, b, c, d, e, and f) | S | —Br | —H | —$OCF_3$ |
| G109 (a, b, c, d, e, and f) | S | —Br | —H | -tert-butyl |
| G110 (a, b, c, d, e, and f) | S | —Br | —H | -iso-propyl |
| G111 (a, b, c, d, e, and f) | S | —I | —Cl | —H |
| G112 (a, b, c, d, e, and f) | S | —I | —Br | —H |
| G113 (a, b, c, d, e, and f) | S | —I | —F | —H |
| G114 (a, b, c, d, e, and f) | S | —I | —$CH_3$ | —H |
| G115 (a, b, c, d, e, and f) | S | —I | —$CF_3$ | —H |
| G116 (a, b, c, d, e, and f) | S | —I | —$OCH_3$ | —H |
| G117 (a, b, c, d, e, and f) | S | —I | —$OCH_2CH_3$ | —H |
| G118 (a, b, c, d, e, and f) | S | —I | —$OCF_3$ | —H |
| G119 (a, b, c, d, e, and f) | S | —I | -tert-butyl | —H |
| G120 (a, b, c, d, e, and f) | S | —I | -iso-propyl | —H |
| G121 (a, b, c, d, e, and f) | S | —I | —$CH_3$ | —$CH_3$ |
| G122 (a, b, c, d, e, and f) | S | —I | —H | —H |
| G123 (a, b, c, d, e, and f) | S | —I | —H | —Cl |
| G124 (a, b, c, d, e, and f) | S | —I | —H | —Br |
| G125 (a, b, c, d, e, and f) | S | —I | —H | —F |
| G126 (a, b, c, d, e, and f) | S | —I | —H | —$CH_3$ |
| G127 (a, b, c, d, e, and f) | S | —I | —H | —$CF_3$ |
| G128 (a, b, c, d, e, and f) | S | —I | —H | —$OCH_3$ |
| G129 (a, b, c, d, e, and f) | S | —I | —H | —$OCH_2CH_3$ |
| G130 (a, b, c, d, e, and f) | S | —I | —H | —$OCF_3$ |
| G131 (a, b, c, d, e, and f) | S | —I | —H | -tert-butyl |
| G132 (a, b, c, d, e, and f) | S | —I | —H | -iso-propyl |
| G133 (a, b, c, d, e, and f) | O | —Cl | —Cl | —H |
| G134 (a, b, c, d, e, and f) | O | —Cl | —Br | —H |
| G135 (a, b, c, d, e, and f) | O | —Cl | —F | —H |
| G136 (a, b, c, d, e, and f) | O | —Cl | —$CH_3$ | —H |
| G137 (a, b, c, d, e, and f) | O | —Cl | —$CF_3$ | —H |
| G138 (a, b, c, d, e, and f) | O | —Cl | —$OCH_3$ | —H |
| G139 (a, b, c, d, e, and f) | O | —Cl | —$OCH_2CH_3$ | —H |
| G140 (a, b, c, d, e, and f) | O | —Cl | —$OCF_3$ | —H |
| G141 (a, b, c, d, e, and f) | O | —Cl | -tert-butyl | —H |
| G142 (a, b, c, d, e, and f) | O | —Cl | -iso-propyl | —H |
| G143 (a, b, c, d, e, and f) | O | —Cl | —$CH_3$ | —$CH_3$ |
| G144 (a, b, c, d, e, and f) | O | —Cl | —H | —H |
| G145 (a, b, c, d, e, and f) | O | —Cl | —H | —$CH_3$ |
| G146 (a, b, c, d, e, and f) | O | —Cl | —H | —Cl |
| G147 (a, b, c, d, e, and f) | O | —Cl | —H | —Br |
| G148 (a, b, c, d, e, and f) | O | —Cl | —H | —F |
| G149 (a, b, c, d, e, and f) | O | —Cl | —H | —$CF_3$ |
| G150 (a, b, c, d, e, and f) | O | —Cl | —H | —$OCH_3$ |

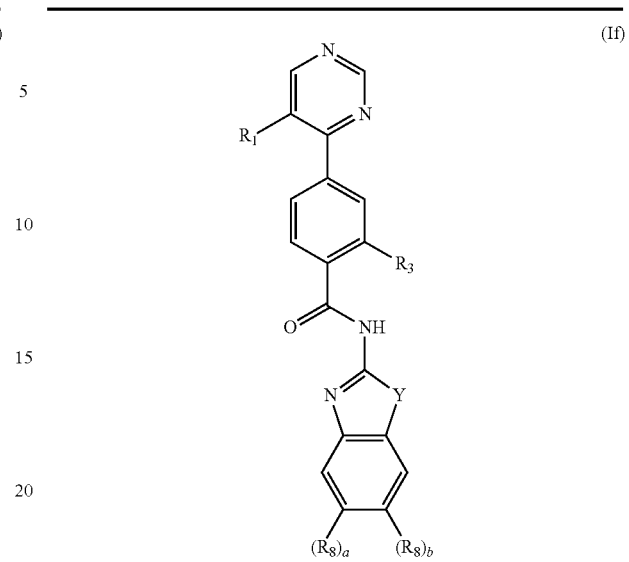

TABLE 7-continued (If)

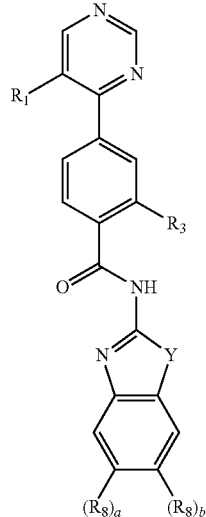

and pharmaceutically acceptable salts thereof, where:

| Compound | Y | R₁ | (R₈)ₐ | (R₈)ᵦ |
|---|---|---|---|---|
| G151 (a, b, c, d, e, and f) | O | —Cl | —H | —OCH₂CH₃ |
| G152 (a, b, c, d, e, and f) | O | —Cl | —H | —OCF₃ |
| G153 (a, b, c, d, e, and f) | O | —Cl | —H | -tert-butyl |
| G154 (a, b, c, d, e, and f) | O | —Cl | —H | -iso-propyl |
| G155 (a, b, c, d, e, and f) | O | —CH₃ | —Cl | —H |
| G156 (a, b, c, d, e, and f) | O | —CH₃ | —Br | —H |
| G157 (a, b, c, d, e, and f) | O | —CH₃ | —F | —H |
| G158 (a, b, c, d, e, and f) | O | —CH₃ | —CH₃ | —H |
| G159 (a, b, c, d, e, and f) | O | —CH₃ | —CF₃ | —H |
| G160 (a, b, c, d, e, and f) | O | —CH₃ | —OCH₃ | —H |
| G161 (a, b, c, d, e, and f) | O | —CH₃ | —OCH₂CH₃ | —H |
| G162 (a, b, c, d, e, and f) | O | —CH₃ | —OCF₃ | —H |
| G163 (a, b, c, d, e, and f) | O | —CH₃ | -tert-butyl | —H |
| G164 (a, b, c, d, e, and f) | O | —CH₃ | -iso-propyl | —H |
| G165 (a, b, c, d, e, and f) | O | —CH₃ | —CH₃ | —CH₃ |
| G166 (a, b, c, d, e, and f) | O | —CH₃ | —H | —H |
| G167 (a, b, c, d, e, and f) | O | —CH₃ | —H | —Cl |
| G168 (a, b, c, d, e, and f) | O | —CH₃ | —H | —Br |
| G169 (a, b, c, d, e, and f) | O | —CH₃ | —H | —F |
| G170 (a, b, c, d, e, and f) | O | —CH₃ | —H | —CH₃ |
| G171 (a, b, c, d, e, and f) | O | —CH₃ | —H | —CF₃ |
| G172 (a, b, c, d, e, and f) | O | —CH₃ | —H | —OCH₃ |
| G173 (a, b, c, d, e, and f) | O | —CH₃ | —H | —OCH₂CH₃ |
| G174 (a, b, c, d, e, and f) | O | —CH₃ | —H | —OCF₃ |
| G175 (a, b, c, d, e, and f) | O | —CH₃ | —H | -tert-butyl |
| G176 (a, b, c, d, e, and f) | O | —CH₃ | —H | -iso-propyl |
| G177 (a, b, c, d, e, and f) | O | —CF₃ | —Cl | —H |
| G178 (a, b, c, d, e, and f) | O | —CF₃ | —Br | —H |
| G179 (a, b, c, d, e, and f) | O | —CF₃ | —F | —H |
| G180 (a, b, c, d, e, and f) | O | —CF₃ | —CH₃ | —H |
| G181 (a, b, c, d, e, and f) | O | —CF₃ | —CF₃ | —H |
| G182 (a, b, c, d, e, and f) | O | —CF₃ | —OCH₃ | —H |
| G183 (a, b, c, d, e, and f) | O | —CF₃ | —OCH₂CH₃ | —H |
| G184 (a, b, c, d, e, and f) | O | —CF₃ | —OCF₃ | —H |
| G185 (a, b, c, d, e, and f) | O | —CF₃ | -tert-butyl | —H |
| G186 (a, b, c, d, e, and f) | O | —CF₃ | -iso-propyl | —H |
| G187 (a, b, c, d, e, and f) | O | —CF₃ | —CH₃ | —CH₃ |
| G188 (a, b, c, d, e, and f) | O | —CF₃ | —H | —H |
| G189 (a, b, c, d, e, and f) | O | —CF₃ | —H | —Cl |
| G190 (a, b, c, d, e, and f) | O | —CF₃ | —H | —Br |
| G191 (a, b, c, d, e, and f) | O | —CF₃ | —FT | —F |
| G192 (a, b, c, d, e, and f) | O | —CF₃ | —H | —CH₃ |
| G193 (a, b, c, d, e, and f) | O | —CF₃ | —H | —CF₃ |
| G194 (a, b, c, d, e, and f) | O | —CF₃ | —H | —OCH₃ |
| G195 (a, b, c, d, e, and f) | O | —CF₃ | —H | —OCH₂CH₃ |
| G196 (a, b, c, d, e, and f) | O | —CF₃ | —H | —OCF₃ |
| G197 (a, b, c, d, e, and f) | O | —CF₃ | —H | -tert-butyl |
| G198 (a, b, c, d, e, and f) | O | —CF₃ | —H | -iso-propyl |
| G199 (a, b, c, d, e, and f) | O | —CHF₂ | —Cl | —H |
| G200 (a, b, c, d, e, and f) | O | —CHF₂ | —Br | —H |
| G201 (a, b, c, d, e, and f) | O | —CHF₂ | —F | —H |
| G202 (a, b, c, d, e, and f) | O | —CHF₂ | —CH₃ | —H |
| G203 (a, b, c, d, e, and f) | O | —CHF₂ | —CF₃ | —H |
| G204 (a, b, c, d, e, and f) | O | —CHF₂ | —OCH₃ | —H |
| G205 (a, b, c, d, e, and f) | O | —CHF₂ | —OCH₂CH₃ | —H |
| G206 (a, b, c, d, e, and f) | O | —CHF₂ | —OCF₃ | —H |
| G207 (a, b, c, d, e, and f) | O | —CHF₂ | -tert-butyl | —H |
| G208 (a, b, c, d, e, and f) | O | —CHF₂ | -iso-propyl | —H |
| G209 (a, b, c, d, e, and f) | O | —CHF₂ | —CH₃ | —CH₃ |
| G210 (a, b, c, d, e, and f) | O | —CHF₂ | —H | —H |
| G211 (a, b, c, d, e, and f) | O | —CHF₂ | —H | —Cl |
| G212 (a, b, c, d, e, and f) | O | —CHF₂ | —H | —Br |
| G213 (a, b, c, d, e, and f) | O | —CHF₂ | —H | —F |
| G214 (a, b, c, d, e, and f) | O | —CHF₂ | —H | —CH₃ |
| G215 (a, b, c, d, e, and f) | O | —CHF₂ | —H | —CF₃ |
| G216 (a, b, c, d, e, and f) | O | —CHF₂ | —H | —OCH₃ |
| G217 (a, b, c, d, e, and f) | O | —CHF₂ | —H | —OCH₂CH₃ |
| G218 (a, b, c, d, e, and f) | O | —CHF₂ | —H | —OCF₃ |
| G219 (a, b, c, d, e, and f) | O | —CHF₂ | —H | -tert-butyl |
| G220 (a, b, c, d, e, and f) | O | —CHF₂ | —H | -iso-propyl |
| G221 (a, b, c, d, e, and f) | O | —Br | —Br | —H |
| G222 (a, b, c, d, e, and f) | O | —Br | —Cl | —H |
| G223 (a, b, c, d, e, and f) | O | —Br | —F | —H |
| G224 (a, b, c, d, e, and f) | O | —Br | —CH₃ | —H |
| G225 (a, b, c, d, e, and f) | O | —Br | —CF₃ | —H |
| G226 (a, b, c, d, e, and f) | O | —Br | —OCH₃ | —H |
| G227 (a, b, c, d, e, and f) | O | —Br | —OCH₂CH₃ | —H |
| G228 (a, b, c, d, e, and f) | O | —Br | —OCF₃ | —H |
| G229 (a, b, c, d, e, and f) | O | —Br | -tert-butyl | —H |
| G230 (a, b, c, d, e, and f) | O | —Br | -iso-propyl | —H |
| G231 (a, b, c, d, e, and f) | O | —Br | —CH₃ | —CH₃ |
| G232 (a, b, c, d, e, and f) | O | —Br | —H | —H |
| G233 (a, b, c, d, e, and f) | O | —Br | —H | —Cl |
| G234 (a, b, c, d, e, and f) | O | —Br | —H | —Br |
| G235 (a, b, c, d, e, and f) | O | —Br | —H | —F |
| G236 (a, b, c, d, e, and f) | O | —Br | —H | —CH₃ |
| G237 (a, b, c, d, e, and f) | O | —Br | —H | —CF₃ |
| G238 (a, b, c, d, e, and f) | O | —Br | —H | —OCH₃ |
| G239 (a, b, c, d, e, and f) | O | —Br | —H | —OCH₂CH₃ |
| G240 (a, b, c, d, e, and f) | O | —Br | —H | —OCF₃ |
| G241 (a, b, c, d, e, and f) | O | —Br | —H | -tert-butyl |
| G242 (a, b, c, d, e, and f) | O | —Br | —H | -iso-propyl |
| G243 (a, b, c, d, e, and f) | O | —I | —Cl | —H |
| G244 (a, b, c, d, e, and f) | O | —I | —Br | —H |
| G245 (a, b, c, d, e, and f) | O | —I | —F | —H |
| G246 (a, b, c, d, e, and f) | O | —I | —CH₃ | —H |
| G247 (a, b, c, d, e, and f) | O | —I | —CF₃ | —H |
| G248 (a, b, c, d, e, and f) | O | —I | —OCH₃ | —H |
| G249 (a, b, c, d, e, and f) | O | —I | —OCH₂CH₃ | —H |
| G250 (a, b, c, d, e, and f) | O | —I | —OCF₃ | —H |

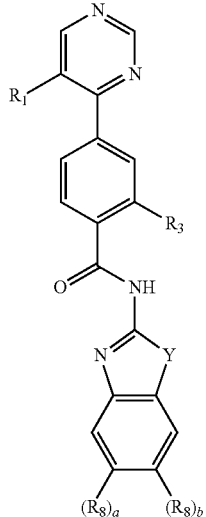

TABLE 7-continued

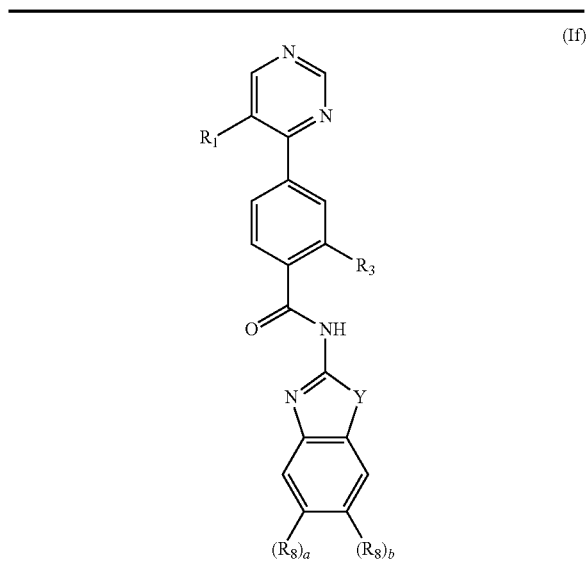

(If)

and pharmaceutically acceptable salts thereof, where:

| Compound | Y | R₁ | (R₈)ₐ | (R₈)ᵦ |
|---|---|---|---|---|
| G251 (a, b, c, d, e, and f) | O | —I | -tert-butyl | —H |
| G252 (a, b, c, d, e, and f) | O | —I | -iso-propyl | —H |
| G253 (a, b, c, d, e, and f) | O | —I | —CH₃ | —CH₃ |
| G254 (a, b, c, d, e, and f) | O | —I | —H | —H |
| G255 (a, b, c, d, e, and f) | O | —I | —H | —Cl |
| G256 (a, b, c, d, e, and f) | O | —I | —H | —Br |
| G257 (a, b, c, d, e, and f) | O | —I | —H | —F |
| G258 (a, b, c, d, e, and f) | O | —I | —H | —CH₃ |
| G259 (a, b, c, d, e, and f) | O | —I | —H | —CF₃ |
| G260 (a, b, c, d, e, and f) | O | —I | —H | —OCH₃ |
| G261 (a, b, c, d, e, and f) | O | —I | —H | —OCH₂CH₃ |
| G262 (a, b, c, d, e, and f) | O | —I | —H | —OCF₃ |
| G263 (a, b, c, d, e, and f) | O | —I | —H | -tert-butyl |
| G264 (a, b, c, d, e, and f) | O | —I | —H | -iso-propyl |
| G265 (a, b, c, d, e, and f) | NH | —Cl | —Cl | —H |
| G266 (a, b, c, d, e, and f) | NH | —Cl | —Br | —H |
| G267 (a, b, c, d, e, and f) | NH | —Cl | —F | —H |
| G268 (a, b, c, d, e, and f) | NH | —Cl | —CH₃ | —H |
| G269 (a, b, c, d, e, and f) | NH | —Cl | —CF₃ | —H |
| G270 (a, b, c, d, e, and f) | NH | —Cl | —OCH₃ | —H |
| G271 (a, b, c, d, e, and f) | NH | —Cl | —OCH₂CH₃ | —H |
| G272 (a, b, c, d, e, and f) | NH | —Cl | —OCF₃ | —H |
| G273 (a, b, c, d, e, and f) | NH | —Cl | -tert-butyl | —H |
| G274 (a, b, c, d, e, and f) | NH | —Cl | -iso-propyl | —H |
| G275 (a, b, c, d, e, and f) | NH | —Cl | —CH₃ | —CH₃ |
| G276 (a, b, c, d, e, and f) | NH | —Cl | —H | —H |
| G277 (a, b, c, d, e, and f) | NH | —Cl | —H | —CH₃ |
| G278 (a, b, c, d, e, and f) | NH | —Cl | —H | —Cl |
| G279 (a, b, c, d, e, and f) | NH | —Cl | —H | —Br |
| G280 (a, b, c, d, e, and f) | NH | —Cl | —H | —F |
| G281 (a, b, c, d, e, and f) | NH | —Cl | —H | —CF₃ |
| G282 (a, b, c, d, e, and f) | NH | —Cl | —H | —OCH₃ |
| G283 (a, b, c, d, e, and f) | NH | —Cl | —H | —OCH₂CH₃ |
| G284 (a, b, c, d, e, and f) | NH | —Cl | —H | —OCF₃ |
| G285 (a, b, c, d, e, and f) | NH | —Cl | —H | -tert-butyl |
| G286 (a, b, c, d, e, and f) | NH | —Cl | —H | -iso-propyl |
| G287 (a, b, c, d, e, and f) | NH | —CH₃ | —Cl | —H |
| G288 (a, b, c, d, e, and f) | NH | —CH₃ | —Br | —H |
| G289 (a, b, c, d, e, and f) | NH | —CH₃ | —F | —H |
| G290 (a, b, c, d, e, and f) | NH | —CH₃ | —CH₃ | —H |
| G291 (a, b, c, d, e, and f) | NH | —CH₃ | —CF₃ | —H |
| G292 (a, b, c, d, e, and f) | NH | —CH₃ | —OCH₃ | —H |
| G293 (a, b, c, d, e, and f) | NH | —CH₃ | —OCH₂CH₃ | —H |
| G294 (a, b, c, d, e, and f) | NH | —CH₃ | —OCF₃ | —H |
| G295 (a, b, c, d, e, and f) | NH | —CH₃ | -tert-butyl | —H |
| G296 (a, b, c, d, e, and f) | NH | —CH₃ | -iso-propyl | —H |
| G297 (a, b, c, d, e, and f) | NH | —CH₃ | —CH₃ | —CH₃ |
| G298 (a, b, c, d, e, and f) | NH | —CH₃ | —H | —H |
| G299 (a, b, c, d, e, and f) | NH | —CH₃ | —H | —Cl |
| G300 (a, b, c, d, e, and f) | NH | —CH₃ | —H | —Br |

TABLE 7-continued

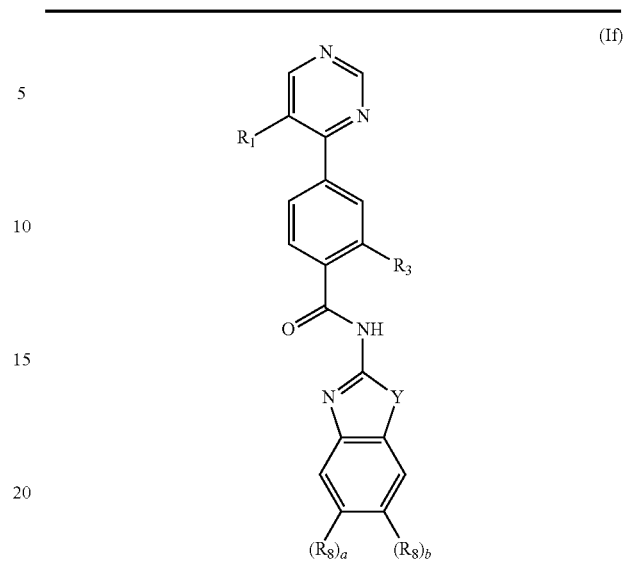

(If)

and pharmaceutically acceptable salts thereof, where:

| Compound | Y | R₁ | (R₈)ₐ | (R₈)ᵦ |
|---|---|---|---|---|
| G301 (a, b, c, d, e, and f) | NH | —CH₃ | —H | —F |
| G302 (a, b, c, d, e, and f) | NH | —CH₃ | —H | —CH₃ |
| G303 (a, b, c, d, e, and f) | NH | —CH₃ | —H | —CF₃ |
| G304 (a, b, c, d, e, and f) | NH | —CH₃ | —H | —OCH₃ |
| G305 (a, b, c, d, e, and f) | NH | —CH₃ | —H | —OCH₂CH₃ |
| G306 (a, b, c, d, e, and f) | NH | —CH₃ | —H | —OCF₃ |
| G307 (a, b, c, d, e, and f) | NH | —CH₃ | —H | -tert-butyl |
| G308 (a, b, c, d, e, and f) | NH | —CH₃ | —H | -iso-propyl |
| G309 (a, b, c, d, e, and f) | NH | —CF₃ | —Cl | —H |
| G310 (a, b, c, d, e, and f) | NH | —CF₃ | —Br | —H |
| G311 (a, b, c, d, e, and f) | NH | —CF₃ | —F | —H |
| G312 (a, b, c, d, e, and f) | NH | —CF₃ | —CH₃ | —H |
| G313 (a, b, c, d, e, and f) | NH | —CF₃ | —CF₃ | —H |
| G314 (a, b, c, d, e, and f) | NH | —CF₃ | —OCH₃ | —H |
| G315 (a, b, c, d, e, and f) | NH | —CF₃ | —OCH₂CH₃ | —H |
| G316 (a, b, c, d, e, and f) | NH | —CF₃ | —OCF₃ | —H |
| G317 (a, b, c, d, e, and f) | NH | —CF₃ | -tert-butyl | —H |
| G318 (a, b, c, d, e, and f) | NH | —CF₃ | -iso-propyl | —H |
| G319 (a, b, c, d, e, and f) | NH | —CF₃ | —CH₃ | —CH₃ |
| G320 (a, b, c, d, e, and f) | NH | —CF₃ | —H | —H |
| G321 (a, b, c, d, e, and f) | NH | —CF₃ | —H | —Cl |
| G322 (a, b, c, d, e, and f) | NH | —CF₃ | —H | —Br |
| G323 (a, b, c, d, e, and f) | NH | —CF₃ | —H | —F |
| G324 (a, b, c, d, e, and f) | NH | —CF₃ | —H | —CH₃ |
| G325 (a, b, c, d, e, and f) | NH | —CF₃ | —H | —CF₃ |
| G326 (a, b, c, d, e, and f) | NH | —CF₃ | —H | —OCH₃ |
| G327 (a, b, c, d, e, and f) | NH | —CF₃ | —H | —OCH₂CH₃ |
| G328 (a, b, c, d, e, and f) | NH | —CF₃ | —H | —OCF₃ |
| G329 (a, b, c, d, e, and f) | NH | —CF₃ | —H | -tert-butyl |
| G330 (a, b, c, d, e, and f) | NH | —CF₃ | —H | -iso-propyl |
| G331 (a, b, c, d, e, and f) | NH | —CHF₂ | —Cl | —H |
| G332 (a, b, c, d, e, and f) | NH | —CHF₂ | —Br | —H |
| G333 (a, b, c, d, e, and f) | NH | —CHF₂ | —F | —H |
| G334 (a, b, c, d, e, and f) | NH | —CHF₂ | —CH₃ | —H |
| G335 (a, b, c, d, e, and f) | NH | —CHF₂ | —CF₃ | —H |
| G336 (a, b, c, d, e, and f) | NH | —CHF₂ | —OCH₃ | —H |
| G337 (a, b, c, d, e, and f) | NH | —CHF₂ | —OCH₂CH₃ | —H |
| G338 (a, b, c, d, e, and f) | NH | —CHF₂ | —OCF₃ | —H |
| G339 (a, b, c, d, e, and f) | NH | —CHF₂ | -tert-butyl | —H |
| G340 (a, b, c, d, e, and f) | NH | —CHF₂ | -iso-propyl | —H |
| G341 (a, b, c, d, e, and f) | NH | —CHF₂ | —CH₃ | —CH₃ |
| G342 (a, b, c, d, e, and f) | NH | —CHF₂ | —H | —H |
| G343 (a, b, c, d, e, and f) | NH | —CHF₂ | —H | —Cl |
| G344 (a, b, c, d, e, and f) | NH | —CHF₂ | —H | —Br |
| G345 (a, b, c, d, e, and f) | NH | —CHF₂ | —H | —F |
| G346 (a, b, c, d, e, and f) | NH | —CHF₂ | —H | —CH₃ |
| G347 (a, b, c, d, e, and f) | NH | —CHF₂ | —H | —CF₃ |
| G348 (a, b, c, d, e, and f) | NH | —CHF₂ | —H | —OCH₃ |
| G349 (a, b, c, d, e, and f) | NH | —CHF₂ | —H | —OCH₂CH₃ |
| G350 (a, b, c, d, e, and f) | NH | —CHF₂ | —H | —OCF₃ |

TABLE 7-continued

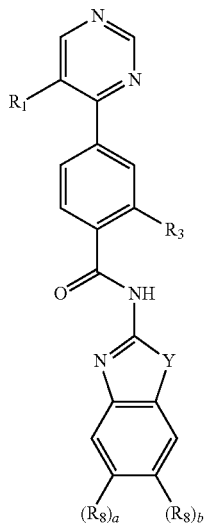

(If)

and pharmaceutically acceptable salts thereof, where:

| Compound | Y | $R_1$ | $(R_8)_a$ | $(R_8)_b$ |
|---|---|---|---|---|
| G351 (a, b, c, d, e, and f) | NH | —CHF$_2$ | —H | -tert-butyl |
| G352 (a, b, c, d, e, and f) | NH | —CHF$_2$ | —H | -iso-propyl |
| G353 (a, b, c, d, e, and f) | NH | —Br | —Br | —H |
| G354 (a, b, c, d, e, and f) | NH | —Br | —Cl | —H |
| G355 (a, b, c, d, e, and f) | NH | —Br | —F | —H |
| G356 (a, b, c, d, e, and f) | NH | —Br | —CH$_3$ | —H |
| G357 (a, b, c, d, e, and f) | NH | —Br | —CF$_3$ | —H |
| G358 (a, b, c, d, e, and f) | NH | —Br | —OCH$_3$ | —H |
| G359 (a, b, c, d, e, and f) | NH | —Br | —OCH$_2$CH$_3$ | —H |
| G360 (a, b, c, d, e, and f) | NH | —Br | —OCF$_3$ | —H |
| G361 (a, b, c, d, e, and f) | NH | —Br | -tert-butyl | —H |
| G362 (a, b, c, d, e, and f) | NH | —Br | -iso-propyl | —H |
| G363 (a, b, c, d, e, and f) | NH | —Br | —CH$_3$ | —CH$_3$ |
| G364 (a, b, c, d, e, and f) | NH | —Br | —H | —H |
| G365 (a, b, c, d, e, and f) | NH | —Br | —H | —Cl |
| G366 (a, b, c, d, e, and f) | NH | —Br | —H | —Br |
| G367 (a, b, c, d, e, and f) | NH | —Br | —H | —F |
| G368 (a, b, c, d, e, and f) | NH | —Br | —H | —CH$_3$ |
| G369 (a, b, c, d, e, and f) | NH | —Br | —H | —CF$_3$ |
| G370 (a, b, c, d, e, and f) | NH | —Br | —H | —OCH$_3$ |
| G371 (a, b, c, d, e, and f) | NH | —Br | —H | —OCH$_2$CH$_3$ |
| G372 (a, b, c, d, e, and f) | NH | —Br | —H | —OCF$_3$ |
| G373 (a, b, c, d, e, and f) | NH | —Br | —H | -tert-butyl |
| G374 (a, b, c, d, e, and f) | NH | —Br | —H | -iso-propyl |
| G375 (a, b, c, d, e, and f) | NH | —I | —Cl | —H |
| G376 (a, b, c, d, e, and f) | NH | —I | —Br | —H |
| G377 (a, b, c, d, e, and f) | NH | —I | —F | —H |
| G378 (a, b, c, d, e, and f) | NH | —I | —CH$_3$ | —H |
| G379 (a, b, c, d, e, and f) | NH | —I | —CF$_3$ | —H |
| G380 (a, b, c, d, e, and f) | NH | —I | —OCH$_3$ | —H |
| G381 (a, b, c, d, e, and f) | NH | —I | —OCH$_2$CH$_3$ | —H |
| G382 (a, b, c, d, e, and f) | NH | —I | —OCF$_3$ | —H |
| G383 (a, b, c, d, e, and f) | NH | —I | -tert-butyl | —H |
| G384 (a, b, c, d, e, and f) | NH | —I | -iso-propyl | —H |
| G385 (a, b, c, d, e, and f) | NH | —I | —CH$_3$ | —CH$_3$ |
| G386 (a, b, c, d, e, and f) | NH | —I | —H | —H |
| G387 (a, b, c, d, e, and f) | NH | —I | —H | —Cl |
| G388 (a, b, c, d, e, and f) | NH | —I | —H | —Br |
| G389 (a, b, c, d, e, and f) | NH | —I | —H | —F |
| G390 (a, b, c, d, e, and f) | NH | —I | —H | —CH$_3$ |
| G391 (a, b, c, d, e, and f) | NH | —I | —H | —CF$_3$ |
| G392 (a, b, c, d, e, and f) | NH | —I | —H | —OCH$_3$ |
| G393 (a, b, c, d, e, and f) | NH | —I | —H | —OCH$_2$CH$_3$ |
| G394 (a, b, c, d, e, and f) | NH | —I | —H | —OCF$_3$ |

TABLE 7-continued

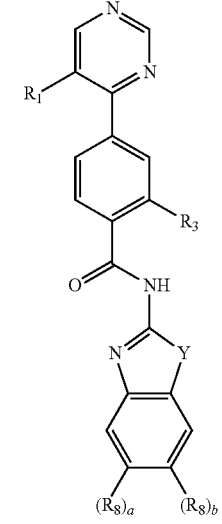

(If)

and pharmaceutically acceptable salts thereof, where:

| Compound | Y | $R_1$ | $(R_8)_a$ | $(R_8)_b$ |
|---|---|---|---|---|
| G395 (a, b, c, d, e, and f) | NH | —I | —H | -tert-butyl |
| G396 (a, b, c, d, e, and f) | NH | —I | —H | -iso-propyl |

In the column labeled "Compound":
(a) means that $R_3$ is —CH$_3$;
(b) means that $R_3$ is —Cl;
(c) means that $R_3$ is —Br;
(d) means that $R_3$ is —I;
(e) means that $R_3$ is —F; and
(f) means that $R_3$ is —H, i.e., in formula (I) m = 0.

TABLE 8

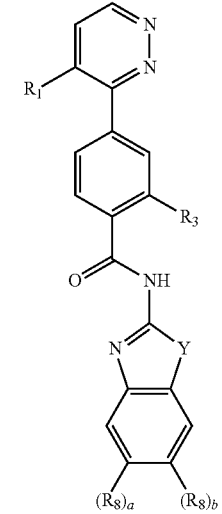

(Ig)

and pharmaceutically acceptable salts thereof, where:

| Compound | Y | $R_1$ | $(R_8)_a$ | $(R_8)_b$ |
|---|---|---|---|---|
| H1 (a, b, c, d, e, and f) | S | —Cl | —Cl | —H |
| H2 (a, b, c, d, e, and f) | S | —Cl | —Br | —H |
| H3 (a, b, c, d, e, and f) | S | —Cl | —F | —H |
| H4 (a, b, c, d, e, and f) | S | —Cl | —CH$_3$ | —H |
| H5 (a, b, c, d, e, and f) | S | —Cl | —CF$_3$ | —H |
| H6 (a, b, c, d, e, and f) | S | —Cl | —OCH$_3$ | —H |
| H7 (a, b, c, d, e, and f) | S | —Cl | —OCH$_2$CH$_3$ | —H |

TABLE 8-continued (Ig)

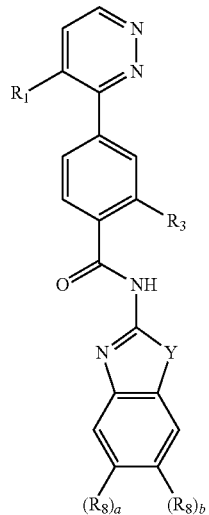

and pharmaceutically acceptable salts thereof, where:

| Compound | Y | R₁ | (R₈)ₐ | (R₈)ᵦ |
|---|---|---|---|---|
| H8 (a, b, c, d, e, and f) | S | —Cl | —OCF₃ | —H |
| H9 (a, b, c, d, e, and f) | S | —Cl | -tert-butyl | —H |
| H10 (a, b, c, d, e, and f) | S | —Cl | -iso-propyl | —H |
| H11 (a, b, c, d, e, and f) | S | —Cl | —CH₃ | —CH₃ |
| H12 (a, b, c, d, e, and f) | S | —Cl | —H | —H |
| H13 (a, b, c, d, e, and f) | S | —Cl | —H | —Cl |
| H14 (a, b, c, d, e, and f) | S | —Cl | —H | —Br |
| H15 (a, b, c, d, e, and f) | S | —Cl | —H | —F |
| H16 (a, b, c, d, e, and f) | S | —Cl | —H | —CH₃ |
| H17 (a, b, c, d, e, and f) | S | —Cl | —H | —CF₃ |
| H18 (a, b, c, d, e, and f) | S | —Cl | —H | —OCH₃ |
| H19 (a, b, c, d, e, and f) | S | —Cl | —H | —OCH₂CH₃ |
| H20 (a, b, c, d, e, and f) | S | —Cl | —H | —OCF₃ |
| H21 (a, b, c, d, e, and f) | S | —Cl | —H | -tert-butyl |
| H22 (a, b, c, d, e, and f) | S | —Cl | —H | -iso-propyl |
| H23 (a, b, c, d, e, and f) | S | —CH₃ | —Cl | —H |
| H24 (a, b, c, d, e, and f) | S | —CH₃ | —Br | —H |
| H25 (a, b, c, d, e, and f) | S | —CH₃ | —F | —H |
| H26 (a, b, c, d, e, and f) | S | —CH₃ | —CH₃ | —H |
| H27 (a, b, c, d, e, and f) | S | —CH₃ | —CF₃ | —H |
| H28 (a, b, c, d, e, and f) | S | —CH₃ | —OCH₃ | —H |
| H29 (a, b, c, d, e, and f) | S | —CH₃ | —OCH₂CH₃ | —H |
| H30 (a, b, c, d, e, and f) | S | —CH₃ | —OCF₃ | —H |
| H31 (a, b, c, d, e, and f) | S | —CH₃ | -tert-butyl | —H |
| H32 (a, b, c, d, e, and f) | S | —CH₃ | -iso-propyl | —H |
| H33 (a, b, c, d, e, and f) | S | —CH₃ | —CH₃ | —CH₃ |
| H34 (a, b, c, d, e, and f) | S | —CH₃ | —H | —H |
| H35 (a, b, c, d, e, and f) | S | —CH₃ | —H | —Cl |
| H36 (a, b, c, d, e, and f) | S | —CH₃ | —H | —Br |
| H37 (a, b, c, d, e, and f) | S | —CH₃ | —H | —F |
| H38 (a, b, c, d, e, and f) | S | —CH₃ | —H | —CH₃ |
| H39 (a, b, c, d, e, and f) | S | —CH₃ | —H | —CF₃ |
| H40 (a, b, c, d, e, and f) | S | —CH₃ | —H | —OCH₃ |
| H41 (a, b, c, d, e, and f) | S | —CH₃ | —H | —OCH₂CH₃ |
| H42 (a, b, c, d, e, and f) | S | —CH₃ | —H | —OCF₃ |
| H43 (a, b, c, d, e, and f) | S | —CH₃ | —H | -tert-butyl |
| H44 (a, b, c, d, e, and f) | S | —CH₃ | —H | -iso-propyl |
| H45 (a, b, c, d, e, and f) | S | —CF₃ | —Cl | —H |
| H46 (a, b, c, d, e, and f) | S | —CF₃ | —Br | —H |
| H47 (a, b, c, d, e, and f) | S | —CF₃ | —F | —H |
| H48 (a, b, c, d, e, and f) | S | —CF₃ | —CH₃ | —H |
| H49 (a, b, c, d, e, and f) | S | —CF₃ | —CF₃ | —H |
| H50 (a, b, c, d, e, and f) | S | —CF₃ | —OCH₃ | —H |
| H51 (a, b, c, d, e, and f) | S | —CF₃ | —OCH₂CH₃ | —H |
| H52 (a, b, c, d, e, and f) | S | —CF₃ | —OCF₃ | —H |
| H53 (a, b, c, d, e, and f) | S | —CF₃ | -tert-butyl | —H |
| H54 (a, b, c, d, e, and f) | S | —CF₃ | -iso-propyl | —H |
| H55 (a, b, c, d, e, and f) | S | —CF₃ | —CH₃ | —CH₃ |
| H56 (a, b, c, d, e, and f) | S | —CF₃ | —H | —H |
| H57 (a, b, c, d, e, and f) | S | —CF₃ | —H | —Cl |
| H58 (a, b, c, d, e, and f) | S | —CF₃ | —H | —Br |
| H59 (a, b, c, d, e, and f) | S | —CF₃ | —H | —F |
| H60 (a, b, c, d, e, and f) | S | —CF₃ | —H | —CH₃ |
| H61 (a, b, c, d, e, and f) | S | —CF₃ | —H | —CF₃ |
| H62 (a, b, c, d, e, and f) | S | —CF₃ | —H | —OCH₃ |
| H63 (a, b, c, d, e, and f) | S | —CF₃ | —H | —OCH₂CH₃ |
| H64 (a, b, c, d, e, and f) | S | —CF₃ | —H | —OCF₃ |
| H65 (a, b, c, d, e, and f) | S | —CF₃ | —H | -tert-butyl |
| H66 (a, b, c, d, e, and f) | S | —CF₃ | —H | -iso-propyl |
| H67 (a, b, c, d, e, and f) | S | —CHF₂ | —Cl | —H |
| H68 (a, b, c, d, e, and f) | S | —CHF₂ | —Br | —H |
| H69 (a, b, c, d, e, and f) | S | —CHF₂ | —F | —H |
| H70 (a, b, c, d, e, and f) | S | —CHF₂ | —CH₃ | —H |
| H71 (a, b, c, d, e, and f) | S | —CHF₂ | —CF₃ | —H |
| H72 (a, b, c, d, e, and f) | S | —CHF₂ | —OCH₃ | —H |
| H73 (a, b, c, d, e, and f) | S | —CHF₂ | —OCH₂CH₃ | —H |
| H74 (a, b, c, d, e, and f) | S | —CHF₂ | —OCF₃ | —H |
| H75 (a, b, c, d, e, and f) | S | —CHF₂ | -tert-butyl | —H |
| H76 (a, b, c, d, e, and f) | S | —CHF₂ | -iso-propyl | —H |
| H77 (a, b, c, d, e, and f) | S | —CHF₂ | —CH₃ | —CH₃ |
| H78 (a, b, c, d, e, and f) | S | —CHF₂ | —H | —H |
| H79 (a, b, c, d, e, and f) | S | —CHF₂ | —H | —Cl |
| H80 (a, b, c, d, e, and f) | S | —CHF₂ | —H | —Br |
| H81 (a, b, c, d, e, and f) | S | —CHF₂ | —H | —F |
| H82 (a, b, c, d, e, and f) | S | —CHF₂ | —H | —CH₃ |
| H83 (a, b, c, d, e, and f) | S | —CHF₂ | —H | —CF₃ |
| H84 (a, b, c, d, e, and f) | S | —CHF₂ | —H | —OCH₃ |
| H85 (a, b, c, d, e, and f) | S | —CHF₂ | —H | —OCH₂CH₃ |
| H86 (a, b, c, d, e, and f) | S | —CHF₂ | —H | —OCF₃ |
| H87 (a, b, c, d, e, and f) | S | —CHF₂ | —H | -tert-butyl |
| H88 (a, b, c, d, e, and f) | S | —CHF₂ | —H | -iso-propyl |
| H89 (a, b, c, d, e, and f) | S | —Br | —Br | —H |
| H90 (a, b, c, d, e, and f) | S | —Br | —Cl | —H |
| H91 (a, b, c, d, e, and f) | S | —Br | —F | —H |
| H92 (a, b, c, d, e, and f) | S | —Br | —CH₃ | —H |
| H93 (a, b, c, d, e, and f) | S | —Br | —CF₃ | —H |
| H94 (a, b, c, d, e, and f) | S | —Br | —OCH₃ | —H |
| H95 (a, b, c, d, e, and f) | S | —Br | —OCH₂CH₃ | —H |
| H96 (a, b, c, d, e, and f) | S | —Br | —OCF₃ | —H |
| H97 (a, b, c, d, e, and f) | S | —Br | -tert-butyl | —H |
| H98 (a, b, c, d, e, and f) | S | —Br | -iso-propyl | —H |
| H99 (a, b, c, d, e, and f) | S | —Br | —CH₃ | —CH₃ |
| H100 (a, b, c, d, e, and f) | S | —Br | —H | —H |
| H101 (a, b, c, d, e, and f) | S | —Br | —H | —Cl |
| H102 (a, b, c, d, e, and f) | S | —Br | —H | —Br |
| H103 (a, b, c, d, e, and f) | S | —Br | —H | —F |
| H104 (a, b, c, d, e, and f) | S | —Br | —H | —CH₃ |
| H105 (a, b, c, d, e, and f) | S | —Br | —H | —CF₃ |
| H106 (a, b, c, d, e, and f) | S | —Br | —H | —OCH₃ |
| H107 (a, b, c, d, e, and f) | S | —Br | —H | —OCH₂CH₃ |

TABLE 8-continued (Ig)

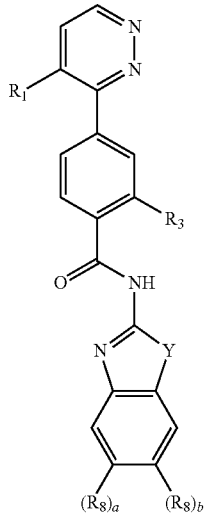

and pharmaceutically acceptable salts thereof, where:

| Compound | Y | R₁ | (R₈)ₐ | (R₈)ᵦ |
|---|---|---|---|---|
| H108 (a, b, c, d, e, and f) | S | —Br | —H | —OCF₃ |
| H109 (a, b, c, d, e, and f) | S | —Br | —H | -tert-butyl |
| H110 (a, b, c, d, e, and f) | S | —Br | —H | -iso-propyl |
| H111 (a, b, c, d, e, and f) | S | —I | —Cl | —H |
| H112 (a, b, c, d, e, and f) | S | —I | —Br | —H |
| H113 (a, b, c, d, e, and f) | S | —I | —F | —H |
| H114 (a, b, c, d, e, and f) | S | —I | —CH₃ | —H |
| H115 (a, b, c, d, e, and f) | S | —I | —CF₃ | —H |
| H116 (a, b, c, d, e, and f) | S | —I | —OCH₃ | —H |
| H117 (a, b, c, d, e, and f) | S | —I | —OCH₂CH₃ | —H |
| H118 (a, b, c, d, e, and f) | S | —I | —OCF₃ | —H |
| H119 (a, b, c, d, e, and f) | S | —I | -tert-butyl | —H |
| H120 (a, b, c, d, e, and f) | S | —I | -iso-propyl | —H |
| H121 (a, b, c, d, e, and f) | S | —I | —CH₃ | —CH₃ |
| H122 (a, b, c, d, e, and f) | S | —I | —H | —H |
| H123 (a, b, c, d, e, and f) | S | —I | —H | —Cl |
| H124 (a, b, c, d, e, and f) | S | —I | —H | —Br |
| H125 (a, b, c, d, e, and f) | S | —I | —H | —F |
| H126 (a, b, c, d, e, and f) | S | —I | —H | —CH₃ |
| H127 (a, b, c, d, e, and f) | S | —I | —H | —CF₃ |
| H128 (a, b, c, d, e, and f) | S | —I | —H | —OCH₃ |
| H129 (a, b, c, d, e, and f) | S | —I | —H | —OCH₂CH₃ |
| H130 (a, b, c, d, e, and f) | S | —I | —H | —OCF₃ |
| H131 (a, b, c, d, e, and f) | S | —I | —H | -tert-butyl |
| H132 (a, b, c, d, e, and f) | S | —I | —H | -iso-propyl |
| H133 (a, b, c, d, e, and f) | O | —Cl | —Cl | —H |
| H134 (a, b, c, d, e, and f) | O | —Cl | —Br | —H |
| H135 (a, b, c, d, e, and f) | O | —Cl | —F | —H |
| H136 (a, b, c, d, e, and f) | O | —Cl | —CH₃ | —H |
| H137 (a, b, c, d, e, and f) | O | —Cl | —CF₃ | —H |
| H138 (a, b, c, d, e, and f) | O | —Cl | —OCH₃ | —H |
| H139 (a, b, c, d, e, and f) | O | —Cl | —OCH₂CH₃ | —H |
| H140 (a, b, c, d, e, and f) | O | —Cl | —OCF₃ | —H |
| H141 (a, b, c, d, e, and f) | O | —Cl | -tert-butyl | —H |
| H142 (a, b, c, d, e, and f) | O | —Cl | -iso-propyl | —H |
| H143 (a, b, c, d, e, and f) | O | —Cl | —CH₃ | —CH₃ |
| H144 (a, b, c, d, e, and f) | O | —Cl | —H | —H |
| H145 (a, b, c, d, e, and f) | O | —Cl | —H | —CH₃ |
| H146 (a, b, c, d, e, and f) | O | —Cl | —H | —Cl |
| H147 (a, b, c, d, e, and f) | O | —Cl | —H | —Br |
| H148 (a, b, c, d, e, and f) | O | —Cl | —H | —F |
| H149 (a, b, c, d, e, and f) | O | —Cl | —H | —CF₃ |
| H150 (a, b, c, d, e, and f) | O | —Cl | —H | —OCH₃ |
| H151 (a, b, c, d, e, and f) | O | —Cl | —H | —OCH₂CH₃ |
| H152 (a, b, c, d, e, and f) | O | —Cl | —H | —OCF₃ |
| H153 (a, b, c, d, e, and f) | O | —Cl | —H | -tert-butyl |
| H154 (a, b, c, d, e, and f) | O | —Cl | —H | -iso-propyl |
| H155 (a, b, c, d, e, and f) | O | —CH₃ | —Cl | —H |
| H156 (a, b, c, d, e, and f) | O | —CH₃ | —Br | —H |
| H157 (a, b, c, d, e, and f) | O | —CH₃ | —F | —H |
| H158 (a, b, c, d, e, and f) | O | —CH₃ | —CH₃ | —H |
| H159 (a, b, c, d, e, and f) | O | —CH₃ | —CF₃ | —H |
| H160 (a, b, c, d, e, and f) | O | —CH₃ | —OCH₃ | —H |
| H161 (a, b, c, d, e, and f) | O | —CH₃ | —OCH₂CH₃ | —H |
| H162 (a, b, c, d, e, and f) | O | —CH₃ | —OCF₃ | —H |
| H163 (a, b, c, d, e, and f) | O | —CH₃ | -tert-butyl | —H |
| H164 (a, b, c, d, e, and f) | O | —CH₃ | -iso-propyl | —H |
| H165 (a, b, c, d, e, and f) | O | —CH₃ | —CH₃ | —CH₃ |
| H166 (a, b, c, d, e, and f) | O | —CH₃ | —H | —H |
| H167 (a, b, c, d, e, and f) | O | —CH₃ | —H | —Cl |
| H168 (a, b, c, d, e, and f) | O | —CH₃ | —H | —Br |
| H169 (a, b, c, d, e, and f) | O | —CH₃ | —H | —F |
| H170 (a, b, c, d, e, and f) | O | —CH₃ | —H | —CH₃ |
| H171 (a, b, c, d, e, and f) | O | —CH₃ | —H | —CF₃ |
| H172 (a, b, c, d, e, and f) | O | —CH₃ | —H | —OCH₃ |
| H173 (a, b, c, d, e, and f) | O | —CH₃ | —H | —OCH₂CH₃ |
| H174 (a, b, c, d, e, and f) | O | —CH₃ | —H | —OCF₃ |
| H175 (a, b, c, d, e, and f) | O | —CH₃ | —H | -tert-butyl |
| H176 (a, b, c, d, e, and f) | O | —CH₃ | —H | -iso-propyl |
| H177 (a, b, c, d, e, and f) | O | —CF₃ | —Cl | —H |
| H178 (a, b, c, d, e, and f) | O | —CF₃ | —Br | —H |
| H179 (a, b, c, d, e, and f) | O | —CF₃ | —F | —H |
| H180 (a, b, c, d, e, and f) | O | —CF₃ | —CH₃ | —H |
| H181 (a, b, c, d, e, and f) | O | —CF₃ | —CF₃ | —H |
| H182 (a, b, c, d, e, and f) | O | —CF₃ | —OCH₃ | —H |
| H183 (a, b, c, d, e, and f) | O | —CF₃ | —OCH₂CH₃ | —H |
| H184 (a, b, c, d, e, and f) | O | —CF₃ | —OCF₃ | —H |
| H185 (a, b, c, d, e, and f) | O | —CF₃ | -tert-butyl | —H |
| H186 (a, b, c, d, e, and f) | O | —CF₃ | -iso-propyl | —H |
| H187 (a, b, c, d, e, and f) | O | —CF₃ | —CH₃ | —CH₃ |
| H188 (a, b, c, d, e, and f) | O | —CF₃ | —H | —H |
| H189 (a, b, c, d, e, and f) | O | —CF₃ | —H | —Cl |
| H190 (a, b, c, d, e, and f) | O | —CF₃ | —H | —Br |
| H191 (a, b, c, d, e, and f) | O | —CF₃ | —H | —F |
| H192 (a, b, c, d, e, and f) | O | —CF₃ | —H | —CH₃ |
| H193 (a, b, c, d, e, and f) | O | —CF₃ | —H | —CF₃ |
| H194 (a, b, c, d, e, and f) | O | —CF₃ | —H | —OCH₃ |
| H195 (a, b, c, d, e, and f) | O | —CF₃ | —H | —OCH₂CH₃ |
| H196 (a, b, c, d, e, and f) | O | —CF₃ | —H | —OCF₃ |
| H197 (a, b, c, d, e, and f) | O | —CF₃ | —H | -tert-butyl |
| H198 (a, b, c, d, e, and f) | O | —CF₃ | —H | -iso-propyl |
| H199 (a, b, c, d, e, and f) | O | —CHF₂ | —Cl | —H |
| H200 (a, b, c, d, e, and f) | O | —CHF₂ | —Br | —H |
| H201 (a, b, c, d, e, and f) | O | —CHF₂ | —F | —H |
| H202 (a, b, c, d, e, and f) | O | —CHF₂ | —CH₃ | —H |
| H203 (a, b, c, d, e, and f) | O | —CHF₂ | —CF₃ | —H |
| H204 (a, b, c, d, e, and f) | O | —CHF₂ | —OCH₃ | —H |
| H205 (a, b, c, d, e, and f) | O | —CHF₂ | —OCH₂CH₃ | —H |
| H206 (a, b, c, d, e, and f) | O | —CHF₂ | —OCF₃ | —H |
| H207 (a, b, c, d, e, and f) | O | —CHF₂ | -tert-butyl | —H |

TABLE 8-continued

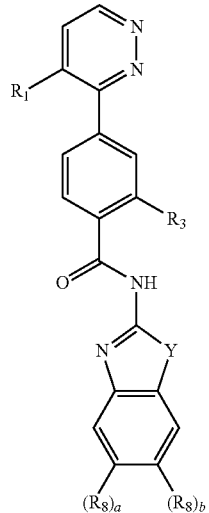

(Ig)

and pharmaceutically acceptable salts thereof, where:

| Compound | Y | R₁ | (R₈)ₐ | (R₈)ᵦ |
|---|---|---|---|---|
| H208 (a, b, c, d, e, and f) | O | —CHF₂ | -iso-propyl | —H |
| H209 (a, b, c, d, e, and f) | O | —CHF₂ | —CH₃ | —CH₃ |
| H210 (a, b, c, d, e, and f) | O | —CHF₂ | —H | —H |
| H211 (a, b, c, d, e, and f) | O | —CHF₂ | —H | —Cl |
| H212 (a, b, c, d, e, and f) | O | —CHF₂ | —H | —Br |
| H213 (a, b, c, d, e, and f) | O | —CHF₂ | —H | —F |
| H214 (a, b, c, d, e, and f) | O | —CHF₂ | —H | —CH₃ |
| H215 (a, b, c, d, e, and f) | O | —CHF₂ | —H | —CF₃ |
| H216 (a, b, c, d, e, and f) | O | —CHF₂ | —H | —OCH₃ |
| H217 (a, b, c, d, e, and f) | O | —CHF₂ | —H | —OCH₂CH₃ |
| H218 (a, b, c, d, e, and f) | O | —CHF₂ | —H | —OCF₃ |
| H219 (a, b, c, d, e, and f) | O | —CHF₂ | —H | -tert-butyl |
| H220 (a, b, c, d, e, and f) | O | —CHF₂ | —H | -iso-propyl |
| H221 (a, b, c, d, e, and f) | O | —Br | —Br | —H |
| H222 (a, b, c, d, e, and f) | O | —Br | —Cl | —H |
| H223 (a, b, c, d, e, and f) | O | —Br | —F | —H |
| H224 (a, b, c, d, e, and f) | O | —Br | —CH₃ | —H |
| H225 (a, b, c, d, e, and f) | O | —Br | —CF₃ | —H |
| H226 (a, b, c, d, e, and f) | O | —Br | —OCH₃ | —H |
| H227 (a, b, c, d, e, and f) | O | —Br | —OCH₂CH₃ | —H |
| H228 (a, b, c, d, e, and f) | O | —Br | —OCF₃ | —H |
| H229 (a, b, c, d, e, and f) | O | —Br | -tert-butyl | —H |
| H230 (a, b, c, d, e, and f) | O | —Br | -iso-propyl | —H |
| H231 (a, b, c, d, e, and f) | O | —Br | —CH₃ | —CH₃ |
| H232 (a, b, c, d, e, and f) | O | —Br | —H | —H |
| H233 (a, b, c, d, e, and f) | O | —Br | —H | —Cl |
| H234 (a, b, c, d, e, and f) | O | —Br | —H | —Br |
| H235 (a, b, c, d, e, and f) | O | —Br | —H | —F |
| H236 (a, b, c, d, e, and f) | O | —Br | —H | —CH₃ |
| H237 (a, b, c, d, e, and f) | O | —Br | —H | —CF₃ |
| H238 (a, b, c, d, e, and f) | O | —Br | —H | —OCH₃ |
| H239 (a, b, c, d, e, and f) | O | —Br | —H | —OCH₂CH₃ |
| H240 (a, b, c, d, e, and f) | O | —Br | —H | —OCF₃ |
| H241 (a, b, c, d, e, and f) | O | —Br | —H | -tert-butyl |
| H242 (a, b, c, d, e, and f) | O | —Br | —H | -iso-propyl |
| H243 (a, b, c, d, e, and f) | O | —I | —Cl | —H |
| H244 (a, b, c, d, e, and f) | O | —I | —Br | —H |
| H245 (a, b, c, d, e, and f) | O | —I | —F | —H |
| H246 (a, b, c, d, e, and f) | O | —I | —CH₃ | —H |
| H247 (a, b, c, d, e, and f) | O | —I | —CF₃ | —H |
| H248 (a, b, c, d, e, and f) | O | —I | —OCH₃ | —H |
| H249 (a, b, c, d, e, and f) | O | —I | —OCH₂CH₃ | —H |
| H250 (a, b, c, d, e, and f) | O | —I | —OCF₃ | —H |
| H251 (a, b, c, d, e, and f) | O | —I | -tert-butyl | —H |
| H252 (a, b, c, d, e, and f) | O | —I | -iso-propyl | —H |
| H253 (a, b, c, d, e, and f) | O | —I | —CH₃ | —CH₃ |
| H254 (a, b, c, d, e, and f) | O | —I | —H | —H |
| H255 (a, b, c, d, e, and f) | O | —I | —H | —Cl |
| H256 (a, b, c, d, e, and f) | O | —I | —H | —Br |
| H257 (a, b, c, d, e, and f) | O | —I | —H | —F |
| H258 (a, b, c, d, e, and f) | O | —I | —H | —CH₃ |
| H259 (a, b, c, d, e, and f) | O | —I | —H | —CF₃ |
| H260 (a, b, c, d, e, and f) | O | —I | —H | —OCH₃ |
| H261 (a, b, c, d, e, and f) | O | —I | —H | —OCH₂CH₃ |
| H262 (a, b, c, d, e, and f) | O | —I | —H | —OCF₃ |
| H263 (a, b, c, d, e, and f) | O | —I | —H | -tert-butyl |
| H264 (a, b, c, d, e, and f) | O | —I | —H | -iso-propyl |
| H265 (a, b, c, d, e, and f) | NH | —Cl | —Cl | —H |
| H266 (a, b, c, d, e, and f) | NH | —Cl | —Br | —H |
| H267 (a, b, c, d, e, and f) | NH | —Cl | —F | —H |
| H268 (a, b, c, d, e, and f) | NH | —Cl | —CH₃ | —H |
| H269 (a, b, c, d, e, and f) | NH | —Cl | —CF₃ | —H |
| H270 (a, b, c, d, e, and f) | NH | —Cl | —OCH₃ | —H |
| H271 (a, b, c, d, e, and f) | NH | —Cl | —OCH₂CH₃ | —H |
| H272 (a, b, c, d, e, and f) | NH | —Cl | —OCF₃ | —H |
| H273 (a, b, c, d, e, and f) | NH | —Cl | -tert-butyl | —H |
| H274 (a, b, c, d, e, and f) | NH | —Cl | -iso-propyl | —H |
| H275 (a, b, c, d, e, and f) | NH | —Cl | —CH₃ | —CH₃ |
| H276 (a, b, c, d, e, and f) | NH | —Cl | —H | —H |
| H277 (a, b, c, d, e, and f) | NH | —Cl | —H | —CH₃ |
| H278 (a, b, c, d, e, and f) | NH | —Cl | —H | —Cl |
| H279 (a, b, c, d, e, and f) | NH | —Cl | —H | —Br |
| H280 (a, b, c, d, e, and f) | NH | —Cl | —H | —F |
| H281 (a, b, c, d, e, and f) | NH | —Cl | —H | —CF₃ |
| H282 (a, b, c, d, e, and f) | NH | —Cl | —H | —OCH₃ |
| H283 (a, b, c, d, e, and f) | NH | —Cl | —H | —OCH₂CH₃ |
| H284 (a, b, c, d, e, and f) | NH | —Cl | —H | —OCF₃ |
| H285 (a, b, c, d, e, and f) | NH | —Cl | —H | -tert-butyl |
| H286 (a, b, c, d, e, and f) | NH | —Cl | —H | -iso-propyl |
| H287 (a, b, c, d, e, and f) | NH | —CH₃ | —Cl | —H |
| H288 (a, b, c, d, e, and f) | NH | —CH₃ | —Br | —H |
| H289 (a, b, c, d, e, and f) | NH | —CH₃ | —F | —H |
| H290 (a, b, c, d, e, and f) | NH | —CH₃ | —CH₃ | —H |
| H291 (a, b, c, d, e, and f) | NH | —CH₃ | —CF₃ | —H |
| H292 (a, b, c, d, e, and f) | NH | —CH₃ | —OCH₃ | —H |
| H293 (a, b, c, d, e, and f) | NH | —CH₃ | —OCH₂CH₃ | —H |
| H294 (a, b, c, d, e, and f) | NH | —CH₃ | —OCF₃ | —H |
| H295 (a, b, c, d, e, and f) | NH | —CH₃ | -tert-butyl | —H |
| H296 (a, b, c, d, e, and f) | NH | —CH₃ | -iso-propyl | —H |
| H297 (a, b, c, d, e, and f) | NH | —CH₃ | —CH₃ | —CH₃ |
| H298 (a, b, c, d, e, and f) | NH | —CH₃ | —H | —H |
| H299 (a, b, c, d, e, and f) | NH | —CH₃ | —H | —Cl |
| H300 (a, b, c, d, e, and f) | NH | —CH₃ | —H | —Br |
| H301 (a, b, c, d, e, and f) | NH | —CH₃ | —H | —F |
| H302 (a, b, c, d, e, and f) | NH | —CH₃ | —H | —CH₃ |
| H303 (a, b, c, d, e, and f) | NH | —CH₃ | —H | —CF₃ |
| H304 (a, b, c, d, e, and f) | NH | —CH₃ | —H | —OCH₃ |
| H305 (a, b, c, d, e, and f) | NH | —CH₃ | —H | —OCH₂CH₃ |
| H306 (a, b, c, d, e, and f) | NH | —CH₃ | —H | —OCF₃ |
| H307 (a, b, c, d, e, and f) | NH | —CH₃ | —H | -tert-butyl |

TABLE 8-continued

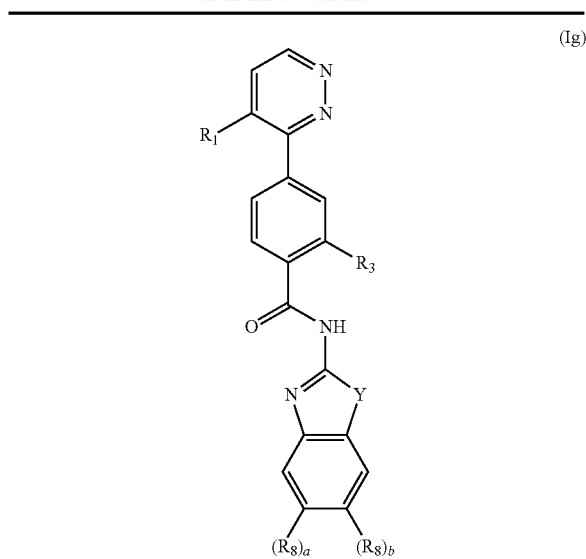

(Ig)

and pharmaceutically acceptable salts thereof, where:

| Compound | Y | R₁ | (R₈)ₐ | (R₈)ᵦ |
|---|---|---|---|---|
| H308 (a, b, c, d, e, and f) | NH | —CH₃ | —H | -iso-propyl |
| H309 (a, b, c, d, e, and f) | NH | —CF₃ | —Cl | —H |
| H310 (a, b, c, d, e, and f) | NH | —CF₃ | —Br | —H |
| H311 (a, b, c, d, e, and f) | NH | —CF₃ | —F | —H |
| H312 (a, b, c, d, e, and f) | NH | —CF₃ | —CH₃ | —H |
| H313 (a, b, c, d, e, and f) | NH | —CF₃ | —CF₃ | —H |
| H314 (a, b, c, d, e, and f) | NH | —CF₃ | —OCH₃ | —H |
| H315 (a, b, c, d, e, and f) | NH | —CF₃ | —OCH₂CH₃ | —H |
| H316 (a, b, c, d, e, and f) | NH | —CF₃ | —OCF₃ | —H |
| H317 (a, b, c, d, e, and f) | NH | —CF₃ | -tert-butyl | —H |
| H318 (a, b, c, d, e, and f) | NH | —CF₃ | -iso-propyl | —H |
| H319 (a, b, c, d, e, and f) | NH | —CF₃ | —CH₃ | —CH₃ |
| H320 (a, b, c, d, e, and f) | NH | —CF₃ | —H | —H |
| H321 (a, b, c, d, e, and f) | NH | —CF₃ | —H | —Cl |
| H322 (a, b, c, d, e, and f) | NH | —CF₃ | —H | —Br |
| H323 (a, b, c, d, e, and f) | NH | —CF₃ | —H | —F |
| H324 (a, b, c, d, e, and f) | NH | —CF₃ | —H | —CH₃ |
| H325 (a, b, c, d, e, and f) | NH | —CF₃ | —H | —CF₃ |
| H326 (a, b, c, d, e, and f) | NH | —CF₃ | —H | —OCH₃ |
| H327 (a, b, c, d, e, and f) | NH | —CF₃ | —H | —OCH₂CH₃ |
| H328 (a, b, c, d, e, and f) | NH | —CF₃ | —H | —OCF₃ |
| H329 (a, b, c, d, e, and f) | NH | —CF₃ | —H | -tert-butyl |
| H330 (a, b, c, d, e, and f) | NH | —CF₃ | —H | -iso-propyl |
| H331 (a, b, c, d, e, and f) | NH | —CHF₂ | —Cl | —H |
| H332 (a, b, c, d, e, and f) | NH | —CHF₂ | —Br | —H |
| H333 (a, b, c, d, e, and f) | NH | —CHF₂ | —F | —H |
| H334 (a, b, c, d, e, and f) | NH | —CHF₂ | —CH₃ | —H |
| H335 (a, b, c, d, e, and f) | NH | —CHF₂ | —CF₃ | —H |
| H336 (a, b, c, d, e, and f) | NH | —CHF₂ | —OCH₃ | —H |
| H337 (a, b, c, d, e, and f) | NH | —CHF₂ | —OCH₂CH₃ | —H |
| H338 (a, b, c, d, e, and f) | NH | —CHF₂ | —OCF₃ | —H |
| H339 (a, b, c, d, e, and f) | NH | —CHF₂ | -tert-butyl | —H |
| H340 (a, b, c, d, e, and f) | NH | —CHF₂ | -iso-propyl | —H |
| H341 (a, b, c, d, e, and f) | NH | —CHF₂ | —CH₃ | —CH₃ |
| H342 (a, b, c, d, e, and f) | NH | —CHF₂ | —H | —H |
| H343 (a, b, c, d, e, and f) | NH | —CHF₂ | —H | —Cl |
| H344 (a, b, c, d, e, and f) | NH | —CHF₂ | —H | —Br |
| H345 (a, b, c, d, e, and f) | NH | —CHF₂ | —H | —F |
| H346 (a, b, c, d, e, and f) | NH | —CHF₂ | —H | —CH₃ |
| H347 (a, b, c, d, e, and f) | NH | —CHF₂ | —H | —CF₃ |
| H348 (a, b, c, d, e, and f) | NH | —CHF₂ | —H | —OCH₃ |
| H349 (a, b, c, d, e, and f) | NH | —CHF₂ | —H | —OCH₂CH₃ |
| H350 (a, b, c, d, e, and f) | NH | —CHF₂ | —H | —OCF₃ |
| H351 (a, b, c, d, e, and f) | NH | —CHF₂ | —H | -tert-butyl |
| H352 (a, b, c, d, e, and f) | NH | —CHF₂ | —H | -iso-propyl |
| H353 (a, b, c, d, e, and f) | NH | —Br | —Br | —H |
| H354 (a, b, c, d, e, and f) | NH | —Br | —Cl | —H |
| H355 (a, b, c, d, e, and f) | NH | —Br | —F | —H |
| H356 (a, b, c, d, e, and f) | NH | —Br | —CH₃ | —H |
| H357 (a, b, c, d, e, and f) | NH | —Br | —CF₃ | —H |

TABLE 8-continued

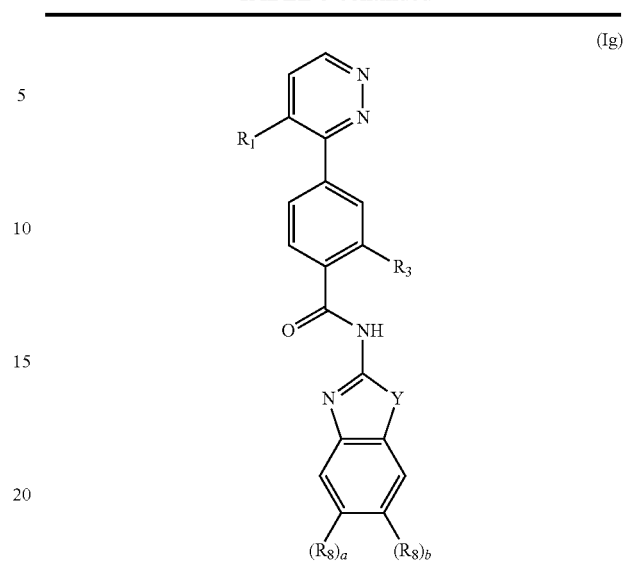

(Ig)

and pharmaceutically acceptable salts thereof, where:

| Compound | Y | R₁ | (R₈)ₐ | (R₈)ᵦ |
|---|---|---|---|---|
| H358 (a, b, c, d, e, and f) | NH | —Br | —OCH₃ | —H |
| H359 (a, b, c, d, e, and f) | NH | —Br | —OCH₂CH₃ | —H |
| H360 (a, b, c, d, e, and f) | NH | —Br | —OCF₃ | —H |
| H361 (a, b, c, d, e, and f) | NH | —Br | -tert-butyl | —H |
| H362 (a, b, c, d, e, and f) | NH | —Br | -iso-propyl | —H |
| H363 (a, b, c, d, e, and f) | NH | —Br | —CH₃ | —CH₃ |
| H364 (a, b, c, d, e, and f) | NH | —Br | —H | —H |
| H365 (a, b, c, d, e, and f) | NH | —Br | —H | —Cl |
| H366 (a, b, c, d, e, and f) | NH | —Br | —H | —Br |
| H367 (a, b, c, d, e, and f) | NH | —Br | —H | —F |
| H368 (a, b, c, d, e, and f) | NH | —Br | —H | —CH₃ |
| H369 (a, b, c, d, e, and f) | NH | —Br | —H | —CF₃ |
| H370 (a, b, c, d, e, and f) | NH | —Br | —H | —OCH₃ |
| H371 (a, b, c, d, e, and f) | NH | —Br | —H | —OCH₂CH₃ |
| H372 (a, b, c, d, e, and f) | NH | —Br | —H | —OCF₃ |
| H373 (a, b, c, d, e, and f) | NH | —Br | —H | -tert-butyl |
| H374 (a, b, c, d, e, and f) | NH | —Br | —H | -iso-propyl |
| H375 (a, b, c, d, e, and f) | NH | —I | —Cl | —H |
| H376 (a, b, c, d, e, and f) | NH | —I | —Br | —H |
| H377 (a, b, c, d, e, and f) | NH | —I | —F | —H |
| H378 (a, b, c, d, e, and f) | NH | —I | —CH₃ | —H |
| H379 (a, b, c, d, e, and f) | NH | —I | —CF₃ | —H |
| H380 (a, b, c, d, e, and f) | NH | —I | —OCH₃ | —H |
| H381 (a, b, c, d, e, and f) | NH | —I | —OCH₂CH₃ | —H |
| H382 (a, b, c, d, e, and f) | NH | —I | —OCF₃ | —H |
| H383 (a, b, c, d, e, and f) | NH | —I | -tert-butyl | —H |
| H384 (a, b, c, d, e, and f) | NH | —I | -iso-propyl | —H |
| H385 (a, b, c, d, e, and f) | NH | —I | —CH₃ | —CH₃ |
| H386 (a, b, c, d, e, and f) | NH | —I | —H | —H |
| H387 (a, b, c, d, e, and f) | NH | —I | —H | —Cl |
| H388 (a, b, c, d, e, and f) | NH | —I | —H | —Br |
| H389 (a, b, c, d, e, and f) | NH | —I | —H | —F |
| H390 (a, b, c, d, e, and f) | NH | —I | —H | —CH₃ |
| H391 (a, b, c, d, e, and f) | NH | —I | —H | —CF₃ |
| H392 (a, b, c, d, e, and f) | NH | —I | —H | —OCH₃ |
| H393 (a, b, c, d, e, and f) | NH | —I | —H | —OCH₂CH₃ |
| H394 (a, b, c, d, e, and f) | NH | —I | —H | —OCF₃ |
| H395 (a, b, c, d, e, and f) | NH | —I | —H | -tert-butyl |
| H396 (a, b, c, d, e, and f) | NH | —I | —H | -iso-propyl |

In the column labeled "Compound":
(a) means that R₃ is —CH₃;
(b) means that R₃ is —Cl;
(c) means that R₃ is —Br;
(d) means that R₃ is —I;
(e) means that R₃ is —F; and
(f) means that R₃ is —H, i.e., in formula (I) m = 0.

TABLE 9

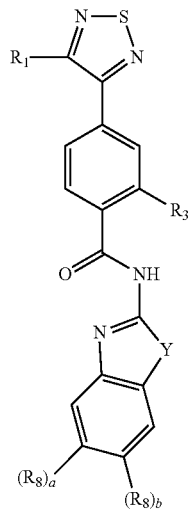

(Ih)

and pharmaceutically acceptable salts thereof, where:

| Compound | Y | $R_1$ | $(R_8)_a$ | $(R_8)_b$ |
|---|---|---|---|---|
| I1 (a, b, c, d, e, and f) | S | —Cl | —Cl | —H |
| I2 (a, b, c, d, e, and f) | S | —Cl | —Br | —H |
| I3 (a, b, c, d, e, and f) | S | —Cl | —F | —H |
| I4 (a, b, c, d, e, and f) | S | —Cl | —$CH_3$ | —H |
| I5 (a, b, c, d, e, and f) | S | —Cl | —$CF_3$ | —H |
| I6 (a, b, c, d, e, and f) | S | —Cl | —$OCH_3$ | —H |
| I7 (a, b, c, d, e, and f) | S | —Cl | —$OCH_2CH_3$ | —H |
| I8 (a, b, c, d, e, and f) | S | —Cl | —$OCF_3$ | —H |
| I9 (a, b, c, d, e, and f) | S | —Cl | -tert-butyl | —H |
| I10 (a, b, c, d, e, and f) | S | —Cl | -iso-propyl | —H |
| I11 (a, b, c, d, e, and f) | S | —Cl | —$CH_3$ | —$CH_3$ |
| I12 (a, b, c, d, e, and f) | S | —Cl | —H | —H |
| I13 (a, b, c, d, e, and f) | S | —Cl | —H | —Cl |
| I14 (a, b, c, d, e, and f) | S | —Cl | —H | —Br |
| I15 (a, b, c, d, e, and f) | S | —Cl | —H | —F |
| I16 (a, b, c, d, e, and f) | S | —Cl | —H | —$CH_3$ |
| I17 (a, b, c, d, e, and f) | S | —Cl | —H | —$CF_3$ |
| I18 (a, b, c, d, e, and f) | S | —Cl | —H | —$OCH_3$ |
| I19 (a, b, c, d, e, and f) | S | —Cl | —H | —$OCH_2CH_3$ |
| I20 (a, b, c, d, e, and f) | S | —Cl | —H | —$OCF_3$ |
| I21 (a, b, c, d, e, and f) | S | —Cl | —H | -tert-butyl |
| I22 (a, b, c, d, e, and f) | S | —Cl | —H | -iso-propyl |
| I23 (a, b, c, d, e, and f) | S | —$CH_3$ | —Cl | —H |
| I24 (a, b, c, d, e, and f) | S | —$CH_3$ | —Br | —H |
| I25 (a, b, c, d, e, and f) | S | —$CH_3$ | —F | —H |
| I26 (a, b, c, d, e, and f) | S | —$CH_3$ | —$CH_3$ | —H |
| I27 (a, b, c, d, e, and f) | S | —$CH_3$ | —$CF_3$ | —H |
| I28 (a, b, c, d, e, and f) | S | —$CH_3$ | —$OCH_3$ | —H |
| I29 (a, b, c, d, e, and f) | S | —$CH_3$ | —$OCH_2CH_3$ | —H |
| I30 (a, b, c, d, e, and f) | S | —$CH_3$ | —$OCF_3$ | —H |
| I31 (a, b, c, d, e, and f) | S | —$CH_3$ | -tert-butyl | —H |
| I32 (a, b, c, d, e, and f) | S | —$CH_3$ | -iso-propyl | —H |
| I33 (a, b, c, d, e, and f) | S | —$CH_3$ | —$CH_3$ | —$CH_3$ |
| I34 (a, b, c, d, e, and f) | S | —$CH_3$ | —H | —H |
| I35 (a, b, c, d, e, and f) | S | —$CH_3$ | —H | —Cl |
| I36 (a, b, c, d, e, and f) | S | —$CH_3$ | —H | —Br |
| I37 (a, b, c, d, e, and f) | S | —$CH_3$ | —H | —F |
| I38 (a, b, c, d, e, and f) | S | —$CH_3$ | —H | —$CH_3$ |
| I39 (a, b, c, d, e, and f) | S | —$CH_3$ | —H | —$CF_3$ |
| I40 (a, b, c, d, e, and f) | S | —$CH_3$ | —H | —$OCH_3$ |
| I41 (a, b, c, d, e, and f) | S | —$CH_3$ | —H | —$OCH_2CH_3$ |
| I42 (a, b, c, d, e, and f) | S | —$CH_3$ | —H | —$OCF_3$ |
| I43 (a, b, c, d, e, and f) | S | —$CH_3$ | —H | -tert-butyl |
| I44 (a, b, c, d, e, and f) | S | —$CH_3$ | —H | -iso-propyl |
| I45 (a, b, c, d, e, and f) | S | —$CF_3$ | —Cl | —H |
| I46 (a, b, c, d, e, and f) | S | —$CF_3$ | —Br | —H |
| I47 (a, b, c, d, e, and f) | S | —$CF_3$ | —F | —H |
| I48 (a, b, c, d, e, and f) | S | —$CF_3$ | —$CH_3$ | —H |
| I49 (a, b, c, d, e, and f) | S | —$CF_3$ | —$CF_3$ | —H |
| I50 (a, b, c, d, e, and f) | S | —$CF_3$ | —$OCH_3$ | —H |
| I51 (a, b, c, d, e, and f) | S | —$CF_3$ | —$OCH_2CH_3$ | —H |
| I52 (a, b, c, d, e, and f) | S | —$CF_3$ | —$OCF_3$ | —H |
| I53 (a, b, c, d, e, and f) | S | —$CF_3$ | -tert-butyl | —H |
| I54 (a, b, c, d, e, and f) | S | —$CF_3$ | -iso-propyl | —H |
| I55 (a, b, c, d, e, and f) | S | —$CF_3$ | —$CH_3$ | —$CH_3$ |
| I56 (a, b, c, d, e, and f) | S | —$CF_3$ | —H | —H |
| I57 (a, b, c, d, e, and f) | S | —$CF_3$ | —H | —Cl |
| I58 (a, b, c, d, e, and f) | S | —$CF_3$ | —H | —Br |
| I59 (a, b, c, d, e, and f) | S | —$CF_3$ | —H | —F |
| I60 (a, b, c, d, e, and f) | S | —$CF_3$ | —H | —$CH_3$ |
| I61 (a, b, c, d, e, and f) | S | —$CF_3$ | —H | —$CF_3$ |
| I62 (a, b, c, d, e, and f) | S | —$CF_3$ | —H | —$OCH_3$ |
| I63 (a, b, c, d, e, and f) | S | —$CF_3$ | —H | —$OCH_2CH_3$ |
| I64 (a, b, c, d, e, and f) | S | —$CF_3$ | —H | —$OCF_3$ |
| I65 (a, b, c, d, e, and f) | S | —$CF_3$ | —H | -tert-butyl |
| I66 (a, b, c, d, e, and f) | S | —$CF_3$ | —H | -iso-propyl |
| I67 (a, b, c, d, e, and f) | S | —$CHF_2$ | —Cl | —H |
| I68 (a, b, c, d, e, and f) | S | —$CHF_2$ | —Br | —H |
| I69 (a, b, c, d, e, and f) | S | —$CHF_2$ | —F | —H |
| I70 (a, b, c, d, e, and f) | S | —$CHF_2$ | —$CH_3$ | —H |
| I71 (a, b, c, d, e, and f) | S | —$CHF_2$ | —$CF_3$ | —H |
| I72 (a, b, c, d, e, and f) | S | —$CHF_2$ | —$OCH_3$ | —H |
| I73 (a, b, c, d, e, and f) | S | —$CHF_2$ | —$OCH_2CH_3$ | —H |
| I74 (a, b, c, d, e, and f) | S | —$CHF_2$ | —$OCF_3$ | —H |
| I75 (a, b, c, d, e, and f) | S | —$CHF_2$ | -tert-butyl | —H |
| I76 (a, b, c, d, e, and f) | S | —$CHF_2$ | -iso-propyl | —H |
| I77 (a, b, c, d, e, and f) | S | —$CHF_2$ | —$CH_3$ | —$CH_3$ |
| I78 (a, b, c, d, e, and f) | S | —$CHF_2$ | —H | —H |
| I79 (a, b, c, d, e, and f) | S | —$CHF_2$ | —H | —Cl |
| I80 (a, b, c, d, e, and f) | S | —$CHF_2$ | —H | —Br |
| I81 (a, b, c, d, e, and f) | S | —$CHF_2$ | —H | —F |
| I82 (a, b, c, d, e, and f) | S | —$CHF_2$ | —H | —$CH_3$ |
| I83 (a, b, c, d, e, and f) | S | —$CHF_2$ | —H | —$CF_3$ |
| I84 (a, b, c, d, e, and f) | S | —$CHF_2$ | —H | —$OCH_3$ |
| I85 (a, b, c, d, e, and f) | S | —$CHF_2$ | —H | —$OCH_2CH_3$ |
| I86 (a, b, c, d, e, and f) | S | —$CHF_2$ | —H | —$OCF_3$ |
| I87 (a, b, c, d, e, and f) | S | —$CHF_2$ | —H | -tert-butyl |
| I88 (a, b, c, d, e, and f) | S | —$CHF_2$ | —H | -iso-propyl |
| I89 (a, b, c, d, e, and f) | S | —Br | —Br | —H |
| I90 (a, b, c, d, e, and f) | S | —Br | —Cl | —H |
| I91 (a, b, c, d, e, and f) | S | —Br | —F | —H |
| I92 (a, b, c, d, e, and f) | S | —Br | —$CH_3$ | —H |
| I93 (a, b, c, d, e, and f) | S | —Br | —$CF_3$ | —H |
| I94 (a, b, c, d, e, and f) | S | —Br | —$OCH_3$ | —H |
| I95 (a, b, c, d, e, and f) | S | —Br | —$OCH_2CH_3$ | —H |
| I96 (a, b, c, d, e, and f) | S | —Br | —$OCF_3$ | —H |
| I97 (a, b, c, d, e, and f) | S | —Br | -tert-butyl | —H |
| I98 (a, b, c, d, e, and f) | S | —Br | -iso-propyl | —H |
| I99 (a, b, c, d, e, and f) | S | —Br | —$CH_3$ | —$CH_3$ |
| I100 (a, b, c, d, e, and f) | S | —Br | —H | —H |
| I101 (a, b, c, d, e, and f) | S | —Br | —H | —Cl |
| I102 (a, b, c, d, e, and f) | S | —Br | —H | —Br |

TABLE 9-continued

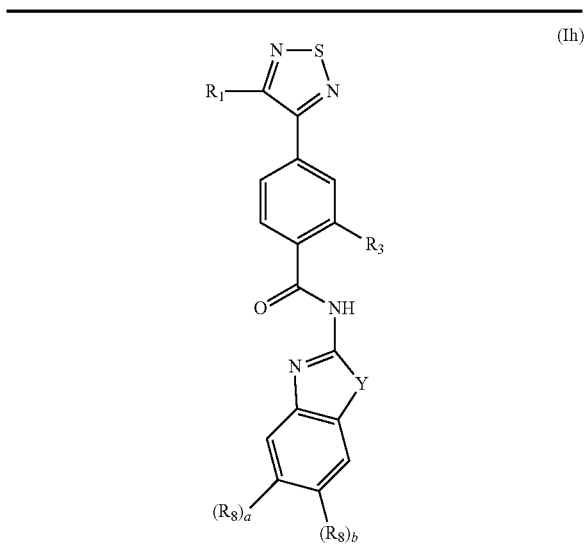

(Ih)

and pharmaceutically acceptable salts thereof, where:

| Compound | Y | $R_1$ | $(R_8)_a$ | $(R_8)_b$ |
|---|---|---|---|---|
| I103 (a, b, c, d, e, and f) | S | —Br | —H | —F |
| I104 (a, b, c, d, e, and f) | S | —Br | —H | —CH$_3$ |
| I105 (a, b, c, d, e, and f) | S | —Br | —H | —CF$_3$ |
| I106 (a, b, c, d, e, and f) | S | —Br | —H | —OCH$_3$ |
| I107 (a, b, c, d, e, and f) | S | —Br | —H | —OCH$_2$CH$_3$ |
| I108 (a, b, c, d, e, and f) | S | —Br | —H | —OCF$_3$ |
| I109 (a, b, c, d, e, and f) | S | —Br | —H | -tert-butyl |
| I110 (a, b, c, d, e, and f) | S | —Br | —H | -iso-propyl |
| I111 (a, b, c, d, e, and f) | S | —I | —Cl | —H |
| I112 (a, b, c, d, e, and f) | S | —I | —Br | —H |
| I113 (a, b, c, d, e, and f) | S | —I | —F | —H |
| I114 (a, b, c, d, e, and f) | S | —I | —CH$_3$ | —H |
| I115 (a, b, c, d, e, and f) | S | —I | —CF$_3$ | —H |
| I116 (a, b, c, d, e, and f) | S | —I | —OCH$_3$ | —H |
| I117 (a, b, c, d, e, and f) | S | —I | —OCH$_2$CH$_3$ | —H |
| I118 (a, b, c, d, e, and f) | S | —I | —OCF$_3$ | —H |
| I119 (a, b, c, d, e, and f) | S | —I | -tert-butyl | —H |
| I120 (a, b, c, d, e, and f) | S | —I | -iso-propyl | —H |
| I121 (a, b, c, d, e, and f) | S | —I | —CH$_3$ | —CH$_3$ |
| I122 (a, b, c, d, e, and f) | S | —I | —H | —H |
| I123 (a, b, c, d, e, and f) | S | —I | —H | —Cl |
| I124 (a, b, c, d, e, and f) | S | —I | —H | —Br |
| I125 (a, b, c, d, e, and f) | S | —I | —H | —F |
| I126 (a, b, c, d, e, and f) | S | —I | —H | —CH$_3$ |
| I127 (a, b, c, d, e, and f) | S | —I | —H | —CF$_3$ |
| I128 (a, b, c, d, e, and f) | S | —I | —H | —OCH$_3$ |
| I129 (a, b, c, d, e, and f) | S | —I | —H | —OCH$_2$CH$_3$ |
| I130 (a, b, c, d, e, and f) | S | —I | —H | —OCF$_3$ |
| I131 (a, b, c, d, e, and f) | S | —I | —H | -tert-butyl |
| I132 (a, b, c, d, e, and f) | S | —I | —H | -iso-propyl |
| I133 (a, b, c, d, e, and f) | O | —Cl | —Cl | —H |
| I134 (a, b, c, d, e, and f) | O | —Cl | —Br | —H |
| I135 (a, b, c, d, e, and f) | O | —Cl | —F | —H |
| I136 (a, b, c, d, e, and f) | O | —Cl | —CH$_3$ | —H |
| I137 (a, b, c, d, e, and f) | O | —Cl | —CF$_3$ | —H |
| I138 (a, b, c, d, e, and f) | O | —Cl | —OCH$_3$ | —H |
| I139 (a, b, c, d, e, and f) | O | —Cl | —OCH$_2$CH$_3$ | —H |
| I140 (a, b, c, d, e, and f) | O | —Cl | —OCF$_3$ | —H |
| I141 (a, b, c, d, e, and f) | O | —Cl | -tert-butyl | —H |
| I142 (a, b, c, d, e, and f) | O | —Cl | -iso-propyl | —H |
| I143 (a, b, c, d, e, and f) | O | —Cl | —CH$_3$ | —CH$_3$ |
| I144 (a, b, c, d, e, and f) | O | —Cl | —H | —H |
| I145 (a, b, c, d, e, and f) | O | —Cl | —H | —CH$_3$ |
| I146 (a, b, c, d, e, and f) | O | —Cl | —H | —Cl |
| I147 (a, b, c, d, e, and f) | O | —Cl | —H | —Br |
| I148 (a, b, c, d, e, and f) | O | —Cl | —H | —F |
| I149 (a, b, c, d, e, and f) | O | —Cl | —H | —CF$_3$ |
| I150 (a, b, c, d, e, and f) | O | —Cl | —H | —OCH$_3$ |
| I151 (a, b, c, d, e, and f) | O | —Cl | —H | —OCH$_2$CH$_3$ |
| I152 (a, b, c, d, e, and f) | O | —Cl | —H | —OCF$_3$ |
| I153 (a, b, c, d, e, and f) | O | —Cl | —H | -tert-butyl |
| I154 (a, b, c, d, e, and f) | O | —Cl | —H | -iso-propyl |
| I155 (a, b, c, d, e, and f) | O | —CH$_3$ | —Cl | —H |
| I156 (a, b, c, d, e, and f) | O | —CH$_3$ | —Br | —H |
| I157 (a, b, c, d, e, and f) | O | —CH$_3$ | —F | —H |
| I158 (a, b, c, d, e, and f) | O | —CH$_3$ | —CH$_3$ | —H |
| I159 (a, b, c, d, e, and f) | O | —CH$_3$ | —CF$_3$ | —H |
| I160 (a, b, c, d, e, and f) | O | —CH$_3$ | —OCH$_3$ | —H |
| I161 (a, b, c, d, e, and f) | O | —CH$_3$ | —OCH$_2$CH$_3$ | —H |
| I162 (a, b, c, d, e, and f) | O | —CH$_3$ | —OCF$_3$ | —H |
| I163 (a, b, c, d, e, and f) | O | —CH$_3$ | -tert-butyl | —H |
| I164 (a, b, c, d, e, and f) | O | —CH$_3$ | -iso-propyl | —H |
| I165 (a, b, c, d, e, and f) | O | —CH$_3$ | —CH$_3$ | —CH$_3$ |
| I166 (a, b, c, d, e, and f) | O | —CH$_3$ | —H | —H |
| I167 (a, b, c, d, e, and f) | O | —CH$_3$ | —H | —Cl |
| I168 (a, b, c, d, e, and f) | O | —CH$_3$ | —H | —Br |
| I169 (a, b, c, d, e, and f) | O | —CH$_3$ | —H | —F |
| I170 (a, b, c, d, e, and f) | O | —CH$_3$ | —H | —CH$_3$ |
| I171 (a, b, c, d, e, and f) | O | —CH$_3$ | —H | —CF$_3$ |
| I172 (a, b, c, d, e, and f) | O | —CH$_3$ | —H | —OCH$_3$ |
| I173 (a, b, c, d, e, and f) | O | —CH$_3$ | —H | —OCH$_2$CH$_3$ |
| I174 (a, b, c, d, e, and f) | O | —CH$_3$ | —H | —OCF$_3$ |
| I175 (a, b, c, d, e, and f) | O | —CH$_3$ | —H | -tert-butyl |
| I176 (a, b, c, d, e, and f) | O | —CH$_3$ | —H | -iso-propyl |
| I177 (a, b, c, d, e, and f) | O | —CF$_3$ | —Cl | —H |
| I178 (a, b, c, d, e, and f) | O | —CF$_3$ | —Br | —H |
| I179 (a, b, c, d, e, and f) | O | —CF$_3$ | —F | —H |
| I180 (a, b, c, d, e, and f) | O | —CF$_3$ | —CH$_3$ | —H |
| I181 (a, b, c, d, e, and f) | O | —CF$_3$ | —CF$_3$ | —H |
| I182 (a, b, c, d, e, and f) | O | —CF$_3$ | —OCH$_3$ | —H |
| I183 (a, b, c, d, e, and f) | O | —CF$_3$ | —OCH$_2$CH$_3$ | —H |
| I184 (a, b, c, d, e, and f) | O | —CF$_3$ | —OCF$_3$ | —H |
| I185 (a, b, c, d, e, and f) | O | —CF$_3$ | -tert-butyl | —H |
| I186 (a, b, c, d, e, and f) | O | —CF$_3$ | -iso-propyl | —H |
| I187 (a, b, c, d, e, and f) | O | —CF$_3$ | —CH$_3$ | —CH$_3$ |
| I188 (a, b, c, d, e, and f) | O | —CF$_3$ | —H | —H |
| I189 (a, b, c, d, e, and f) | O | —CF$_3$ | —H | —Cl |
| I190 (a, b, c, d, e, and f) | O | —CF$_3$ | —H | —Br |
| I191 (a, b, c, d, e, and f) | O | —CF$_3$ | —H | —F |
| I192 (a, b, c, d, e, and f) | O | —CF$_3$ | —H | —CH$_3$ |
| I193 (a, b, c, d, e, and f) | O | —CF$_3$ | —H | —CF$_3$ |
| I194 (a, b, c, d, e, and f) | O | —CF$_3$ | —H | —OCH$_3$ |
| I195 (a, b, c, d, e, and f) | O | —CF$_3$ | —H | —OCH$_2$CH$_3$ |
| I196 (a, b, c, d, e, and f) | O | —CF$_3$ | —H | —OCF$_3$ |
| I197 (a, b, c, d, e, and f) | O | —CF$_3$ | —H | -tert-butyl |
| I198 (a, b, c, d, e, and f) | O | —CF$_3$ | —H | -iso-propyl |
| I199 (a, b, c, d, e, and f) | O | —CHF$_2$ | —Cl | —H |
| I200 (a, b, c, d, e, and f) | O | —CHF$_2$ | —Br | —H |
| I201 (a, b, c, d, e, and f) | O | —CHF$_2$ | —F | —H |
| I202 (a, b, c, d, e, and f) | O | —CHF$_2$ | —CH$_3$ | —H |
| I203 (a, b, c, d, e, and f) | O | —CHF$_2$ | —CF$_3$ | —H |
| I204 (a, b, c, d, e, and f) | O | —CHF$_2$ | —OCH$_3$ | —H |

TABLE 9-continued (Ih)

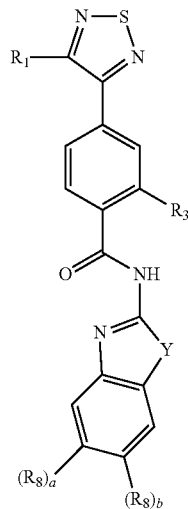

and pharmaceutically acceptable salts thereof, where:

| Compound | Y | R₁ | (R₈)ₐ | (R₈)ᵦ |
|---|---|---|---|---|
| I205 (a, b, c, d, e, and f) | O | —CHF₂ | —OCH₂CH₃ | —H |
| I206 (a, b, c, d, e, and f) | O | —CHF₂ | —OCF₃ | —H |
| I207 (a, b, c, d, e, and f) | O | —CHF₂ | -tert-butyl | —H |
| I208 (a, b, c, d, e, and f) | O | —CHF₂ | -iso-propyl | —H |
| I209 (a, b, c, d, e, and f) | O | —CHF₂ | —CH₃ | —CH₃ |
| I210 (a, b, c, d, e, and f) | O | —CHF₂ | —H | —H |
| I211 (a, b, c, d, e, and f) | O | —CHF₂ | —H | —Cl |
| I212 (a, b, c, d, e, and f) | O | —CHF₂ | —H | —Br |
| I213 (a, b, c, d, e, and f) | O | —CHF₂ | —H | —F |
| I214 (a, b, c, d, e, and f) | O | —CHF₂ | —H | —CH₃ |
| I215 (a, b, c, d, e, and f) | O | —CHF₂ | —H | —CF₃ |
| I216 (a, b, c, d, e, and f) | O | —CHF₂ | —H | —OCH₃ |
| I217 (a, b, c, d, e, and f) | O | —CHF₂ | —H | —OCH₂CH₃ |
| I218 (a, b, c, d, e, and f) | O | —CHF₂ | —H | —OCF₃ |
| I219 (a, b, c, d, e, and f) | O | —CHF₂ | —H | -tert-butyl |
| I220 (a, b, c, d, e, and f) | O | —CHF₂ | —H | -iso-propyl |
| I221 (a, b, c, d, e, and f) | O | —Br | —Br | —H |
| I222 (a, b, c, d, e, and f) | O | —Br | —Cl | —H |
| I223 (a, b, c, d, e, and f) | O | —Br | —F | —H |
| I224 (a, b, c, d, e, and f) | O | —Br | —CH₃ | —H |
| I225 (a, b, c, d, e, and f) | O | —Br | —CF₃ | —H |
| I226 (a, b, c, d, e, and f) | O | —Br | —OCH₃ | —H |
| I227 (a, b, c, d, e, and f) | O | —Br | —OCH₂CH₃ | —H |
| I228 (a, b, c, d, e, and f) | O | —Br | —OCF₃ | —H |
| I229 (a, b, c, d, e, and f) | O | —Br | -tert-butyl | —H |
| I230 (a, b, c, d, e, and f) | O | —Br | -iso-propyl | —H |
| I231 (a, b, c, d, e, and f) | O | —Br | —CH₃ | —CH₃ |
| I232 (a, b, c, d, e, and f) | O | —Br | —H | —H |
| I233 (a, b, c, d, e, and f) | O | —Br | —H | —Cl |
| I234 (a, b, c, d, e, and f) | O | —Br | —H | —Br |
| I235 (a, b, c, d, e, and f) | O | —Br | —H | —F |
| I236 (a, b, c, d, e, and f) | O | —Br | —H | —CH₃ |
| I237 (a, b, c, d, e, and f) | O | —Br | —H | —CF₃ |
| I238 (a, b, c, d, e, and f) | O | —Br | —H | —OCH₃ |
| I239 (a, b, c, d, e, and f) | O | —Br | —H | —OCH₂CH₃ |
| I240 (a, b, c, d, e, and f) | O | —Br | —H | —OCF₃ |
| I241 (a, b, c, d, e, and f) | O | —Br | —H | -tert-butyl |
| I242 (a, b, c, d, e, and f) | O | —Br | —H | -iso-propyl |
| I243 (a, b, c, d, e, and f) | O | —I | —Cl | —H |
| I244 (a, b, c, d, e, and f) | O | —I | —Br | —H |
| I245 (a, b, c, d, e, and f) | O | —I | —F | —H |
| I246 (a, b, c, d, e, and f) | O | —I | —CH₃ | —H |
| I247 (a, b, c, d, e, and f) | O | —I | —CF₃ | —H |
| I248 (a, b, c, d, e, and f) | O | —I | —OCH₃ | —H |
| I249 (a, b, c, d, e, and f) | O | —I | —OCH₂CH₃ | —H |
| I250 (a, b, c, d, e, and f) | O | —I | —OCF₃ | —H |
| I251 (a, b, c, d, e, and f) | O | —I | -tert-butyl | —H |
| I252 (a, b, c, d, e, and f) | O | —I | -iso-propyl | —H |
| I253 (a, b, c, d, e, and f) | O | —I | —CH₃ | —CH₃ |
| I254 (a, b, c, d, e, and f) | O | —I | —H | —H |
| I255 (a, b, c, d, e, and f) | O | —I | —H | —Cl |

TABLE 9-continued (Ih)

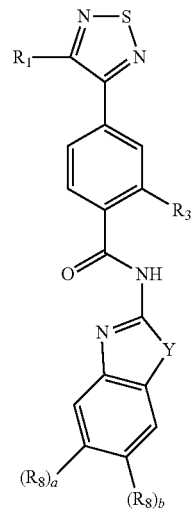

and pharmaceutically acceptable salts thereof, where:

| Compound | Y | R₁ | (R₈)ₐ | (R₈)ᵦ |
|---|---|---|---|---|
| I256 (a, b, c, d, e, and f) | O | —I | —H | —Br |
| I257 (a, b, c, d, e, and f) | O | —I | —H | —F |
| I258 (a, b, c, d, e, and f) | O | —I | —H | —CH₃ |
| I259 (a, b, c, d, e, and f) | O | —I | —H | —CF₃ |
| I260 (a, b, c, d, e, and f) | O | —I | —H | —OCH₃ |
| I261 (a, b, c, d, e, and f) | O | —I | —H | —OCH₂CH₃ |
| I262 (a, b, c, d, e, and f) | O | —I | —H | —OCF₃ |
| I263 (a, b, c, d, e, and f) | O | —I | —H | -tert-butyl |
| I264 (a, b, c, d, e, and f) | O | —I | —H | -iso-propyl |
| I265 (a, b, c, d, e, and f) | NH | —Cl | —Cl | —H |
| I266 (a, b, c, d, e, and f) | NH | —Cl | —Br | —H |
| I267 (a, b, c, d, e, and f) | NH | —Cl | —F | —H |
| I268 (a, b, c, d, e, and f) | NH | —Cl | —CH₃ | —H |
| I269 (a, b, c, d, e, and f) | NH | —Cl | —CF₃ | —H |
| I270 (a, b, c, d, e, and f) | NH | —Cl | —OCH₃ | —H |
| I271 (a, b, c, d, e, and f) | NH | —Cl | —OCH₂CH₃ | —H |
| I272 (a, b, c, d, e, and f) | NH | —Cl | —OCF₃ | —H |
| I273 (a, b, c, d, e, and f) | NH | —Cl | -tert-butyl | —H |
| I274 (a, b, c, d, e, and f) | NH | —Cl | -iso-propyl | —H |
| I275 (a, b, c, d, e, and f) | NH | —Cl | —CH₃ | —CH₃ |
| I276 (a, b, c, d, e, and f) | NH | —Cl | —H | —H |
| I277 (a, b, c, d, e, and f) | NH | —Cl | —H | —CH₃ |
| I278 (a, b, c, d, e, and f) | NH | —Cl | —H | —Cl |
| I279 (a, b, c, d, e, and f) | NH | —Cl | —H | —Br |
| I280 (a, b, c, d, e, and f) | NH | —Cl | —H | —F |
| I281 (a, b, c, d, e, and f) | NH | —Cl | —H | —CF₃ |
| I282 (a, b, c, d, e, and f) | NH | —Cl | —H | —OCH₃ |
| I283 (a, b, c, d, e, and f) | NH | —Cl | —H | —OCH₂CH₃ |
| I284 (a, b, c, d, e, and f) | NH | —Cl | —H | —OCF₃ |
| I285 (a, b, c, d, e, and f) | NH | —Cl | —H | -tert-butyl |
| I286 (a, b, c, d, e, and f) | NH | —Cl | —H | -iso-propyl |
| I287 (a, b, c, d, e, and f) | NH | —CH₃ | —Cl | —H |
| I288 (a, b, c, d, e, and f) | NH | —CH₃ | —Br | —H |
| I289 (a, b, c, d, e, and f) | NH | —CH₃ | —F | —H |
| I290 (a, b, c, d, e, and f) | NH | —CH₃ | —CH₃ | —H |
| I291 (a, b, c, d, e, and f) | NH | —CH₃ | —CF₃ | —H |
| I292 (a, b, c, d, e, and f) | NH | —CH₃ | —OCH₃ | —H |
| I293 (a, b, c, d, e, and f) | NH | —CH₃ | —OCH₂CH₃ | —H |
| I294 (a, b, c, d, e, and f) | NH | —CH₃ | —OCF₃ | —H |
| I295 (a, b, c, d, e, and f) | NH | —CH₃ | -tert-butyl | —H |
| I296 (a, b, c, d, e, and f) | NH | —CH₃ | -iso-propyl | —H |
| I297 (a, b, c, d, e, and f) | NH | —CH₃ | —CH₃ | —CH₃ |
| I298 (a, b, c, d, e, and f) | NH | —CH₃ | —H | —H |
| I299 (a, b, c, d, e, and f) | NH | —CH₃ | —H | —Cl |
| I300 (a, b, c, d, e, and f) | NH | —CH₃ | —H | —Br |
| I301 (a, b, c, d, e, and f) | NH | —CH₃ | —H | —F |
| I302 (a, b, c, d, e, and f) | NH | —CH₃ | —H | —CH₃ |
| I303 (a, b, c, d, e, and f) | NH | —CH₃ | —H | —CF₃ |
| I304 (a, b, c, d, e, and f) | NH | —CH₃ | —H | —OCH₃ |
| I305 (a, b, c, d, e, and f) | NH | —CH₃ | —H | —OCH₂CH₃ |
| I306 (a, b, c, d, e, and f) | NH | —CH₃ | —H | —OCF₃ |

TABLE 9-continued

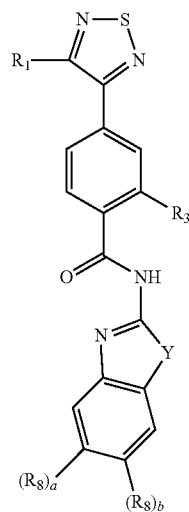

(Ih)

and pharmaceutically acceptable salts thereof, where:

| Compound | Y | $R_1$ | $(R_8)_a$ | $(R_8)_b$ |
|---|---|---|---|---|
| I307 (a, b, c, d, e, and f) | NH | —CH$_3$ | —H | -tert-butyl |
| I308 (a, b, c, d, e, and f) | NH | —CH$_3$ | —H | -iso-propyl |
| I309 (a, b, c, d, e, and f) | NH | —CF$_3$ | —H | —H |
| I310 (a, b, c, d, e, and f) | NH | —CF$_3$ | —Br | —H |
| I311 (a, b, c, d, e, and f) | NH | —CF$_3$ | —F | —H |
| I312 (a, b, c, d, e, and f) | NH | —CF$_3$ | —CH$_3$ | —H |
| I313 (a, b, c, d, e, and f) | NH | —CF$_3$ | —CF$_3$ | —H |
| I314 (a, b, c, d, e, and f) | NH | —CF$_3$ | —OCH$_3$ | —H |
| I315 (a, b, c, d, e, and f) | NH | —CF$_3$ | —OCH$_2$CH$_3$ | —H |
| I316 (a, b, c, d, e, and f) | NH | —CF$_3$ | —OCF$_3$ | —H |
| I317 (a, b, c, d, e, and f) | NH | —CF$_3$ | -tert-butyl | —H |
| I318 (a, b, c, d, e, and f) | NH | —CF$_3$ | -iso-propyl | —H |
| I319 (a, b, c, d, e, and f) | NH | —CF$_3$ | —CH$_3$ | —CH$_3$ |
| I320 (a, b, c, d, e, and f) | NH | —CF$_3$ | —H | —H |
| I321 (a, b, c, d, e, and f) | NH | —CF$_3$ | —H | —Cl |
| I322 (a, b, c, d, e, and f) | NH | —CF$_3$ | —H | —Br |
| I323 (a, b, c, d, e, and f) | NH | —CF$_3$ | —H | —F |
| I324 (a, b, c, d, e, and f) | NH | —CF$_3$ | —H | —CH$_3$ |
| I325 (a, b, c, d, e, and f) | NH | —CF$_3$ | —H | —CF$_3$ |
| I326 (a, b, c, d, e, and f) | NH | —CF$_3$ | —H | —OCH$_3$ |
| I327 (a, b, c, d, e, and f) | NH | —CF$_3$ | —H | —OCH$_2$CH$_3$ |
| I328 (a, b, c, d, e, and f) | NH | —CF$_3$ | —H | —OCF$_3$ |
| I329 (a, b, c, d, e, and f) | NH | —CF$_3$ | —H | -tert-butyl |
| I330 (a, b, c, d, e, and f) | NH | —CF$_3$ | —H | -iso-propyl |
| I331 (a, b, c, d, e, and f) | NH | —CHF$_2$ | —Cl | —H |
| I332 (a, b, c, d, e, and f) | NH | —CHF$_2$ | —Br | —H |
| I333 (a, b, c, d, e, and f) | NH | —CHF$_2$ | —F | —H |
| I334 (a, b, c, d, e, and f) | NH | —CHF$_2$ | —CH$_3$ | —H |
| I335 (a, b, c, d, e, and f) | NH | —CHF$_2$ | —CF$_3$ | —H |
| I336 (a, b, c, d, e, and f) | NH | —CHF$_2$ | —OCH$_3$ | —H |
| I337 (a, b, c, d, e, and f) | NH | —CHF$_2$ | —OCH$_2$CH$_3$ | —H |
| I338 (a, b, c, d, e, and f) | NH | —CHF$_2$ | —OCF$_3$ | —H |
| I339 (a, b, c, d, e, and f) | NH | —CHF$_2$ | -tert-butyl | —H |
| I340 (a, b, c, d, e, and f) | NH | —CHF$_2$ | -iso-propyl | —H |
| I341 (a, b, c, d, e, and f) | NH | —CHF$_2$ | —CH$_3$ | —CH$_3$ |
| I342 (a, b, c, d, e, and f) | NH | —CHF$_2$ | —H | —H |
| I343 (a, b, c, d, e, and f) | NH | —CHF$_2$ | —H | —Cl |
| I344 (a, b, c, d, e, and f) | NH | —CHF$_2$ | —H | —Br |
| I345 (a, b, c, d, e, and f) | NH | —CHF$_2$ | —H | —F |
| I346 (a, b, c, d, e, and f) | NH | —CHF$_2$ | —H | —CH$_3$ |
| I347 (a, b, c, d, e, and f) | NH | —CHF$_2$ | —H | —CF$_3$ |
| I348 (a, b, c, d, e, and f) | NH | —CHF$_2$ | —H | —OCH$_3$ |
| I349 (a, b, c, d, e, and f) | NH | —CHF$_2$ | —H | —OCH$_2$CH$_3$ |
| I350 (a, b, c, d, e, and f) | NH | —CHF$_2$ | —H | —OCF$_3$ |
| I351 (a, b, c, d, e, and f) | NH | —CHF$_2$ | —H | -tert-butyl |
| I352 (a, b, c, d, e, and f) | NH | —CHF$_2$ | —H | -iso-propyl |
| I353 (a, b, c, d, e, and f) | NH | —Br | —Br | —H |
| I354 (a, b, c, d, e, and f) | NH | —Br | —Cl | —H |
| I355 (a, b, c, d, e, and f) | NH | —Br | —F | —H |
| I356 (a, b, c, d, e, and f) | NH | —Br | —CH$_3$ | —H |
| I357 (a, b, c, d, e, and f) | NH | —Br | —CF$_3$ | —H |

TABLE 9-continued

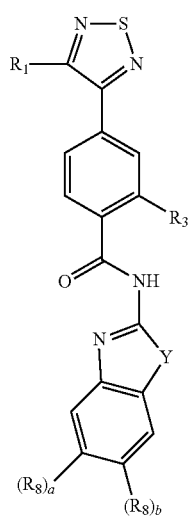

(Ih)

and pharmaceutically acceptable salts thereof, where:

| Compound | Y | $R_1$ | $(R_8)_a$ | $(R_8)_b$ |
|---|---|---|---|---|
| I358 (a, b, c, d, e, and f) | NH | —Br | —OCH$_3$ | —H |
| I359 (a, b, c, d, e, and f) | NH | —Br | —OCH$_2$CH$_3$ | —H |
| I360 (a, b, c, d, e, and f) | NH | —Br | —OCF$_3$ | —H |
| I361 (a, b, c, d, e, and f) | NH | —Br | -tert-butyl | —H |
| I362 (a, b, c, d, e, and f) | NH | —Br | -iso-propyl | —H |
| I363 (a, b, c, d, e, and f) | NH | —Br | —CH$_3$ | —CH$_3$ |
| I364 (a, b, c, d, e, and f) | NH | —Br | —H | —H |
| I365 (a, b, c, d, e, and f) | NH | —Br | —H | —Cl |
| I366 (a, b, c, d, e, and f) | NH | —Br | —H | —Br |
| I367 (a, b, c, d, e, and f) | NH | —Br | —H | —F |
| I368 (a, b, c, d, e, and f) | NH | —Br | —H | —CH$_3$ |
| I369 (a, b, c, d, e, and f) | NH | —Br | —H | —CF$_3$ |
| I370 (a, b, c, d, e, and f) | NH | —Br | —H | —OCH$_3$ |
| I371 (a, b, c, d, e, and f) | NH | —Br | —H | —OCH$_2$CH$_3$ |
| I372 (a, b, c, d, e, and f) | NH | —Br | —H | —OCF$_3$ |
| I373 (a, b, c, d, e, and f) | NH | —Br | —H | -tert-butyl |
| I374 (a, b, c, d, e, and f) | NH | —Br | —H | -iso-propyl |
| I375 (a, b, c, d, e, and f) | NH | —I | —Cl | —H |
| I376 (a, b, c, d, e, and f) | NH | —I | —Br | —H |
| I377 (a, b, c, d, e, and f) | NH | —I | —F | —H |
| I378 (a, b, c, d, e, and f) | NH | —I | —CH$_3$ | —H |
| I379 (a, b, c, d, e, and f) | NH | —I | —CF$_3$ | —H |
| I380 (a, b, c, d, e, and f) | NH | —I | —OCH$_3$ | —H |
| I381 (a, b, c, d, e, and f) | NH | —I | —OCH$_2$CH$_3$ | —H |
| I382 (a, b, c, d, e, and f) | NH | —I | —OCF$_3$ | —H |
| I383 (a, b, c, d, e, and f) | NH | —I | -tert-butyl | —H |
| I384 (a, b, c, d, e, and f) | NH | —I | -iso-propyl | —H |
| I385 (a, b, c, d, e, and f) | NH | —I | —CH$_3$ | —CH$_3$ |
| I386 (a, b, c, d, e, and f) | NH | —I | —H | —H |
| I387 (a, b, c, d, e, and f) | NH | —I | —H | —Cl |
| I388 (a, b, c, d, e, and f) | NH | —I | —H | —Br |
| I389 (a, b, c, d, e, and f) | NH | —I | —H | —F |
| I390 (a, b, c, d, e, and f) | NH | —I | —H | —CH$_3$ |
| I391 (a, b, c, d, e, and f) | NH | —I | —H | —CF$_3$ |
| I392 (a, b, c, d, e, and f) | NH | —I | —H | —OCH$_3$ |
| I393 (a, b, c, d, e, and f) | NH | —I | —H | —OCH$_2$CH$_3$ |
| I394 (a, b, c, d, e, and f) | NH | —I | —H | —OCF$_3$ |
| I395 (a, b, c, d, e, and f) | NH | —I | —H | -tert-butyl |
| I396 (a, b, c, d, e, and f) | NH | —I | —H | -iso-propyl |

In the column labeled "Compound":
(a) means that $R_3$ is —CH$_3$;
(b) means that $R_3$ is —Cl;
(c) means that $R_3$ is —Br;
(d) means that $R_3$ is —I;
(e) means that $R_3$ is —F; and
(f) means that $R_3$ is —H, i.e., in formula (I) m = 0.

TABLE 10

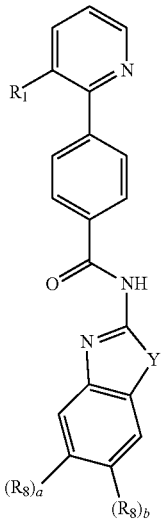

(IIb)

and pharmaceutically acceptable salts thereof, where:

| Compound | Y | R₁ | (R₈)ₐ | (R₈)ᵦ |
|---|---|---|---|---|
| J1 | S | —Cl | —Cl | —H |
| J2 | S | —Cl | —Br | —H |
| J3 | S | —Cl | —F | —H |
| J4 | S | —Cl | —CH₃ | —H |
| J5 | S | —Cl | —CF₃ | —H |
| J6 | S | —Cl | —OCH₃ | —H |
| J7 | S | —Cl | —OCH₂CH₃ | —H |
| J8 | S | —Cl | —OCF₃ | —H |
| J9 | S | —Cl | -tert-butyl | —H |
| J10 | S | —Cl | -iso-propyl | —H |
| J11 | S | —Cl | —CH₃ | —CH₃ |
| J12 | S | —Cl | —H | —H |
| J13 | S | —Cl | —H | —Cl |
| J14 | S | —Cl | —H | —Br |
| J15 | S | —Cl | —H | —F |
| J16 | S | —Cl | —H | —CH₃ |
| J17 | S | —Cl | —H | —CF₃ |
| J18 | S | —Cl | —H | —OCH₃ |
| J19 | S | —Cl | —H | —OCH₂CH₃ |
| J20 | S | —Cl | —H | —OCF₃ |
| J21 | S | —Cl | —H | -tert-butyl |
| J22 | S | —Cl | —H | -iso-propyl |
| J23 | S | —CH₃ | —Cl | —H |
| J24 | S | —CH₃ | —Br | —H |
| J25 | S | —CH₃ | —F | —H |
| J26 | S | —CH₃ | —CH₃ | —H |
| J27 | S | —CH₃ | —CF₃ | —H |
| J28 | S | —CH₃ | —OCH₃ | —H |
| J29 | S | —CH₃ | —OCH₂CH₃ | —H |
| J30 | S | —CH₃ | —OCF₃ | —H |
| J31 | S | —CH₃ | -tert-butyl | —H |
| J32 | S | —CH₃ | -iso-propyl | —H |
| J33 | S | —CH₃ | —CH₃ | —CH₃ |
| J34 | S | —CH₃ | —H | —H |
| J35 | S | —CH₃ | —H | —Cl |
| J36 | S | —CH₃ | —H | —Br |
| J37 | S | —CH₃ | —H | —F |
| J38 | S | —CH₃ | —H | —CH₃ |
| J39 | S | —CH₃ | —H | —CF₃ |
| J40 | S | —CH₃ | —H | —OCH₃ |
| J41 | S | —CH₃ | —H | —OCH₂CH₃ |
| J42 | S | —CH₃ | —H | —OCF₃ |
| J43 | S | —CH₃ | —H | -tert-butyl |
| J44 | S | —CH₃ | —H | -iso-propyl |
| J45 | S | —CF₃ | —Cl | —H |
| J46 | S | —CF₃ | —Br | —H |
| J47 | S | —CF₃ | —F | —H |
| J48 | S | —CF₃ | —CH₃ | —H |
| J49 | S | —CF₃ | —CF₃ | —H |
| J50 | S | —CF₃ | —OCH₃ | —H |
| J51 | S | —CF₃ | —OCH₂CH₃ | —H |
| J52 | S | —CF₃ | —OCF₃ | —H |
| J53 | S | —CF₃ | -tert-butyl | —H |
| J54 | S | —CF₃ | iso-propyl | —H |
| J55 | S | —CF₃ | —CH₃ | —CH₃ |
| J56 | S | —CF₃ | —H | —H |
| J57 | S | —CF₃ | —H | —Cl |
| J58 | S | —CF₃ | —H | —Br |
| J59 | S | —CF₃ | —H | —F |
| J60 | S | —CF₃ | —H | —CH₃ |
| J61 | S | —CF₃ | —H | —CF₃ |
| J62 | S | —CF₃ | —H | —OCH₃ |
| J63 | S | —CF₃ | —H | —OCH₂CH₃ |
| J64 | S | —CF₃ | —H | —OCF₃ |
| J65 | S | —CF₃ | —H | -tert-butyl |
| J66 | S | —CF₃ | —H | -iso-propyl |
| J67 | S | —CHF₂ | —Cl | —H |
| J68 | S | —CHF₂ | —Br | —H |
| J69 | S | —CHF₂ | —F | —H |
| J70 | S | —CHF₂ | —CH₃ | —H |
| J71 | S | —CHF₂ | —CF₃ | —H |
| J72 | S | —CHF₂ | —OCH₃ | —H |
| J73 | S | —CHF₂ | —OCH₂CH₃ | —H |
| J74 | S | —CHF₂ | —OCF₃ | —H |
| J75 | S | —CHF₂ | -tert-butyl | —H |
| J76 | S | —CHF₂ | -iso-propyl | —H |
| J77 | S | —CHF₂ | —CH₃ | —CH₃ |
| J78 | S | —CHF₂ | —H | —H |
| J79 | S | —CHF₂ | —H | —Cl |
| J80 | S | —CHF₂ | —H | —Br |
| J81 | S | —CHF₂ | —H | —F |
| J82 | S | —CHF₂ | —H | —CH₃ |
| J83 | S | —CHF₂ | —H | —CF₃ |
| J84 | S | —CHF₂ | —H | —OCH₃ |
| J85 | S | —CHF₂ | —H | —OCH₂CH₃ |
| J86 | S | —CHF₂ | —H | —OCF₃ |
| J87 | S | —CHF₂ | —H | -tert-butyl |
| J88 | S | —CHF₂ | —H | -iso-propyl |
| J89 | S | —Br | —Br | —H |
| J90 | S | —Br | —Cl | —H |
| J91 | S | —Br | —F | —H |
| J92 | S | —Br | —CH₃ | —H |
| J93 | S | —Br | —CF₃ | —H |
| J94 | S | —Br | —OCH₃ | —H |
| J95 | S | —Br | —OCH₂CH₃ | —H |
| J96 | S | —Br | —OCF₃ | —H |
| J97 | S | —Br | -tert-butyl | —H |
| J98 | S | —Br | -iso-propyl | —H |
| J99 | S | —Br | —CH₃ | —CH₃ |
| J100 | S | —Br | —H | —H |

TABLE 10-continued

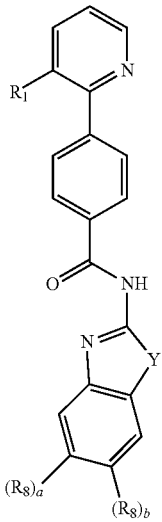

(IIb)

and pharmaceutically acceptable salts thereof, where:

| Compound | Y | R₁ | (R₈)ₐ | (R₈)ᵦ |
|---|---|---|---|---|
| J101 | S | —Br | —H | —Cl |
| J102 | S | —Br | —H | —Br |
| J103 | S | —Br | —H | —F |
| J104 | S | —Br | —H | —CH₃ |
| J105 | S | —Br | —H | —CF₃ |
| J106 | S | —Br | —H | —OCH₃ |
| J107 | S | —Br | —H | —OCH₂CH₃ |
| J108 | S | —Br | —H | —OCF₃ |
| J109 | S | —Br | —H | -tert-butyl |
| J110 | S | —Br | —H | -iso-propyl |
| J111 | S | —I | —Cl | —H |
| J112 | S | —I | —Br | —H |
| J113 | S | —I | —F | —H |
| J114 | S | —I | —CH₃ | —H |
| J115 | S | —I | —CF₃ | —H |
| J116 | S | —I | —OCH₃ | —H |
| J117 | S | —I | —OCH₂CH₃ | —H |
| J118 | S | —I | —OCF₃ | —H |
| J119 | S | —I | -tert-butyl | —H |
| J120 | S | —I | -iso-propyl | —H |
| J121 | S | —I | —CH₃ | —CH₃ |
| J122 | S | —I | —H | —H |
| J123 | S | —I | —H | —Cl |
| J124 | S | —I | —H | —Br |
| J125 | S | —I | —H | —F |
| J126 | S | —I | —H | —CH₃ |
| J127 | S | —I | —H | —CF₃ |
| J128 | S | —I | —H | —OCH₃ |
| J129 | S | —I | —H | —OCH₂CH₃ |
| J130 | S | —I | —H | —OCF₃ |
| J131 | S | —I | —H | -tert-butyl |
| J132 | S | —I | —H | -iso-propyl |
| J133 | O | —Cl | —Cl | —H |
| J134 | O | —Cl | —Br | —H |
| J135 | O | —Cl | —F | —H |
| J136 | O | —Cl | —CH₃ | —H |
| J137 | O | —Cl | —CF₃ | —H |
| J138 | O | —Cl | —OCH₃ | —H |
| J139 | O | —Cl | —OCH₂CH₃ | —H |
| J140 | O | —Cl | —OCF₃ | —H |
| J141 | O | —Cl | -tert-butyl | —H |
| J142 | O | —Cl | -iso-propyl | —H |
| J143 | O | —Cl | —CH₃ | —CH₃ |
| J144 | O | —Cl | —H | —H |
| J145 | O | —Cl | —H | —CH₃ |
| J146 | O | —Cl | —H | —Cl |
| J147 | O | —Cl | —H | —Br |
| J148 | O | —Cl | —H | —F |
| J149 | O | —Cl | —H | —CF₃ |
| J150 | O | —Cl | —H | —OCH₃ |
| J151 | O | —Cl | —H | —OCH₂CH₃ |
| J152 | O | —Cl | —H | —OCF₃ |
| J153 | O | —Cl | —H | -tert-butyl |
| J154 | O | —Cl | —H | -iso-propyl |
| J155 | O | —CH₃ | —Cl | —H |
| J156 | O | —CH₃ | —Br | —H |
| J157 | O | —CH₃ | —F | —H |
| J158 | O | —CH₃ | —CH₃ | —H |
| J159 | O | —CH₃ | —CF₃ | —H |
| J160 | O | —CH₃ | —OCH₃ | —H |
| J161 | O | —CH₃ | —OCH₂CH₃ | —H |
| J162 | O | —CH₃ | —OCF₃ | —H |
| J163 | O | —CH₃ | -tert-butyl | —H |
| J164 | O | —CH₃ | -iso-propyl | —H |
| J165 | O | —CH₃ | —CH₃ | —CH₃ |
| J166 | O | —CH₃ | —H | —H |
| J167 | O | —CH₃ | —H | —Cl |
| J168 | O | —CH₃ | —H | —Br |
| J169 | O | —CH₃ | —H | —F |
| J170 | O | —CH₃ | —H | —CH₃ |
| J171 | O | —CH₃ | —H | —CF₃ |
| J172 | O | —CH₃ | —H | —OCH₃ |
| J173 | O | —CH₃ | —H | —OCH₂CH₃ |
| J174 | O | —CH₃ | —H | —OCF₃ |
| J175 | O | —CH₃ | —H | -tert-butyl |
| J176 | O | —CH₃ | —H | -iso-propyl |
| J177 | O | —CF₃ | —Cl | —H |
| J178 | O | —CF₃ | —Br | —H |
| J179 | O | —CF₃ | —F | —H |
| J180 | O | —CF₃ | —CH₃ | —H |
| J181 | O | —CF₃ | —CF₃ | —H |
| J182 | O | —CF₃ | —OCH₃ | —H |
| J183 | O | —CF₃ | —OCH₂CH₃ | —H |
| J184 | O | —CF₃ | —OCF₃ | —H |
| J185 | O | —CF₃ | -tert-butyl | —H |
| J186 | O | —CF₃ | -iso-propyl | —H |
| J187 | O | —CF₃ | —CH₃ | —CH₃ |
| J188 | O | —CF₃ | —H | —H |
| J189 | O | —CF₃ | —H | —Cl |
| J190 | O | —CF₃ | —H | —Br |
| J191 | O | —CF₃ | —H | —F |
| J192 | O | —CF₃ | —H | —CH₃ |
| J193 | O | —CF₃ | —H | —CF₃ |
| J194 | O | —CF₃ | —H | —OCH₃ |
| J195 | O | —CF₃ | —H | —OCH₂CH₃ |
| J196 | O | —CF₃ | —H | —OCF₃ |
| J197 | O | —CF₃ | —H | -tert-butyl |
| J198 | O | —CF₃ | —H | -iso-propyl |
| J199 | O | —CHF₂ | —Cl | —H |
| J200 | O | —CHF₂ | —Br | —H |

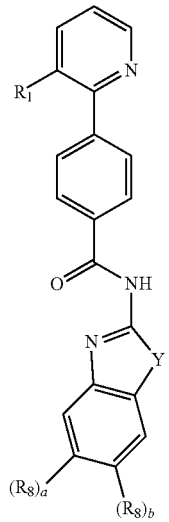

TABLE 10-continued

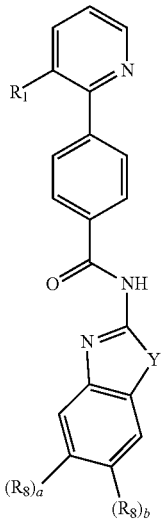

(IIb)

and pharmaceutically acceptable salts thereof, where:

| Compound | Y | R₁ | (R₈)ₐ | (R₈)ᵦ |
|---|---|---|---|---|
| J201 | O | —CHF₂ | —F | —H |
| J202 | O | —CHF₂ | —CH₃ | —H |
| J203 | O | —CHF₂ | —CF₃ | —H |
| J204 | O | —CHF₂ | —OCH₃ | —H |
| J205 | O | —CHF₂ | —OCH₂CH₃ | —H |
| J206 | O | —CHF₂ | —OCF₃ | —H |
| J207 | O | —CHF₂ | -tert-butyl | —H |
| J208 | O | —CHF₂ | -iso-propyl | —H |
| J209 | O | —CHF₂ | —CH₃ | —CH₃ |
| J210 | O | —CHF₂ | —H | —H |
| J211 | O | —CHF₂ | —H | —Cl |
| J212 | O | —CHF₂ | —H | —Br |
| J213 | O | —CHF₂ | —H | —F |
| J214 | O | —CHF₂ | —H | —CH₃ |
| J215 | O | —CHF₂ | —H | —CF₃ |
| J216 | O | —CHF₂ | —H | —OCH₃ |
| J217 | O | —CHF₂ | —H | —OCH₂CH₃ |
| J218 | O | —CHF₂ | —H | —OCF₃ |
| J219 | O | —CHF₂ | —H | -tert-butyl |
| J220 | O | —CHF₂ | —H | -iso-propyl |
| J221 | O | —Br | —Br | —H |
| J222 | O | —Br | —Cl | —H |
| J223 | O | —Br | —F | —H |
| J224 | O | —Br | —CH₃ | —H |
| J225 | O | —Br | —CF₃ | —H |
| J226 | O | —Br | —OCH₃ | —H |
| J227 | O | —Br | —OCH₂CH₃ | —H |
| J228 | O | —Br | —OCF₃ | —H |
| J229 | O | —Br | -tert-butyl | —H |
| J230 | O | —Br | -iso-propyl | —H |
| J231 | O | —Br | —CH₃ | —CH₃ |
| J232 | O | —Br | —H | —H |
| J233 | O | —Br | —H | —Cl |
| J234 | O | —Br | —H | —Br |
| J235 | O | —Br | —H | —F |
| J236 | O | —Br | —H | —CH₃ |
| J237 | O | —Br | —H | —CF₃ |
| J238 | O | —Br | —H | —OCH₃ |
| J239 | O | —Br | —H | —OCH₂CH₃ |
| J240 | O | —Br | —H | —OCF₃ |
| J241 | O | —Br | —H | -tert-butyl |
| J242 | O | —Br | —H | -iso-propyl |
| J243 | O | —I | —Cl | —H |
| J244 | O | —I | —Br | —H |
| J245 | O | —I | —F | —H |
| J246 | O | —I | —CH₃ | —H |
| J247 | O | —I | —CF₃ | —H |
| J248 | O | —I | —OCH₃ | —H |
| J249 | O | —I | —OCH₂CH₃ | —H |
| J250 | O | —I | —OCF₃ | —H |
| J251 | O | —I | -tert-butyl | —H |
| J252 | O | —I | -iso-propyl | —H |
| J253 | O | —I | —CH₃ | —CH₃ |
| J254 | O | —I | —H | —H |
| J255 | O | —I | —H | —Cl |
| J256 | O | —I | —H | —Br |
| J257 | O | —I | —H | —F |
| J258 | O | —I | —H | —CH₃ |
| J259 | O | —I | —H | —CF₃ |
| J260 | O | —I | —H | —OCH₃ |
| J261 | O | —I | —H | —OCH₂CH₃ |
| J262 | O | —I | —H | —OCF₃ |
| J263 | O | —I | —H | -tert-butyl |
| J264 | O | —I | —H | -iso-propyl |
| J265 | NH | —Cl | —Cl | —H |
| J266 | NH | —Cl | —Br | —H |
| J267 | NH | —Cl | —F | —H |
| J268 | NH | —Cl | —CH₃ | —H |
| J269 | NH | —Cl | —CF₃ | —H |
| J270 | NH | —Cl | —OCH₃ | —H |
| J271 | NH | —Cl | —OCH₂CH₃ | —H |
| J272 | NH | —Cl | —OCF₃ | —H |
| J273 | NH | —Cl | -tert-butyl | —H |
| J274 | NH | —Cl | iso-propyl | —H |
| J275 | NH | —Cl | —CH₃ | —CH₃ |
| J276 | NH | —Cl | —H | —H |
| J277 | NH | —Cl | —H | —CH₃ |
| J278 | NH | —Cl | —H | —Cl |
| J279 | NH | —Cl | —H | —Br |
| J280 | NH | —Cl | —H | —F |
| J281 | NH | —Cl | —H | —CF₃ |
| J282 | NH | —Cl | —H | —OCH₃ |
| J283 | NH | —Cl | —H | —OCH₂CH₃ |
| J284 | NH | —Cl | —H | —OCF₃ |
| J285 | NH | —Cl | —H | -tert-butyl |
| J286 | NH | —Cl | —H | -iso-propyl |
| J287 | NH | —CH₃ | —Cl | —H |
| J288 | NH | —CH₃ | —Br | —H |
| J289 | NH | —CH₃ | —F | —H |
| J290 | NH | —CH₃ | —CH₃ | —H |
| J291 | NH | —CH₃ | —CF₃ | —H |
| J292 | NH | —CH₃ | —OCH₃ | —H |
| J293 | NH | —CH₃ | —OCH₂CH₃ | —H |
| J294 | NH | —CH₃ | —OCF₃ | —H |
| J295 | NH | —CH₃ | -tert-butyl | —H |
| J296 | NH | —CH₃ | -iso-propyl | —H |
| J297 | NH | —CH₃ | —CH₃ | —CH₃ |
| J298 | NH | —CH₃ | —H | —H |
| J299 | NH | —CH₃ | —H | —Cl |
| J300 | NH | —CH₃ | —H | —Br |

TABLE 10-continued

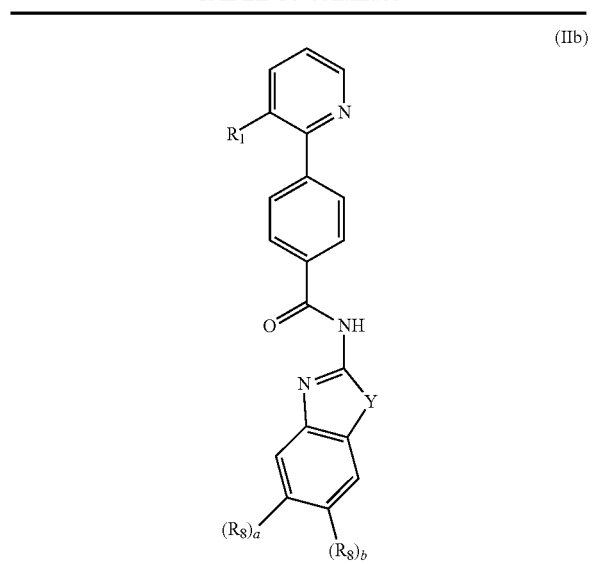

(IIb)

and pharmaceutically acceptable salts thereof, where:

| Compound | Y | R$_1$ | (R$_8$)$_a$ | (R$_8$)$_b$ |
|---|---|---|---|---|
| J301 | NH | —CH$_3$ | —H | —F |
| J302 | NH | —CH$_3$ | —H | —CH$_3$ |
| J303 | NH | —CH$_3$ | —H | —CF$_3$ |
| J304 | NH | —CH$_3$ | —H | —OCH$_3$ |
| J305 | NH | —CH$_3$ | —H | —OCH$_2$CH$_3$ |
| J306 | NH | —CH$_3$ | —H | —OCF$_3$ |
| J307 | NH | —CH$_3$ | —H | -tert-butyl |
| J308 | NH | —CH$_3$ | —H | -iso-propyl |
| J309 | NH | —CF$_3$ | —Cl | —H |
| J310 | NH | —CF$_3$ | —Br | —H |
| J311 | NH | —CF$_3$ | —F | —H |
| J312 | NH | —CF$_3$ | —CH$_3$ | —H |
| J313 | NH | —CF$_3$ | —CF$_3$ | —H |
| J314 | NH | —CF$_3$ | —OCH$_3$ | —H |
| J315 | NH | —CF$_3$ | —OCH$_2$CH$_3$ | —H |
| J316 | NH | —CF$_3$ | —OCF$_3$ | —H |
| J317 | NH | —CF$_3$ | -tert-butyl | —H |
| J318 | NH | —CF$_3$ | -iso-propyl | —H |
| J319 | NH | —CF$_3$ | —CH$_3$ | —CH$_3$ |
| J320 | NH | —CF$_3$ | —H | —H |
| J321 | NH | —CF$_3$ | —H | —Cl |
| J322 | NH | —CF$_3$ | —H | —Br |
| J323 | NH | —CF$_3$ | —H | —F |
| J324 | NH | —CF$_3$ | —H | —CH$_3$ |
| J325 | NH | —CF$_3$ | —H | —CF$_3$ |
| J326 | NH | —CF$_3$ | —H | —OCH$_3$ |
| J327 | NH | —CF$_3$ | —H | —OCH$_2$CH$_3$ |
| J328 | NH | —CF$_3$ | —H | —OCF$_3$ |
| J329 | NH | —CF$_3$ | —H | -tert-butyl |
| J330 | NH | —CF$_3$ | —H | -iso-propyl |
| J331 | NH | —CHF$_2$ | —Cl | —H |
| J332 | NH | —CHF$_2$ | —Br | —H |
| J333 | NH | —CHF$_2$ | —F | —H |
| J334 | NH | —CHF$_2$ | —CH$_3$ | —H |
| J335 | NH | —CHF$_2$ | —CF$_3$ | —H |
| J336 | NH | —CHF$_2$ | —OCH$_3$ | —H |
| J337 | NH | —CHF$_2$ | —OCH$_2$CH$_3$ | —H |
| J338 | NH | —CHF$_2$ | —OCF$_3$ | —H |
| J339 | NH | —CHF$_2$ | -tert-butyl | —H |
| J340 | NH | —CHF$_2$ | -iso-propyl | —H |
| J341 | NH | —CHF$_2$ | —CH$_3$ | —CH$_3$ |
| J342 | NH | —CHF$_2$ | —H | —H |
| J343 | NH | —CHF$_2$ | —H | —Cl |
| J344 | NH | —CHF$_2$ | —H | —Br |
| J345 | NH | —CHF$_2$ | —H | —F |
| J346 | NH | —CHF$_2$ | —H | —CH$_3$ |
| J347 | NH | —CHF$_2$ | —H | —CF$_3$ |
| J348 | NH | —CHF$_2$ | —H | —OCH$_3$ |
| J349 | NH | —CHF$_2$ | —H | —OCH$_2$CH$_3$ |
| J350 | NH | —CHF$_2$ | —H | —OCF$_3$ |

TABLE 10-continued

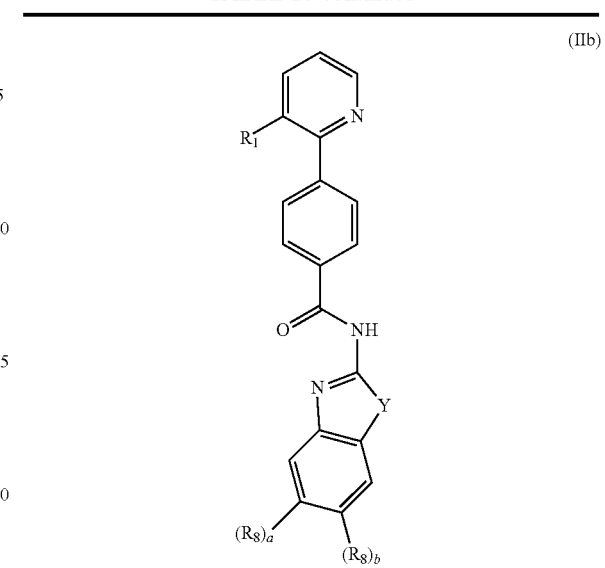

(IIb)

and pharmaceutically acceptable salts thereof, where:

| Compound | Y | R$_1$ | (R$_8$)$_a$ | (R$_8$)$_b$ |
|---|---|---|---|---|
| J351 | NH | —CHF$_2$ | —H | -tert-butyl |
| J352 | NH | —CHF$_2$ | —H | -iso-propyl |
| J353 | NH | —Br | —Br | —H |
| J354 | NH | —Br | —Cl | —H |
| J355 | NH | —Br | —F | —H |
| J356 | NH | —Br | —CH$_3$ | —H |
| J357 | NH | —Br | —CF$_3$ | —H |
| J358 | NH | —Br | —OCH$_3$ | —H |
| J359 | NH | —Br | —OCH$_2$CH$_3$ | —H |
| J360 | NH | —Br | —OCF$_3$ | —H |
| J361 | NH | —Br | -tert-butyl | —H |
| J362 | NH | —Br | -iso-propyl | —H |
| J363 | NH | —Br | —CH$_3$ | —CH$_3$ |
| J364 | NH | —Br | —H | —H |
| J365 | NH | —Br | —H | —Cl |
| J366 | NH | —Br | —H | —Br |
| J367 | NH | —Br | —H | —F |
| J368 | NH | —Br | —H | —CH$_3$ |
| J369 | NH | —Br | —H | —CF$_3$ |
| J370 | NH | —Br | —H | —OCH$_3$ |
| J371 | NH | —Br | —H | —OCH$_2$CH$_3$ |
| J372 | NH | —Br | —H | —OCF$_3$ |
| J373 | NH | —Br | —H | -tert-butyl |
| J374 | NH | —Br | —H | -iso-propyl |
| J375 | NH | —I | —Cl | —H |
| J376 | NH | —I | —Br | —H |
| J377 | NH | —I | —F | —H |
| J378 | NH | —I | —CH$_3$ | —H |
| J379 | NH | —I | —CF$_3$ | —H |
| J380 | NH | —I | —OCH$_3$ | —H |
| J381 | NH | —I | —OCH$_2$CH$_3$ | —H |
| J382 | NH | —I | —OCF$_3$ | —H |
| J383 | NH | —I | -tert-butyl | —H |
| J384 | NH | —I | -iso-propyl | —H |
| J385 | NH | —I | —CH$_3$ | —CH$_3$ |
| J386 | NH | —I | —H | —H |
| J387 | NH | —I | —H | —Cl |
| J388 | NH | —I | —H | —Br |
| J389 | NH | —I | —H | —F |
| J390 | NH | —I | —H | —CH$_3$ |
| J391 | NH | —I | —H | —CF$_3$ |
| J392 | NH | —I | —H | —OCH$_3$ |
| J393 | NH | —I | —H | —OCH$_2$CH$_3$ |
| J394 | NH | —I | —H | —OCF$_3$ |
| J395 | NH | —I | —H | -tert-butyl |
| J396 | NH | —I | —H | -iso-propyl |

4.4 Definitions

As used in connection with the Phenylene Compounds herein, the terms used herein having following meaning:

"—$(C_1-C_{10})$alkyl" means a straight chain or branched non-cyclic hydrocarbon having from 1 to 10 carbon atoms. Representative straight chain —$(C_1-C_{10})$alkyls include -methyl, -ethyl, -n-propyl, -n-butyl, -n-pentyl, -n-hexyl, -n-heptyl, -n-octyl, -n-nonyl, and -n-decyl. Representative branched —$(C_1-C_{10})$alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—$(C_1-C_6)$alkyl" means a straight chain or branched non-cyclic hydrocarbon having from 1 to 6 carbon atoms. Representative straight chain —$(C_1-C_6)$alkyls include -methyl, -ethyl, -n-propyl, -n-butyl, -n-pentyl, and -n-hexyl. Representative branched —$(C_1-C_6)$alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

"—$(C_1-C_4)$alkyl" means a straight chain or branched non-cyclic hydrocarbon having from 1 to 4 carbon atoms. Representative straight chain —$(C_1-C_4)$alkyls include -methyl, -ethyl, -n-propyl, and -n-butyl. Representative branched —$(C_1-C_4)$alkyls include -iso-propyl, -sec-butyl, -iso-butyl, and -tert-butyl.

"—$(C_2-C_{10})$alkenyl" means a straight chain or branched non-cyclic hydrocarbon having from 2 to 10 carbon atoms and including at least one carbon-carbon double bond. Representative straight chain and branched $(C_2-C_{10})$alkenyls include -vinyl, -allyl, -1-butenyl, -2-butenyl, -iso-butylenyl, -1-pentenyl, -2-pentenyl, -3-methyl-1-butenyl, methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

"—$(C_2-C_6)$alkenyl" means a straight chain or branched non-cyclic hydrocarbon having from 2 to 6 carbon atoms and including at least one carbon-carbon double bond. Representative straight chain and branched $(C_2-C_6)$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, 2-hexenyl, 3-hexenyl and the like.

"—$(C_2-C_{10})$alkynyl" means a straight chain or branched non-cyclic hydrocarbon having from 2 to 10 carbon atoms and including at least one carbon-carbon triple bond. Representative straight chain and branched —$(C_2-C_{10})$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl and the like.

"—$(C_2-C_6)$alkynyl" means a straight chain or branched non-cyclic hydrocarbon having from 2 to 6 carbon atoms and including at least one carbon-carbon triple bond. Representative straight chain and branched $(C_2-C_6)$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl and the like.

"—$(C_3-C_{10})$cycloalkyl" means a saturated cyclic hydrocarbon having from 3 to 10 carbon atoms. Representative $(C_3-C_{10})$cycloalkyls are -cyclopropyl, -cyclobutyl, -cyclopentyl, -cyclohexyl, -cycloheptyl, -cyclooctyl, -cyclononyl, and -cyclodecyl.

"—$(C_3-C_8)$cycloalkyl" means a saturated cyclic hydrocarbon having from 3 to 8 carbon atoms. Representative $(C_3-C_8)$ cycloalkyls include -cyclopropyl, -cyclobutyl, -cyclopentyl, -cyclohexyl, -cycloheptyl, and -cyclooctyl.

"—$(C_8-C_{14})$bicycloalkyl" means a bi-cyclic hydrocarbon ring system having from 8 to 14 carbon atoms and at least one saturated cyclic alkyl ring. Representative —$(C_8-C_{14})$bicycloalkyls include -indanyl, -1,2,3,4-tetrahydronaphthyl, -5,6,7,8-tetrahydronaphthyl, -perhydronaphthyl and the like.

"—$(C_8-C_{14})$tricycloalkyl" means a tri-cyclic hydrocarbon ring system having from 8 to 14 carbon atoms and at least one saturated cyclic alkyl ring. Representative —$(C_8-C_{14})$tricycloalkyls include -pyrenyl, -1,2,3,4-tetrahydroanthracenyl, -perhydroanthracenyl -aceanthreneyl, -1,2,3,4-tetrahydropenanthrenyl, -5,6,7,8-tetrahydrophenanthrenyl, -perhydrophenanthrenyl and the like.

"—$(C_5-C_{10})$cycloalkenyl" means a cyclic non-aromatic hydrocarbon having at least one carbon-carbon double bond in the cyclic system and from 5 to 10 carbon atoms. Representative $(C_5-C_{10})$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl and the like.

"—$(C_5-C_8)$cycloalkenyl" means a cyclic non-aromatic hydrocarbon having at least one carbon-carbon double bond in the cyclic system and from 5 to 8 carbon atoms. Representative $(C_5-C_8)$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl and the like.

"—$(C_8-C_{14})$bicycloalkenyl" means a bi-cyclic hydrocarbon ring system having at least one carbon-carbon double bond in each ring and from 8 to 14 carbon atoms. Representative —$(C_8-C_{14})$bicycloalkenyls include -indenyl, -pentalenyl, -naphthalenyl, -azulenyl, -heptalenyl, -1,2,7,8-tetrahydronaphthalenyl and the like.

"—$(C_8-C_{14})$tricycloalkenyl" means a tri-cyclic hydrocarbon ring system having at least one carbon-carbon double bond in each ring and from 8 to 14 carbon atoms. Representative —$(C_8-C_{14})$tricycloalkenyls include -anthracenyl, -phenanthrenyl, -phenalenyl, -acenaphthalenyl, as-indacenyl, s-indacenyl and the like.

"—(3- to 7-membered)heterocycle" or "-(3- to 7-membered)heterocyclo" means a 3- to 7-membered monocyclic heterocyclic ring which is either saturated, unsaturated non-aromatic, or aromatic. A 3- or a 4-membered heterocycle can contain up to 3 heteroatoms, a 5-membered heterocycle can contain up to 4 heteroatoms, a 6-membered heterocycle can contain up to 6 heteroatoms, and a 7-membered heterocycle can contain up to 7 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative-(3- to 7-membered)heterocycles include pyridyl, furyl, thiophenyl, pyrrolyl, oxazolyl, imidazolyl, thiazolyl, thiadiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl and the like.

"-(3- to 5-membered)heterocycle" or "-(3- to 5-membered)heterocyclo" means a 3- to 5-membered monocyclic heterocyclic ring which is either saturated, unsaturated non-aromatic, or aromatic. A 3- or a 4-membered heterocycle can contain up to 3 heteroatoms, and a 5-membered heterocycle can contain up to 4 heteroatoms. Each heteroatom is independently selected from nitrogen, which can be quaternized; oxygen; and sulfur, including sulfoxide and sulfone. The -(3- to 5-membered)heterocycle can be attached via a nitrogen or carbon atom. Representative -(3- to 5-membered)heterocycles include furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl, tetrahydrothiophenyl and the like.

"-(7- to 10-membered)bicycloheterocycle" or "-(7- to 10-membered)bicycloheterocyclo" means a 7- to 10-membered bicyclic, heterocyclic ring which is either saturated, unsaturated non-aromatic, or aromatic. A -(7- to 10-membered)bicycloheterocycle contains from 1 to 4 heteroatoms independently selected from nitrogen, which can be quaternized; oxygen; and sulfur, including sulfoxide and sulfone. The -(7- to 10-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, -β-carbolinyl and the like.

"—(C$_{14}$)aryl" means a 14-membered aromatic carbocyclic moiety such as -anthryl or -phenanthryl.

"-(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur. In one embodiment, one of the -(5- to 10-membered)heteroaryl's rings contain at least one carbon atom. In another embodiment, both of the -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidyl, pyrimidinyl, thiadiazolyl, triazinyl, cinnolinyl, phthalazinyl, and quinazolinyl.

"—CH$_2$(halo)" means a methyl group where one of the hydrogens of the methyl group has been replaced with a halogen. Representative —CH$_2$(halo) groups include —CH$_2$F, —CH$_2$Cl, —CH$_2$Br, and —CH$_2$I.

"—CH(halo)$_2$" means a methyl group where two of the hydrogens of the methyl group have been replaced with a halogen. Representative —CH(halo)$_2$ groups include —CHF$_2$, —CHCl$_2$, —CHBr$_2$, —CHBrCl, —CHClI, and —CHI$_2$.

"—C(halo)$_3$" means a methyl group where each of the hydrogens of the methyl group has been replaced with a halogen. Representative —C(halo)$_3$ groups include —CF$_3$, —CCl$_3$, —CBr$_3$, and —CI$_3$.

"-Halogen" or "-halo" means —F, —Cl, —Br, or —I.

The phrase "pyridyl group" means

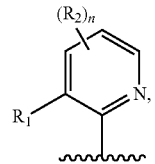

where $R_1$, $R_2$, and n are defined above for the Phenylene Compounds of formula (II).

The phrase "pyrazinyl group" means,

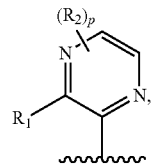

where $R_1$, $R_2$, and p are defined above for the Phenylene Compounds of formula (I).

The phrase "pyrimidinyl group" means

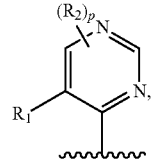

where $R_1$, $R_2$, and p are defined above for the Phenylene Compounds of formula (I).

The phrase "pyridazinyl group" means

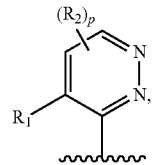

where $R_1$, $R_2$, and p are defined above for the Phenylene Compounds of formula (I).

The phrase "thiadiazolyl group" means

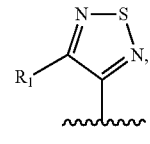

where $R_1$ is defined above for the Phenylene Compounds of formula (I).

The phrase "benzoimidiazolyl group" means

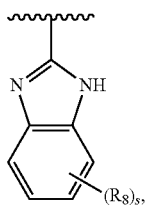

where $R_8$ and s are defined above for the Phenylene Compounds of formula (I) or (II).

The phrase "benzothiazolyl group" means

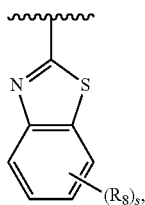

where $R_8$ and s are defined above for the Phenylene Compounds of formula (I) or (II).

The phrase "benzooxazolyl group" means

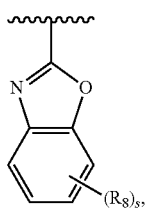

where $R_8$ and s are defined above for the Phenylene Compounds of formula (I) or (II).

The phrase "phenylene ring" means

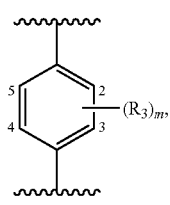

where $R_3$ and m are defined above for the Phenylene Compounds of formula (I) and the numbers designate the position of each atom of the phenylene ring.

The term "animal" includes, but is not limited to, a cow, monkey, baboon, chimpanzee, horse, sheep, pig, chicken, turkey, quail, cat, dog, mouse, rat, rabbit, guinea pig, and human.

The phrase "pharmaceutically acceptable salt," as used herein, is any pharmaceutically acceptable salt that can be prepared from a Phenylene Compound including a salt formed from an acid and a basic functional group, such as a nitrogen group, of one of the Phenylene Compounds. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a Phenylene Compound having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine and the like.

The phrase "effective amount," when used in connection with a Phenylene Compound means an amount effective for: (a) treating or preventing a Condition; or (b) inhibiting VR1, mGluR1, or mGluR5 function in a cell.

The phrase "effective amount," when used in connection with another therapeutic agent means an amount for providing the therapeutic effect of the therapeutic agent.

When a first group is "substituted with one or more" second groups, one or more hydrogen atoms of the first group is replaced with a corresponding number of second groups. When the number of second groups is two or greater, each second group can be the same or different. In one embodiment, the number of second groups is one or two. In another embodiment, the number of second groups is one.

The term "EtOAc" means ethyl acetate.

The term "THF" means tetrahydrofuran.

The term "DMF" means dimethylformamide.

The term "HOBT" means 1-hydroxybenzotriazole hydrate.

The term "EDCI" means 1-ethyl-3-[3-(dimethylamino) propyl]carbodiimide.

The term "IBD" means inflammatory-bowel disease.

The term "IBS" means irritable-bowel syndrome.

The term "ALS" means amyotrophic lateral sclerosis.

The phrases "treatment of," "treating" and the like include the amelioration or cessation of a Condition or a symptom thereof.

In one embodiment, treating includes inhibiting, for example, decreasing the overall frequency of episodes of a Condition or a symptom thereof.

The phrases "prevention of," "preventing" and the like include the avoidance of the onset of a Condition or a symptom thereof.

4.5 Methods for Making the Phenylene Compounds

The Phenylene Compounds can be made using conventional organic synthesis including the following illustrative methods shown in the schemes below.

4.5.1 Methods for Making the Phenylene Compounds where X is O
The Phenylene Compounds where X is O can be obtained by the following illustrative method shown below in Scheme 1.
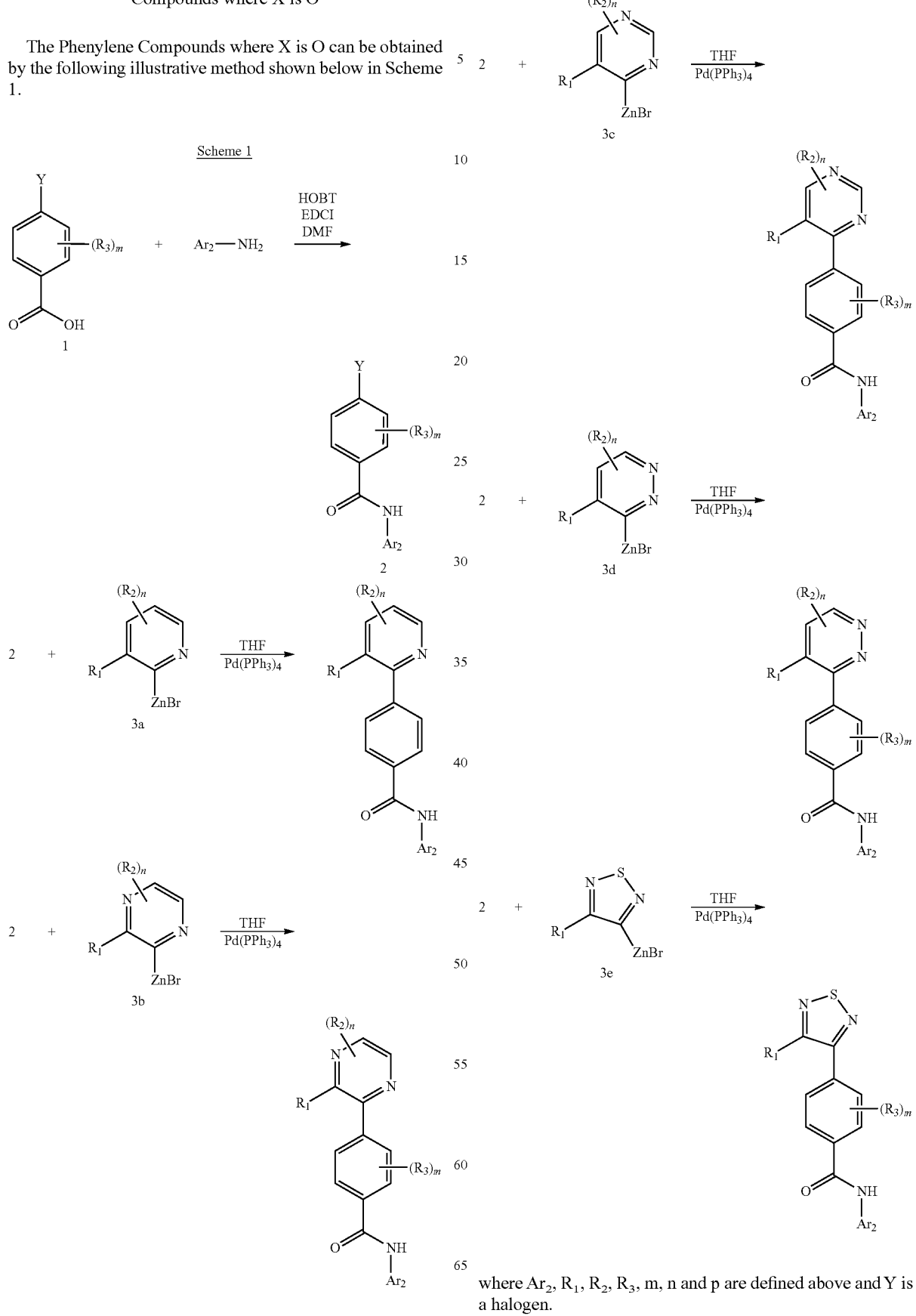
where $Ar_2$, $R_1$, $R_2$, $R_3$, m, n and p are defined above and Y is a halogen.

To a solution of a 4-halobenzoic acid 1 in DMF (0.22 M) is added 1 equivalent of amine $Ar_2$—$NH_2$, and the resulting solution is allowed to stir for about 5 min at a temperature of about 25° C. To the resulting solution is then added 1 equivalent of HOBT and 1 eq. of EDCI, and the resulting mixture is allowed to stir for about 6 h at a temperature of about 25° C. Typically, a solid forms during stirring and the reaction mixture is filtered to remove the resultant solid. If a solid does not form the reaction mixture is diluted with 2N aq. sodium hydroxide and extracted between 2 and 3 times with EtOAc, the organic layers are combined, dried (with $Na_2SO_4$), and the solvent removed under reduced pressure to provide a residue. The residue is then washed with methanol and dried under reduced pressure. The solid or residue is then suspended in THF (0.04 moles/liter) under an argon atmosphere and about 3 equivalent of zinc bromide 3a-e and about 0.05 equivalent of $Pd(PPh_3)_4$ are added to the suspension. The suspension is allowed to stir for about 2 h at a temperature of about 70° C. The solvent is then removed under reduced pressure to provide a solid that is purified using a silica gel column eluted with an ethyl acetate/hexane gradient to provide the Phenylene Compound where X is O.

If the compound of formula 2 is substituted with a hydroxyl or amino group, the hydroxyl or amino group is protected using a suitable protecting group before being reacted with zinc bromide 3a-e. Similarly, if $R_2$ is a hydroxyl or amino group, the hydroxyl or amino group is protected before forming the zinc bromide reagent. Suitable protecting groups for hydroxyl group include, but are not limited to, methyl ether, methoxymethyl ether, methoxythiomethyl ether, 2-methoxyethoxymethyl ether, bis(2-chloroethoxy)ethyl ether, tetrahydropyranyl ether, tetrahydrothiopyranyl ether, 4-methoxytetrahydropyranyl ether, methoxytetrahydrothiopyranyl ether, tetrahydrofuranyl ether, tetrahydrothiofuranyl ether, 1-ethoxyethyl ether, 1-methyl-1-methoxyethyl ether, 2-(phenylselenyl ether), tert-butyl ether, allyl ether, benzyl ether, o-nitrobenzyl ether, triphenylmethyl ether, o-napthyldiphenylmethyl ether, p-methoxydiphenylmethyl ether, 9-(9-phenyl-10-oxo)anthryl ether (tritylone), trimethylsilyl ether, isopropyldimethylsilyl ether, tert-butyldimethylsilyl ether, tert-butyldiphenylsilyl ether, tribenzylsilyl ether, tri-isopropylsilyl ether, formate ester, acetate ester, trichloroacetate ester, phenoxyacetate ester, iso-butyrate ester, pivaloate ester, adamantoate ester, benzoate ester, 2,4,6-trimethyl (mesitoate) ester, methyl carbonate, 2,2,2-trichlorocarbonate, allyl carbonate, p-nitrophenyl carbonate, benzyl carbonate, p-nitrobenzyl carbonate, S-benzylthiocarbonate, N-phenylcarbamate, nitrate ester, and 2,4-dinitrophenylsulfenate ester (See, e.g., T. W. Greene, *Protective Groups in Organic Synthesis*, John Wiley-Interscience Publication, New York, (1981)). Suitable protecting groups for an amino group include, but are not limited to, 1,1-dimethyl-2,2,2-trichloroethyl carbamate, 1-methyl-1-(4-biphenylyl)ethyl carbamate, 2-trimethylsilylethyl carbamate, and tert-butyl carbamate (T. W. Greene et al., *Protective Groups in Organic Synthesis*, 309-405 (2d ed. 1991)).

The 4-halobenzoic acids 1 and the amines of formula $Ar_2NH_2$ are commercially available or can be prepared by methods known to those skilled in the art. Compounds of formula 3a-e can be prepared by methods known to those skilled in the art (See, M. B. Smith and J. March, *March's Advanced Organic Chemistry: Reaction Mechanisms and Structure*, 805-807 (5$^{th}$ ed. 2001); H. Fillon et al., *Tett. Lett.* 42:3843-46 (2001); M. Amadji et al., *Tetrahedron* 9:1657-60 (1998); and S. Billotte, *Synlett.* 379-380 (1998)).

4.5.2 Methods for Making the Phenylene Compounds where X is S

The Phenylene Compounds where X is S can be obtained by reacting a Phenylene Compound where X is O, prepared as described above in section 4.5.1, with Lawesson's reagent at a temperature of about 100° C. (See, M. B. Smith and J. March, *March's Advanced Organic Chemistry: Reaction Mechanisms and Structure*, 1184-1185 (5$^{th}$ ed. 2001)).

4.6 Therapeutic Uses of the Phenylene Compounds

In accordance with the invention, the Phenylene Compounds are administered to an animal in need of treatment or prevention of a Condition.

In one embodiment, an effective amount of a Phenylene Compound can be used to treat or prevent any condition treatable or preventable by inhibiting VR1. Examples of conditions that are treatable or preventable by inhibiting VR1 include, but are not limited to, pain, UI, an ulcer, IBD, and IBS.

In another embodiment, an effective amount of a Phenylene Compound can be used to treat or prevent any condition treatable or preventable by inhibiting mGluR5. Examples of conditions that are treatable or preventable by inhibiting mGluR5 include, but are not limited to, pain, an addictive disorder, Parkinson's disease, parkinsonism, anxiety, a pruritic condition, and psychosis.

In another embodiment, an effective amount of a Phenylene Compound can be used to treat or prevent any condition treatable or preventable by inhibiting mGluR1. Examples of conditions that are treatable or preventable by inhibiting mGluR1 include, but are not limited to, pain, UI, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, and depression.

The Phenylene Compounds can be used to treat or prevent acute or chronic pain. Examples of pain treatable or preventable using the Phenylene Compounds include, but are not limited to, cancer pain, labor pain, myocardial infarction pain, pancreatic pain, colic pain, post-operative pain, headache pain, muscle pain, arthritic pain, and pain associated with a periodontal disease, including gingivitis and periodontitis.

The Phenylene Compounds can also be used for treating or preventing pain associated with inflammation or with an inflammatory disease in an animal. Such pain can arise where there is an inflammation of the body tissue which can be a local inflammatory response and/or a systemic inflammation. For example, the Phenylene Compounds can be used to treat or prevent pain associated with inflammatory diseases including, but not limited to: organ transplant rejection; reoxygenation injury resulting from organ transplantation (see Grupp et al., *J. Mol, Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis;

chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. The Phenylene Compounds can also be used for treating or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The Phenylene Compounds can be used to treat or prevent UI. Examples of UI treatable or preventable using the Phenylene Compounds include, but are not limited to, urge incontinence, stress incontinence, overflow incontinence, neurogenic incontinence, and total incontinence.

The Phenylene Compounds can be used to treat or prevent an ulcer. Examples of ulcers treatable or preventable using the Phenylene Compounds include, but are not limited to, a duodenal ulcer, a gastric ulcer, a marginal ulcer, an esophageal ulcer, and a stress ulcer.

The Phenylene Compounds can be used to treat or prevent IBD, including Crohn's disease and ulcerative colitis.

The Phenylene Compounds can be used to treat or prevent IBS. Examples of IBS treatable or preventable using the Phenylene Compounds include, but are not limited to, spastic-colon-type IBS and constipation-predominant IBS.

The Phenylene Compounds can be used to treat or prevent an addictive disorder, including but not limited to, an eating disorder, an impulse-control disorder, an alcohol-related disorder, a nicotine-related disorder, an amphetamine-related disorder, a *cannabis*-related disorder, a cocaine-related disorder, an hallucinogen-related disorder, an inhalant-related disorders, and an opioid-related disorder, all of which are further sub-classified as listed below.

Eating disorders include, but are not limited to, Bulimia Nervosa, Nonpurging Type; Bulimia Nervosa, Purging Type; Anorexia; and Eating Disorder not otherwise specified (NOS).

Impulse control disorders include, but are not limited to, Intermittent Explosive Disorder, Kleptomania, Pyromania, Pathological Gambling, Trichotillomania, and Impulse Control Disorder not otherwise specified (NOS).

Alcohol-related disorders include, but are not limited to, Alcohol-Induced Psychotic Disorder with delusions, Alcohol Abuse, Alcohol Intoxication, Alcohol Withdrawal, Alcohol Intoxication Delirium, Alcohol Withdrawal Delirium, Alcohol-Induced Persisting Dementia, Alcohol-Induced Persisting Amnestic Disorder, Alcohol Dependence, Alcohol-Induced Psychotic Disorder with hallucinations, Alcohol-Induced Mood Disorder, Alcohol-Induced Anxiety Disorder, Alcohol-Induced Sexual Dysfunction, Alcohol-Induced Sleep Disorder, and Alcohol-Related Disorder not otherwise specified (NOS).

Nicotine-related disorders include, but are not limited to, Nicotine Dependence, Nicotine Withdrawal, and Nicotine-Related Disorder not otherwise specified (NOS).

Amphetamine-related disorders include, but are not limited to, Amphetamine Dependence, Amphetamine Abuse, Amphetamine Intoxication, Amphetamine Withdrawal, Amphetamine Intoxication Delirium, Amphetamine-Induced Psychotic Disorder with delusions, Amphetamine-Induced Psychotic Disorders with hallucinations, Amphetamine-Induced Mood Disorder, Amphetamine-Induced Anxiety Disorder, Amphetamine-Induced Sexual Dysfunction, Amphetamine-Induced Sleep Disorder, and Amphetamine Related Disorder not otherwise specified (NOS).

*Cannabis*-related disorders include, but are not limited to, *Cannabis* Dependence, *Cannabis* Abuse, *Cannabis* Intoxication, *Cannabis* Intoxication Delirium, *Cannabis*-Induced Psychotic Disorder with delusions, *Cannabis*-Induced Psychotic Disorder with hallucinations, *Cannabis*-Induced Anxiety Disorder, and *Cannabis* Related Disorder not otherwise specified (NOS).

Cocaine-related disorders include, but are not limited to, Cocaine Dependence, Cocaine Abuse, Cocaine Intoxication, Cocaine Withdrawal, Cocaine Intoxication Delirium, Cocaine-Induced Psychotic Disorder with delusions, Cocaine-Induced Psychotic Disorders with hallucinations, Cocaine-Induced Mood Disorder, Cocaine-Induced Anxiety Disorder, Cocaine-Induced Sexual Dysfunction, Cocaine-Induced Sleep Disorder, and Cocaine Related Disorder not otherwise specified (NOS).

Hallucinogen-related disorders include, but are not limited to, Hallucinogen Dependence, Hallucinogen Abuse, Hallucinogen Intoxication, Hallucinogen Withdrawal, Hallucinogen Intoxication Delirium, Hallucinogen Persisting Perception Disorder (Flashbacks), Hallucinogen-Induced Psychotic Disorder with delusions, Hallucinogen-Induced Psychotic Disorders with hallucinations, Hallucinogen-Induced Mood Disorder, Hallucinogen-Induced Anxiety Disorder, Hallucinogen-Induced Sexual Dysfunction, Hallucinogen-Induced Sleep Disorder, and Hallucinogen Related Disorder not otherwise specified (NOS).

Inhalant-related disorders include, but are not limited to, Inhalant Dependence, Inhalant Abuse, Inhalant Intoxication, Inhalant Intoxication Delirium, Inhalant-Induced Psychotic Disorder with delusions, Inhalant-Induced Psychotic Disorder with hallucinations, Inhalant-Induced Anxiety Disorder, and Inhalant Related Disorder not otherwise specified (NOS).

Opioid-related disorders include, but are not limited to, Opioid Dependence, Opioid Abuse, Opioid Withdrawal, Opioid Intoxication, Opioid Intoxication Delirium, Opioid-Induced Psychotic Disorder with delusions, Opioid-Induced Psychotic Disorder with hallucinations, Opioid-Induced Anxiety Disorder, and Opioid Related Disorder not otherwise specified (NOS).

The Phenylene Compounds can be used to treat or prevent Parkinson's disease and parkinsonism and the symptoms associated with Parkinson's disease and parkinsonism, including but not limited to, bradykinesia, muscular rigidity, resting tremor, and impairment of postural balance.

The Phenylene Compounds can be used to treat or prevent generalized anxiety or severe anxiety and the symptoms associated with anxiety, including but not limited to, restlessness; tension; tachycardia; dyspnea; depression, including chronic "neurotic" depression; panic disorder; agoraphobia and other specific phobias; eating disorders; and personality disorders.

The Phenylene Compounds can be used to treat or prevent epilepsy, including but not limited to, partial epilepsy, generalized epilepsy, and the symptoms associated with epilepsy, including but not limited to, simple partial seizures, jacksonian seizures, complex partial (psychomotor) seizures, convulsive seizures (grand mal or tonic-clonic seizures), petit mal (absence) seizures, and status epilepticus.

The Phenylene Compounds can be used to treat or prevent strokes, including but not limited to, ischemic strokes and hemorrhagic strokes.

The Phenylene Compounds can be used to treat or prevent a seizure, including but not limited to, infantile spasms, febrile seizures, and epileptic seizures.

The Phenylene Compounds can be used to treat or prevent a pruritic condition, including but not limited to, pruritus caused by dry skin, scabies, dermatitis, herpetiformis, atopic dermatitis, pruritus vulvae et ani, miliaria, insect bites, pediculosis, contact dermatitis, drug reactions, urticaria, urticarial eruptions of pregnancy, psoriasis, lichen planus, lichen simplex chronicus, exfoliative dermatitis, folliculitis, bullous pemphigoid, or fiberglass dermatitis.

The Phenylene Compounds can be used to treat or prevent psychosis, including but not limited to, schizophrenia, including paranoid schizophrenia, hebephrenic or disorganized schizophrenia, catatonic schizophrenia, undifferentiated schizophrenia, negative or deficit subtype schizophrenia, and non-deficit schizophrenia; a delusional disorder, including erotomanic subtype delusional disorder, grandiose subtype delusional disorder, jealous subtype delusional disorder, persecutory subtype delusional disorder, and somatic subtype delusional disorder; and brief psychosis.

The Phenylene Compounds can be used to treat or prevent a cognitive disorder, including but not limited to, delirium and dementia such as multi-infarct dementia, dementia pugilistica, dementia caused by AIDS, and dementia caused by Alzheimer's disease.

The Phenylene Compounds can be used to treat or prevent a memory deficiency, including but not limited to, dissociative amnesia and dissociative fugue.

The Phenylene Compounds can be used to treat or prevent restricted brain function, including but not limited to, that caused by surgery or an organ transplant, restricted blood supply to the brain, a spinal cord injury, a head injury, hypoxia, cardiac arrest, or hypoglycemia.

The Phenylene Compounds can be used to treat or prevent Huntington's chorea.

The Phenylene Compounds can be used to treat or prevent ALS.

The Phenylene Compounds can be used to treat or prevent retinopathy, including but not limited to, arteriosclerotic retinopathy, diabetic arteriosclerotic retinopathy, hypertensive retinopathy, non-proliferative retinopathy, and proliferative retinopathy.

The Phenylene Compounds can be used to treat or prevent a muscle spasm.

The Phenylene Compounds can be used to treat or prevent a migraine including, but not limited to, migraine without aura ("common migraine"), migraine with aura ("classic migraine"), migraine without headache, basilar migraine, familial hemiplegic migraine, migrainous infarction, and migraine with prolonged aura.

The Phenylene Compounds can be used to treat or prevent vomiting, including but not limited to, nausea vomiting, dry vomiting (retching), and regurgitation.

The Phenylene Compounds can be used to treat or prevent dyskinesia, including but not limited to, tardive dyskinesia and biliary dyskinesia.

The Phenylene Compounds can be used to treat or prevent depression, including but not limited to, major depression and bipolar disorder.

Applicants believe that the Phenylene Compounds are antagonists for VR1.

The invention also relates to methods for inhibiting VR1 function in a cell comprising contacting a cell capable of expressing VR1 with an amount of a Phenylene Compound effective to inhibit VR1 function in the cell. This method can be used in vitro, for example, as an assay to select cells that express VR1 and, accordingly, are useful as part of an assay to select compounds useful for treating or preventing pain, UI, an ulcer, IBD, or IBS. The method is also useful for inhibiting VR1 function in a cell in vivo, in an animal (e.g., a human), by contacting a cell in an animal with an effective amount of a Phenylene Compound. In one embodiment, the method is useful for treating or preventing pain in an animal in need thereof. In another embodiment, the method is useful for treating or preventing UI in an animal in need thereof. In another embodiment, the method is useful for treating or preventing an ulcer in an animal in need thereof. In another embodiment, the method is useful for treating or preventing IBD in an animal in need thereof. In another embodiment, the method is useful for treating or preventing IBS in an animal in need thereof.

Examples of tissue comprising cells capable of expressing VR1 include, but are not limited to, neuronal, brain, kidney, urothelium, and bladder tissue. Methods for assaying cells that express VR1 are known in the art.

Applicants believe that the Phenylene Compounds are antagonists for mGluR5.

The invention further relates to methods for inhibiting mGluR5 function in a cell comprising contacting a cell capable of expressing mGluR5 with an amount of a Phenylene Compound effective to inhibit mGluR5 function in the cell. This method can be used in vitro, for example, as an assay to select cells that express mGluR5 and, accordingly, are useful as part of an assay to select compounds useful for treating or preventing pain, an addictive disorder, Parkinson's disease, parkinsonism, anxiety, a pruritic condition, or psychosis. The method is also useful for inhibiting mGluR5 function in a cell in vivo, in an animal (e.g., a human), by contacting a cell in an animal with an amount of a Phenylene Compound effective to inhibit mGluR5 function in the cell. In one embodiment, the method is useful for treating or preventing pain in an animal in need thereof. In another embodiment, the method is useful for treating or preventing an addictive disorder in an animal in need thereof. In another embodiment, the method is useful for treating or preventing Parkinson's disease in an animal in need thereof. In another embodiment, the method is useful for treating or preventing parkinsonism in an animal in need thereof. In another embodiment, the method is useful for treating or preventing anxiety in an animal in need thereof. In another embodiment, the method is useful for treating or preventing a pruritic condition in an animal in need thereof. In another embodiment, the method is useful for treating or preventing psychosis in an animal in need thereof.

Examples of cells capable of expressing mGluR5 are neuronal and glial cells of the central nervous system, particularly the brain, especially in the nucleus accumbens. Methods for assaying cells that express mGluR5 are known in the art.

Applicants believe that the Phenylene Compounds are antagonists for mGluR1.

The invention also relates to methods for inhibiting mGluR1 function in a cell comprising contacting a cell capable of expressing mGluR1 with an amount of a Phenylene Compound effective to inhibit mGluR1 function in the cell. This method can be used in vitro, for example, as an assay to select cells that express mGluR1 and, accordingly, are useful as part of an assay to select compounds useful for treating or preventing pain, UI, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression. The method is also useful for inhibiting mGluR1 function in a cell in vivo, in an animal (e.g., a human), by contacting a cell in an animal with an effective amount of a Phenylene Compound. In one embodiment, the method is useful for treating or preventing pain in an animal in need thereof. In another embodiment, the method is useful for treating or preventing UI in an animal in need thereof. In another embodiment, the method is useful for treating or preventing an addictive disorder in an animal in need thereof. In another embodiment, the method is useful for treating or preventing Parkinson's disease in an animal in need thereof. In another embodiment, the method is useful for treating or preventing parkinsonism in an animal in need thereof. In another embodiment, the method is useful for treating or preventing anxiety in an animal in need thereof. In another embodiment, the method is useful for treating or preventing epilepsy in an animal in need thereof. In another embodiment, the method is useful for treating or preventing stroke in an animal in need thereof. In another embodiment, the method is useful for treating or preventing a seizure in an animal in need thereof. In another embodiment, the method is useful for treating or preventing a pruritic condition in an animal in need thereof. In another embodiment, the method is useful for treating or preventing psychosis in an animal in need thereof. In another embodiment, the method is useful for treating or preventing a cognitive disorder in an animal in need thereof. In another embodiment, the method is useful for treating or preventing a memory deficit in an animal in need thereof. In another embodiment, the method is useful for treating or preventing restricted brain function in an animal in need thereof. In another embodiment, the method is useful for treating or preventing Huntington's chorea in an animal in need thereof. In another embodiment, the method is useful for treating or preventing ALS in an animal in need thereof. In another embodiment, the method is useful for treating or preventing dementia in an animal in need thereof. In another embodiment, the method is useful for treating or preventing retinopathy in an animal in need thereof. In another embodiment, the method is useful for treating or preventing a muscle spasm in an animal in need thereof. In another embodiment, the method is useful for treating or preventing a migraine in an animal in need thereof. In another embodiment, the method is useful for treating or preventing vomiting in an animal in need thereof. In another embodiment, the method is useful for treating or preventing dyskinesia in an animal in need thereof.

In another embodiment, the method is useful for treating or preventing depression in an animal in need thereof.

Examples of cells capable of expressing mGluR1 include, but are not limited to, cerebellar Purkinje neuron cells, Purkinje cell bodies (punctate), cells of spine(s) of the cerebellum; neurons and neurophil cells of olfactory-bulb glomeruli; cells of the superficial layer of the cerebral cortex; hippocampus cells; thalamus cells; superior colliculus cells; and spinal trigeminal nucleus cells. Methods for assaying cells that express mGluR1 are known in the art.

4.7 Therapeutic/Prophylactic Administration and Compositions of the Invention Due to their activity, the Phenylene Compounds are advantageously useful in veterinary and human medicine. As described above, the Phenylene Compounds are useful for treating or preventing a Condition in an animal in need thereof.

When administered to an animal, the Phenylene Compounds can be administered as a component of a composition that comprises a pharmaceutically acceptable carrier or excipient. The present compositions, which comprise a Phenylene Compound, can be administered orally. The Phenylene Compounds of the invention can also be administered by any other convenient route, for example, by infusion or bolus injection, by absorption through epithelial or mucocutaneous linings (e.g., oral, rectal, and intestinal mucosa, etc.) and can be administered together with another therapeutically active agent. Administration can be systemic or local. Various delivery systems are known, e.g., encapsulation in liposomes, microparticles, microcapsules, capsules, etc., and can be used to administer the Phenylene Compound.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of the Phenylene Compounds into the bloodstream.

In specific embodiments, it can be desirable to administer the Phenylene Compounds locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Phenylene Compounds into the central nervous system or gastrointestinal tract by any suitable route, including intraventricular, intrathecal, and epidural injection, and enema.

Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Phenylene Compounds can be formulated as a suppository, with traditional binders and excipients such as triglycerides.

In another embodiment, the Phenylene Compounds can be delivered in a vesicle, in particular a liposome (see Langer, Science 249:1527-1533 (1990); and Treat et al., *Liposomes in the Therapy of Infectious Disease and Cancer* 317-327 and 353-365 (1989)).

In yet another embodiment, the Phenylene Compounds can be delivered in a controlled-release system or sustained-release system (see, e.g., Goodson, in Medical Applications of Controlled Release, supra, vol. 2, pp. 115-138 (1984)). Other controlled- or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of the Phenylene Compounds, e.g., the spinal column, brain, or gastrointestinal tract, thus requiring only a fraction of the systemic dose.

The present compositions can optionally comprise a suitable amount of a pharmaceutically acceptable excipient so as to provide the form for proper administration to the animal. Such a pharmaceutical excipient can be a liquid, such as water or an oil, including those of petroleum, animal, vegetable, or synthetic origin, such as peanut oil, soybean oil, mineral oil, sesame oil and the like. The pharmaceutical excipient can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipient is sterile when administered to an animal. Water is a particularly useful excipient when the Phenylene Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

In one embodiment, the Phenylene Compounds are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Phenylene Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lidocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the Phenylene Compounds are to be administered by infusion, they can be dispensed, for example, with an infusion bottle containing sterile pharmaceutical grade water or saline. Where the Phenylene Compounds are administered by injection, an ampule of sterile water for injection or saline can be provided so that the ingredients can be mixed prior to administration.

The Phenylene Compounds can be administered by controlled-release or sustained-release means or by delivery devices that are known to those in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of a Phenylene Compound to treat or prevent the Condition or a symptom thereof in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the Phenylene Compound, and can thus reduce the occurrence of adverse side effects.

Controlled- or sustained-release compositions can initially release an amount of a Phenylene Compound that promptly produces the desired therapeutic or prophylactic effect, and gradually and continually release other amounts of the Phenylene Compound to maintain this level of therapeutic or prophylactic effect over an extended period of time. To maintain a constant level of the Phenylene Compound in the body, the Phenylene Compound can be released from the dosage form at a rate that will replace the amount of Phenylene Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Phenylene Compound that is effective for the treatment or prevention of a condition can be determined by standard clinical techniques. In addition, in vitro or in vivo assays can optionally be employed to help identify optimal dosage ranges. The precise dose to be employed will also depend on the route of administration, and the seriousness of the Condition and can be decided according to the judgment of a practitioner and/or each animal's circumstances. Suitable effective dosage amounts, however, range from about 0.01 mg/kg of body weight to about 2500 mg/kg of body weight, although they are typically about 100 mg/kg of body weight or less. In one embodiment, the effective dosage amount ranges from about 0.01 mg/kg of body weight to about 100 mg/kg of body weight of a Phenylene Compound, in another embodiment, about 0.02 mg/kg of body weight to about 50 mg/kg of body weight, and in another embodiment, about 0.025 mg/kg of body weight to about 20 mg/kg of body weight. In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated. The effective dosage amounts described herein refer to total amounts administered; that is, if more than one Phenylene Compound is administered, the effective dosage amounts correspond to the total amount administered.

Where a cell capable of expressing VR1, mGluR5, or mGluR1 is contacted with a Phenylene Compound in vitro, the amount effective for inhibiting the VR1, mGluR5, or mGluR1 receptor function in a cell will typically range from about 0.01 µg/L to about 5 mg/L, in one embodiment, from about 0.01 µg/L to about 2.5 mg/L, in another embodiment, from about 0.01 µg/L to about 0.5 mg/L, and in another embodiment, from about 0.01 µg/L to about 0.25 mg/L of a solution or suspension of a pharmaceutically acceptable carrier or excipient. In one embodiment, the volume of solution or suspension comprising the Phenylene Compound is from about 0.01 µL to about 1 mL. In another embodiment, the volume of solution or suspension is about 200 µL.

Where a cell capable of expressing VR1, mGluR5, or mGluR1 is contacted with a Phenylene Compound in vivo, the amount effective for inhibiting the receptor function in a cell will typically range from about 0.01 mg/kg of body weight to about 2500 mg/kg of body weight, although it typically ranges from about 100 mg/kg of body weight or less. In one embodiment, the effective dosage amount ranges from about 0.01 mg/kg of body weight to about 100 mg/kg of body weight of a Phenylene Compound, in another embodiment, about 0.02 mg/kg of body weight to about 50 mg/kg of body weight, and in another embodiment, about 0.025 mg/kg of body weight to about 20 mg/kg of body weight. In one embodiment, an effective dosage amount is administered about every 24 h. In another embodiment, an effective dosage amount is administered about every 12. In another embodiment, an effective dosage amount is administered about every 8. In another embodiment, an effective dosage amount is administered about every 6 h. In another embodiment, an effective dosage amount is administered about every 4 h.

The Phenylene Compounds can be assayed in vitro or in vivo for the desired therapeutic or prophylactic activity prior to use in humans. Animal model systems can be used to demonstrate safety and efficacy.

The present methods for treating or preventing a Condition in an animal in need thereof can further comprise administering to the animal being administered a Phenylene Compound another therapeutic agent. In one embodiment, the other therapeutic agent is administered in an effective amount.

The present methods for inhibiting VR1 function in a cell capable of expressing VR1 can further comprise contacting the cell with an effective amount of another therapeutic agent that may or may not inhibit VR1.

The present methods for inhibiting mGluR5 function in a cell capable of expressing mGluR5 can further comprise contacting the cell with an effective amount of another therapeutic agent that may or may not inhibit mGluR5.

The present methods for inhibiting mGluR1 function in a cell capable of expressing mGluR1 can further comprise contacting the cell with an effective amount of another therapeutic agent that may or may not inhibit mGluR1.

Effective amounts of the other therapeutic agents are known to those skilled in the art. However, it is well within the skilled artisan's purview to determine the other therapeutic agent's optimal effective-amount range. In one embodiment of the invention, where another therapeutic agent is administered to an animal, the minimal effective amount of the Phenylene Compound is less than its minimal effective amount would be where the other therapeutic agent is not administered. In this embodiment, without being bound by theory, it is believed that the Phenylene Compounds and the other therapeutic agent act synergistically to treat or prevent a Condition.

The other therapeutic agent can be, but is not limited to, an opioid agonist, a non-opioid analgesic, a non-steroidal anti-inflammatory agent, an antimigraine agent, a Cox-II inhibitor, an antiemetic, a β-adrenergic blocker, an anticonvulsant, an antidepressant, a Ca2+-channel blocker, an anticancer agent, an agent for treating or preventing UI, an agent for treating or preventing an ulcer, an agent for treating or preventing IBD, an agent for treating or preventing IBS, an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating a migraine, an agent for inhibiting vomiting, an agent for treating dyskinesia, or an agent for treating depression, and mixtures thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic-Antipyretic and Anti-inflammatory Agents and Drugs Employed in the Treatment of Gout*, in Goodman & Gilman's The Pharmacological Basis of Therapeutics 617-57 (Perry B. Molinhoff and Raymond W. Ruddon eds., 9$^{th}$ ed 1996); and Glen R. Hanson, *Analgesic, Antipyretic and Anti-Inflammatory Drugs in Remington: The Science and Practice of Pharmacy Vol II* 1196-1221 (A. R. Gennaro ed. 19$^{th}$ ed. 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib.

Examples of useful antimigraine agents include, but are not limited to, alpiropride, bromocriptine, dihydroergotamine, dolasetron, ergocornine, ergocominine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

The other therapeutic agent can also be an antiemetic agent. Examples of useful antiemetic agents include, but are not limited to, metoclopromide, domperidone, prochlorperazine, promethazine, chlorpromazine, trimethobenzamide, odansteron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimelidine.

Examples of useful Ca2+-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexyline.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozotocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti-cancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor;

mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; odansteron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of useful therapeutic agents for treating or preventing UI include, but are not limited to, propantheline, imipramine, hyoscyamine, oxybutynin, and dicyclomine.

Examples of useful therapeutic agents for treating or preventing an ulcer include, antacids such as aluminum hydroxide, magnesium hydroxide, sodium bicarbonate, and calcium bicarbonate; sucraflate; bismuth compounds such as bismuth subsalicylate and bismuth subcitrate; $H_2$ antagonists such as cimetidine, ranitidine, famotidine, and nizatidine; $H^+$, $K^+$-ATPase inhibitors such as omeprazole, iansoprazole, and lansoprazole; carbenoxolone; misprostol; and antibiotics such as tetracycline, metronidazole, timidazole, clarithromycin, and amoxicillin.

Examples of useful therapeutic agents for treating or preventing IBD include, but are not limited to, anticholinergic drugs; diphenoxylate; loperamide; deodorized opium tincture; codeine; broad-spectrum antibiotics such as metronidazole; sulfasalazine; olsalazine; mesalamine; prednisone; azathioprine; mercaptopurine; and methotrexate.

Examples of useful therapeutic agents for treating or preventing IBS include, but are not limited to, propantheline; muscarine receptor antagonists such as pirenzapine, methoctramine, ipratropium, tiotropium, scopolamine, methscopolamine, homatropine, homatropine methylbromide, and methantheline; and antidiarrheal drugs such as diphenoxylate and loperamide.

Examples of useful therapeutic agents for treating or preventing an addictive disorder include, but are not limited to, methadone, desipramine, amantadine, fluoxetine, buprenorphine, an opiate agonist, 3-phenoxypyridine, levomethadyl acetate hydrochloride, and serotonin antagonists.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy include, but are not limited to, carbamazepine, ethosuximide, gabapentin, lamotrigine, phenobarbital, phenyloin, primidone, valproic acid, trimethadione, benzodiazepines, γ-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a seizure include, but are not limited to, carbamazepine, ethosuximide, gabapentin, lamotrigine, phenobarbital, phenyloin, primidone, valproic acid, trimethadione, benzodiazepines, gabapentin, lamotrigine, γ-vinyl GABA, acetazolamide, and felbamate.

Examples of useful therapeutic agents for treating or preventing a pruritic condition include, but are not limited to, naltrexone; nalmefene; danazol; tricyclics such as amitriptyline, imipramine, and doxepin; antidepressants such as those given below, menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing Huntington's chorea include, but are not limited to, haloperidol and pimozide.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating, inhibiting, or preventing vomiting include, but are not limited to, $5\text{-HT}_3$ receptor antagonists such as odansteron, dolasetron, granisetron, and tropisetron; dopamine receptor antagonists such as prochlorperazine, thiethylperazine, chlorpromazin, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A Phenylene Compound and the other therapeutic agent combined can act additively or, in one embodiment, synergistically. In one embodiment, a Phenylene Compound is administered concurrently with another therapeutic agent, for example, a composition comprising an effective amount of a Phenylene Compound and an effective amount of another therapeutic agent can be administered. Alternatively, a composition comprising an effective amount of a Phenylene Compound and a different composition comprising an effective amount of another therapeutic agent can be concurrently administered. In another embodiment, an effective amount of a Phenylene Compound is administered prior or subsequent to administration of an effective amount of another therapeutic agent. In this embodiment, the Phenylene Compound is administered while the other therapeutic agent exerts its therapeutic effect, or the other therapeutic agent is administered while the Phenylene Compound exerts its therapeutic effect for treating or preventing a Condition.

A composition of the invention is prepared by a method comprising admixing a Phenylene Compound or a pharmaceutically acceptable salt and a pharmaceutically acceptable carrier or excipient. Admixing can be accomplished using methods known for admixing a compound (or salt) and a pharmaceutically acceptable carrier or excipient. In one embodiment, the Phenylene Compound is present in the composition in an effective amount.

4.8 Kits

The invention encompasses kits that can simplify the administration of a Phenylene Compound to an animal.

A typical kit of the invention comprises a unit dosage form of a Phenylene Compound. In one embodiment, the unit dosage form is a container, which can be sterile, containing an effective amount of a Phenylene Compound and a pharmaceutically acceptable carrier or excipient. The kit can further comprise a label or printed instructions instructing the use of the Phenylene Compound to treat or prevent a Condition. The kit can also further comprise a unit dosage form of another therapeutic agent, for example, a second container containing an effective amount of the other therapeutic agent and a pharmaceutically acceptable carrier or excipient. In another embodiment, the kit comprises a container containing an effective amount of a Phenylene Compound, an effective amount of another therapeutic agent and a pharmaceutically acceptable carrier or excipient. Examples of other therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes

5. EXAMPLES

5.1 Example 1

Synthesis of Compound E35

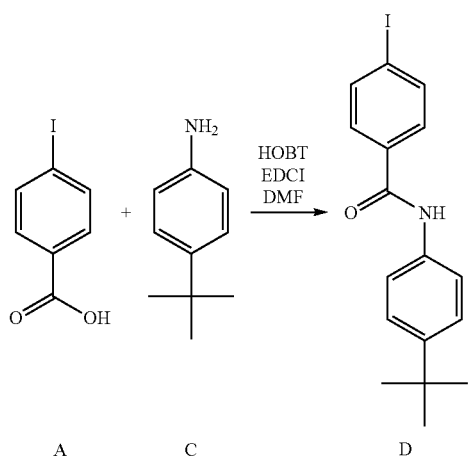

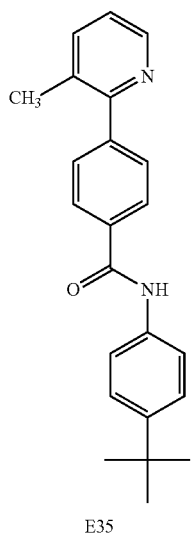

E35

To a solution of 4-iodobenzoic acid A (commercially available from Sigma-Aldrich, St. Louis, Mo.) in DMF (0.22 M) was added 1 equivalent of 4-tert-butylaniline B (commercially available from Sigma-Aldrich), and the resulting solution was stirred for about 5 min at a temperature of about 25° C. To the resulting reaction mixture was added about 1 equivalent of HOBT and about 1 equivalent of EDCI and the mixture was allowed to stir for about 6 h at a temperature of about 25° C. The reaction mixture was diluted with 2N aq. sodium hydroxide and extracted 3 times with EtOAc. The EtOAc layers were combined, dried (with $Na_2SO_4$), and the solvent removed under reduced pressure to provide a residue that was washed with methanol and dried under reduced pressure. The residue was then suspended in THF (0.04 moles/liter) under a nitrogen atmosphere and 3 equivalent of Compound E (commercially available from Sigma-Aldrich) and 0.05 equivalent of $Pd(PPh_3)_4$ (commercially available from Sigma-Aldrich) were added to the reaction mixture. The reaction mixture was then heated to about 70° C. and stirred for about 2 h. The solvent was removed under reduced pressure to provide a residue that was purified using a silica gel column eluted with a gradient of 5:95 ethyl acetate:hexane to 50:50 ethyl acetate:hexane to provide Compound E35 as an off-white solid (28% yield).

The identity of Compound E35 was confirmed using $^1$H NMR.

Compound E35: $^1$H NMR (MeOD) δ 8.335 (s, 1H), 7.939 (d, 2H), 7.681 (d, 1H), 7.513 (t, 4H), 7.300 (d, 2H), 7.251 (dd, 1H), 2.230 (s, 3H), 1.227 (s, 9H) ppm.

5.2 Example 2

Synthesis of Compound E42

Compound E42 was made by a procedure that is analogous to the procedure used to make Compound E35 except that 4-trifluoromethylaniline (commercially available from Sigma-Aldrich) was used in place of 4-tert-butylaniline. Compound E42 was obtained as a white solid (80% yield).

The identity of Compound E42 was confirmed using $^1$H NMR.

Compound E42: $^1$H NMR (CDCl$_3$) δ 8.560 (s, 1H), 8.138 (s, 1H), 7.954 (d, 2H), 7.813 (d, 2H), 7.684-7.604 (m, 5H), 7.267-7.223 (m, 1H+CDCl$_3$), 2.369 (s, 3H), 1.559 (s, H$_2$O) ppm.

5.3 Example 3

Synthesis of Compound J35

Compound J35 was made by a procedure that is analogous to the procedure used to make Compound E35 except that 6-chlorobenzothiazol-2-ylamine (commercially available from Sigma-Aldrich) was used in place of 4-tert-butylaniline. Compound J35 was obtained as a white solid.

The identity of Compound J35 was confirmed using $^1$H NMR.

Compound J35: $^1$H NMR (DMSO$_6$), δ 8.65-8.60 (M, 1 h), 8.22-8.17 (M, 2h), 7.93-7.89 (M, 1 h), 7.86-7.84 (M, 1h0, 7.74-7.67 (M, 3H), 7.52-7.47 (m, 1H), 7.45-7.41 (m, 1H), 2.43 (s, 3H) ppm.

5.4 Example 4

Synthesis of Compound J37

Compound J37 was made by a procedure analogous to the procedure used to make Compound E35 except that 6-fluorobenzothiazol-2-ylamine (commercially available from Sigma-Aldrich) was used in place of 4-tert-butylaniline. Compound J37 was obtained as an off-white solid.

The identity of Compound J37 was confirmed using $^1$H NMR.

Compound J37: $^1$H NMR (DMSO-d$_6$) δ 8.29-8.24 (m, 1H), 8.15-8.09 (m, 2H), 7.65-7.61 (m, 1H), 7.52-7.34 (m, 4H), 7.22-7.16 (m, 1H), 6.98-6.91 (m, 1H), 2.19 (s, 3H) ppm.

5.5 Example 5

Synthesis of Compound E50

Compound 50 was made by a procedure that is analogous to the procedure used to make Compound E35 except that the following zinc bromide compound, prepared according to the procedure provided in M. B. Smith and J. March, *March's Advanced Organic Chemistry Reaction Mechanisms and Structure*, 805-807 (5$^{th}$ ed. 2001); H. Fillon et al., *Tett. Lett.* 42:3843-46 (2001); M. Amadji et al., *Tettrahedron* 9:1657-60 (1998); and S. Billotte, *Synlett*. 379-380 (1998), was used in place of Compound E:

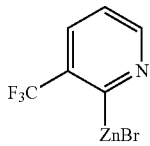

Compound E50 was obtained as a white solid.

The identity of Compound E50 was confirmed using $^1$H NMR.

Compound E50: $^1$H NMR (CDCl$_3$) δ 8.87 (dd, 1H), 8.12 (dd, 1H), 7.96 (d, 2H), 7.83 (s, 1H), 7.64 (d, 2H), 7.58 (d, 2H), 7.48 (dd, 1H), 7.41 (d, 2H), 1.33 (s, 9H) ppm.

5.6 Example 6

Binding of Phenylene Compounds to mGluR5

The following assay can be used to demonstrate that Phenylene Compounds bind to and modulate the activity of mGluR5.

Cell Cultures: Primary glial cultures are prepared from cortices of Sprague-Dawley 18 days old embryos. The cortices are dissected and then dissociated by trituration. The resulting cell homogenate is plated onto poly-D-lysine pre-coated T175 flasks (BIOCOAT, commercially available from Becton Dickinson and Company Inc. of Franklin Lakes, N.J.) in Dulbecco's Modified Eagle's Medium ("DMEM," pH 7.4), buffered with 25 mM HEPES, and supplemented with 15% fetal calf serum ("FCS," commercially available from Hyclone Laboratories Inc. of Omaha, Nebr.), and incubated at 37° C. and 5% CO$_2$. After 24 hours, FCS supplementation is reduced to 10%. On day six, oligodendrocytes and microglia are removed by strongly tapping the sides of the flasks. One day following this purification step, secondary astrocyte cultures are established by subplating onto 96 poly-D-lysine precoated T175 flasks (BIOCOAT) at a density of 65,000 cells/well in DMEM and 10% FCS. After 24 hours, the astrocytes are washed with serum free medium and then cultured in DMEM, without glutamate, supplemented with 0.5% FCS, 20 mM HEPES, 10 ng/mL epidermal growth factor ("EGF"), 1 mM sodium pyruvate, and 1× penicillin/streptomycin at pH 7.5 for 3 to 5 days at 37° C. and 5% CO$_2$. The procedure allows the expression of the mGluR5 receptor by astrocytes, as demonstrated by S. Miller et al., *J. Neuroscience* 15(9): 6103-6109 (1995).

Assay Protocol: After 3-5 days incubation with EGF, the astrocytes are washed with 127 mM NaCl, 5 mM KCl, 2 mM MgCl$_2$, 700 mM NaH$_2$PO$_4$, 2 mM CaCl$_2$, 5 mM NaHCO$_3$, 8 mM HEPES, 10 mM Glucose at pH 7.4 ("Assay Buffer") and loaded with the dye Fluo-4 (commercially available from Molecular Probes Inc. of Eugene, Oreg.) using 0.1 mL of Assay Buffer containing Fluo-4 (3 mM final). After 90 minutes of dye loading, the cells are then washed twice with 0.2 mL Assay Buffer and resuspended in 0.1 mL of Assay Buffer. The plates containing the astrocytes are then transferred to a Fluorometric Imaging Plate reader ("FLIPR," commercially available from Molecular Devices Corporation of Sunnyvale, Calif.) for the assessment of calcium mobilization flux in the presence of glutamate and in the presence or absence of antagonist. After monitoring fluorescence for 15 seconds to establish a baseline, DMSO solutions containing various concentrations of a Phenylene Compound diluted in Assay Buffer (0.05 mL of 4× dilutions for competition curves) are added to the cell plate and fluorescence is monitored for 2 minutes. 0.05 mL of a 4× glutamate solution (agonist) is then added to each well to provide a final glutamate concentration in each well of 10 mM. Plate fluorescence is then monitored for an additional 60 seconds after agonist addition. The final DMSO concentration in the assay is 1.0%. In each experiment, fluorescence is monitored as a function of time and the data analyzed using Microsoft Excel and GraphPad Prism. Dose-response curves are fit using a non-linear regression to determine the IC$_{50}$ value. In each experiment, each data point is determined two times.

5.7 Example 7

In Vivo Assays for Prevention or Treatment of Pain

Test Animals: Each experiment uses rats weighing between 200-260 g at the start of the experiment. The rats are group-housed and have free access to food and water at all times, except prior to oral administration of a Phenylene Compound when food is removed for 16 hours before dosing. A control group acts as a comparison to rats treated with a Phenylene Compound. The control group is administered the carrier for the Phenylene Compound. The volume of carrier administered to the control group is the same as the volume of carrier and Phenylene Compound administered to the test group.

Acute Pain: To assess the actions of the Phenylene Compounds for the treatment or prevention of acute pain, the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Phenylene Compound. Data are expressed as tail flick latency(s) and the percentage of the maximal possible effect (% MPE), i.e., 20 seconds, is calculated as follows:

$$\% MPE = \frac{[(\text{post administration latency}) - (\text{pre-administration latency})]}{(20 \text{ s pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

Acute pain can also be assessed by measuring the animal's response to noxious mechanical stimuli by determining the paw withdrawal threshold ("PWT"), as described below.

Inflammatory Pain: To assess the actions of the Phenylene Compounds for the treatment or prevention of inflammatory pain, the Freund's complete adjuvant ("FCA") model of inflammatory pain is used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 µL intraplantar injection of 50% FCA. 24 hour post injection, the animal is assessed for response to noxious mechanical stimuli by determining the PWT, as described below. Rats are then administered a single injection of 1, 3, 10 or 30 mg/kg of either a Phenylene Compound; 30 mg/kg of a control selected from Celebrex, indomethacin or naproxen; or carrier. Responses to noxious mechanical stimuli are then determined 1, 3, 5 and 24 hours post administration. Percentage reversal of hyperalgesia for each animal is defined as:

$$\% \text{Reversal} = \frac{[(\text{post administration } PWT) - (\text{pre-administration } PWT)]}{[(\text{baseline } PWT) - (\text{pre-administration } PWT)]} \times 100$$

Neuropathic Pain: To assess the actions of the Phenylene Compounds for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \text{Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Phenylene Compound for the left rear paw of the animal. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that can be applied to the hind paw is set at 250 g and the end point is taken as complete withdrawal of the paw. PWT is determined once for each rat at each time point and only the affected (ipsilateral) paw is tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Only the affected (ipsilateral) paw is tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

5.8 Example 8

In Vivo Assays for Prevention or Treatment of Anxiety

The elevated plus maze test or the shock-probe burying test can be used to assess the anxiolytic activity of Phenylene Compounds in rats or mice.

The Elevated Plus Maze Test: The elevated plus maze consists of a platform with 4 arms, two open and two closed (50×10×50 cm enclosed with an open roof). Rats (or mice) are placed in the center of the platform, at the crossroad of the 4 arms, facing one of the closed arms. Time spent in the open arms vs the closed arms and number of open arm entries during the testing period are recorded. This test is conducted prior to drug administration and again after drug administration. Test results are expressed as the mean time spent in open arms and the mean number of entries into open arms. Known anxiolytic drugs increase both the time spent in open arms and number of open arm entries. The elevated plus maze test is described in D. Treit, "Animal Models for the Study of Antianxiety Agents: A Review," *Neuroscience & Biobehavioral Reviews* 9(2):203-222 (1985).

The Shock-Probe Burying Test: For the shock-probe burying test the testing apparatus consists of a plexiglass box measuring 40×30×40 cm, evenly covered with approximately 5 cm of bedding material (odor absorbent kitty litter) with a small hole in one end through which a shock probe (6.5 cm long and 0.5 cm in diameter) is inserted. The plexiglass shock probe is helically wrapped with two copper wires through which an electric current is administered. The current is set at 2 mA. Rats are habituated to the testing apparatus for 30 min on 4 consecutive days without the shock probe in the box. On test day, rats are placed in one corner of the test chamber following drug administration. The probe is not electrified until the rat touches it with its snout or fore paws, at which point the rat receives a brief 2 mA shock. The 15 min testing period begins once the rat receives its first shock and the probe remains electrified for the remainder of the testing period. The shock elicits burying behavior by the rat. Following the first shock, the duration of time the rat spends spraying bedding material toward or over the probe with its snout or fore paws (burying behavior) is measured as well as the number of contact-induced shocks the rat receives from the probe. Known anxiolytic drugs reduce the amount of burying behavior. In addition, an index of the rat's reactivity to each shock is scored on a 4 point scale. The total time spent immobile during the 15 min testing period is used as an index of general activity. The shock-probe burying test is described in D. Treit, 1985, supra.

5.9 Example 9

In Vivo Assays for Prevention or Treatment of an Addictive Disorder

The conditioned place preference test or drug self-administration test can be used to assess the ability of Phenylene Compounds to attenuate the rewarding properties of known drugs of abuse.

The Conditioned Place Preference Test: The apparatus for the conditioned place preference test consists of two large compartments (45×45×30 cm) made of wood with a plexiglass front wall. These two large compartments are distinctly different. Doors at the back of each large compartment lead to a smaller box (36×18×20 cm) made of wood, painted grey, with a ceiling of wire mesh. The two large compartments differ in terms of shading (white vs black), level of illumination (the plexiglass door of the white compartment is covered with aluminum foil except for a window of 7×7 cm), texture (the white compartment has a 3 cm thick floor board (40×40 cm) with nine equally spaced 5 cm diameter holes and the black has a wire mesh floor), and olfactory cues (saline in the white compartment and 1 mL of 10% acetic acid in the black compartment). On habituation and testing days, the doors to the small box remain open, giving the rat free access to both large compartments.

The first session that a rat is placed in the apparatus is a habituation session and entrances to the smaller grey compartment remain open giving the rat free access to both large compartments. During habituation, rats generally show no preference for either compartment. Following habituation, rats are given 6 conditioning sessions. Rats are divided into 4 groups: carrier pre-treatment+carrier (control group), Phenylene Compound pre-treatment+carrier, carrier pre-treatment+morphine, Phenylene Compound pre-treatment+morphine. During each conditioning session the rat is injected with one of the drug combinations and confined to one compartment for 30 min. On the following day, the rat receives a carrier+carrier treatment and is confined to the other large compartment. Each rat receives three conditioning sessions consisting of 3 drug combination-compartment and 3 carrier-compartment pairings. The order of injections and the drug/compartment pairings are counterbalanced within groups. On the test day, rats are injected prior to testing (30 min to 1 hour) with either morphine or carrier and the rat is placed in the apparatus, the doors to the grey compartment remain open and the rat is allowed to explore the entire apparatus for 20 min. The time spent in each compartment is recorded. Known drugs of abuse increase the time spent in the drug-paired compartment during the testing session. If the Phenylene Compound blocks or reduces the acquisition of morphine conditioned place preference (reward), there will be no difference or less of a difference in time spent in each side in rats pre-treated with a Phenylene Compound and the group will not be different from the group of rats that was given carrier+ carrier in both compartments. Data will be analyzed as time spent in each compartment (drug combination-paired vs carrier-paired). Generally, the experiment is repeated with a minimum of 3 doses of a Phenylene Compound.

The Drug Self-Administration Test: The apparatus for the drug self-administration test is a standard commercially available operant conditioning chamber. Before drug trials begin rats are trained to press a lever for a food reward. After stable lever pressing behavior is acquired, rats are tested for acquisition of lever pressing for drug reward. Rats are implanted with chronically indwelling jugular catheters for i.v. administration of compounds and are allowed to recover for 7 days before training begins. Experimental sessions are conducted daily for 5 days in 3 hour sessions. Rats are trained to self-administer a known drug of abuse, such as morphine. Rats are then presented with two levers, an "active" lever and an "inactive" lever. Pressing of the active lever results in drug infusion on a fixed ratio 1 (FR1) schedule (i.e., one lever press gives an infusion) followed by a 20 second time out period (signaled by illumination of a light above the levers). Pressing of the inactive lever results in infusion of excipient. Training continues until the total number of morphine infusions stabilizes to within ±10% per session. Trained rats are then used to evaluate the effect of Phenylene Compounds pre-treatment on drug self-administration. On test day, rats are pre-treated with a Phenylene Compound or excipient and then are allowed to self-administer drug as usual. If the Phenylene Compound blocks or reduces the rewarding effects of morphine, rats pre-treated with the Phenylene Compound will show a lower rate of responding compared to their previous rate of responding and compared to excipient pre-treated rats. Data are analyzed as the change in number of drug infusions per testing session (number of infusions during test session−number of infusions during training session).

5.10 Example 10

Functional Assay for Characterizing mGluR1 Antagonistic Properties

Functional assays for the characterization of mGluR 1 antagonistic properties are known in the art. For example, the following procedure can be used.

A CHO-rat mGluR1 cell line is generated using cDNA encoding rat mGluR1 receptor (M. Masu and S. Nakanishi, *Nature* 349: 760-765 (1991)). The cDNA encoding rat mGluR1 receptor can be obtained from, e.g., Prof. S. Nakanishi (Kyoto, Japan).

40,000 CHO-rat mGluR1 cells/well are plated into a Costar 3409, black, clear bottom, 96 well, tissue culture treated plate (commercially available from Fisher Scientific of Chicago, Ill.) and are incubated in Dulbecco's Modified Eagle's Medium (DMEM, pH 7.4) supplemented with glutamine, 10% FBS, 1% Pen/Strep, and 500 µg/mL Geneticin for about 12 h. The CHO-rat mGluR1 cells are then washed and treated with Optimem medium (commercially available from Invitrogen, Carlsbad, Calif.) and incubated for a time period ranging from 1 to 4 hours prior to loading the cells with the dye Fluo-4. After incubation, the cell plates are washed with loading buffer (127 mM NaCl, 5 mM KCl, 2 mM $MgCl_2$, 700 µM, $NaH_2PO_4$, 2 mM $CaCl_2$, 5 mM $NaHCO_3$, 8 mM HEPES, and 10 mM glucose, pH 7.4) and incubated with 3 µM Fluo-4 in 0.1 mL loading buffer for 90 min. The cells are then washed twice with 0.2 mL loading buffer, resuspended in 0.1 mL of loading buffer, and transferred to a FLIPR for measurement of calcium mobilization flux in the presence of glutamate and in the presence or absence of a Phenylene Compound.

To measure calcium mobilization flux, fluoresence is monitored for about 15 s to establish a baseline and DMSO solutions containing various concentrations of a Phenylene Compound ranging from about 50 µM to about 0.8 nM diluted in loading buffer (0.05 mL of a 4× dilution) are added to the cell plate and fluoresence is monitored for about 2 min. 0.05 mL of a 4× Glutamate solution (agonist) is then added to each well to provide a final glutamate concentration in each well of 10 µM and fluoresence is monitored for about 1 additional min. The final DMSO concentration in the assay is 1%. In each experiment fluoresence is monitored as a function of time and the data is analyzed using a non-linear regression to determine the $IC_{50}$ value. In each experiment each data point is determined twice.

5.11 Example 11

Binding of Phenylene Compounds to VR1

Methods for assaying compounds capable of inhibiting VR1 are known to those skilled in the art, for example, those methods disclosed in U.S. Pat. No. 6,239,267 to Duckworth et al.; U.S. Pat. No. 6,406,908 to McIntyre et al.; or U.S. Pat. No. 6,335,180 to Julius et al.

Binding of Compound E35 to VR1

Assay Protocol

Human VR1 Cloning: Human spinal cord RNA (commercially available from Clontech, Palo Alto, Calif.) was used. Reverse transcription was conducted on 1.0 µg total RNA using Thermoscript Reverse Transcriptase (commercially available from Invitrogen) and oligo dT primers as detailed in its product description. Reverse transcription reactions were incubated at 55° C. for 1 h, heat-inactivated at 85° C. for 5 min, and RNase H-treated at 37° C. for 20 min.

Human VR1 cDNA sequence was obtained by comparison of the human genomic sequence, prior to annotation, to the published rat sequence. Intron sequences were removed and flanking exonic sequences were joined to generate the hypothetical human cDNA. Primers flanking the coding region of human VR1 were designed as follows: forward primer, GAA-GATCTTCGCTGGTTGCACACTGGGCCACA; and reverse primer, GAAGATCTTCGGGGACAGTGACGGT-TGGATGT.

PCR of VR1 was performed on one tenth of the Reverse transcription reaction mixture using Expand Long Template Polymerase and Expand Buffer 2 in a final volume of 50 µL according to the manufacturer's instructions (Roche Applied Sciences, Indianapolis, Ind.). After denaturation at 94° C. for 2 min, PCR amplification was performed for 25 cycles at 94° C. for 15 sec, 58° C. for 30 sec, and 68° C. for 3 min followed by a final incubation at 72° C. for 7 min to complete the amplification. A PCR product of ~2.8 kb was gel-isolated using a 1.0% agarose, Tris-Acetate gel containing 1.6 µg/mL of crystal violet and purified with a S.N.A.P. UV-Free Gel Purification Kit (commercially available from Invitrogen). The VR1 PCR product was cloned into the pIND/V5-His-TOPO vector (commercially available from Invitrogen) according to the manufacturer's instructions. DNA preparations, restriction enzyme digestions, and preliminary DNA sequencing were performed according to standard protocols. Full-length sequencing confirmed the identity of the human VR1.

Generation of Inducible Cell Lines: Unless noted otherwise, cell culture reagents were purchased from Life Technologies of Rockville, Md. HEK 293-EcR cells expressing the ecdysone receptor (commercially available from Invitrogen) were cultured in Growth Medium (Dulbecco's Modified Eagles Medium containing 10% fetal bovine serum (commercially available from HYCLONE, Logan, Utah), 1× penicillin/streptomycin, 1× glutamine, 1 mM sodium pyruvate and 400 µg/mL Zeocin (commercially available from Invitrogen)). The VR1-pIND constructs were transfected into the HEK293-EcR cell line using Fugene transfection reagent (commercially available from Roche Applied Sciences, Basel, Switzerland). After 48 h, cells were transferred to Selection Medium (Growth Medium containing 300 µg/mL G418 (commercially available from Invitrogen)). Approximately 3 weeks later, individual Zeocin/G418 resistant colonies were isolated and expanded. To identify functional clones, multiple colonies were plated into 96-well plates and expression was induced for 48 h using Selection Medium supplemented with 5 µM ponasterone A ("PonA") (commercially available from Invitrogen). On the day of assay, cells were loaded with Fluo-4 (a calcium-sensitive dye that is commercially available from Molecular Probes) and CAP-mediated calcium influx was measured using a FLIPR as described below. Functional clones were re-assayed, expanded, and cryopreserved.

pH-Based Assay: Two days prior to performing this assay, cells were seeded on poly-D-lysine-coated 96-well clear-bottom black plates (commercially available from Becton-Dickinson) at 75,000 cells/well in growth media containing 5 µM PonA to induce expression. On the day of the assay, the plates were washed with 0.2 mL 1× Hank's Balanced Salt Solution (commercially available from Life Technologies) containing 1.6 mM $CaCl_2$ and 20 mM HEPES, pH 7.4 ("wash buffer"), and loaded using 0.1 mL of wash buffer containing Fluo-4 (3 µM final concentration, commercially available from Molecular Probes). After 1 h, the cells were washed twice with 0.2 mL wash buffer and resuspended in 0.05 mL 1× Hank's Balanced Salt Solution containing 3.5 mM $CaCl_2$ and 10 mM Citrate, pH 7.4 ("assay buffer"). Plates were then transferred to a FLIPR for assay. Compound E35 was diluted in assay buffer, and 50 mL of the resultant solution were added to the cell plates and the solution monitored for two minutes. The final concentration of Compound E35 ranged from about 50 µM to about 3 µM. Agonist buffer (wash buffer titrated with 1N HCl to provide a solution having a pH of 5.5 when mixed 1:1 with assay buffer) (0.1 mL) was then added to each well, and the plates were incubated for 1 additional minute. Data were collected over the entire time course and analyzed using Excel and Graph Pad Prism. Compound E35 when assayed according to this protocol had an $IC_{50}$ of 11.2±5.5 nM (n=5).

Capsaicin-Based Assay: Two days prior to performing this assay, cells were seeded in poly-D-lysine-coated 96-well clear-bottom black plates (50,000 cells/well) in growth media containing 5 µM PonA to induce expression. On the day of the assay, the plates were washed with 0.2 mL 1× Hank's Balanced Salt Solution containing 1 mM $CaCl_2$ and 20 mM HEPES, pH 7.4, and cells were loaded using 0.1 mL of wash buffer containing Fluo-4 (3 µM final). After one hour, the cells were washed twice with 0.2 mL of wash buffer and resuspended in 0.1 mL of wash buffer. The plates were transferred to a FLIPR for assay. 50 µL of Compound E35 diluted with assay buffer were added to the cell plates and incubated for 2 min. The final concentration of Compound E35 ranged from about 50 µM to about 3 µM. Human VR1 was activated by the addition of 50 µL of capsaicin (400 nM), and the plates were incubated for an additional 3 min. Data were collected over the entire time course and analyzed using Excel and Graph-Pad Prism. Compound E35 when assayed according to this protocol had an $IC_{50}$ of 128.1±26 nM (n=4).

The results of the pH-based assay and the capsaicin-based assay demonstrate that Compound E35, an illustrative Phenylene Compound, binds to and modulates the activity of human VR1 and accordingly is useful for treating or preventing pain, UI, an ulcer, IBD or IBS in an animal.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A compound of formula:

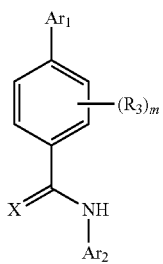

(I)

or a pharmaceutically acceptable salt thereof, wherein:

$Ar_1$ is

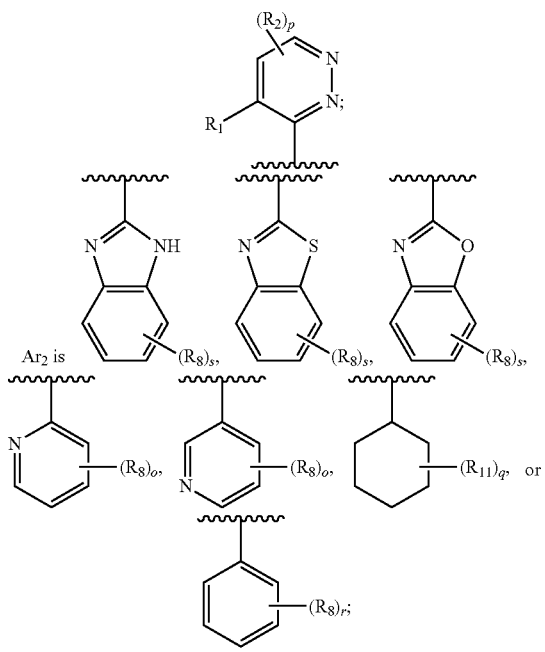

X is O or S;

$R_1$ is -halo, —$CH_3$, —C(halo)$_3$, —CH(halo)$_2$, or —$CH_2$(halo);

each $R_2$ is independently:
(a) -halo, —OH, —$NH_2$, —CN, or —$NO_2$;
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups; or
(c) -phenyl, -naphthyl, —($C_{14}$)aryl, or -(5- to 10-membered)heteroaryl, each of which is unsubstituted or substituted with one or more $R_6$ groups;

each $R_3$ is independently:
(a) -halo, —CN, —OH, —$NO_2$, or —$NH_2$;
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups; or
(c) -phenyl, -naphthyl, —($C_{14}$)aryl, or -(5- to 10-membered)heteroaryl, each of which is unsubstituted or substituted with one or more $R_6$ groups;

each $R_5$ is independently —CN, —OH, —($C_1$-$C_6$)alkyl, —($C_2$-$C_6$)alkenyl, -halo, —$N_3$, —$NO_2$, —N($R_7$)$_2$, —CH=$NR_7$, —$NR_7$OH, —$OR_7$, —$COR_7$, —C(O)OR$_7$, —OC(O)R$_7$, —OC(O)OR$_7$, —SR$_7$, —S(O)R$_7$, or —S(O)$_2$R$_7$;

each $R_6$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —$CH_2$(halo), —CN, —OH, -halo, —$N_3$, —$NO_2$, N($R_7$)$_2$, —CH=$NR_7$, —$NR_7$OH, —$OR_7$, —$COR_7$, —C(O)OR$_7$, —OC(O)R$_7$, —OC(O)OR$_7$, —SR$_7$, —S(O)R$_7$, or —S(O)$_2$R$_7$;

each $R_7$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, or —$CH_2$(halo);

each $R_8$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —$CH_2$(halo), —CN, —OH, -halo, —$N_3$, —$NO_2$, —N($R_7$)$_2$, —CH=$NR_7$, —$NR_7$OH, —$OR_7$, —$COR_7$, —C(O)OR$_7$, —OC(O)R$_7$, —OC(O)OR$_7$, —SR$_7$, —S(O)R$_7$, or —S(O)$_2$R$_7$;

each $R_{11}$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —$CH_2$(halo), —CN, —OH, -halo, —$N_3$, —$NO_2$, —N($R_7$)$_2$, —CH=$NR_7$, —$NR_7$OH, —$COR_7$, —C(O)OR$_7$, —OC(O)R$_7$, —OC(O)OR$_7$, —SR$_7$, —S(O)R$_7$, or —S(O)$_2$R$_7$;

each halo is independently —F, —Cl, —Br, or —I;

m is an integer ranging from 0 to 4;

o is an integer ranging from 0 to 4;

p is an integer ranging from 0 to 2;

q is an integer ranging from 0 to 6;

r is an integer ranging from 0 to 5; and
s is an integer ranging from 0 to 4.

2. The compound of claim 1, wherein p is 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

3. The compound of claim 2, wherein $R_2$ is —($C_1$-$C_{10}$)alkyl which is substituted with two $R_5$ groups.

4. The compound of claim 1, wherein:
$Ar_2$ is

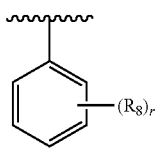

X is O; and
$R_1$ is —F, —Cl, —$CH_3$, or —$CF_3$.

5. The compound of claim 4, wherein p is 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

6. The compound of claim 5, wherein $R_2$ is —($C_1$-$C_{10}$)alkyl which is substituted with two $R_5$ groups.

7. The compound of claim 4, wherein:
m is 0;
r is 1; and
$R_8$ is —($C_1$-$C_6$)alkyl, -halo, —$OCF_3$, or —$CF_3$.

8. The compound of claim 7, wherein p is 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

9. The compound of claim 8, wherein $R_2$ is —($C_1$-$C_{10}$)alkyl which is substituted with two $R_5$ groups.

10. The compound of claim 7, wherein the —($C_1$-$C_6$)alkyl is a tert-butyl group, optionally substituted at the 4-position of $Ar_2$.

11. The compound of claim 1, wherein:
$Ar_2$ is

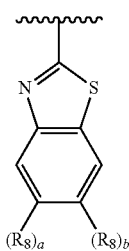

X is O;
$R_1$ is —$CH_3$, —$CF_3$, —Cl, —Br, —I, or —F;
m is 0;
$(R_8)_a$ is —H; and
$(R_8)_b$ is —H, —$CH_3$, —$OCH_3$, —$CF_3$, —$OCF_3$, —$OCH_2CH_3$, iso-propyl, tert-butyl, —Cl, —Br, —I, or —F.

12. The compound of claim 11, wherein p is 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

13. The compound of claim 12, wherein $R_2$ is —($C_1$-$C_{10}$)alkyl which is substituted with two $R_5$ groups.

14. The compound of claim 11, wherein $R_1$ is —$CH_3$, —$CF_3$, or —Cl and $(R_8)_b$ is —Cl, —F, —$CF_3$, —$OCF_3$, or tert-butyl.

15. The compound of claim 1, wherein:
$Ar_2$ is

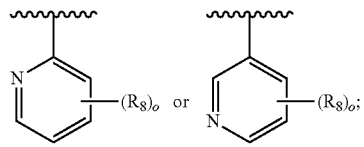

X is O; and
$R_1$ is —F, —Cl, —$CH_3$ or —$CF_3$.

16. The compound of claim 15, wherein p is 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

17. The compound of claim 16, wherein $R_2$ is —($C_1$-$C_{10}$)alkyl which is substituted with two $R_5$ groups.

18. The compound of claim 15, wherein:
m is 0;
o is 1; and
$R_8$ is —($C_1$-$C_6$)alkyl or -halo.

19. The compound of claim 18, wherein p is 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

20. The compound of claim 19, wherein $R_2$ is —($C_1$-$C_{10}$)alkyl which is substituted with two $R_5$ groups.

21. A composition comprising an effective amount of the compound or a pharmaceutically acceptable salt of the compound of claim 1 and a pharmaceutically acceptable carrier or excipient.

22. An in vitro method for inhibiting VR1 function in a cell comprising:
contacting a cell expressing VR1 in vitro with a compound of claim 1, or a pharmaceutically acceptable salt thereof, in an amount sufficient to reduce calcium ion mobilization into said cell treated with an activator of VR1 as compared to said cell expressing VR1 in vitro treated with an activator of VR1 and not contacted with said compound.

23. A method for treating pain in an animal, comprising administering to an animal in need thereof an effective amount of the compound or a pharmaceutically acceptable salt of the compound of claim 1.

* * * * *